(12) United States Patent
Gao et al.

(10) Patent No.: US 12,016,242 B2
(45) Date of Patent: Jun. 18, 2024

(54) HETEROCYCLIC COMPOUND AND APPLICATION THEREOF

(71) Applicants: Wuhan Tianma Micro-Electronics Co., Ltd., Wuhan (CN); Wuhan Tianma Microelectronics Co., Ltd. Shanghai Branch, Shanghai (CN)

(72) Inventors: Wei Gao, Shanghai (CN); Wenpeng Dai, Shanghai (CN); Lei Zhang, Shanghai (CN); Quan Ran, Shanghai (CN); Lu Zhai, Shanghai (CN); Lilian Kuang, Shanghai (CN)

(73) Assignees: Wuhan Tianma Micro-Electronics Co., Ltd., Wuhan (CN); Wuhan Tianma Microelectronics Co., Ltd. Shanghai Branch, Shanghai (CN)

( * ) Notice: Subject to any disclaimer, the term of this patent is extended or adjusted under 35 U.S.C. 154(b) by 646 days.

(21) Appl. No.: 17/191,837

(22) Filed: Mar. 4, 2021

(65) Prior Publication Data
US 2022/0223794 A1 Jul. 14, 2022

(30) Foreign Application Priority Data
Jan. 5, 2021 (CN) .......................... 202110009324.1

(51) Int. Cl.
*H10K 50/15* (2023.01)
*C07D 491/048* (2006.01)
(Continued)

(52) U.S. Cl.
CPC ....... *H10K 85/636* (2023.02); *C07D 491/048* (2013.01); *C07D 491/147* (2013.01);
(Continued)

(58) Field of Classification Search
None
See application file for complete search history.

(56) References Cited

U.S. PATENT DOCUMENTS

2010/0187984 A1* 7/2010 Lin ...................... H10K 50/156
546/89
2013/0255780 A1 10/2013 Iwanaga et al.
(Continued)

FOREIGN PATENT DOCUMENTS

CN 107056746 A 8/2017

*Primary Examiner* — Robert S Loewe
(74) *Attorney, Agent, or Firm* — Anova Law Group, PLLC

(57) ABSTRACT

A heterocyclic compound containing heteroatom substituted fluorene is provided in the present disclosure. The heterocyclic compound includes a structure:

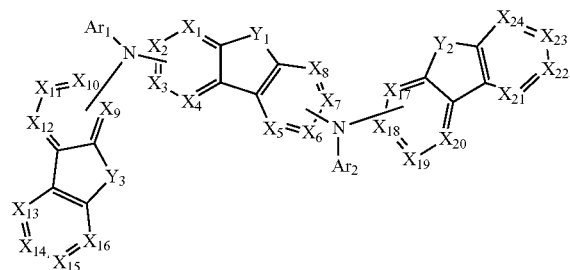

Y1 is selected from O or S; $X_1, X_2, X_3, X_4, X_5, X_6, X_7$, and $X_8$ are independently selected from $CR_a$ or N; $X_9, X_{10}, X_{11}, X_{12}, X_{13}, X_{14}, X_{15}, X_{16}, X_{17}, X_{18}, X_{19}, X_{20}, X_{21}, X_{22}, X_{23}$, and $X_{24}$ are independently selected from $CR_1$ or N; $R_a$ is independently selected from hydrogen, deuterium, tritium, halogen, nitrile, cyano, nitro, hydroxyl, carbonyl, ester, carboxyl, imide, amide, C1-C20 alkoxy, C1-C20 alkyl, C3-C20 cycloalkyl, C2-C20 alkenyl, C3-C20 cycloalkenyl, silyl, boron, phosphine oxide, phosphine, sulfonyl, amine, C6-C30 aryl, C3-C30 heteroaryl, or a ring structure; $Y_2$, and $Y_3$ (Continued)

are independently selected from O, S or $NR_2$; $Ar_1$ and $Ar_2$ are independently selected from aryl or heteroaryl; and $R_1$ and $R_2$ are independently selected from hydrogen, deuterium, C1-C20 alkyl, C6-C30 aryl, or C3-C30 heteroaryl.

26 Claims, 1 Drawing Sheet

(51) Int. Cl.
    *C07D 491/147*     (2006.01)
    *C07D 495/14*     (2006.01)
    *C09K 11/06*     (2006.01)
    *H10K 85/60*     (2023.01)
    *H10K 50/16*     (2023.01)
    *H10K 50/858*     (2023.01)

(52) U.S. Cl.
    CPC ............ *C07D 495/14* (2013.01); *C09K 11/06* (2013.01); *H10K 85/633* (2023.02); *C09K 2211/1018* (2013.01); *H10K 50/15* (2023.02); *H10K 50/16* (2023.02); *H10K 50/858* (2023.02); *H10K 85/626* (2023.02); *H10K 85/657* (2023.02); *H10K 85/6574* (2023.02)

(56) References Cited

U.S. PATENT DOCUMENTS

2016/0351817 A1*   12/2016   Kim .................... H10K 85/624
2016/0351818 A1*   12/2016   Kim ....................... H10K 85/40
2019/0074449 A1*    3/2019   Chen ................... C07D 413/04

* cited by examiner

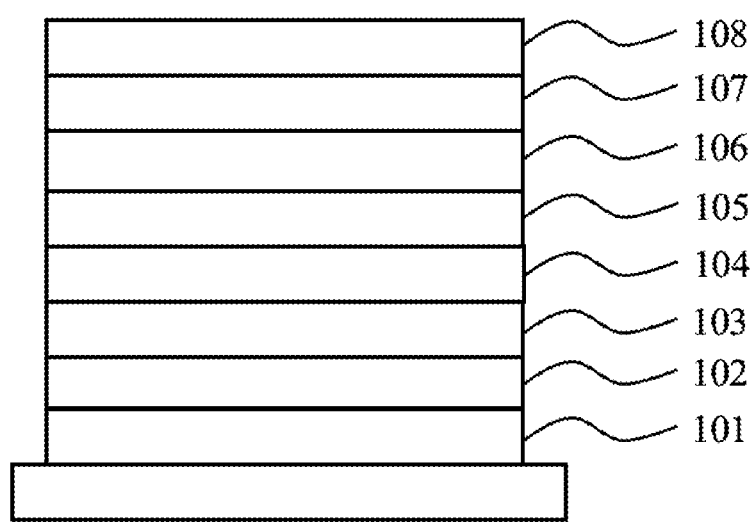

HETEROCYCLIC COMPOUND AND APPLICATION THEREOF

CROSS-REFERENCE TO RELATED APPLICATION

This application claims the priority of Chinese Patent Application No. 202110009324.1, filed on Jan. 5, 2021, the content of which is incorporated herein by reference in its entirety.

TECHNICAL FIELD

The present disclosure generally relates to the field of organic electroluminescent material technology and, more particularly, relates to a heterocyclic compound containing heteroatom substituted fluorene and its application.

BACKGROUND

According to the direction in which an organic light-emitting layer emits light, OLED displays are divided into bottom-emitting OLED displays and top-emitting OLED displays. In the bottom-emitting OLED display, the light is emitted toward a substrate, a reflective electrode is formed on the organic light-emitting layer, and a transparent electrode is formed under the organic light-emitting layer. If the OLED display is an active-matrix OLED display, a part of thin film transistors formed therein may not transmit light, such that the light-emitting area may be reduced. On the other hand, in the top-emitting OLED display, the transparent electrode is formed on the organic light-emitting layer, and the reflective electrode is formed under the organic light-emitting layer, such that the light is emitted along a direction opposite to the substrate, thereby increasing the light-transmitting area and improving the brightness.

There are a number of commonly used manners to improve luminous efficiency, including forming structures such as wrinkles, photonic crystals, micro-lens arrays (MLA) on a light-exiting surface of the substrate and adding a high-refractive-index surface capping layer on a low-refractive-index semi-reflective semi-transparent electrode. The first two structures may affect the angular distribution of the radiation spectrum of the OLED display, and the third structure may have a complicated fabrication process. However, the process of using the surface capping layer is simple, and the luminous efficiency is significantly improved, which gains more popularity.

Surface capping materials are divided into two categories: inorganic materials and organic materials.

When preparing the OLED devices by an evaporation method, in order to form the capping layer, a solution of using a high-precision metal mask is required, but the metal mask has a problem that the deformation caused by heat may cause poor positioning accuracy. That is, the melting point of ZnSe is as high as 1100° C. or more (Appl. Phys. Lett., 2003, 82, 466), and the high-precision mask may not be evaporated on an accurate position. Meantime, most inorganic substances have high vapor evaporation temperatures, which is not suitable for the use of the high-precision mask. The inorganic film formation manner based on a sputtering method may also cause damages to the light-emitting devices. For at least this reason, it is impossible to use the inorganic material as a constituting material for the capping layer.

In view of current low light extraction efficiency of the OLED device, it is necessary to add a capping layer (CPL), that is, a light extraction material, to the device structure. According to the principle of optical absorption and refraction, the refractive index of the surface capping layer material should be as high as possible.

Current CPL materials are mainly hole transport layer materials and electron transport type materials; the refractive index may not meet the increasing market demand, and the light extraction effect may not be sufficiently desirable; meanwhile, the difference in the refractive indexes measured in the respective wavelength regions of blue, green, and red may be large. For at least this reason, it is impossible to simultaneously obtain high light extraction efficiency for all of the light in blue, green, and red light-emitting devices.

SUMMARY

One aspect of the present disclosure provides a heterocyclic compound containing heteroatom substituted fluorene, having a structure shown in formula I:

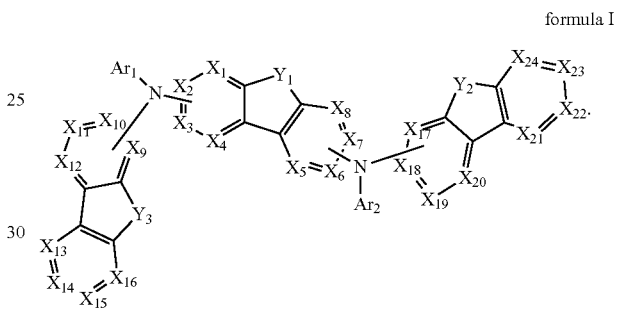

formula I where:

$Y_1$ is selected from O or S;

$X_1$, $X_2$, $X_3$, $X_4$, $X_5$, $X_6$, $X_7$, and $X_8$ are independently selected from $CR_a$ or N, and at least one of $X_1$, $X_2$, $X_3$, $X_4$, $X_5$, $X_6$, $X_7$, and $X_8$ is N;

$X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, and $X_{24}$ are independently selected from $CR_1$ or N;

when there are a plurality of $CR_a$ in $X_1$-$X_8$, $R_a$ are same or different; and $R_a$ is independently selected from hydrogen, deuterium, tritium, halogen, nitrile, cyano, nitro, hydroxyl, carbonyl, ester, carboxyl, imide, amide, substituted or unsubstituted C1-C20 alkoxy, substituted or unsubstituted C1-C20 alkyl, substituted or unsubstituted C3-C20 cycloalkyl, substituted or unsubstituted C2-C20 alkenyl, substituted or unsubstituted C3-C20 cycloalkenyl, substituted or unsubstituted silyl, substituted or unsubstituted boron, substituted or unsubstituted phosphine oxide, substituted or unsubstituted phosphine, substituted or unsubstituted sulfonyl, substituted or unsubstituted amine, substituted or unsubstituted C6-C30 aryl, substituted or unsubstituted C3-C30 heteroaryl, or a ring structure formed by bonding adjacent groups;

$Y_2$ and $Y_3$ are independently selected from O, S or $NR_2$;

$Ar_1$ and $Ar_2$ are independently selected from substituted or unsubstituted aryl, or substituted or unsubstituted heteroaryl; and $R_1$ and $R_2$ are independently selected from hydrogen, deuterium, substituted or unsubstituted C1-C20 alkyl, substituted or unsubstituted C6-C30 aryl, or substituted or unsubstituted C3-C30 heteroaryl.

Another aspect of the present disclosure provides a display panel, including an organic light-emitting device. The organic light-emitting device includes an anode, a cathode, and an organic thin film layer between the anode and the cathode; the cathode is covered with a capping layer (CPL); and the CPL layer contains at least a heterocyclic compound containing heteroatom substituted fluorene, having a structure shown in formula I, the heterocyclic compound comprising:

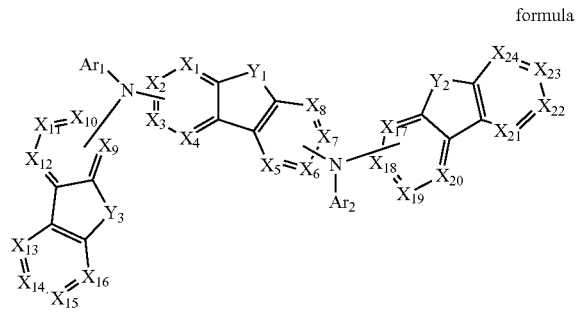

formula I where:

Y1 is selected from O or S;

$X_1$, $X_2$, $X_3$, $X_4$, $X_5$, $X_6$, $X_7$, and $X_8$ are independently selected from $CR_a$ or N, and at least one of $X_1$, $X_2$, $X_3$, $X_4$, $X_5$, $X_6$, $X_7$, and $X_8$ is N;

$X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, and $X_{24}$ are independently selected from $CR_1$ or N;

when there are a plurality of $CR_a$ in $X_1$-$X_8$, $R_a$ are same or different; and $R_a$ is independently selected from hydrogen, deuterium, tritium, halogen, nitrile, cyano, nitro, hydroxyl, carbonyl, ester, carboxyl, imide, amide, substituted or unsubstituted C1-C20 alkoxy, substituted or unsubstituted C1-C20 alkyl, substituted or unsubstituted C3-C20 cycloalkyl, substituted or unsubstituted C2-C20 alkenyl, substituted or unsubstituted C3-C20 cycloalkenyl, substituted or unsubstituted silyl, substituted or unsubstituted boron, substituted or unsubstituted phosphine oxide, substituted or unsubstituted phosphine, substituted or unsubstituted sulfonyl, substituted or unsubstituted amine, substituted or unsubstituted C6-C30 aryl, substituted or unsubstituted C3-C30 heteroaryl, or a ring structure formed by bonding adjacent groups;

$Y_2$, and $Y_3$ are independently selected from O, S or $NR_2$;

$Ar_1$ and $Ar_2$ are independently selected from substituted or unsubstituted aryl, or substituted or unsubstituted heteroaryl; and $R_1$ and $R_2$ are independently selected from hydrogen, deuterium, substituted or unsubstituted C1-C20 alkyl, substituted or unsubstituted C6-C30 aryl, or substituted or unsubstituted C3-C30 heteroaryl.

Another aspect of the present disclosure provides a display panel, including an organic light-emitting device. The organic light-emitting device includes an anode, a cathode, and an organic thin film layer between the anode and the cathode; the organic thin film layer includes a hole transport layer and/or an electron transport layer, where at least one of the hole transport layer and the electron transport layer contains at least a heterocyclic compound containing heteroatom substituted fluorene, having a structure shown in formula I, the heterocyclic compound comprising:

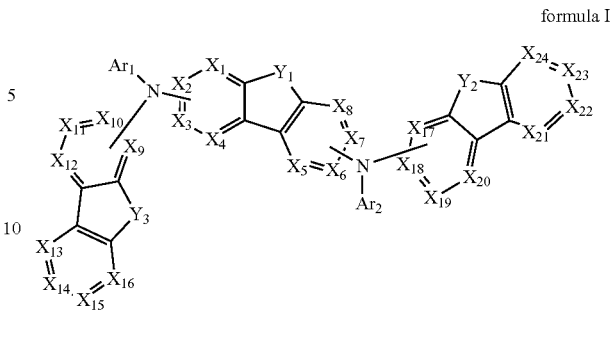

formula I where:

$Y_1$ is selected from O or S;

$X_1$, $X_2$, $X_3$, $X_4$, $X_5$, $X_6$, $X_7$, and $X_8$ are independently selected from $CR_a$ or N, and at least one of $X_1$, $X_2$, $X_3$, $X_4$, $X_5$, $X_6$, $X_7$, and $X_8$ is N;

$X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, and $X_{24}$ are independently selected from $CR_1$ or N;

when there are a plurality of $CR_a$ in $X_1$-$X_8$, $R_a$ are same or different; and $R_a$ is independently selected from hydrogen, deuterium, tritium, halogen, nitrile, cyano, nitro, hydroxyl, carbonyl, ester, carboxyl, imide, amide, substituted or unsubstituted C1-C20 alkoxy, substituted or unsubstituted C1-C20 alkyl, substituted or unsubstituted C3-C20 cycloalkyl, substituted or unsubstituted C2-C20 alkenyl, substituted or unsubstituted C3-C20 cycloalkenyl, substituted or unsubstituted silyl, substituted or unsubstituted boron, substituted or unsubstituted phosphine oxide, substituted or unsubstituted phosphine, substituted or unsubstituted sulfonyl, substituted or unsubstituted amine, substituted or unsubstituted C6-C30 aryl, substituted or unsubstituted C3-C30 heteroaryl, or a ring structure formed by bonding adjacent groups;

$Y_2$, and $Y_3$ are independently selected from O, S or $NR_2$;

$Ar_1$ and $Ar_2$ are independently selected from substituted or unsubstituted aryl, or substituted or unsubstituted heteroaryl; and $R_1$ and $R_2$ are independently selected from hydrogen, deuterium, substituted or unsubstituted C1-C20 alkyl, substituted or unsubstituted C6-C30 aryl, or substituted or unsubstituted C3-C30 heteroaryl.

Other aspects of the present disclosure can be understood by those skilled in the art in light of the description, the claims, and the drawing of the present disclosure.

BRIEF DESCRIPTION OF THE DRAWING

The drawing incorporated in the specification and forming a part of the specification demonstrates the embodiments of the present disclosure and, together with the specification, describes the principles of the present disclosure.

The Figure illustrates a structural schematic of an organic light-emitting diode (OLED) device according to various embodiments of the present disclosure.

DETAILED DESCRIPTION

The present disclosure provides a heterocyclic compound containing heteroatom substituted fluorene, which may have the structure shown in formula I:

formula I

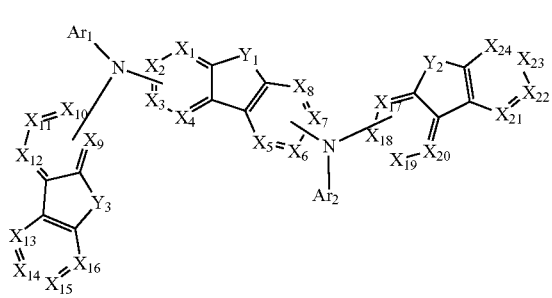

where, Y1 is selected from O or S;

$X_1$, $X_2$, $X_3$, $X_4$, $X_5$, $X_6$, $X_7$, and $X_8$ are independently selected from $CR_a$ or N, and at least one of $X_1$, $X_2$, $X_3$, $X_4$, $X_5$, $X_6$, $X_7$, and $X_8$ is N;

$X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, and $X_{24}$ are independently selected from $CR_1$ or N;

when there are a plurality of $CR_a$ in $X_1$-$X_8$, $R_a$ are same or different; and $R_a$ is independently selected from hydrogen, deuterium, tritium, halogen, nitrile, cyano, nitro, hydroxyl, carbonyl, ester, carboxyl, imide, amide, substituted or unsubstituted C1-C20 alkoxy, substituted or unsubstituted C1-C20 alkyl, substituted or unsubstituted C3-C20 cycloalkyl, substituted or unsubstituted C2-C20 alkenyl, substituted or unsubstituted C3-C20 cycloalkenyl, substituted or unsubstituted silyl, substituted or unsubstituted boron, substituted or unsubstituted phosphine oxide, substituted or unsubstituted phosphine, substituted or unsubstituted sulfonyl, substituted or unsubstituted amine, substituted or unsubstituted C6-C30 aryl, substituted or unsubstituted C3-C30 heteroaryl, or a ring structure formed by bonding adjacent groups which may not be limited according to various embodiments of the present disclosure;

$Y_2$, and $Y_3$ are independently selected from O, S or $NR_2$;

$Ar_1$ and $Ar_2$ are independently selected from substituted or unsubstituted aryl, or substituted or unsubstituted heteroaryl; and $R_1$ and $R_2$ are independently selected from hydrogen, deuterium, substituted or unsubstituted C1-C20 alkyl, substituted or unsubstituted C6-C30 aryl, or substituted or unsubstituted C3-C30 heteroaryl.

Optionally, in the present disclosure, $Ar_1$ and $Ar_2$ are independently selected from any of the following structures:

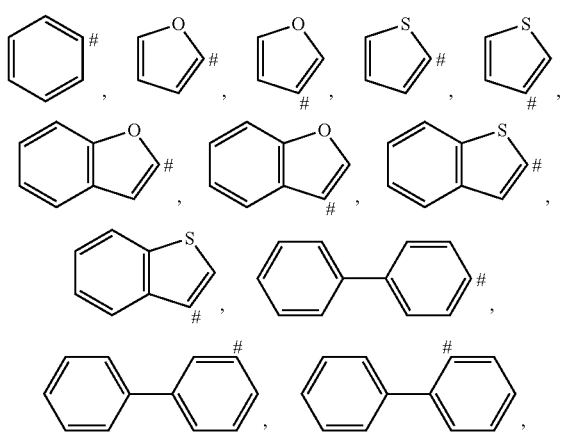

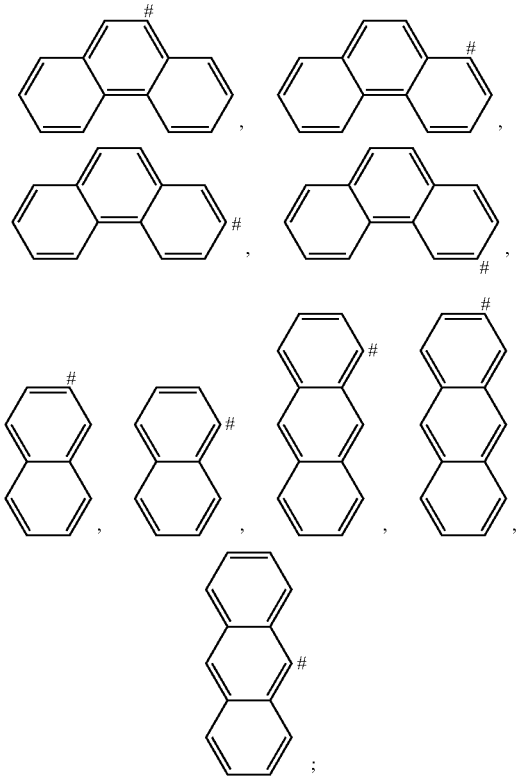

where, #denotes a connection location.

Optionally, in the present disclosure, $Y_2$ and $Y_3$ are independently selected from O, S, or $NR_2$, where $R_2$ is selected from phenyl, biphenyl, terphenyl, naphthyl, anthryl, phenanthryl, pyrenyl, fluoranthyl, triphenyl, pyrrolyl, pyranyl, thienyl, pyridyl, pyrimidinyl, triazinyl, benzofuranyl, benzothienyl, dibenzofuranyl, or dibenzothienyl.

Optionally, in the present disclosure, for the structure

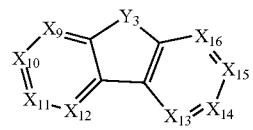

in the heterocyclic compound, $X_9$, $X_{10}$, $X_{11}$, $X_{12}$, $X_{13}$, $X_{14}$, $X_{15}$, and $X_{16}$ are independently selected from $CR_1$ or N, and at least one of $X_9$, $X_{10}$, $X_{11}$, $X_{12}$, $X_{13}$, $X_{14}$, $X_{15}$, and $X_{16}$ is N.

$R_1$ is selected from hydrogen, deuterium, substituted or unsubstituted C1-C20 alkyl, substituted or unsubstituted C6-C30 aryl or substituted or unsubstituted C3-C30 heteroaryl.

Optionally, $X_9$, $X_{10}$, $X_{11}$, $X_{12}$, $X_{13}$, $X_{14}$, $X_{15}$, and $X_{16}$ are independently selected from $CR_1$ or N, and optionally, 1 to 3 of $X_9$, $X_{10}$, $X_{11}$, $X_{12}$, $X_{13}$, $X_{14}$, $X_{15}$, and $X_{16}$ are N.

$R_1$ is selected from hydrogen, deuterium, substituted or unsubstituted C1-C20 alkyl, substituted or unsubstituted C6-C30 aryl or substituted or unsubstituted C3-C30 heteroaryl.

Optionally, in the present disclosure,

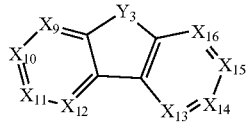

is selected from any one of the following structures:

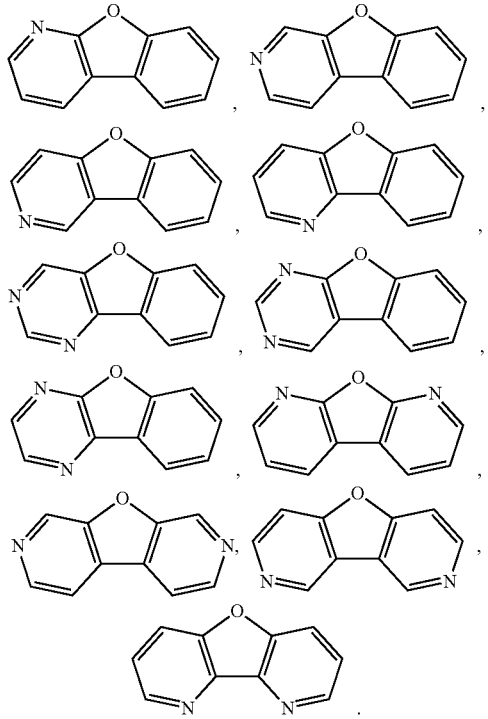

Optionally, in the present disclosure, in the heterocyclic compound,

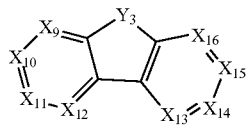

is selected from:

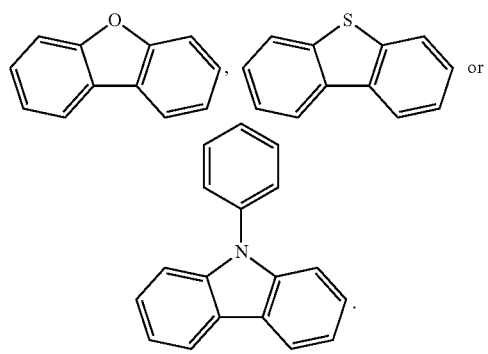

Optionally, in the heterocyclic compound of the present disclosure,
for the structure

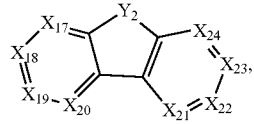

$X_{17}$, $X_{18}$, $X_{19}$, $X_{20}$, $X_{21}$, $X_{22}$, $X_{23}$, and $X_{24}$ are independently selected from $CR_1$ or N, and at least one of $X_{17}$, $X_{18}$, $X_{19}$, $X_{20}$, $X_{21}$, $X_{22}$, $X_{23}$, and $X_{24}$ is N.

$R_1$ is selected from hydrogen, deuterium, substituted or unsubstituted C1-C20 alkyl, substituted or unsubstituted C6-C30 aryl or substituted or unsubstituted C3-C30 heteroaryl.

Optionally, $X_{17}$, $X_{18}$, $X_{19}$, $X_{20}$, $X_{21}$, $X_{22}$, $X_{23}$, and $X_{24}$ are independently selected from $CR_1$ or N, and optionally 1 to 3 of $X_{17}$, $X_{18}$, $X_{19}$, $X_{20}$, $X_{21}$, $X_{22}$, $X_{23}$, and $X_{24}$ are N.

$R_1$ is selected from hydrogen, deuterium, substituted or unsubstituted C1-C20 alkyl, substituted or unsubstituted C6-C30 aryl or substituted or unsubstituted C3-C30 heteroaryl.

Optionally, in the present disclosure,

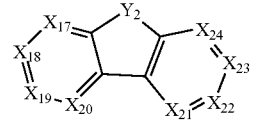

is selected from any one of the following structures:

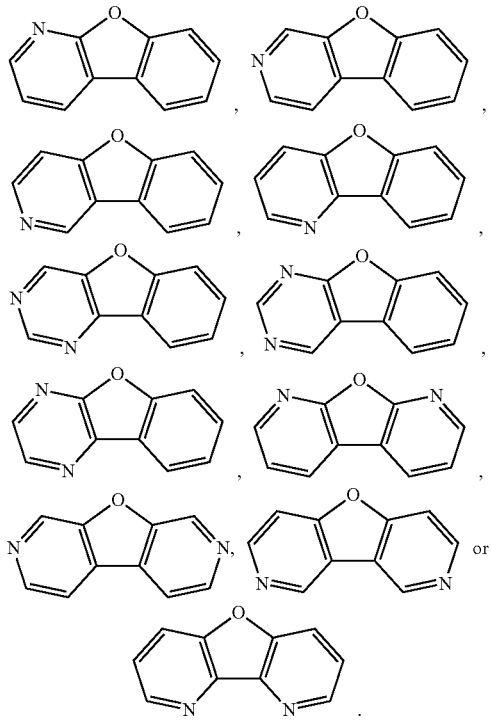

Optionally, in the heterocyclic compound of the present disclosure,

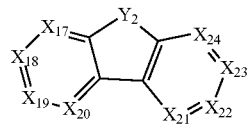

is selected from:

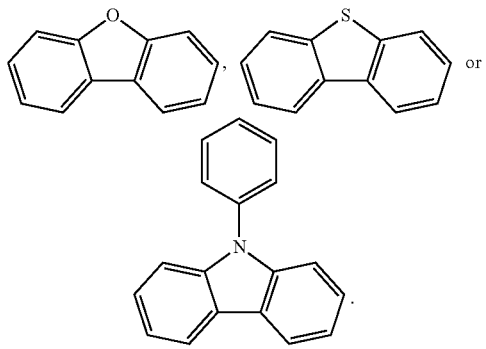

Optionally, in the present disclosure, any 1 to 6 of $X_1$, $X_2$, $X_3$, $X_4$, $X_5$, $X_6$, $X_7$, and $X_8$ are N.

Optionally, in the present disclosure, any 1 to 4 of $X_1$, $X_2$, $X_3$, $X_4$, $X_5$, $X_6$, $X_7$, and $X_8$ are N.

Optionally, in the present disclosure, any 1 to 3 of $X_1$, $X_2$, $X_3$, $X_4$, $X_5$, $X_6$, $X_7$, and $X_8$ are N.

Optionally, in the heterocyclic compound of the present disclosure,

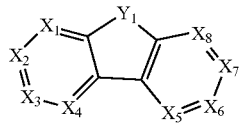

is selected from any one of the following structures:

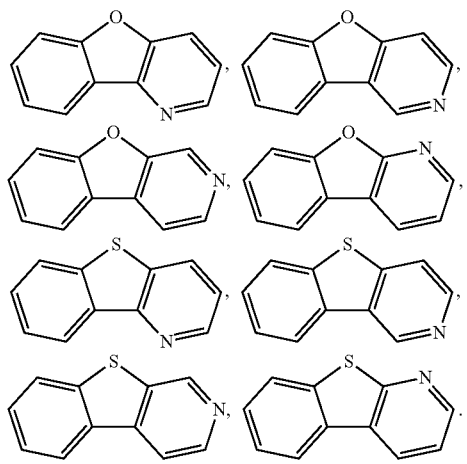

Optionally, in the heterocyclic compound of the present disclosure,

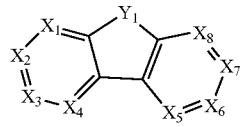

is selected from any one of the following structures:

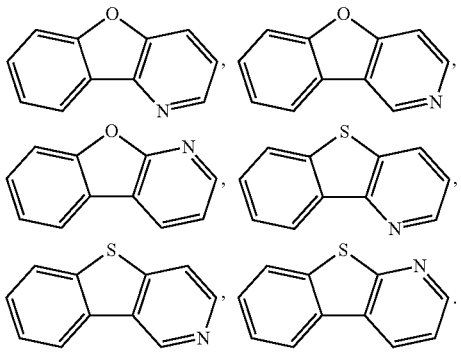

Optionally, in the heterocyclic compound of the present disclosure,

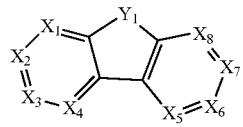

is selected from any one of the following structures:

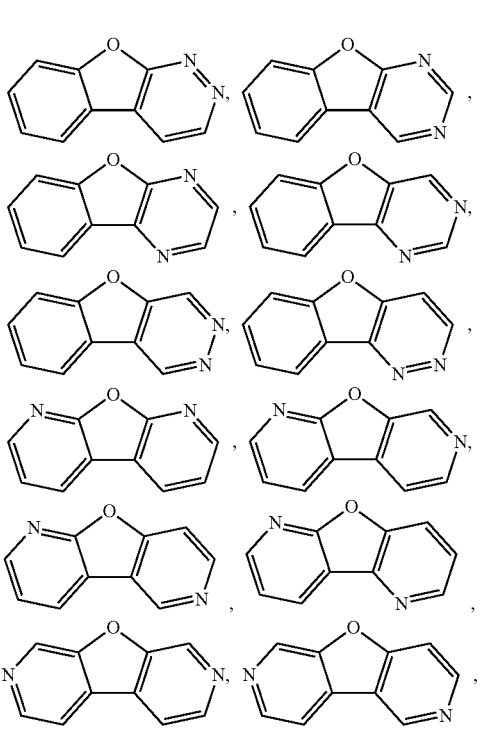

-continued
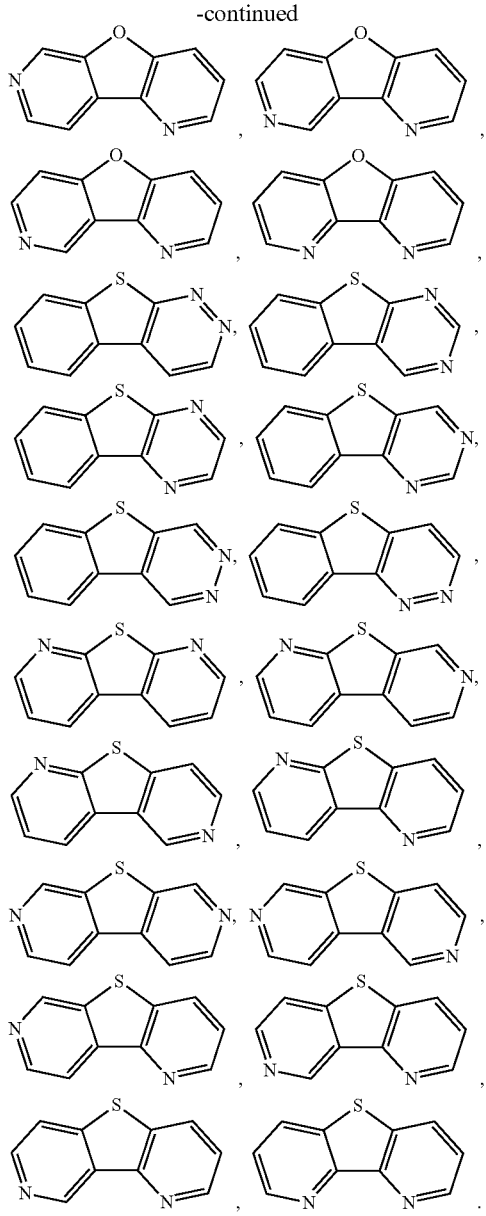
Optionally, in the heterocyclic compound of the present disclosure,
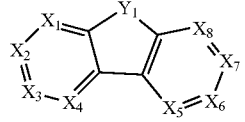
is selected from any one of the following structures:
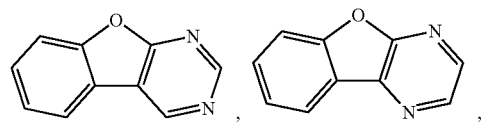
-continued
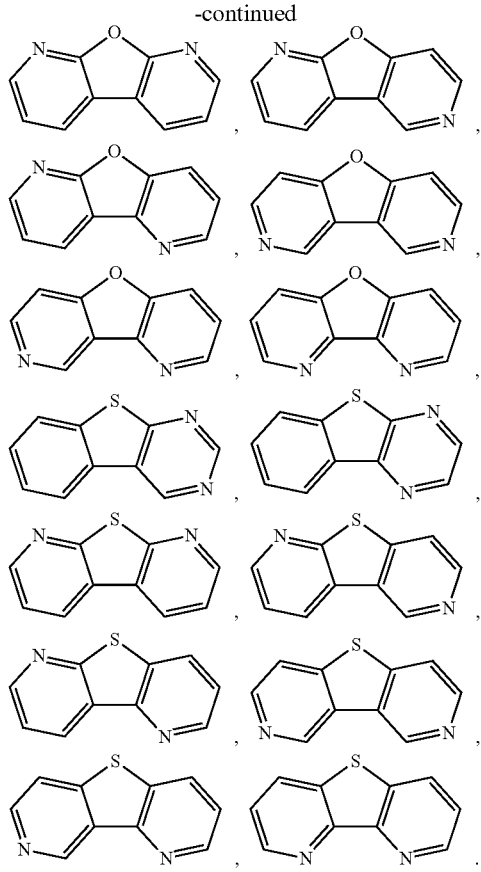
Optionally, in the heterocyclic compound of the present disclosure,
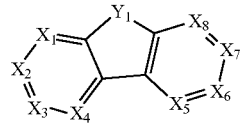
is selected from any one of the following structures:
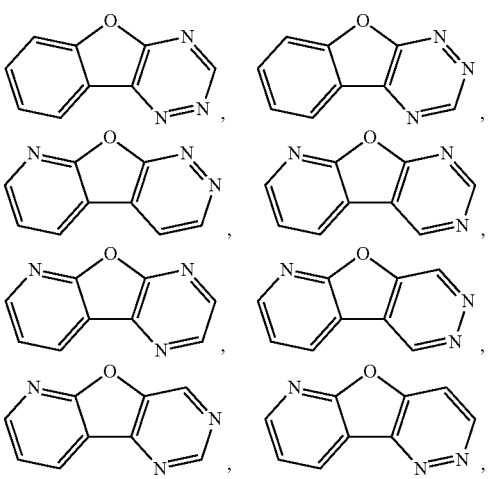
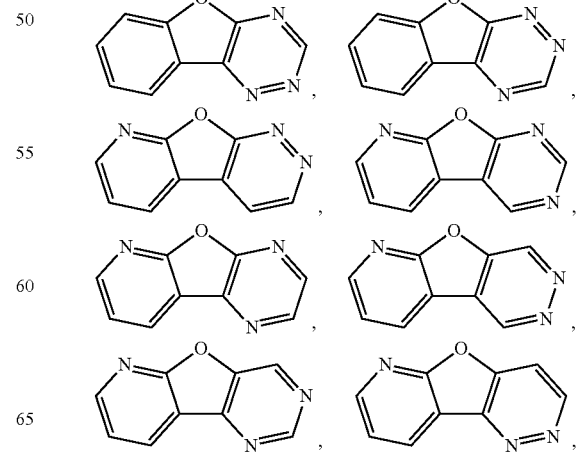

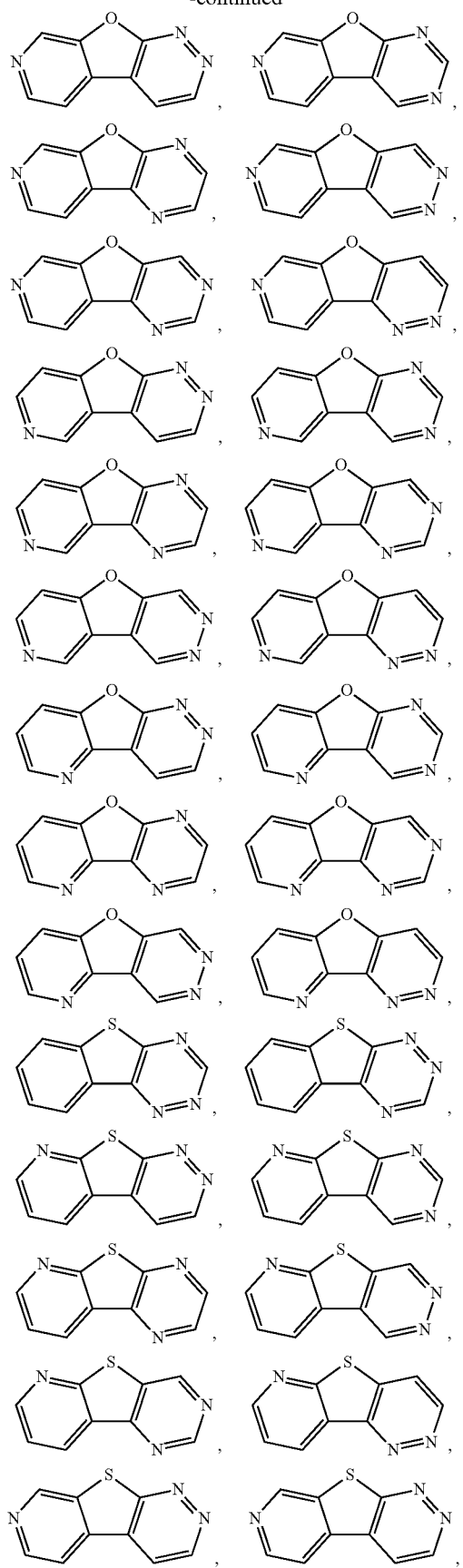
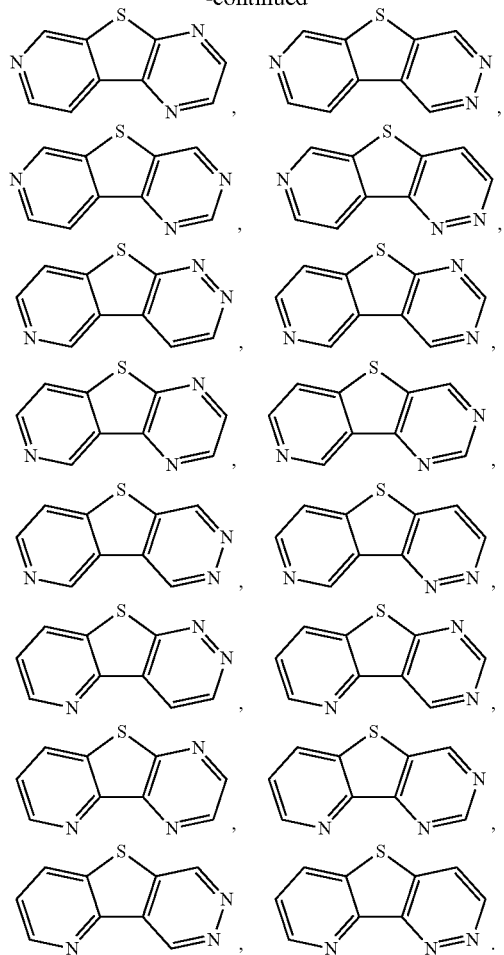
Optionally, in the heterocyclic compound of the present disclosure,
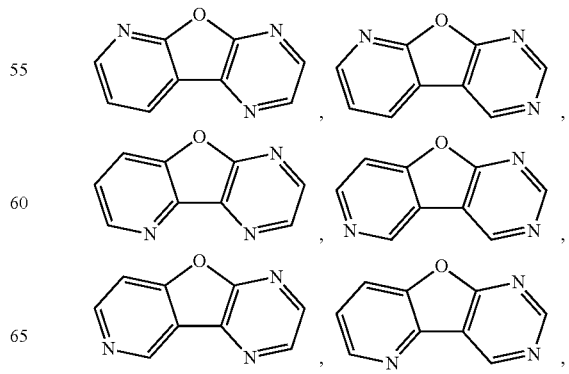
is selected from any one of the following structures:

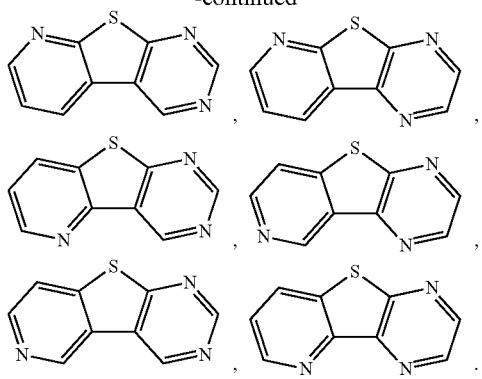
Optionally, in the heterocyclic compound of the present disclosure,
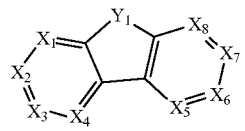
is selected from any one of the following structures:
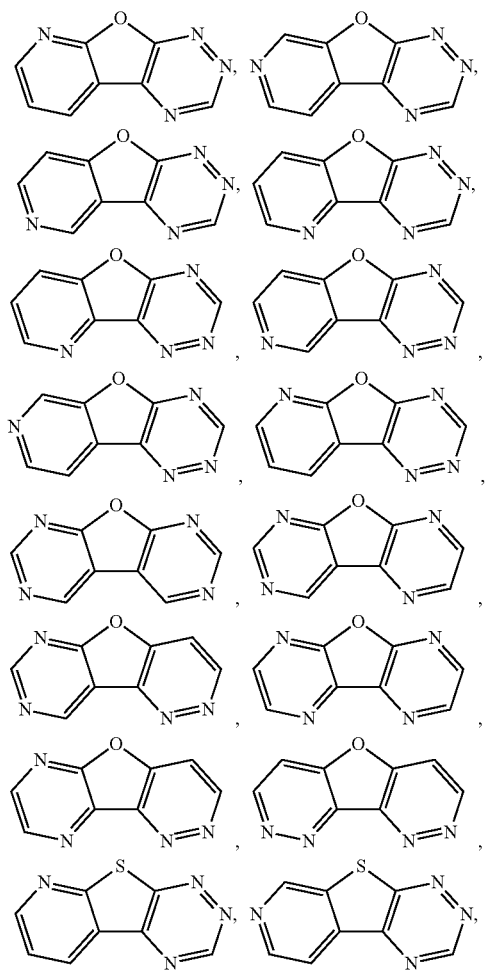
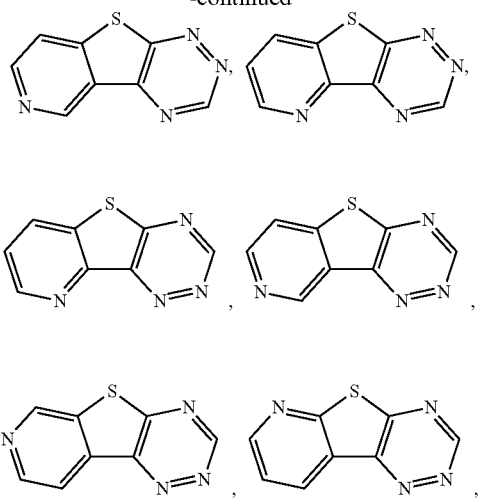
Optionally, the heterocyclic compound of the present disclosure may be any one of the following structures:
M001
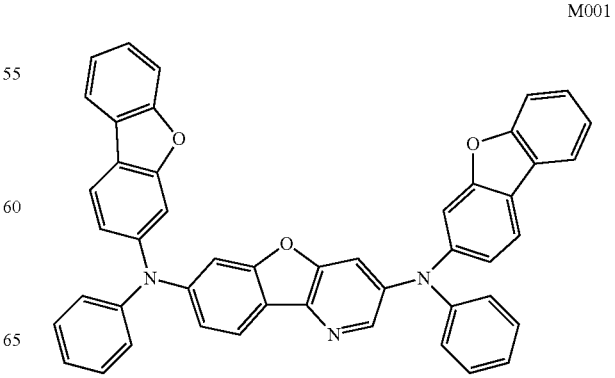

M002
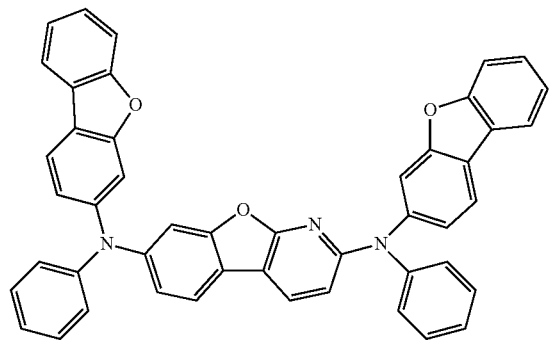
M003
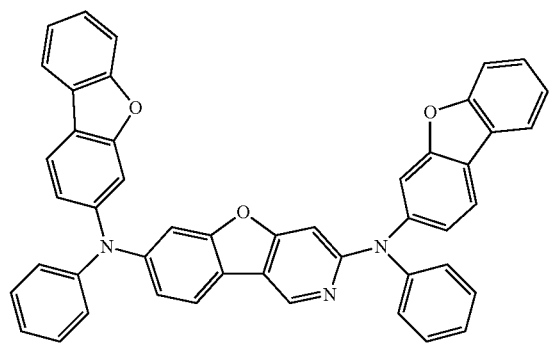
M004
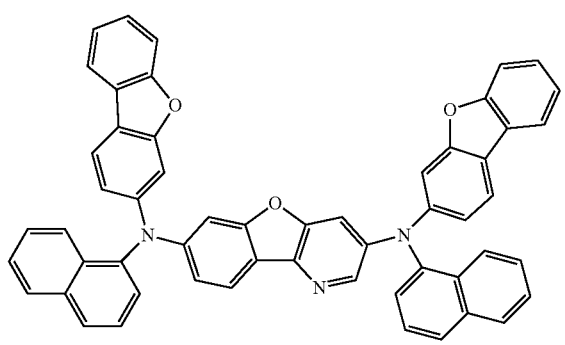
M005
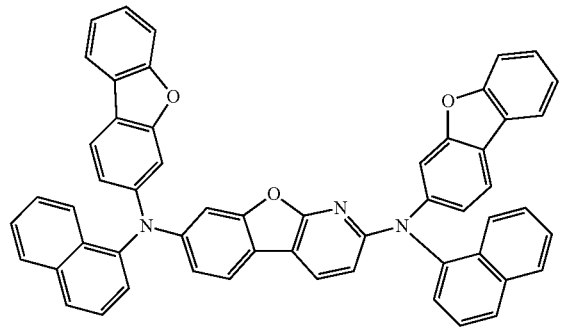
M006
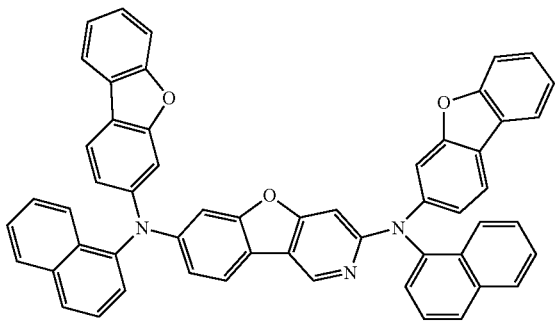
M007
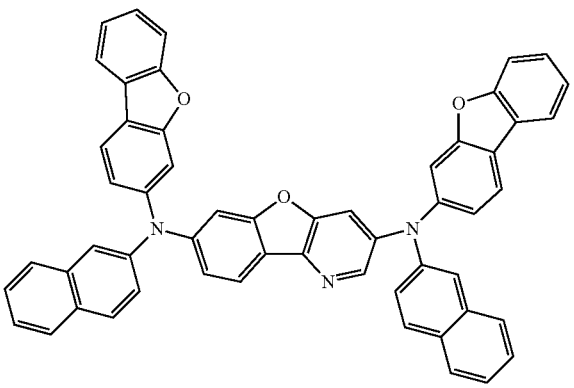
M008
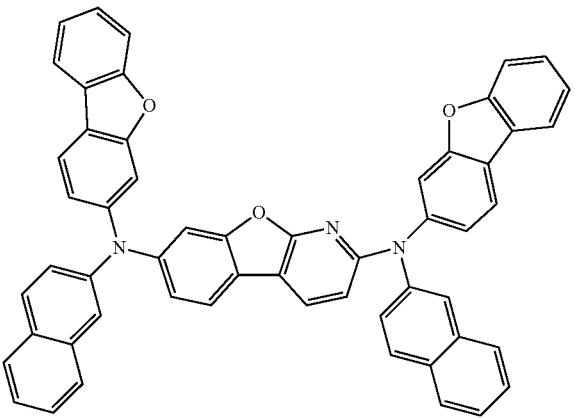
M009
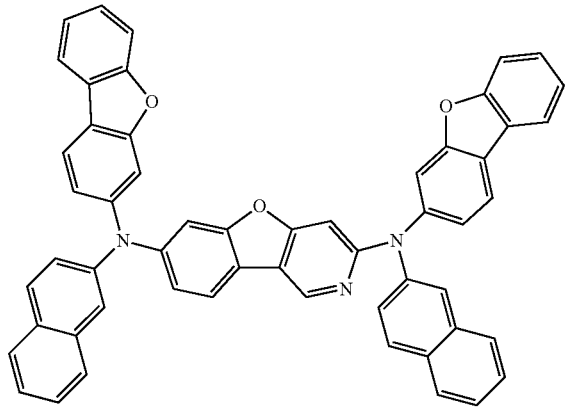

M010
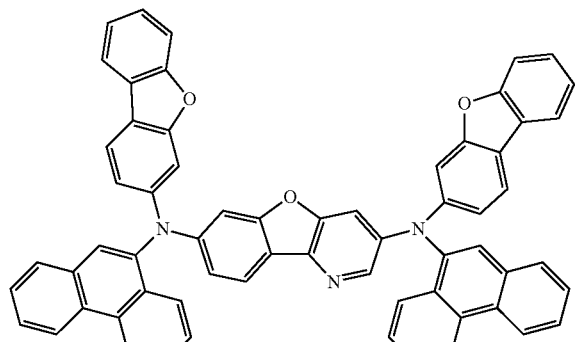
M011
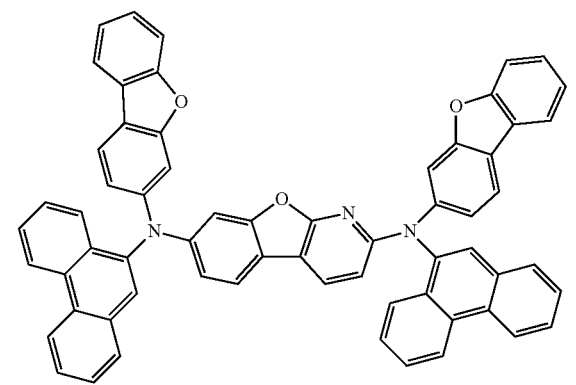
M012
M013
M014
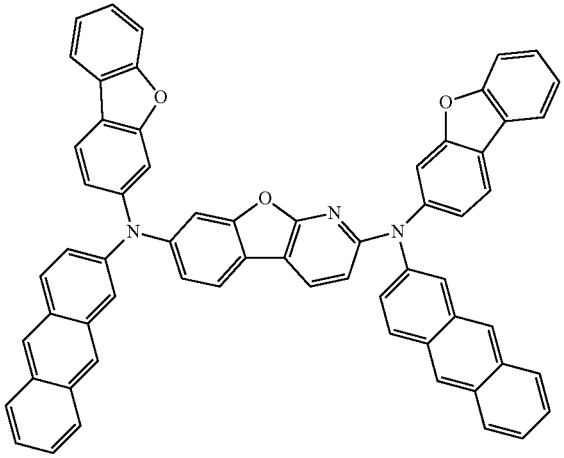
M015
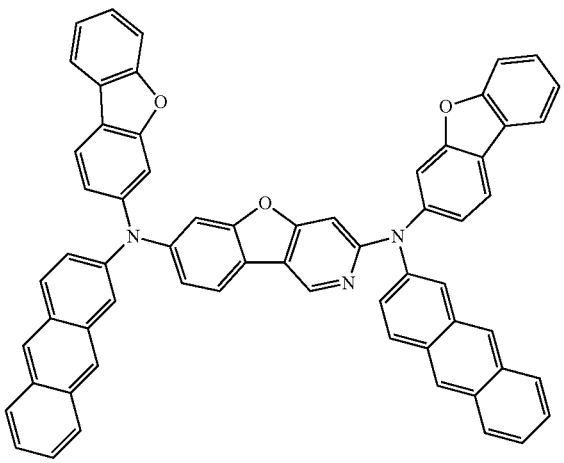
M016
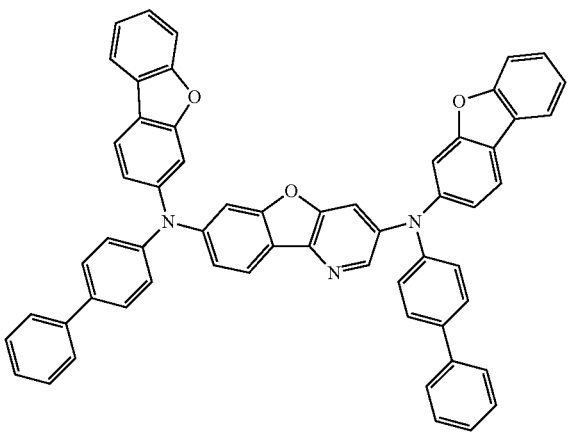

M017
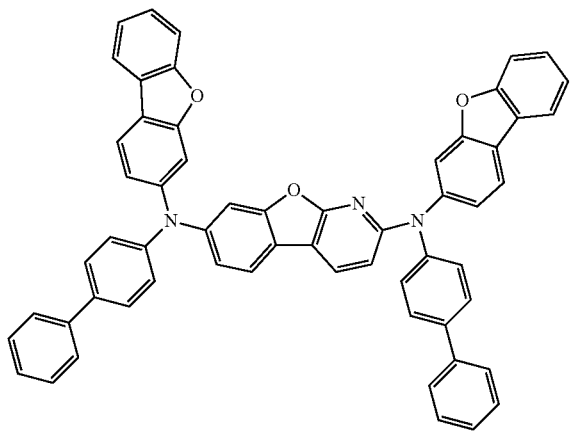
M018
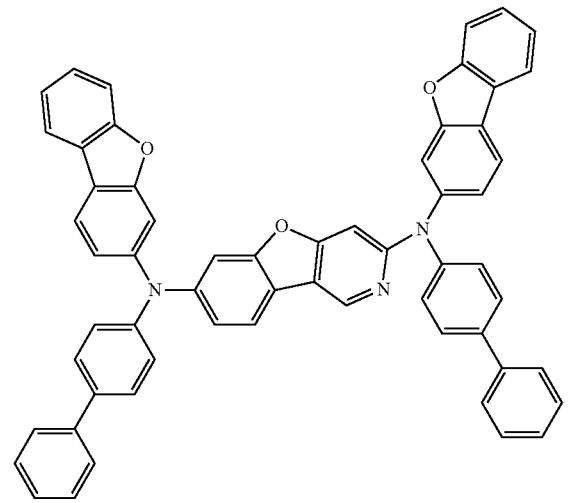
M019
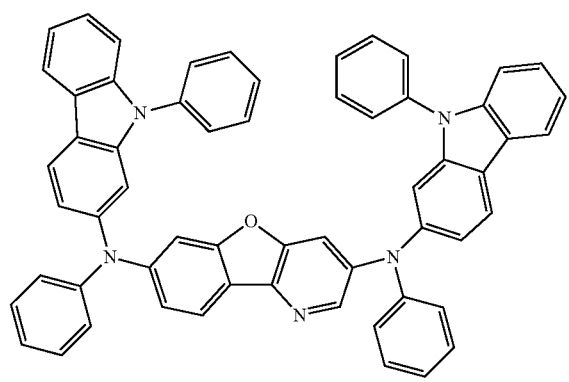
M020
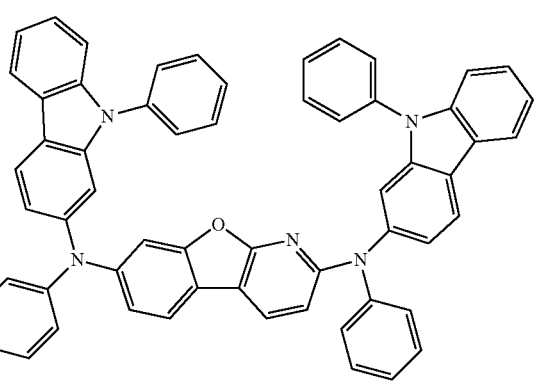
M021
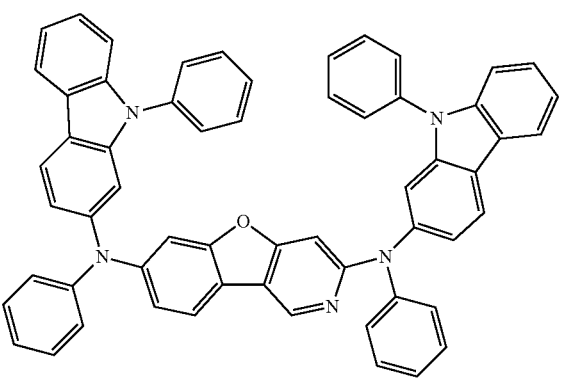
M022
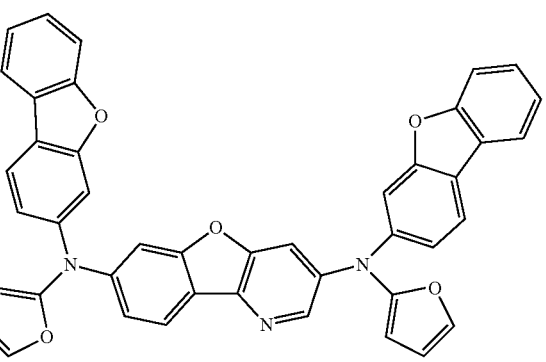
M023
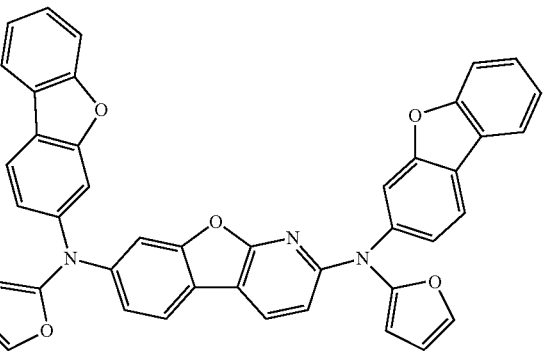

M024
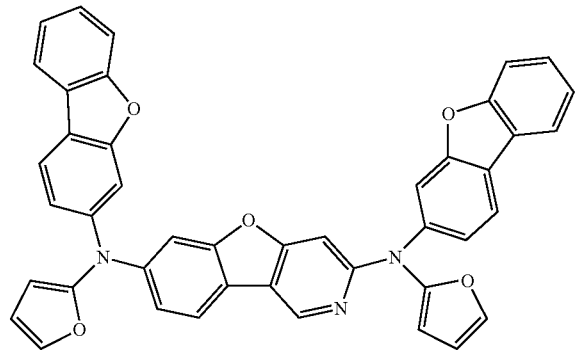
M025
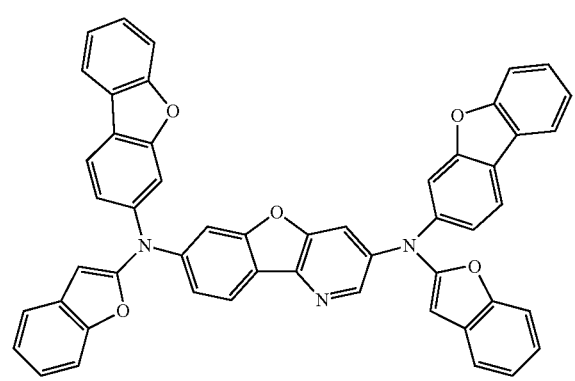
M026
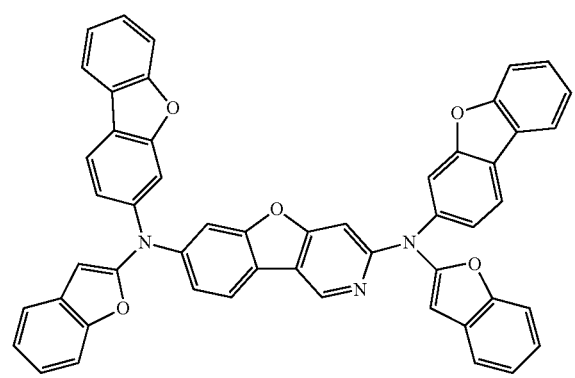
M027
M028
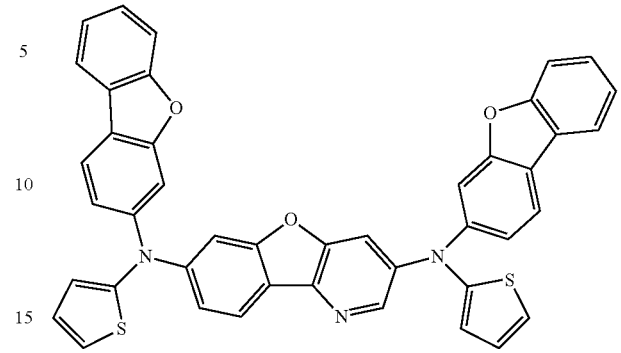
M029
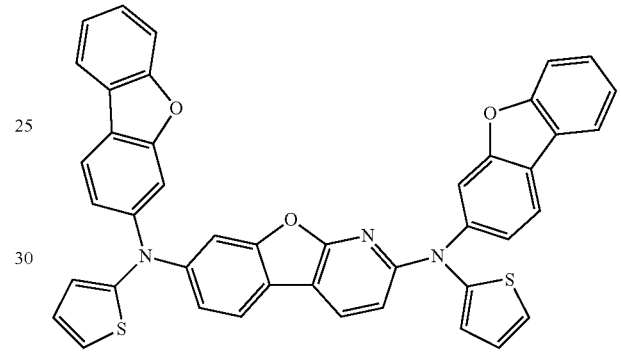
M030
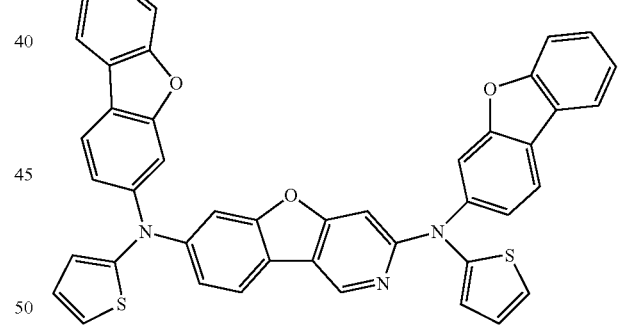
M031
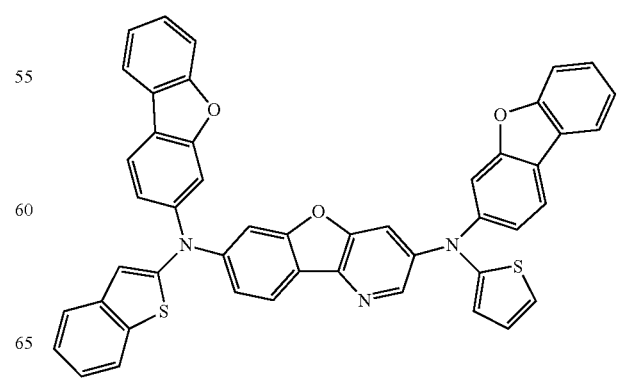

-continued
M032
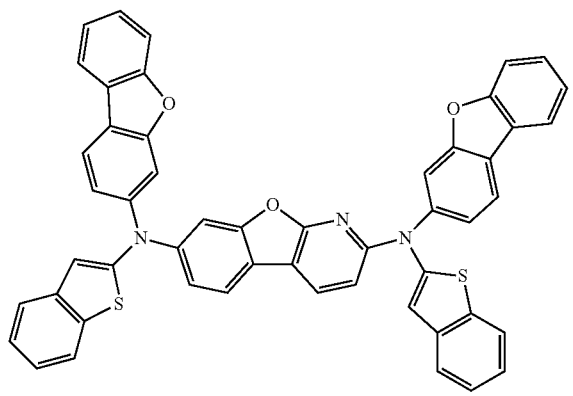
M033
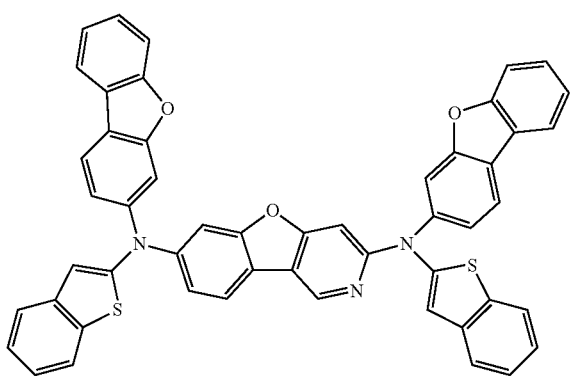
M034
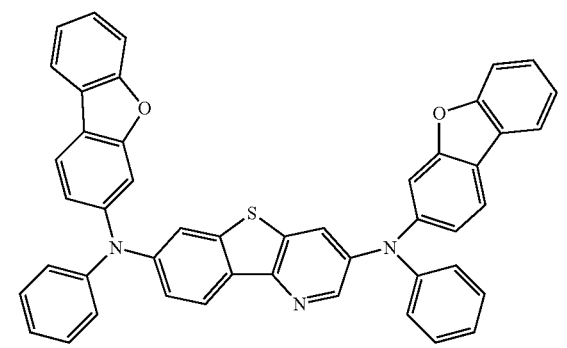
M035
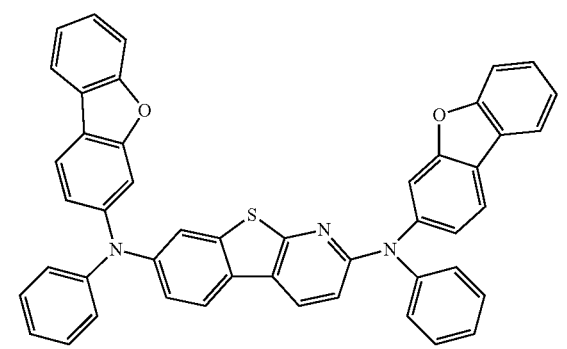
M036
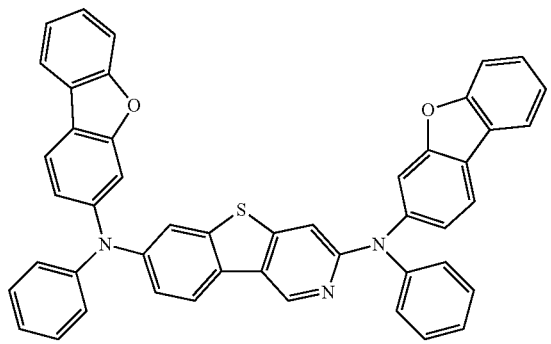
M037
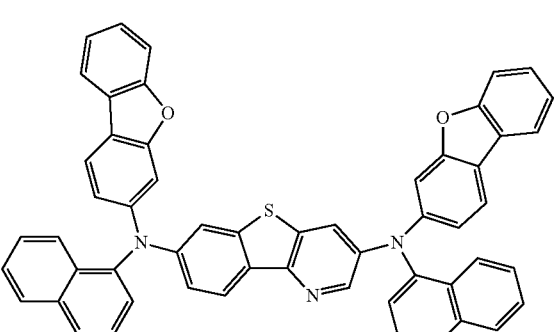
M038
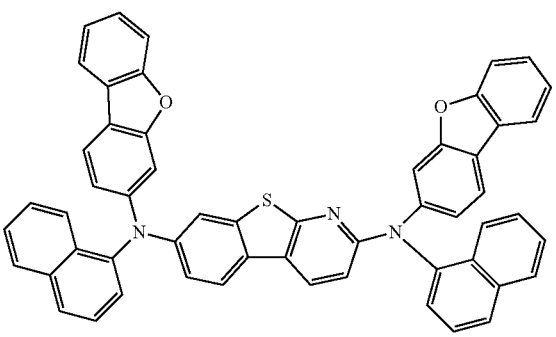
M039
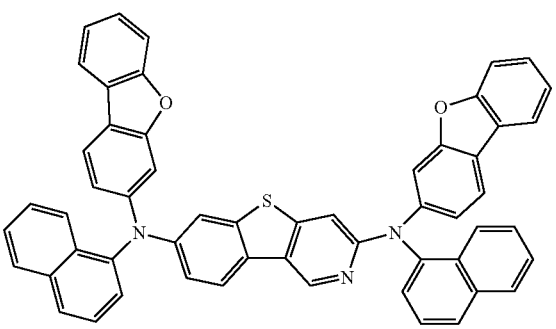

M040
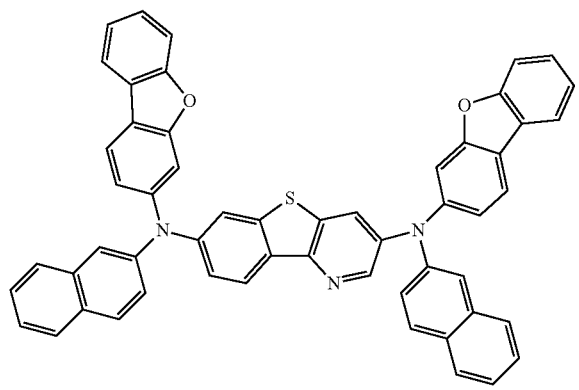
M041
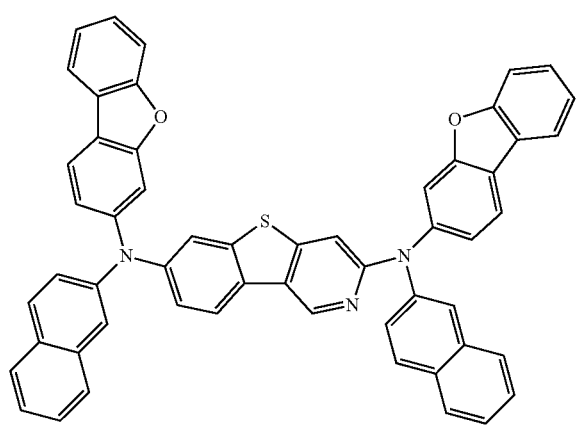
M042
M043
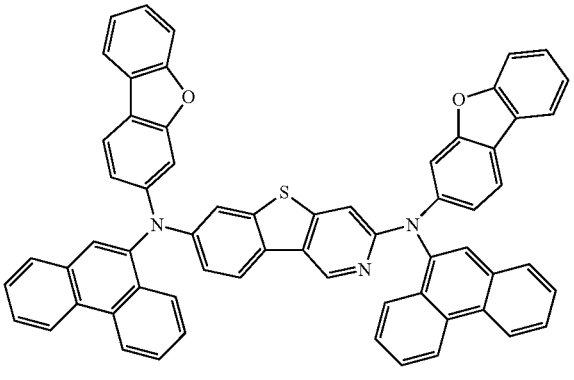
M044
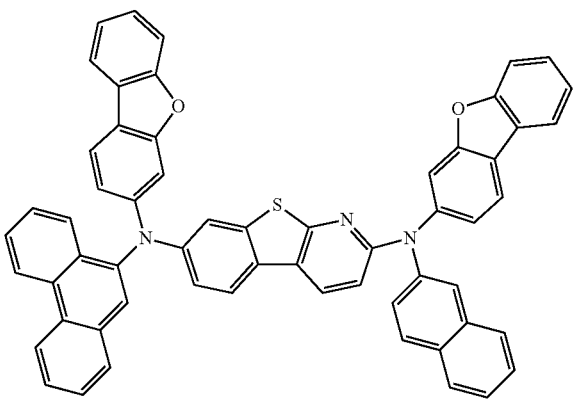
M045
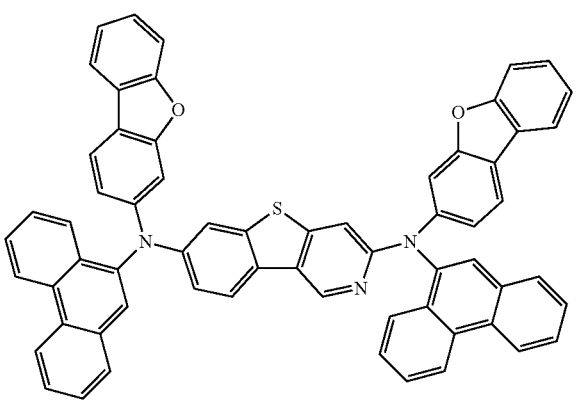
M046

M047
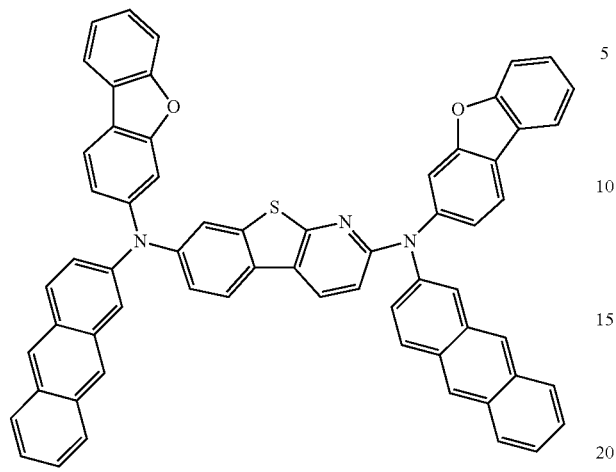
M048
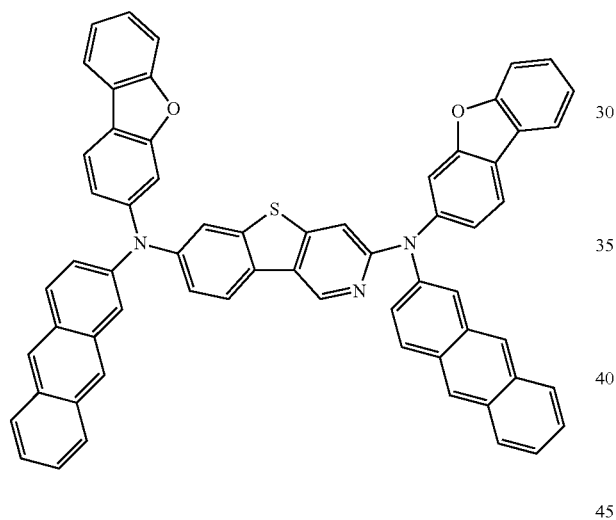
M049
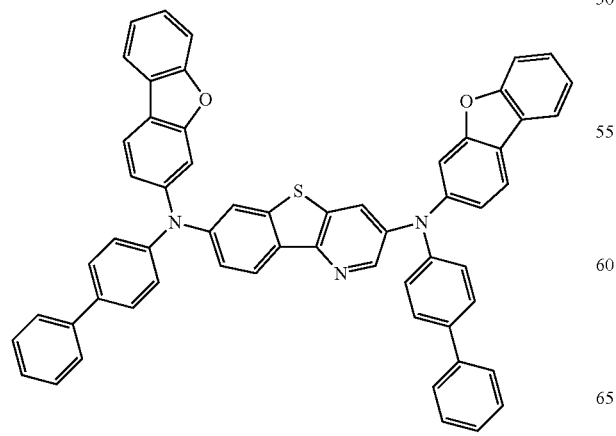
M050
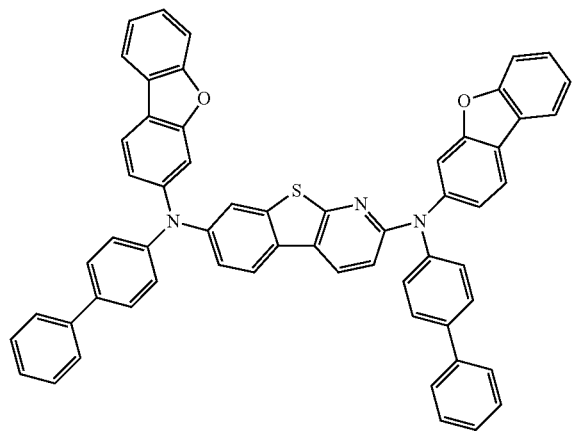
M051
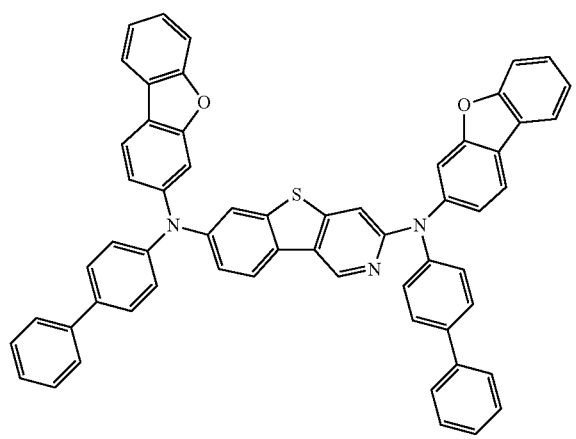
M052
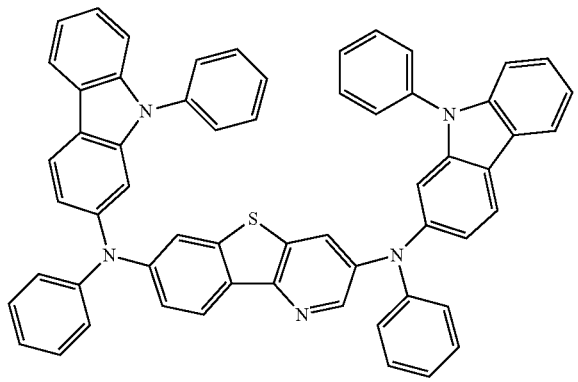

M053
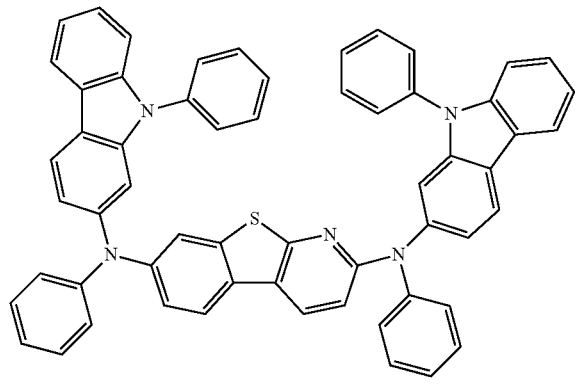
M054
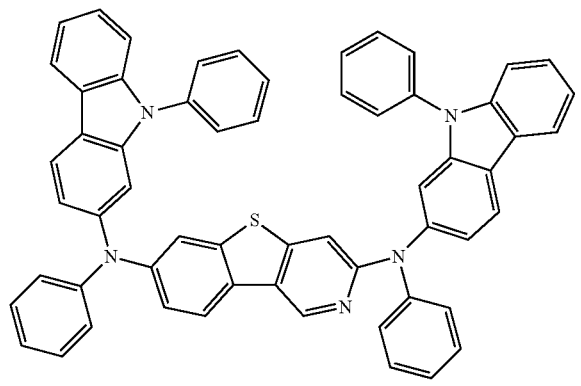
M055
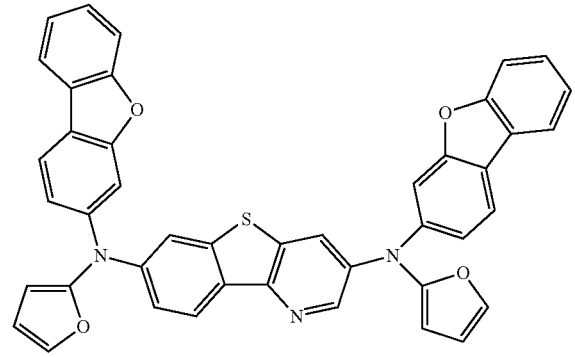
M056
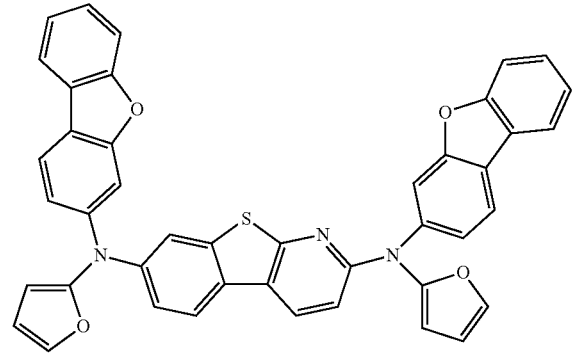
M057
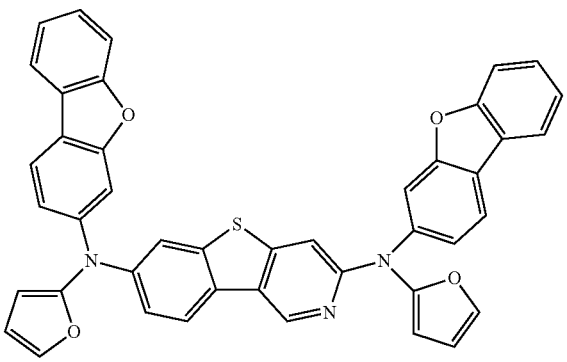
M058
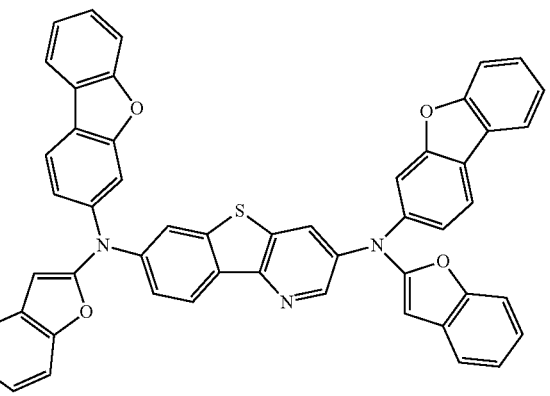
M059
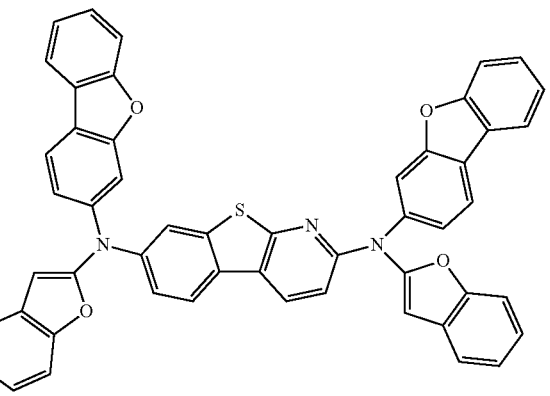
M060
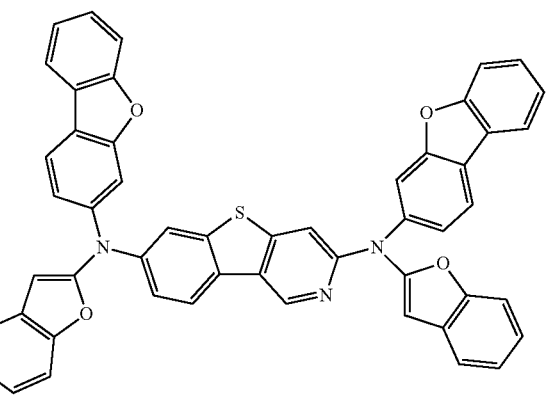

-continued
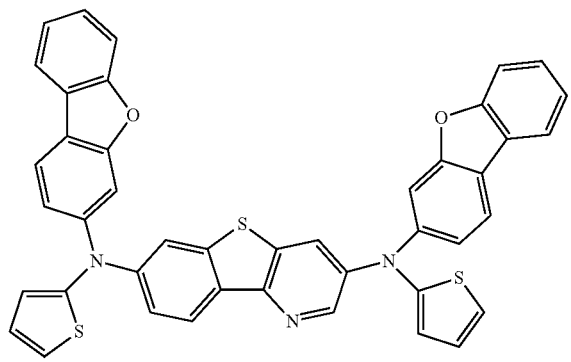
M061
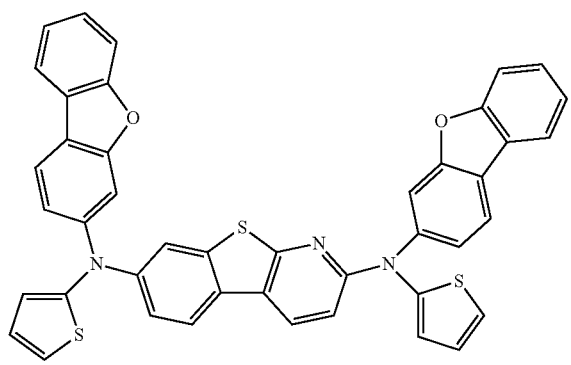
M062
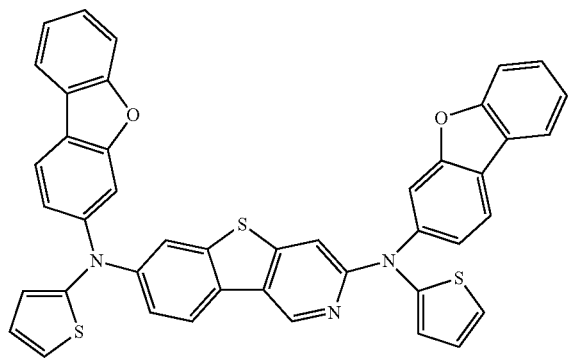
M063
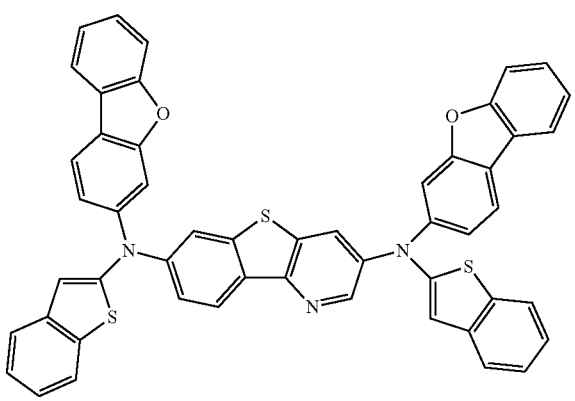
M064
-continued
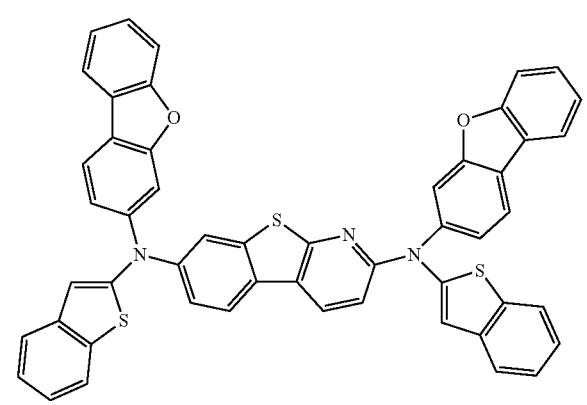
M065
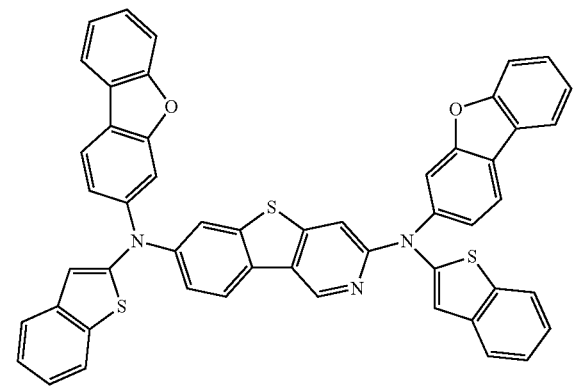
M066
Optionally, the heterocyclic compound of the present disclosure may be any one of the following structures:
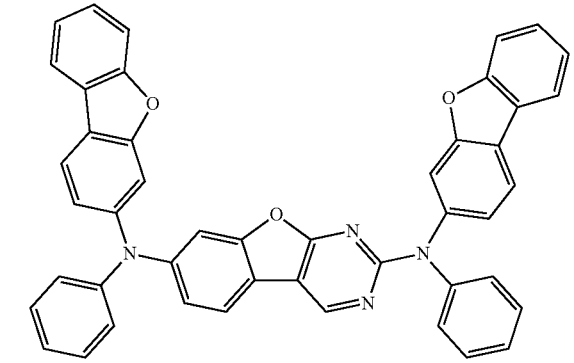
M067

M068
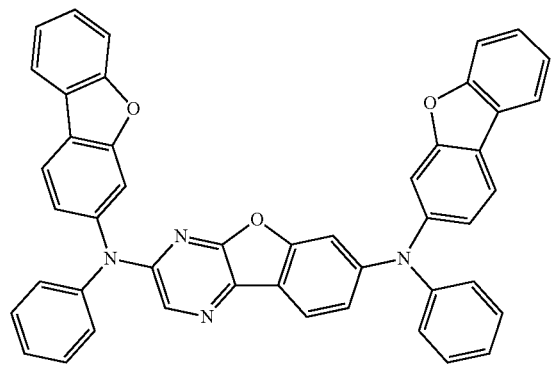
M069
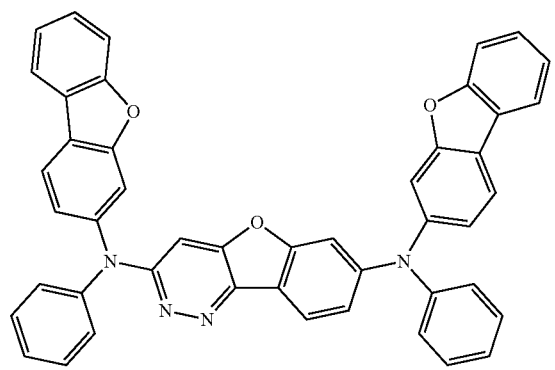
M070
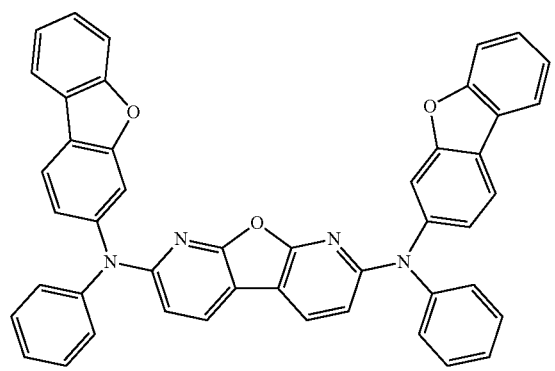
M071
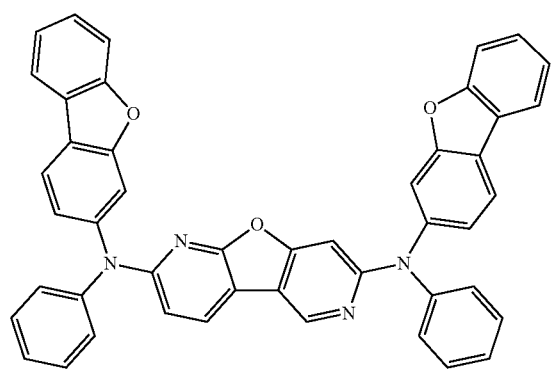
M072
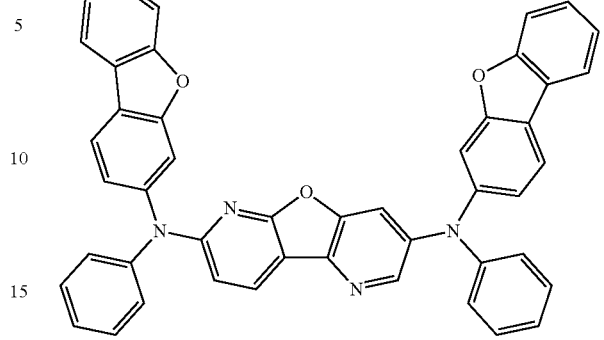
M073
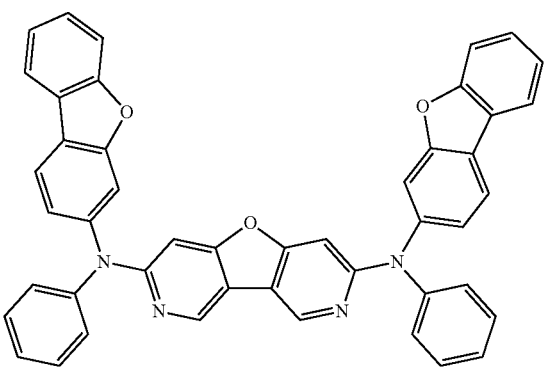
M074
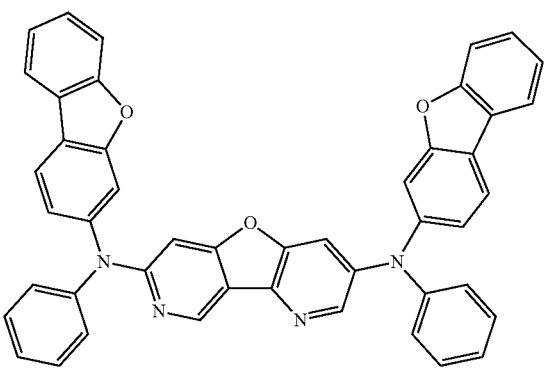
M075
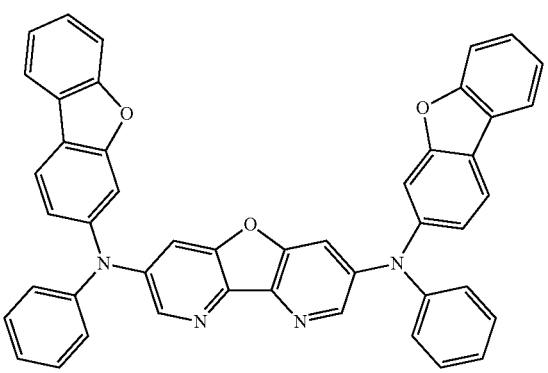

M076
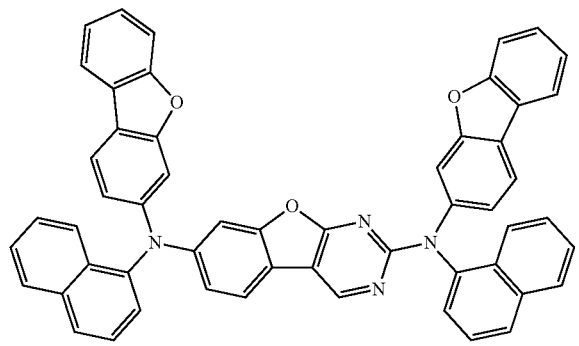
M077
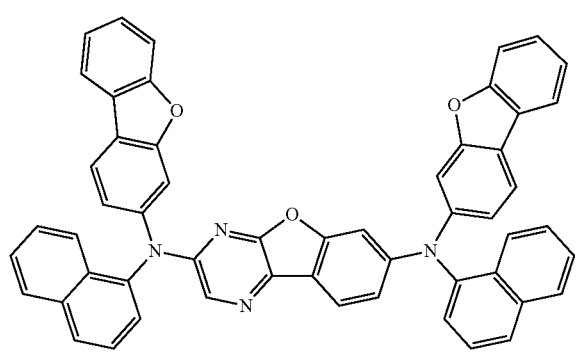
M078
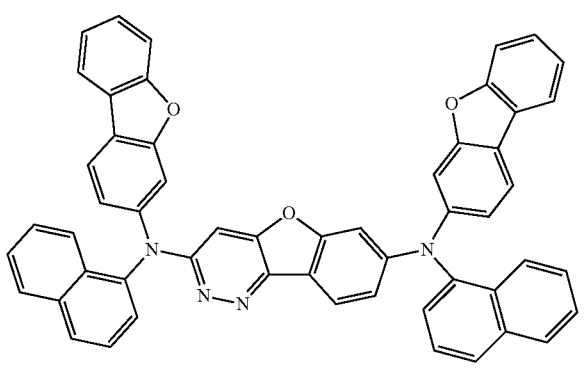
M079
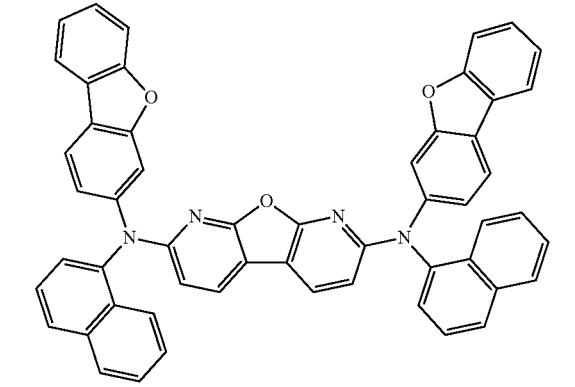
M080
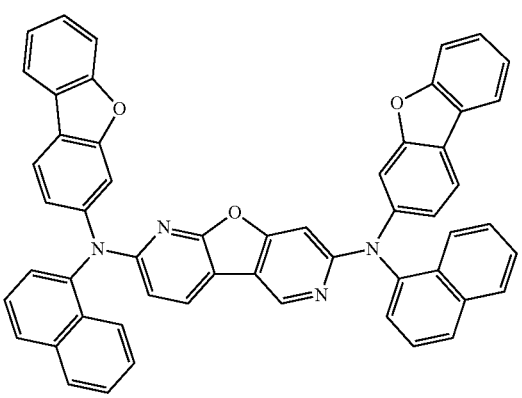
M081
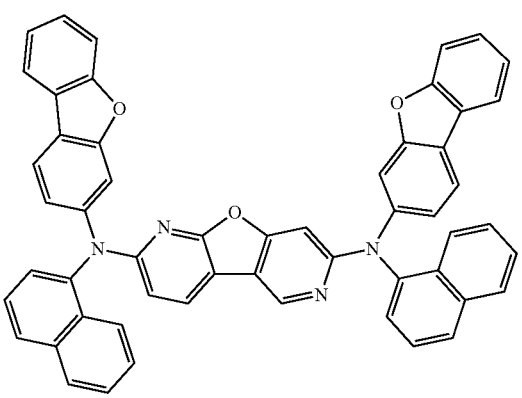
M082
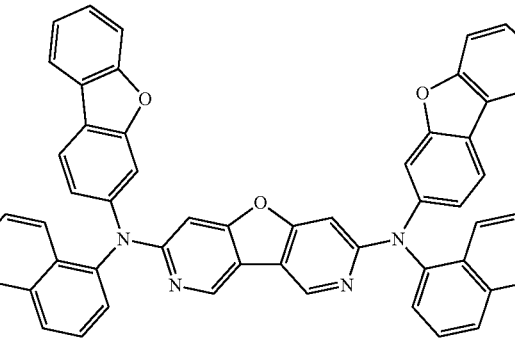
M083

M084
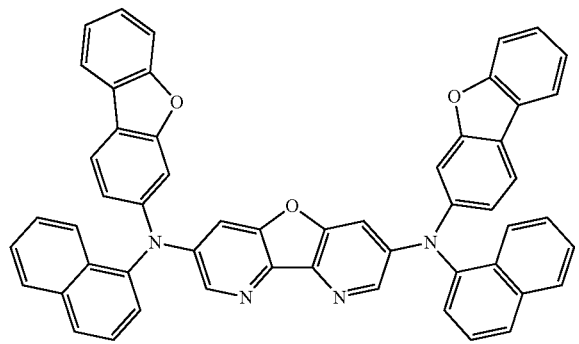
M085
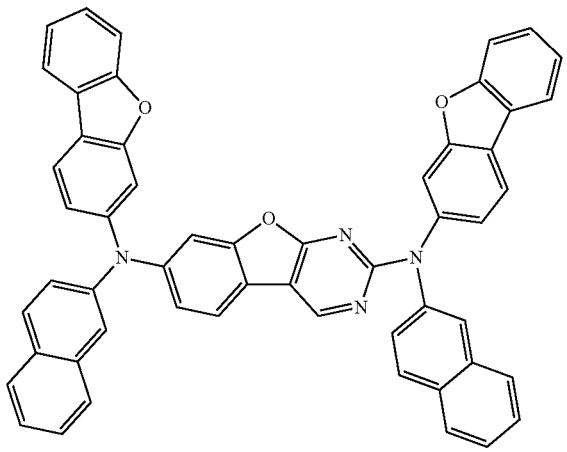
M086
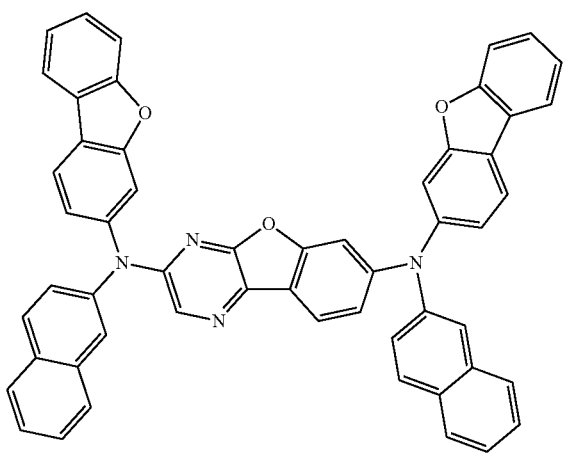
M087
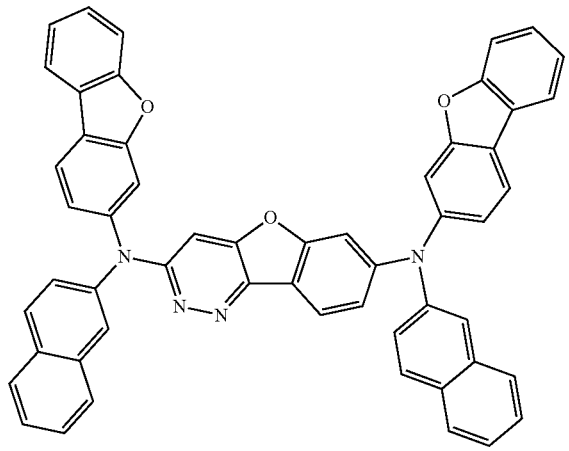
M088
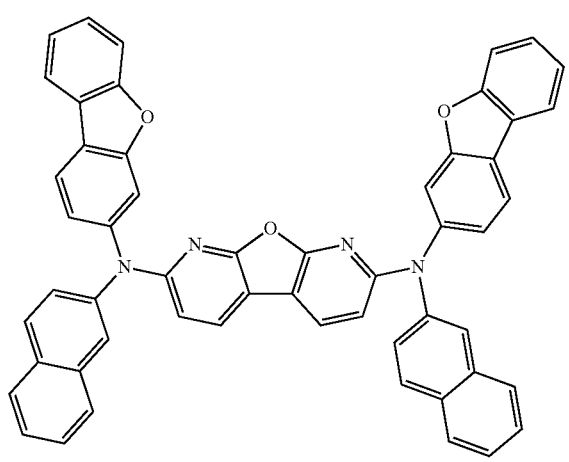
M089
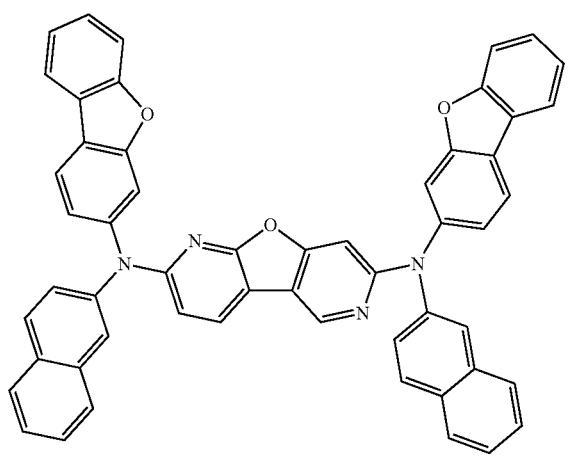

M090
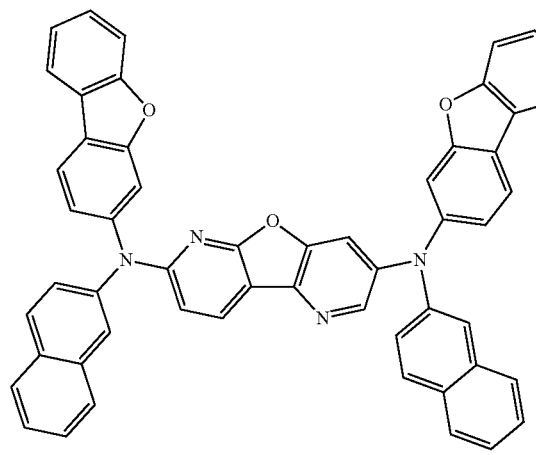
M093
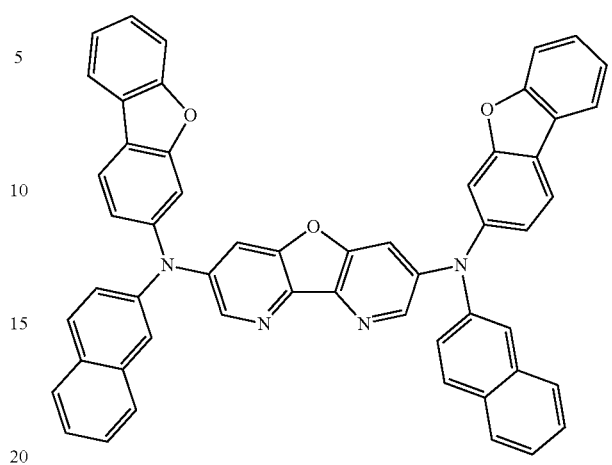
M091
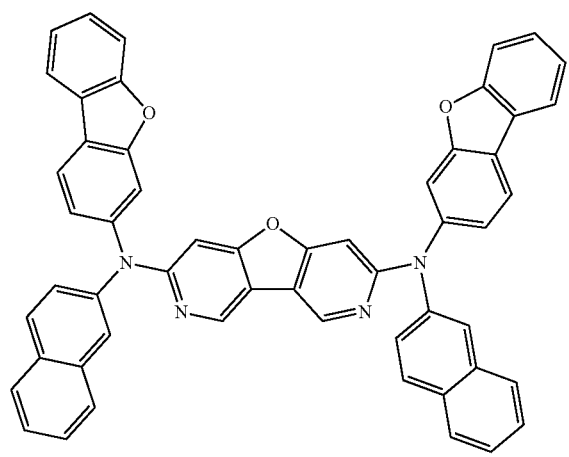
M094
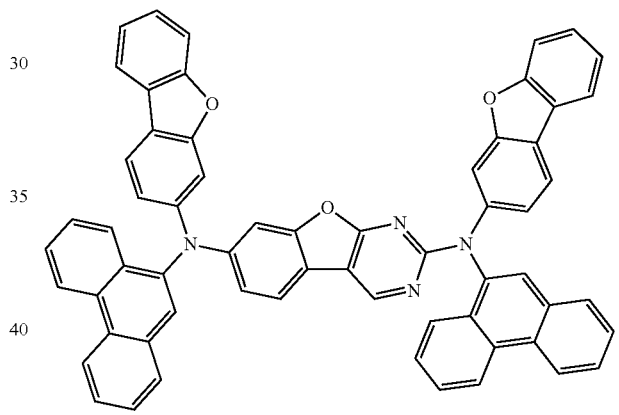
M092
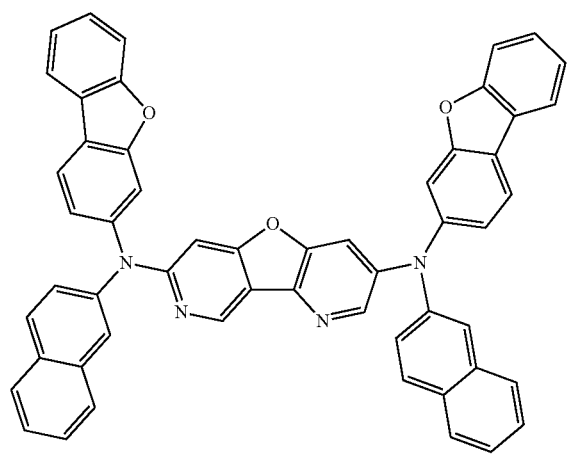
M095
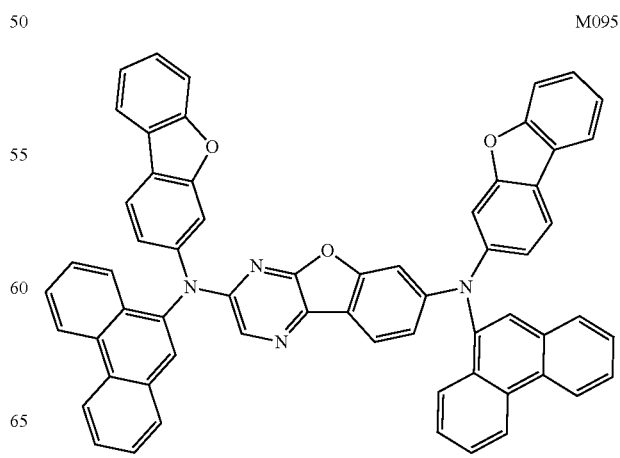

M096
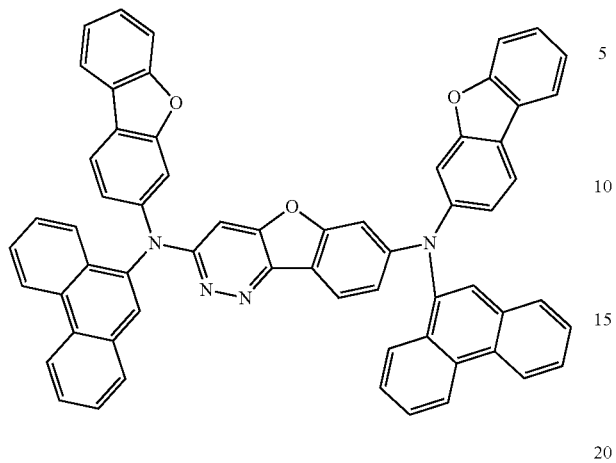
M099
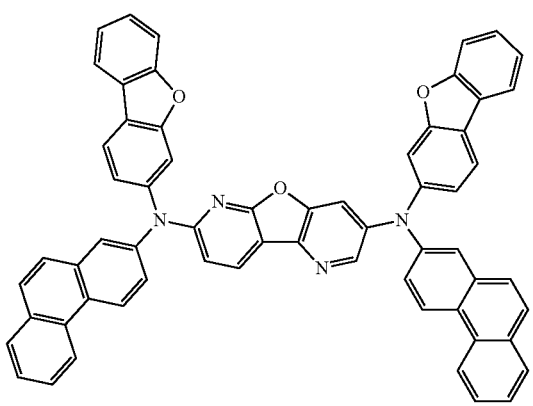
M097
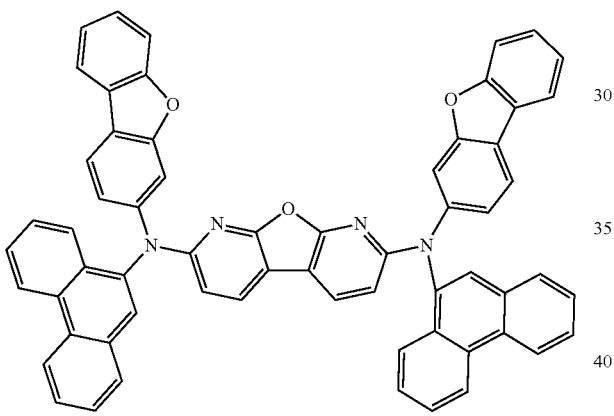
M100
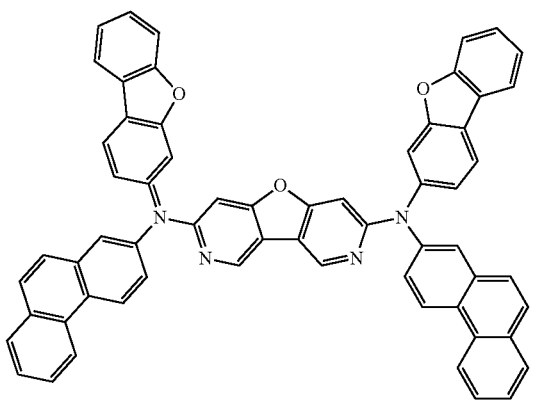
M098
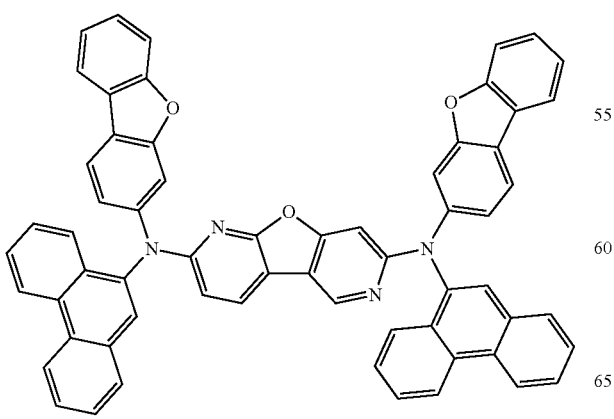
M101
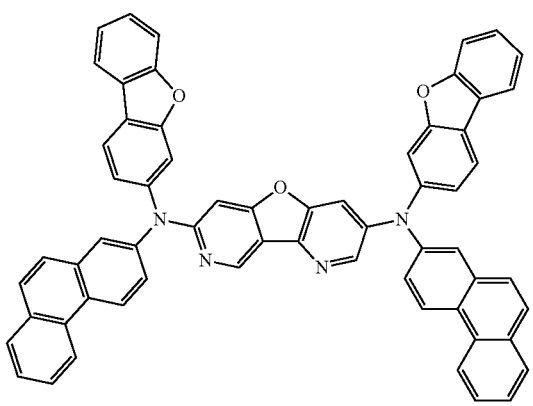

-continued
M102
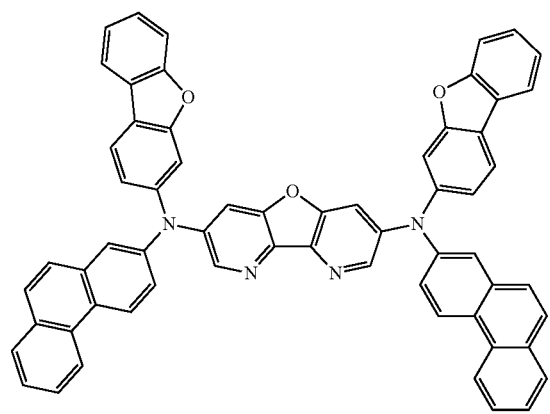
M103
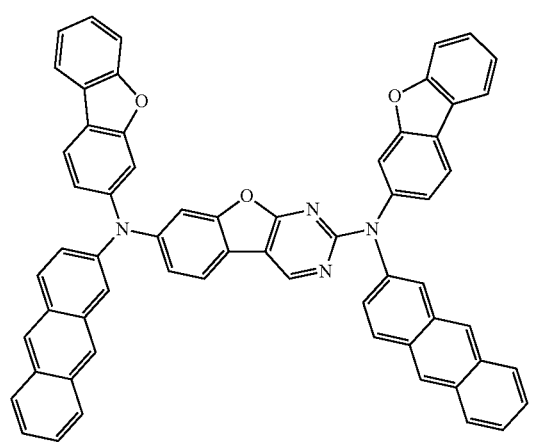
M104
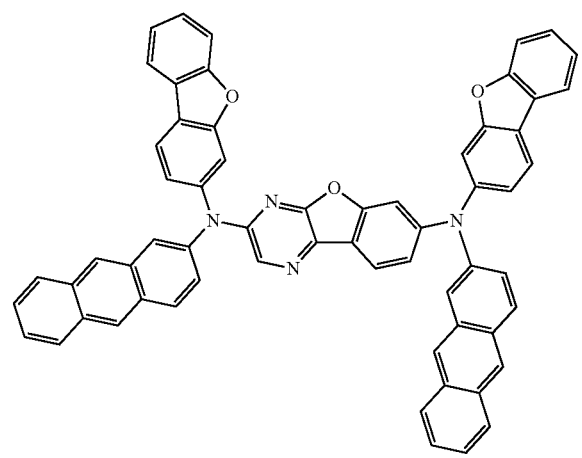
M105
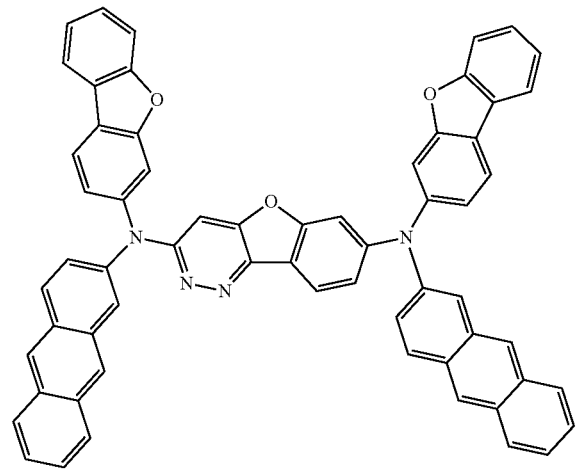
M106
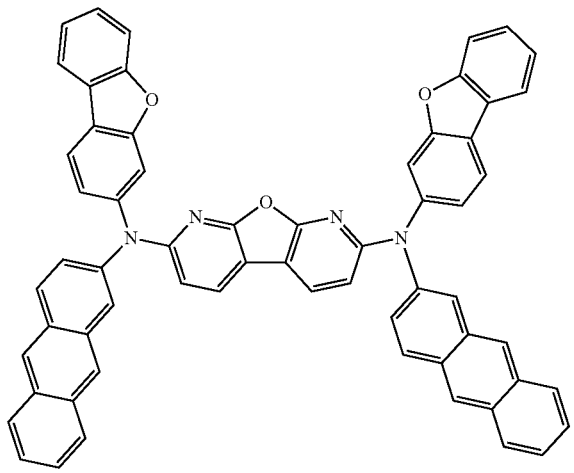
M107
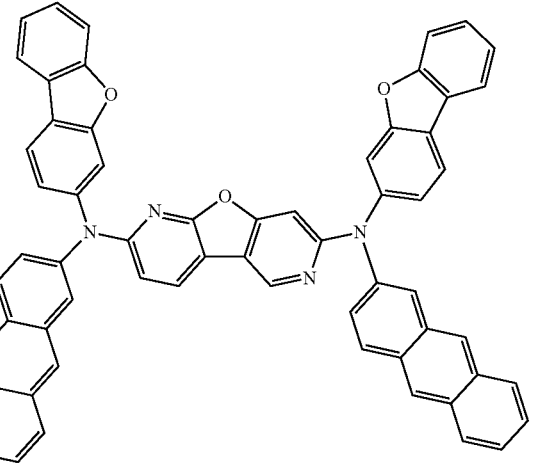

M108
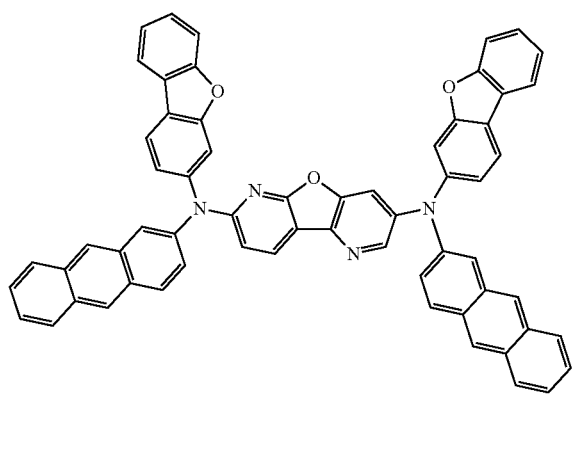
M111
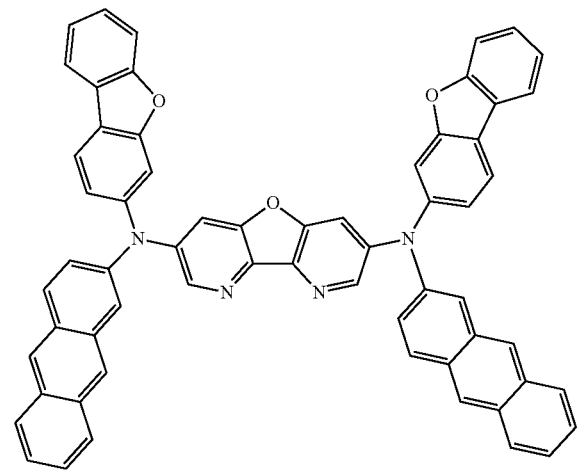
M109
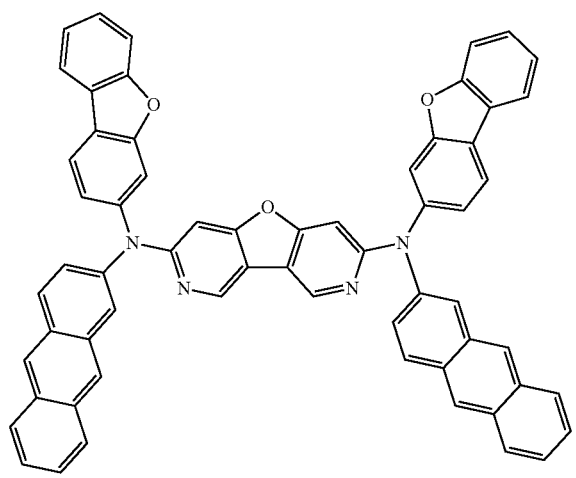
M112
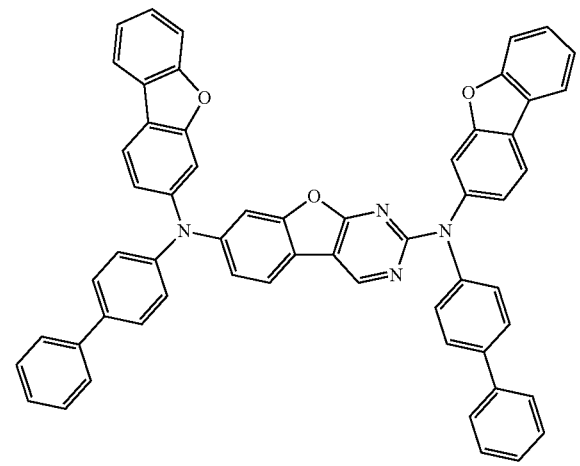
M110
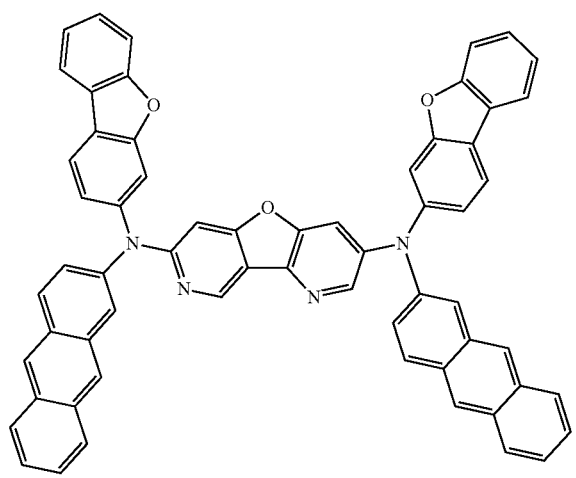
M113
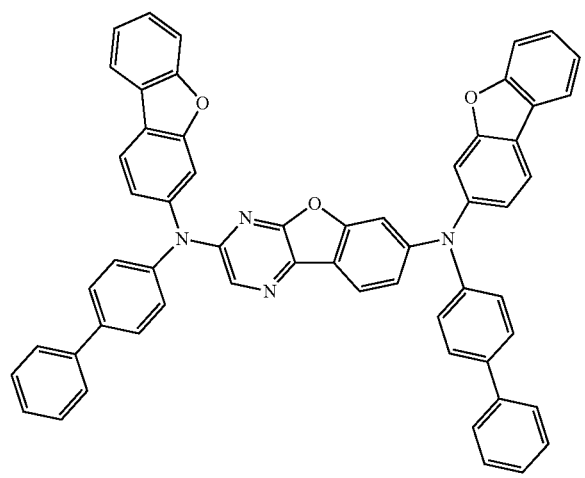

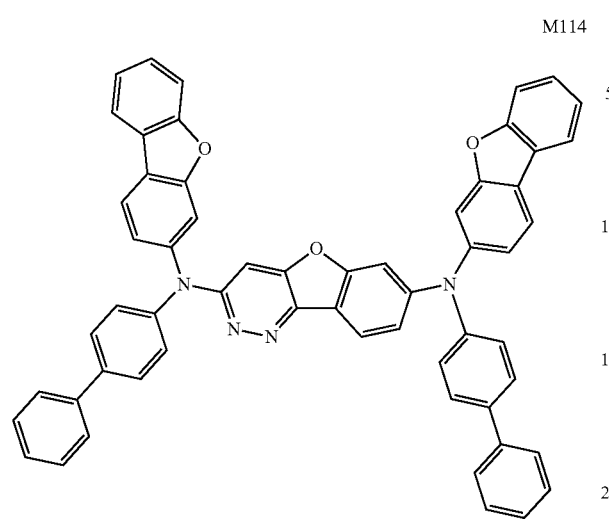
M114
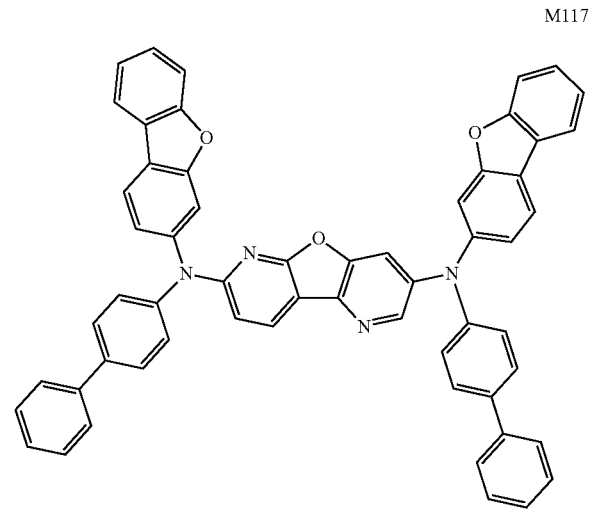
M117
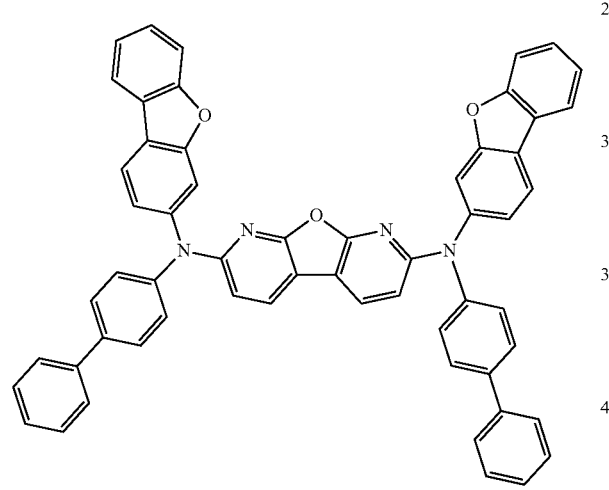
M115
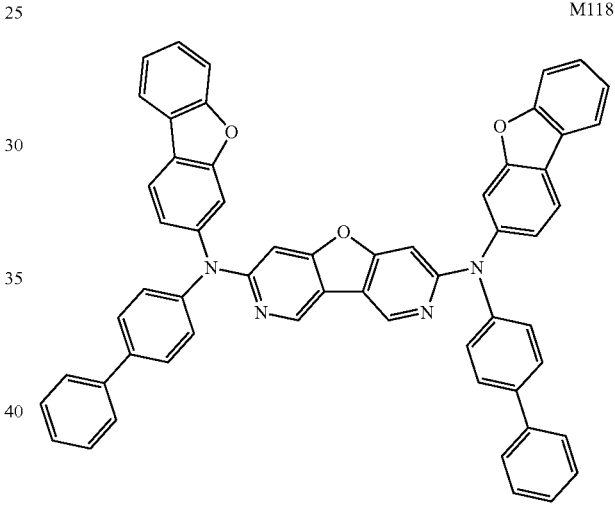
M118
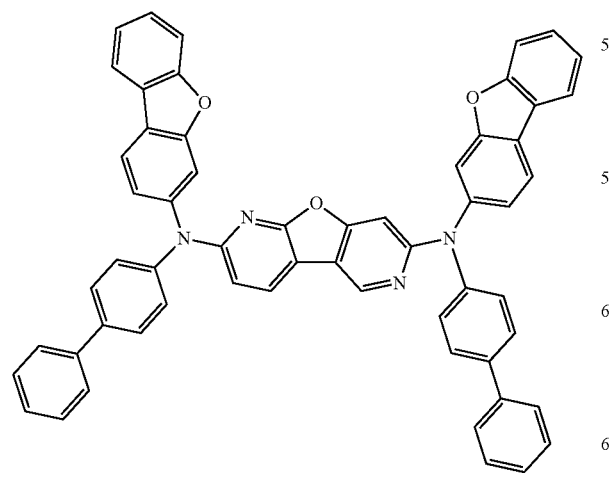
M116
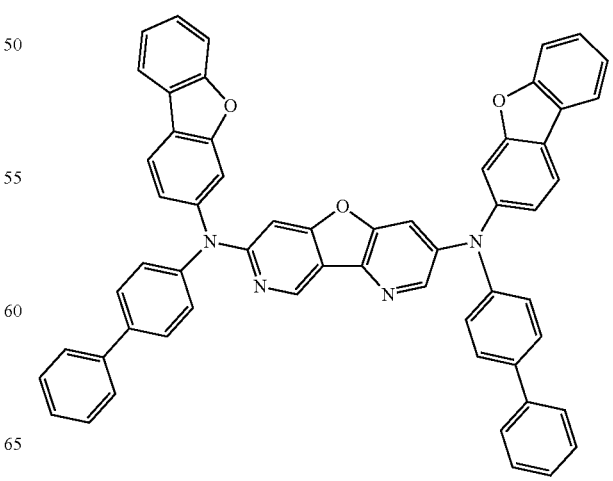
M119

M120
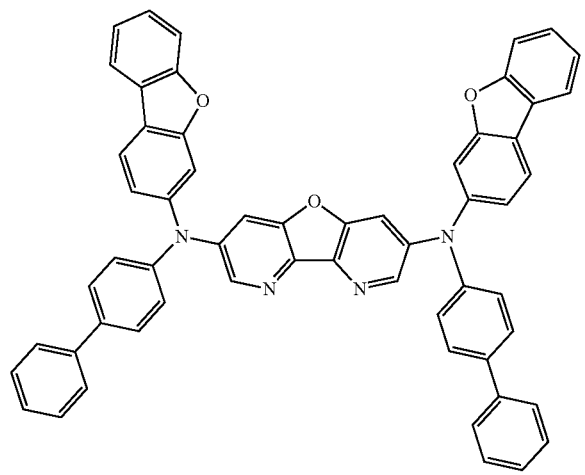
M123
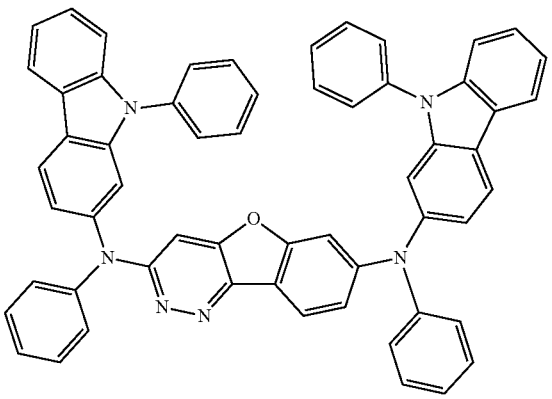
M121
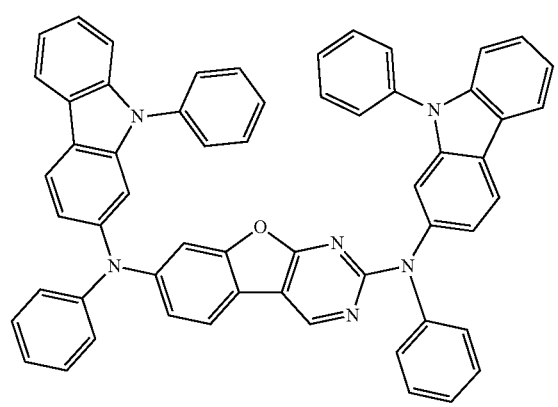
M124
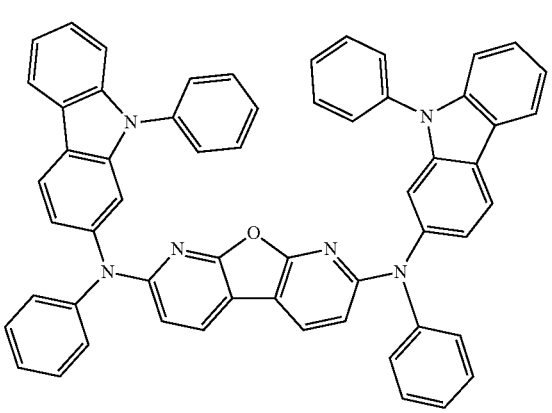
M122
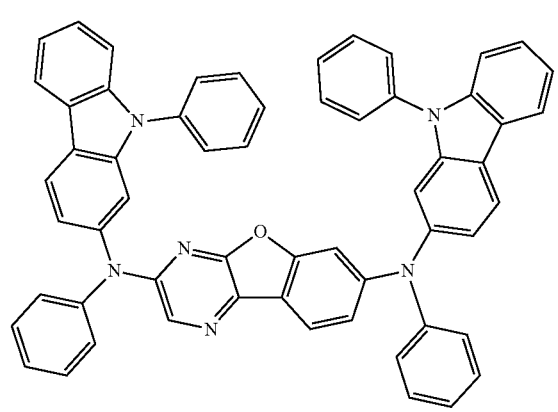
M125
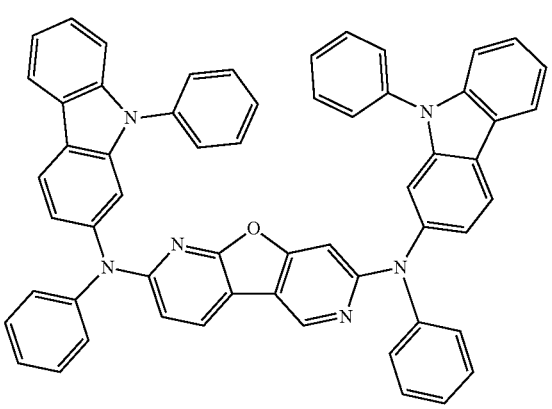

M126
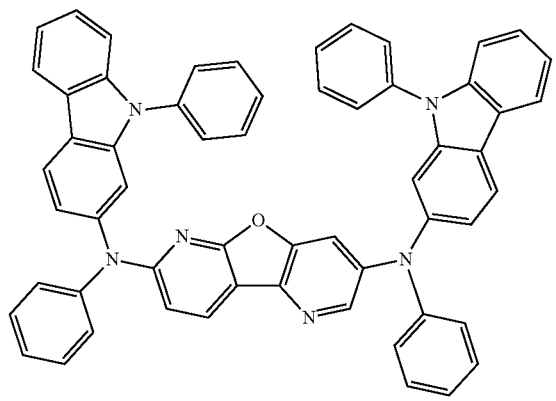
M127
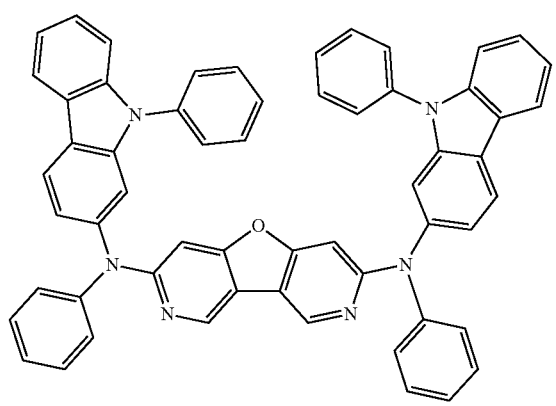
M128
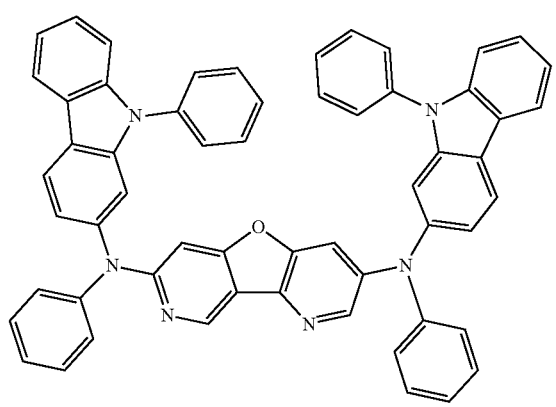
M129
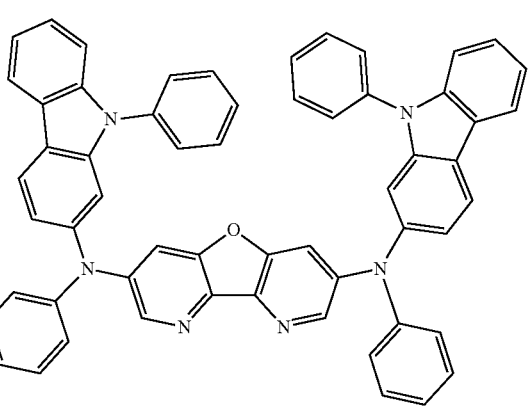
M130
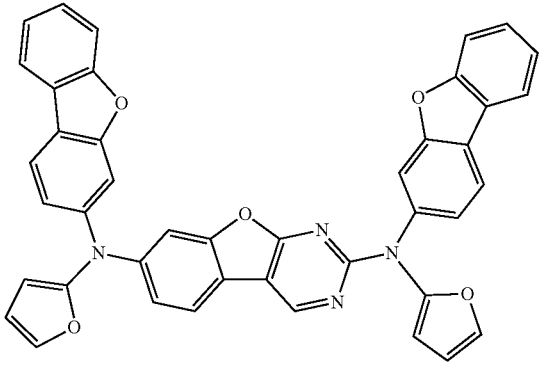
M131
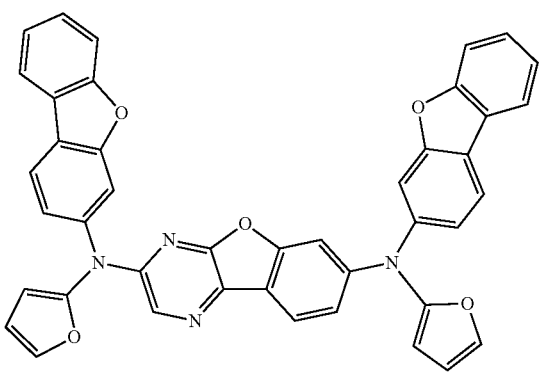
M132
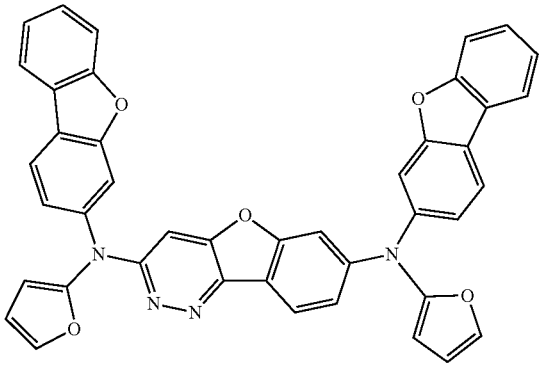

M133
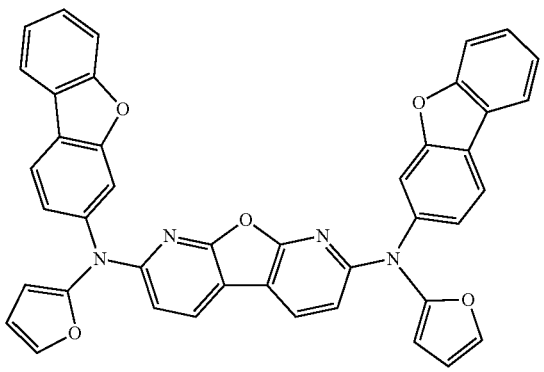
M134
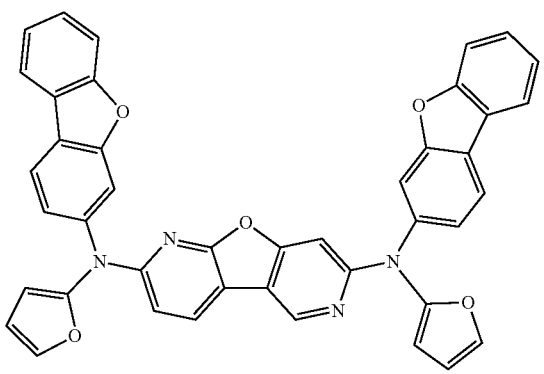
M135
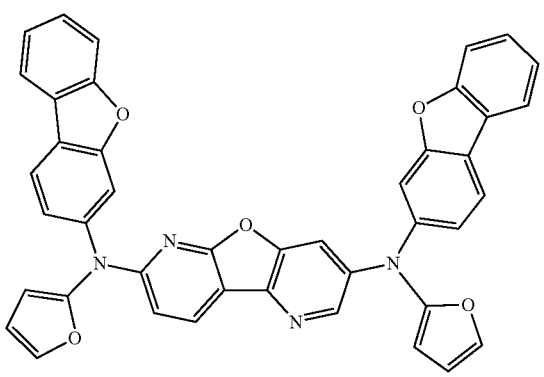
M136
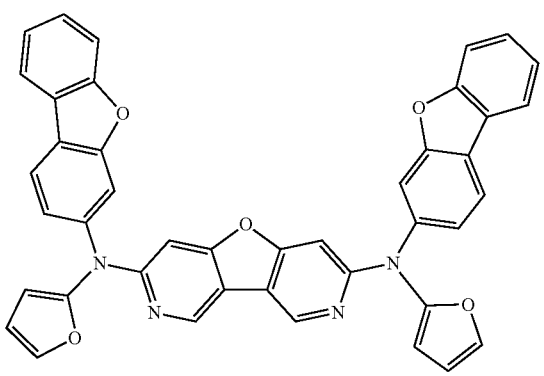
M136
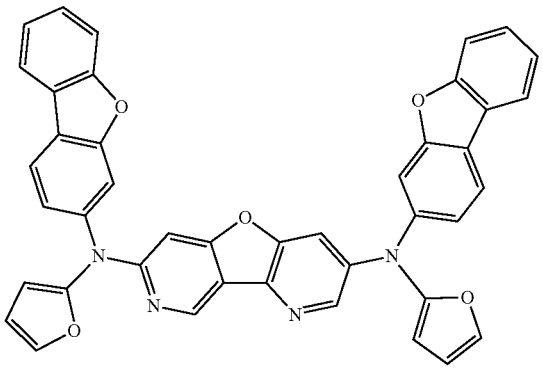
M138
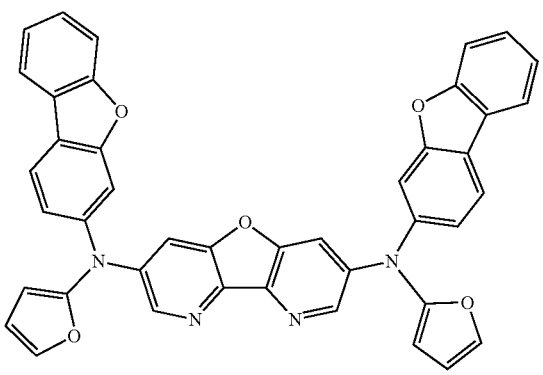
M139
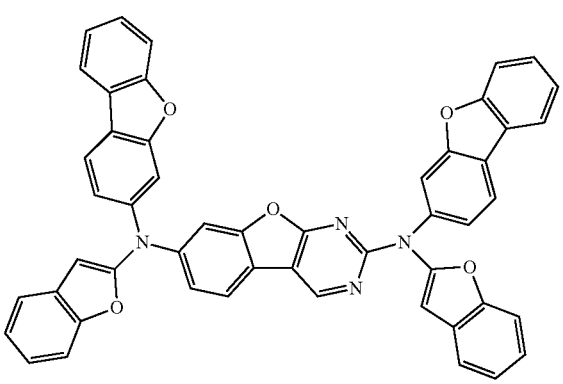
M140
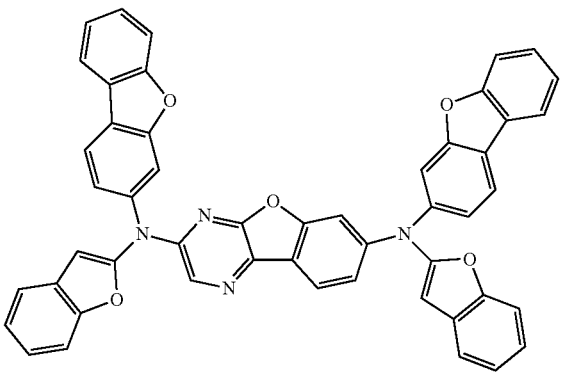

M141
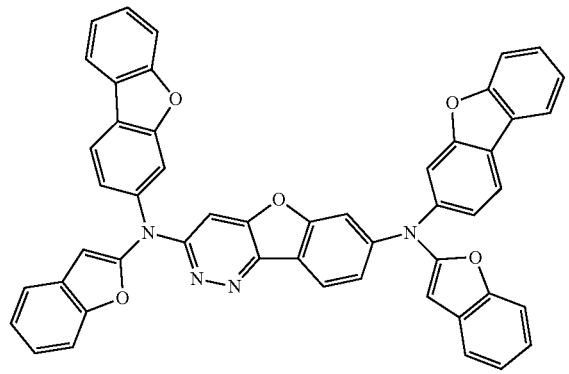
M142
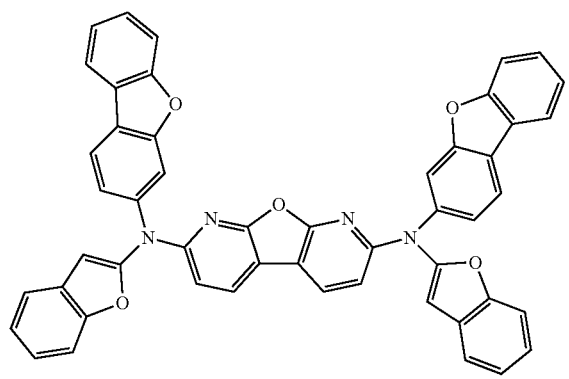
M143

M144
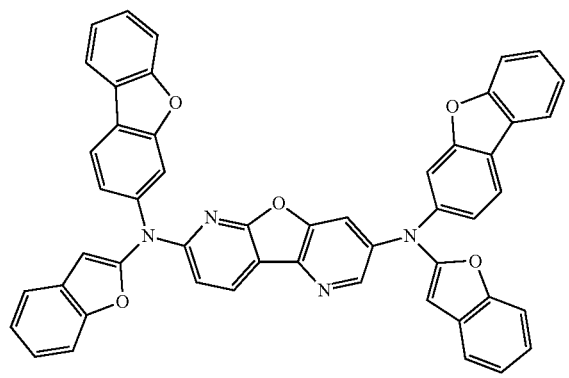
M145
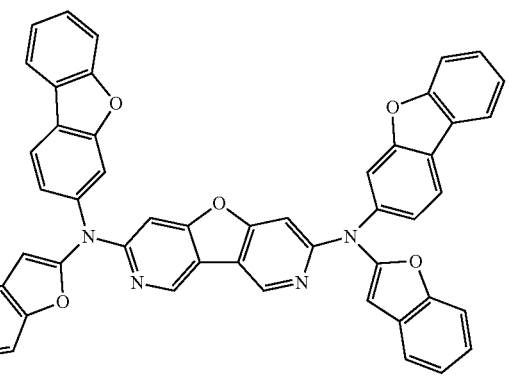
M146
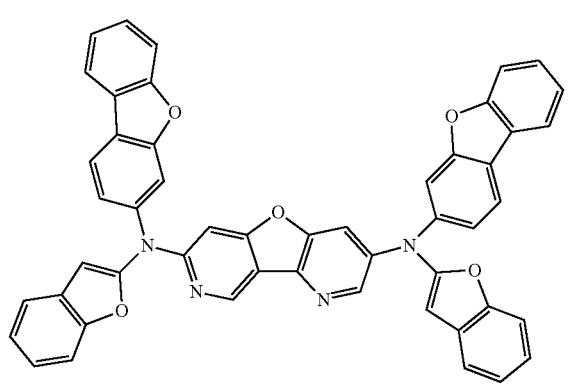
M147
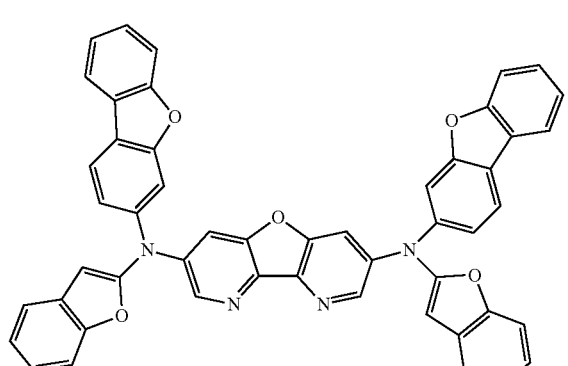
M148
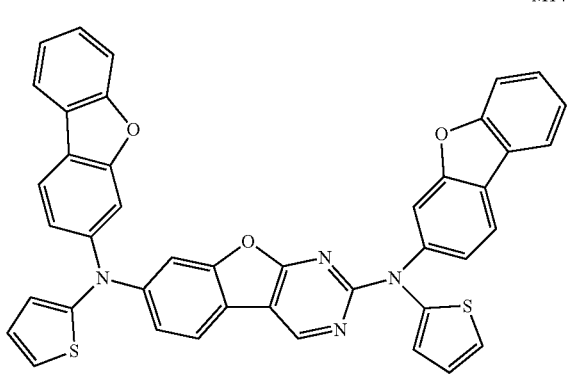

M149
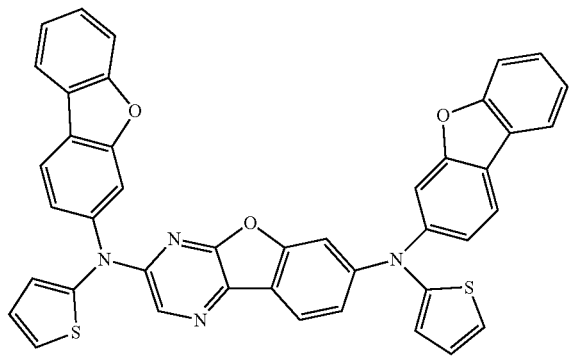
M150
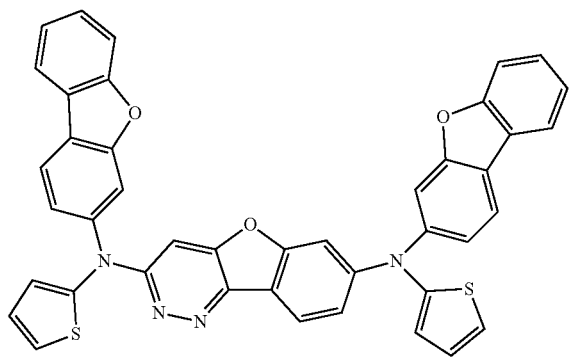
M151
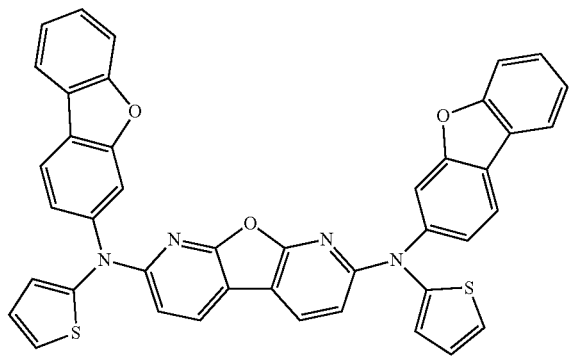
M152
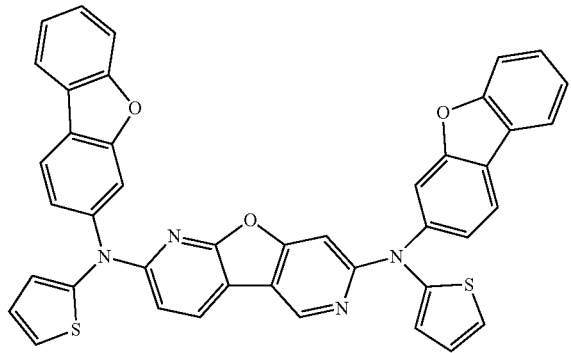
M153
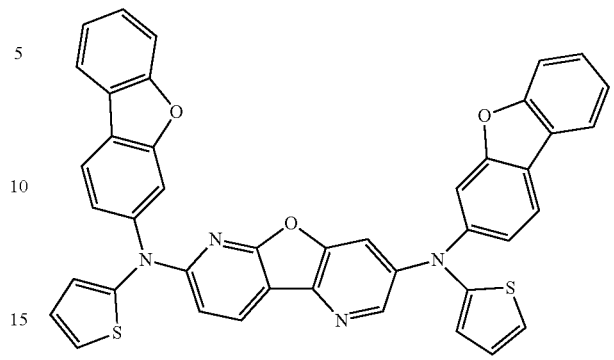
M154
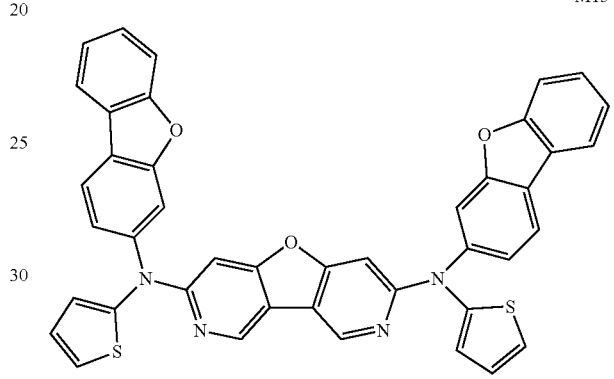
M155
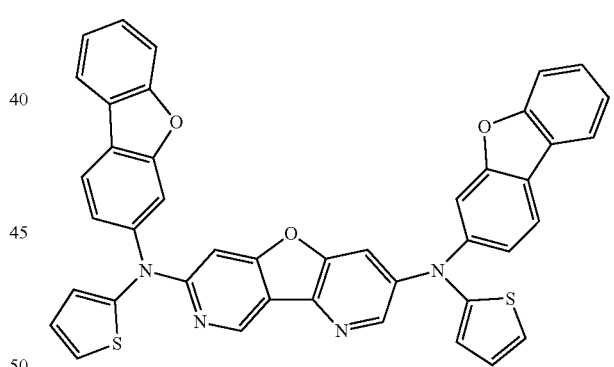
M156
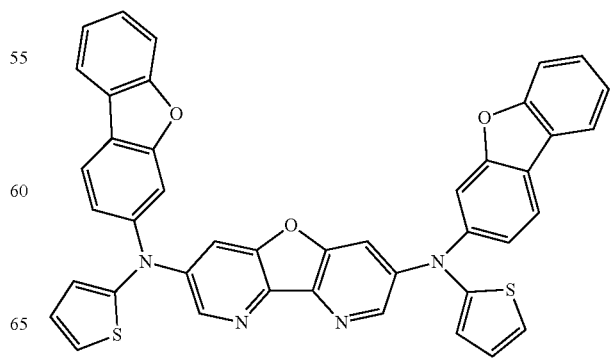

M157
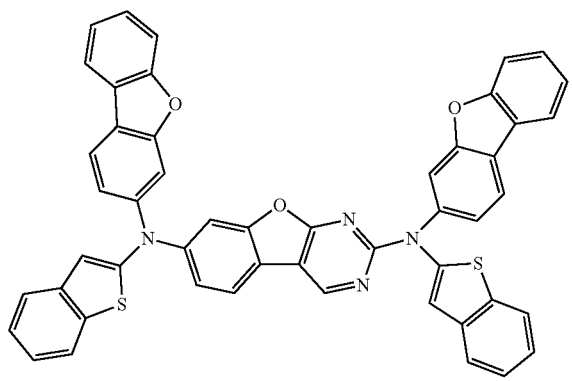
M161
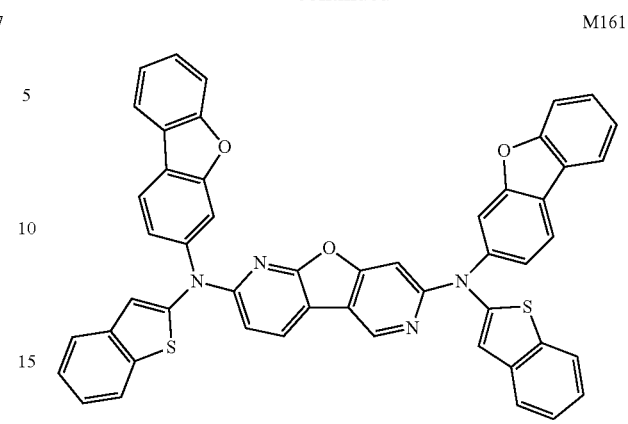
M158
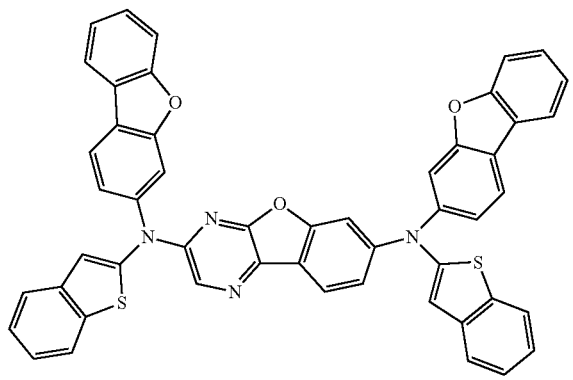
M162
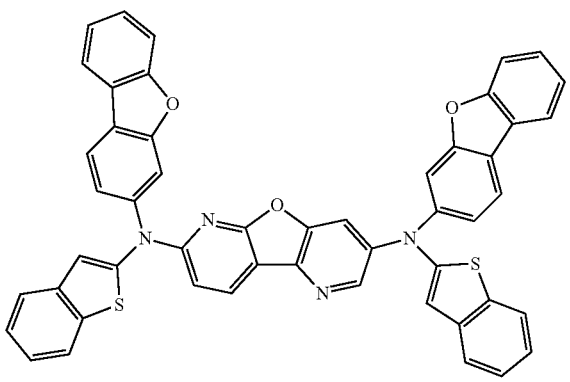
M159
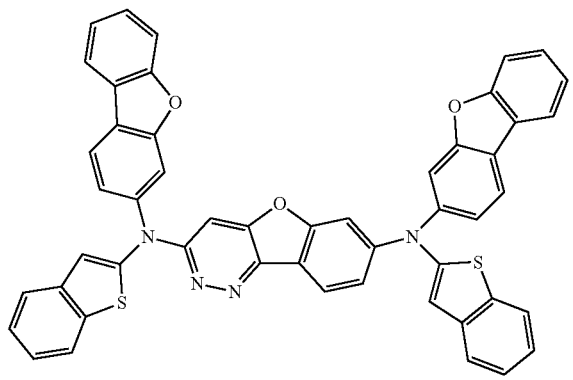
M163
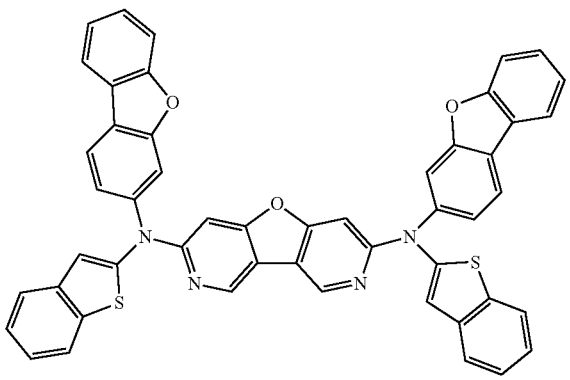
M160
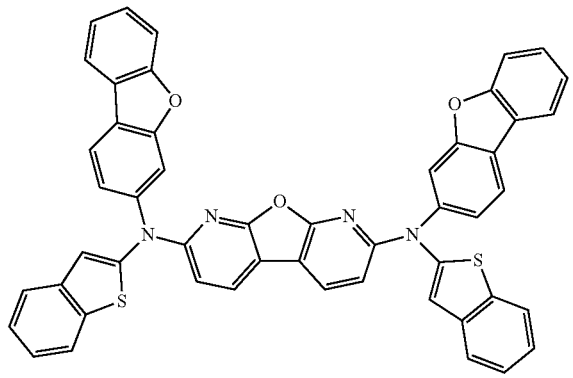
M164
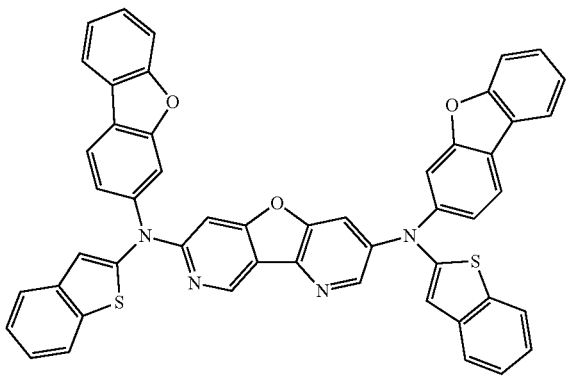

M165
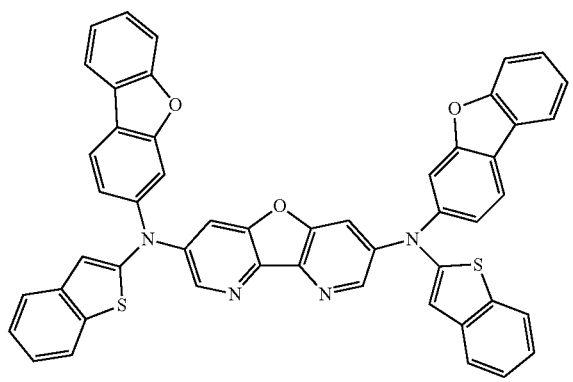
M166
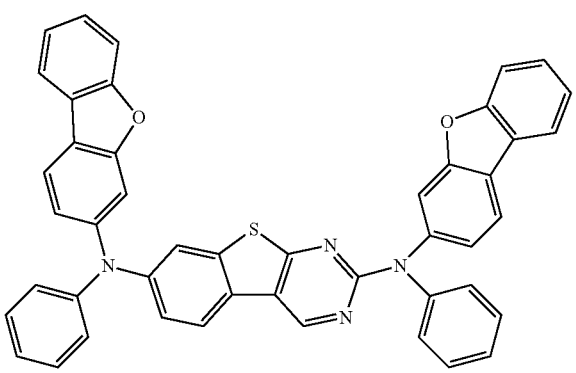
M167
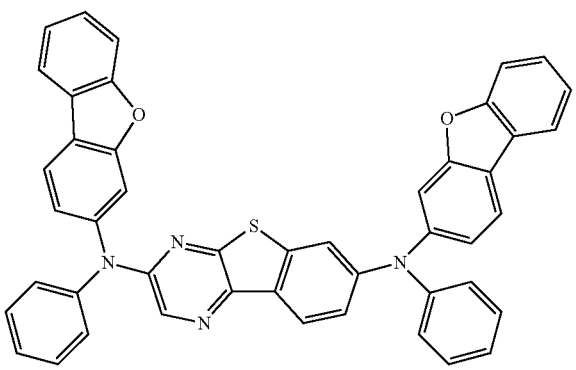
M168
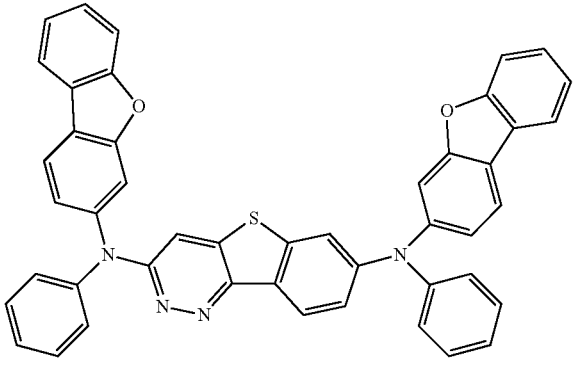
M169
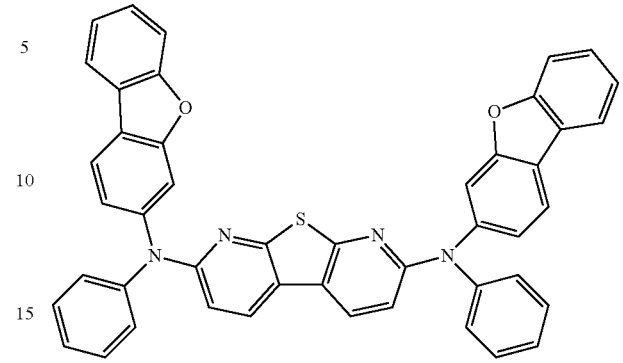
M170
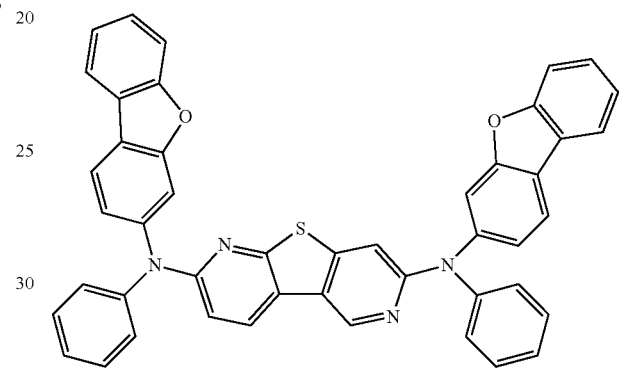
M171
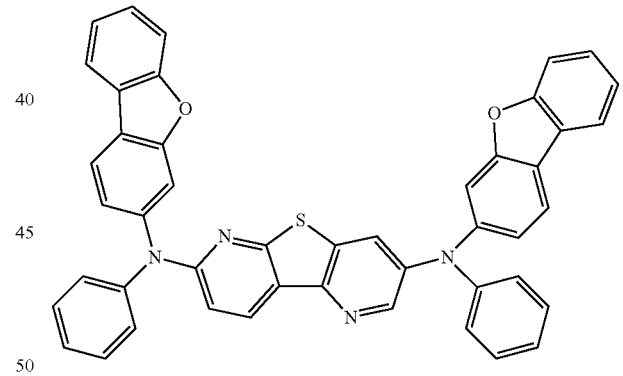
M172
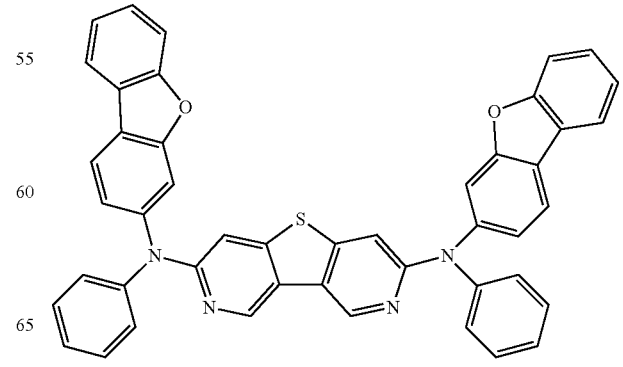

M173
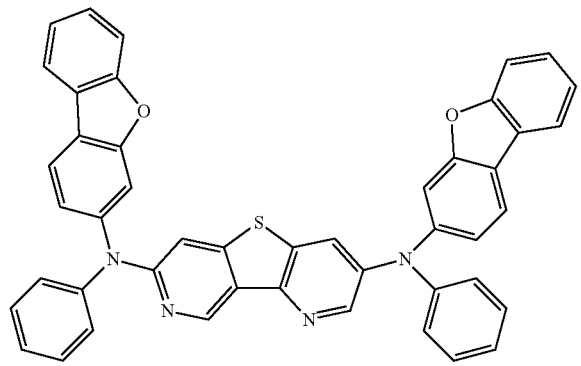
M174
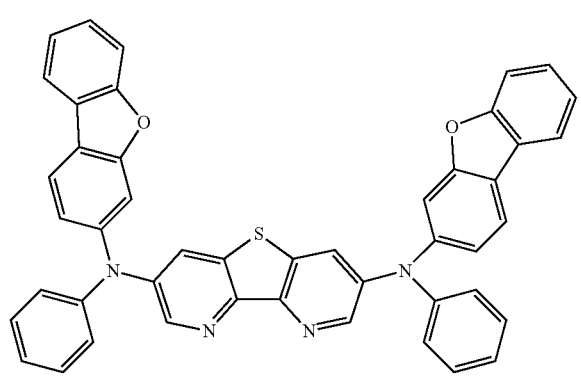
M175
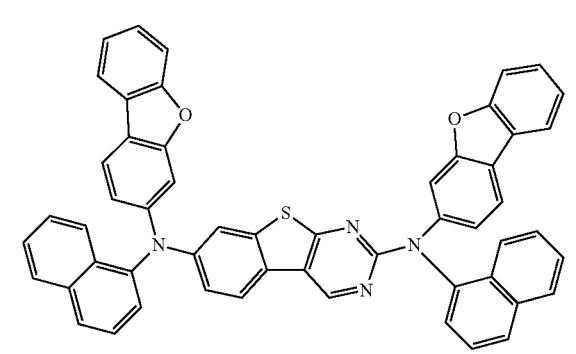
M176
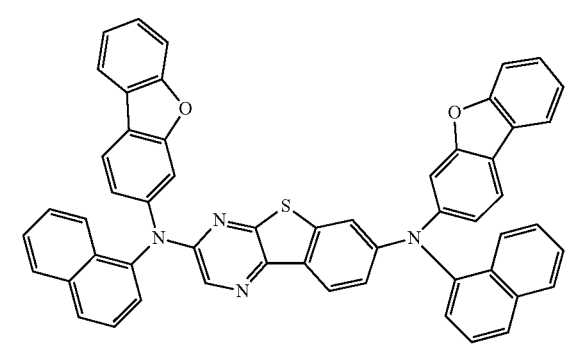
M177
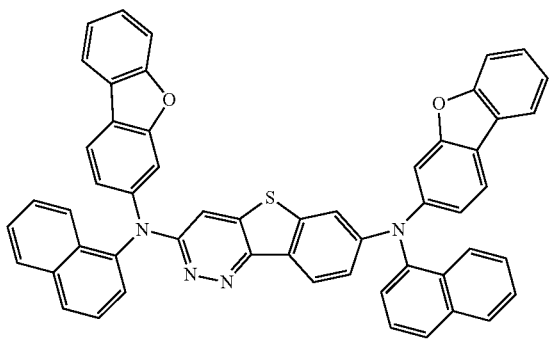
M178
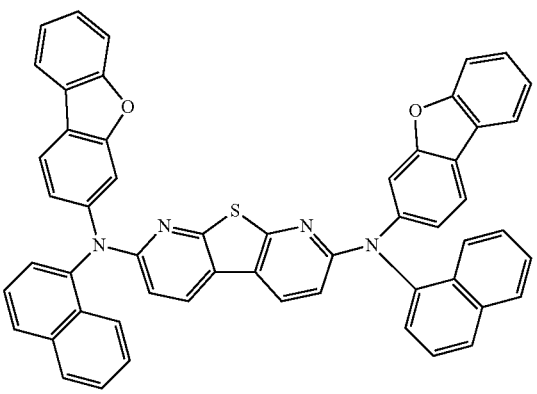
M179
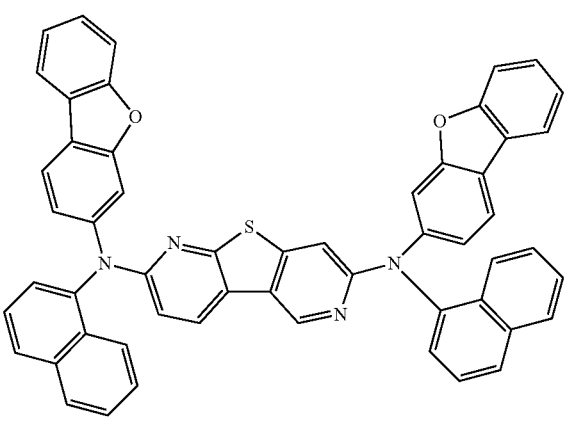
M180
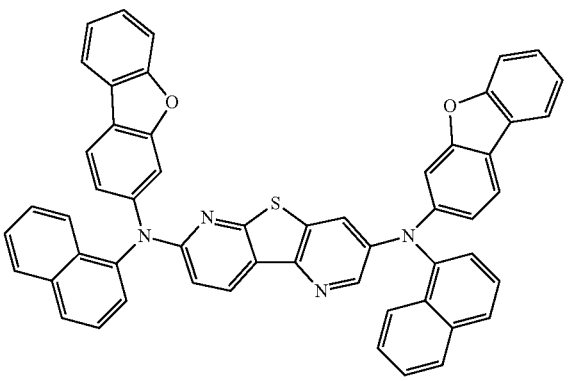

M181
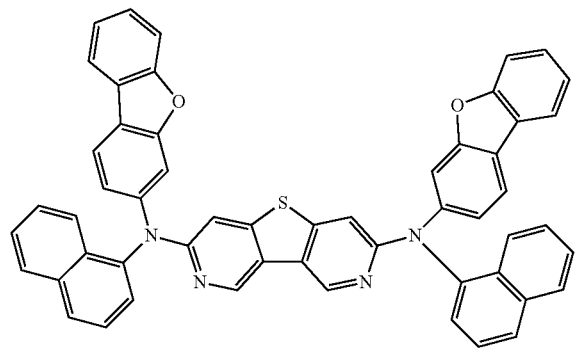
M182
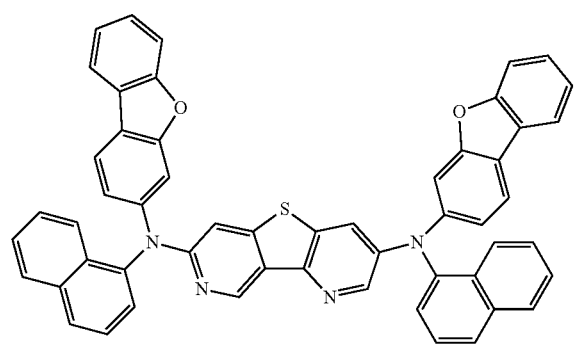
M183
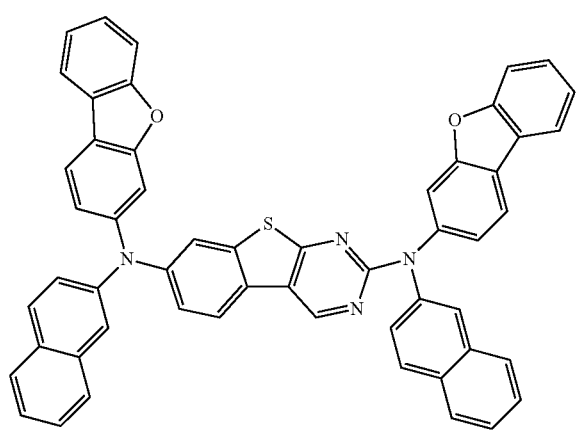
M184
M185
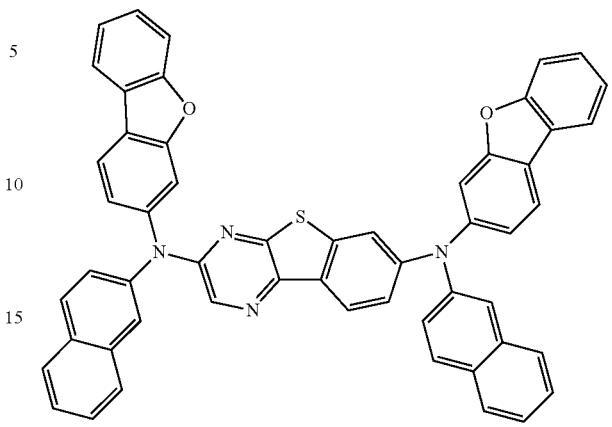
M186
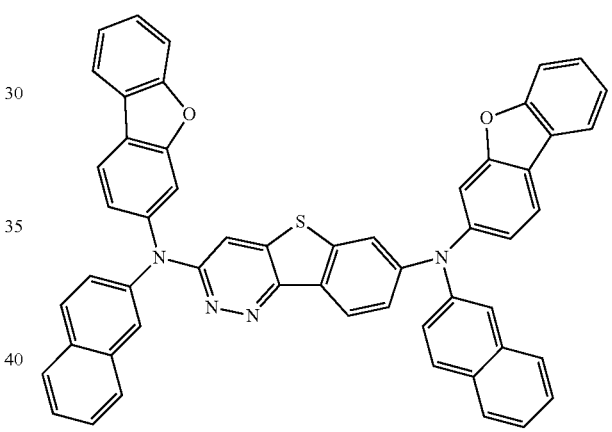
M187
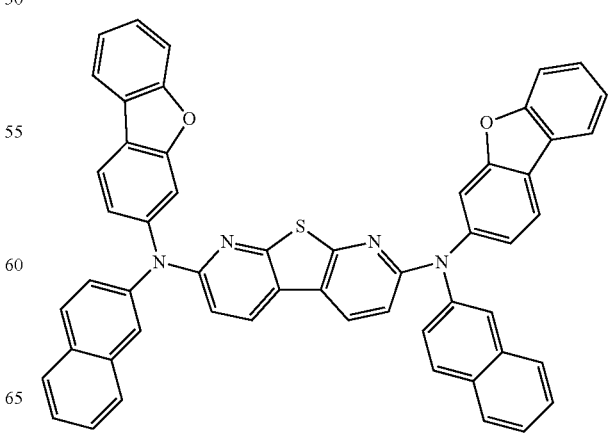

M188
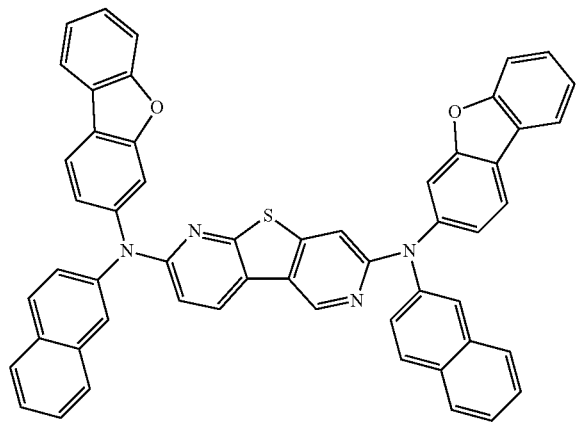
M189
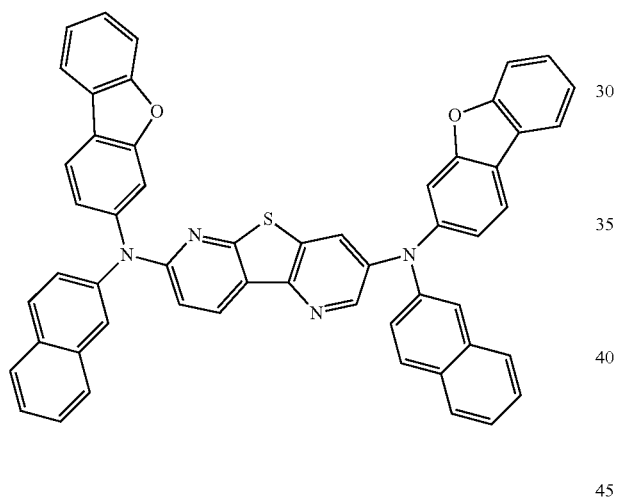
M190
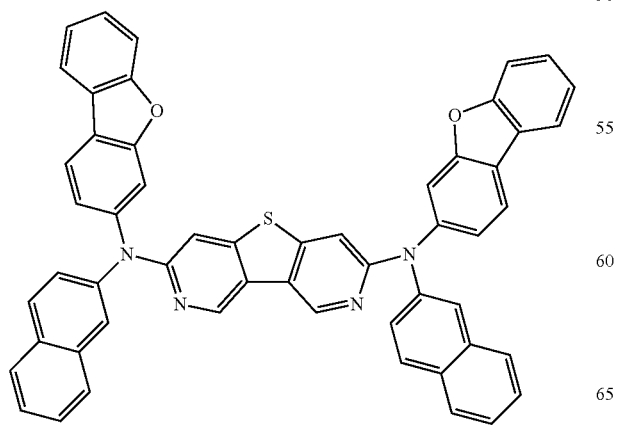
M191
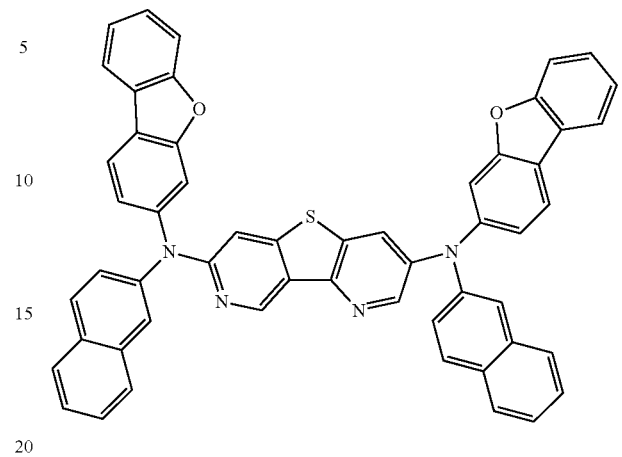
M192
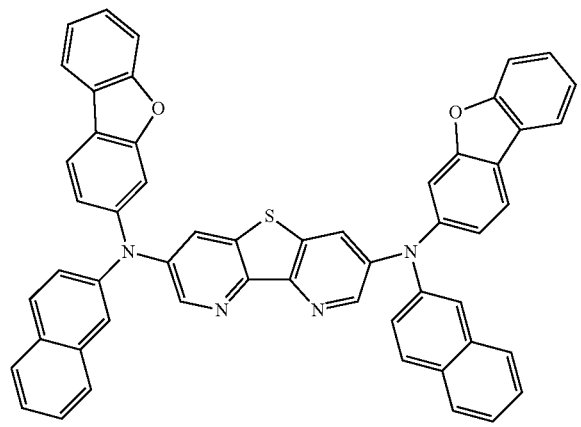
M193
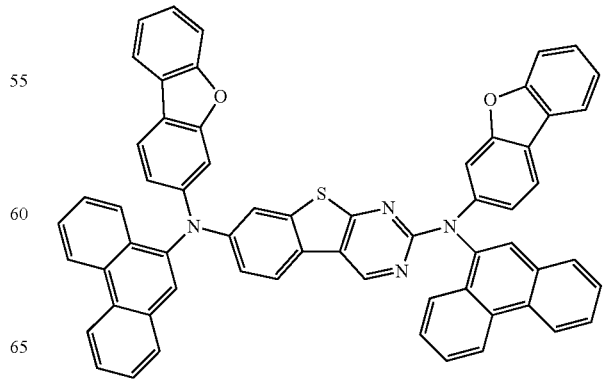

M194
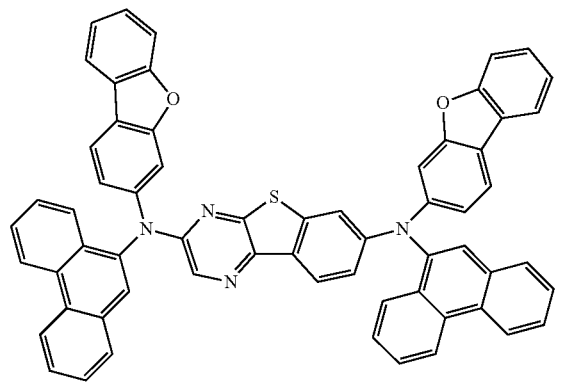
M195
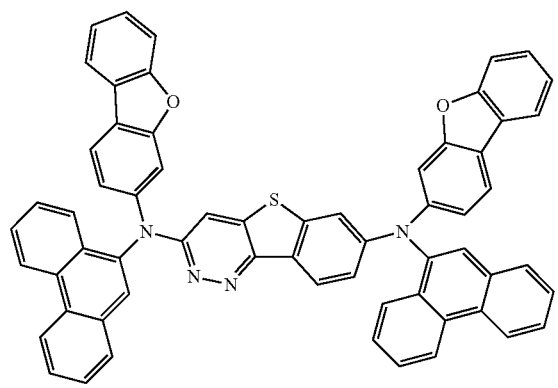
M196
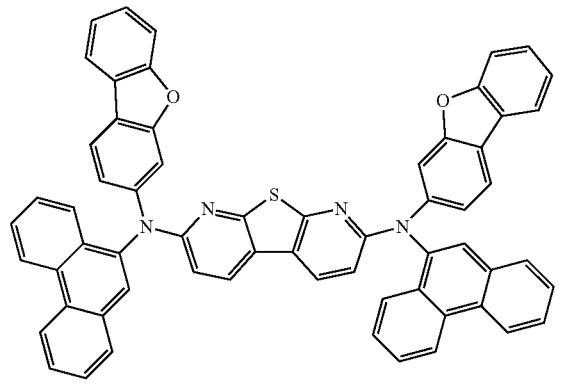
M197
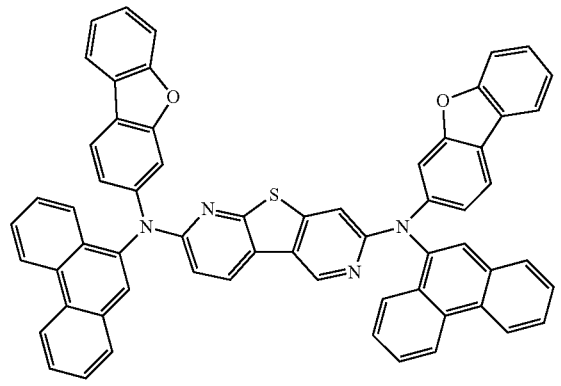
M198
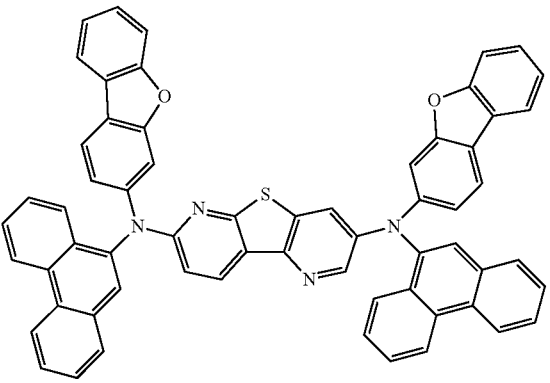
M199
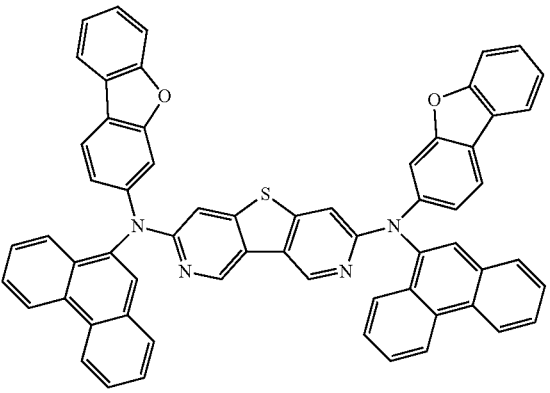
M200
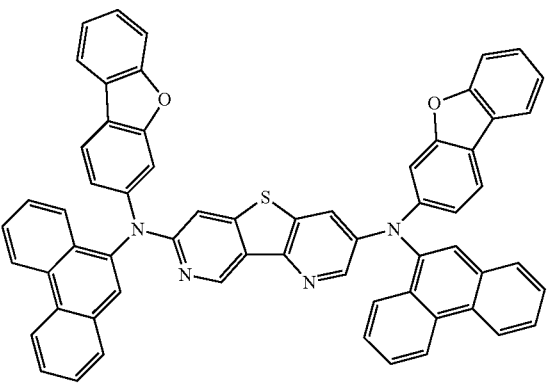
M201
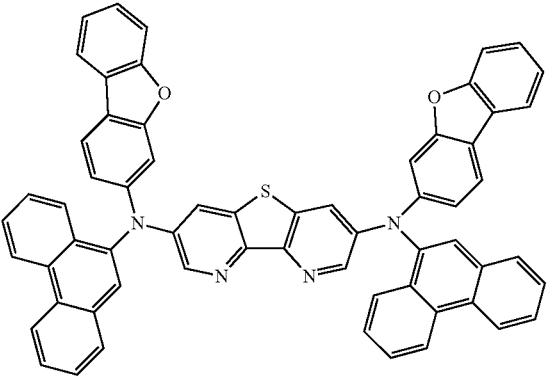

-continued
M202
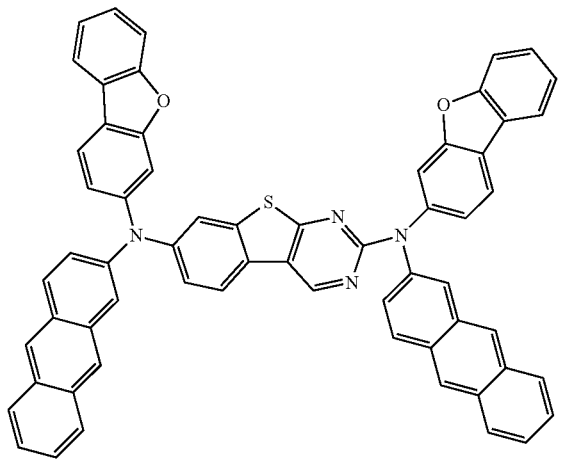
M203
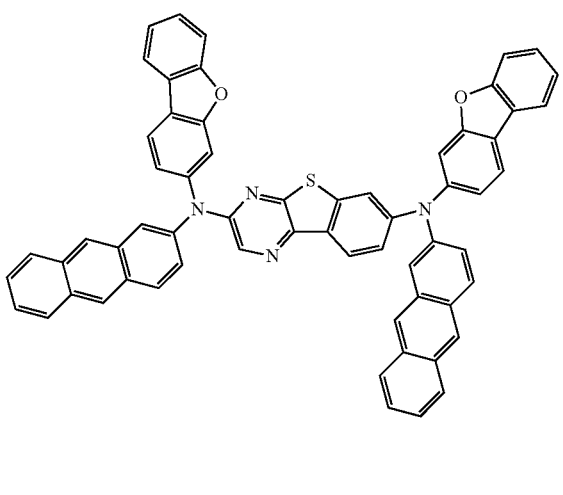
M204
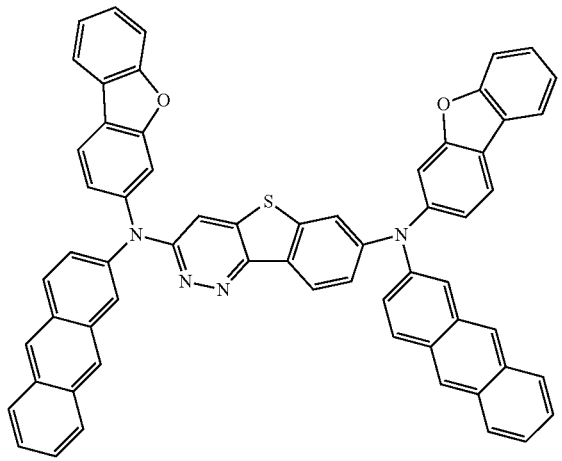
-continued
M205
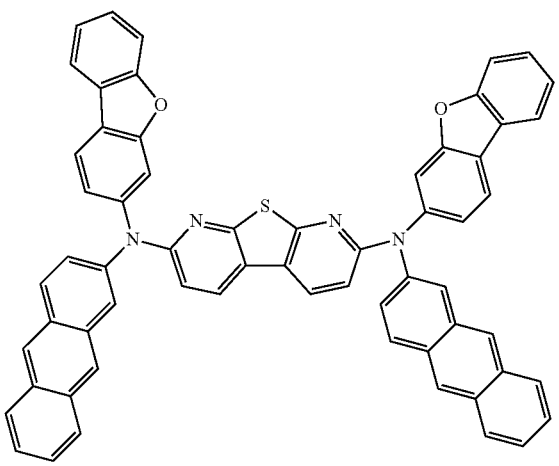
M206
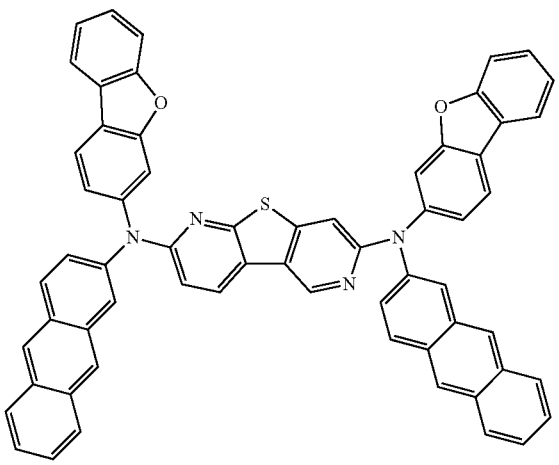
M207
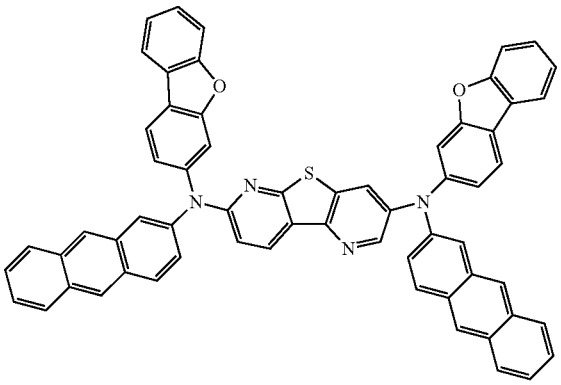

M208
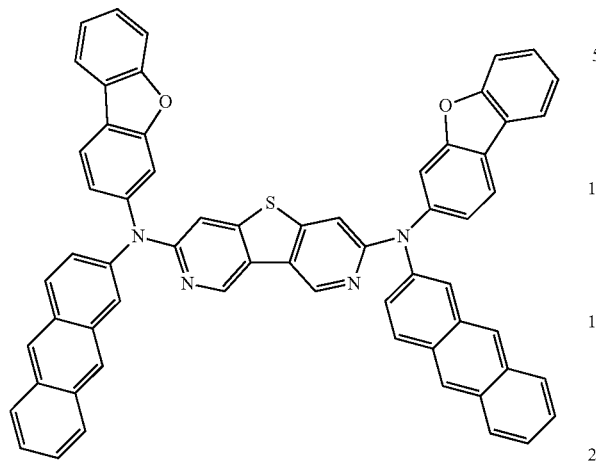
M209
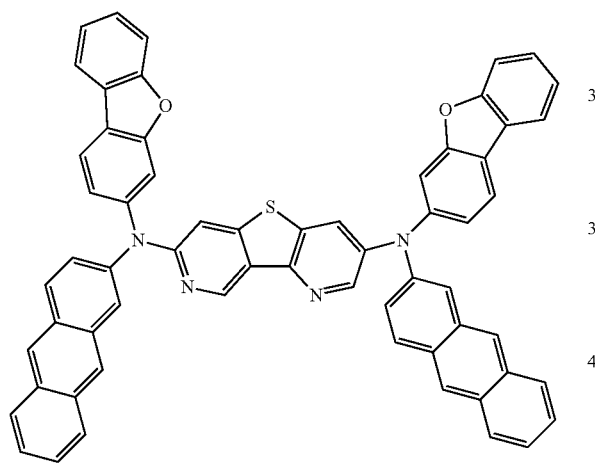
M210
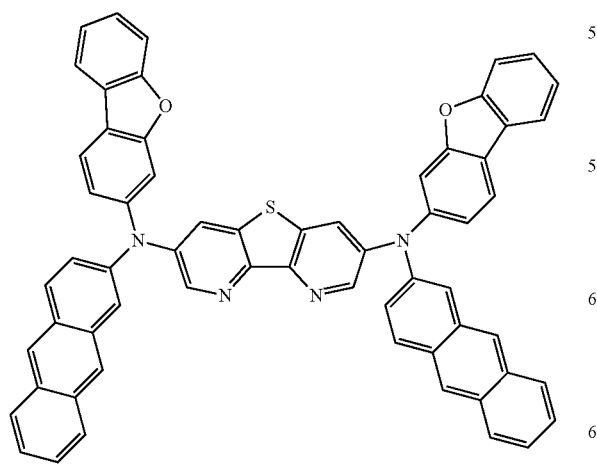
M211
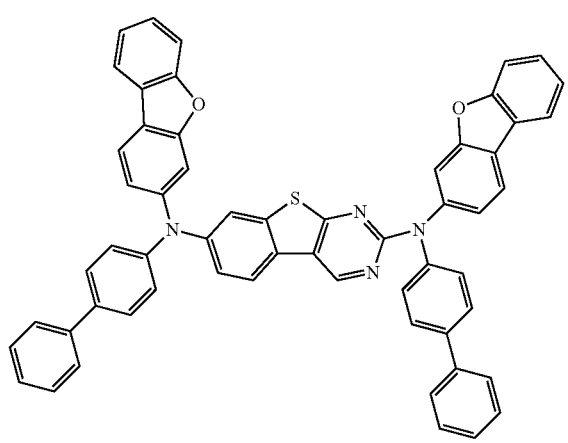
M212
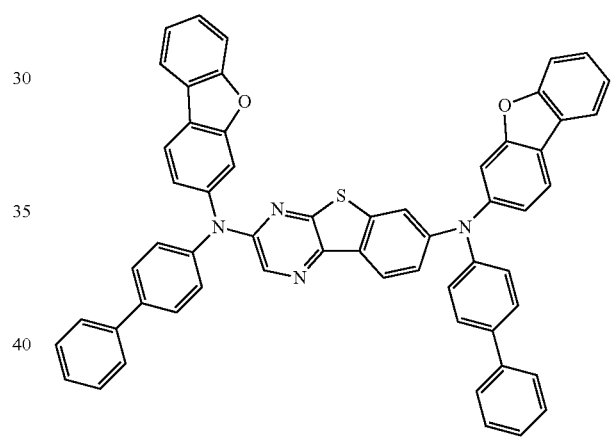
M213
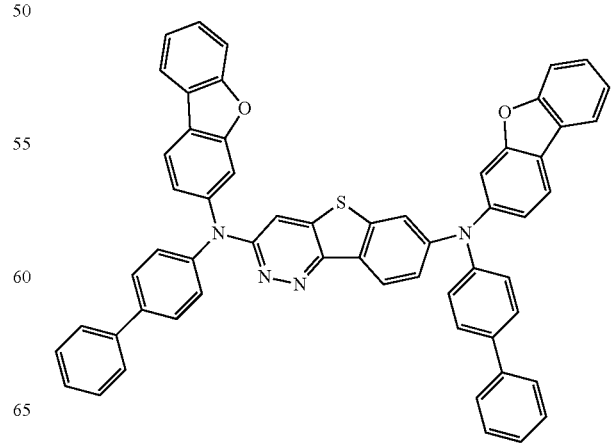

M214
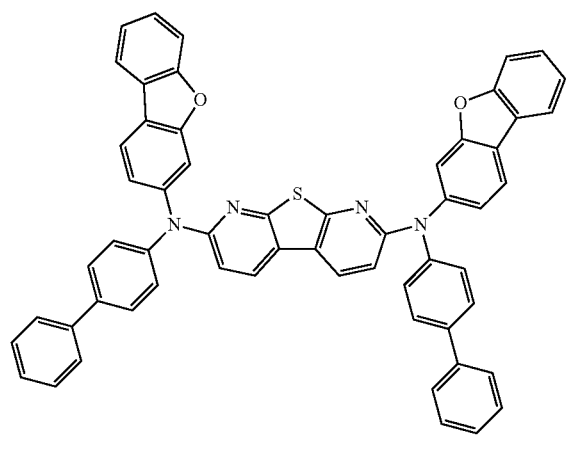
M215
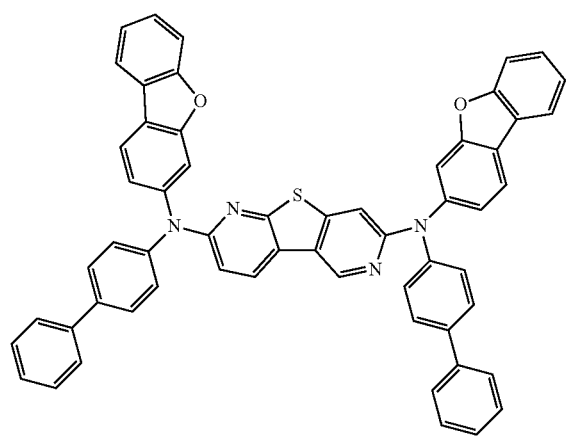
M216
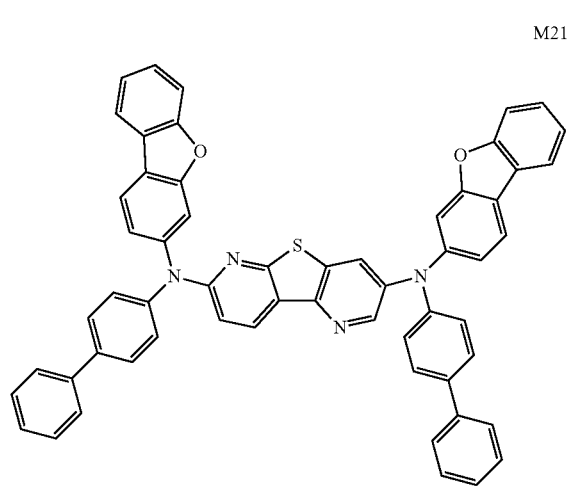
M217
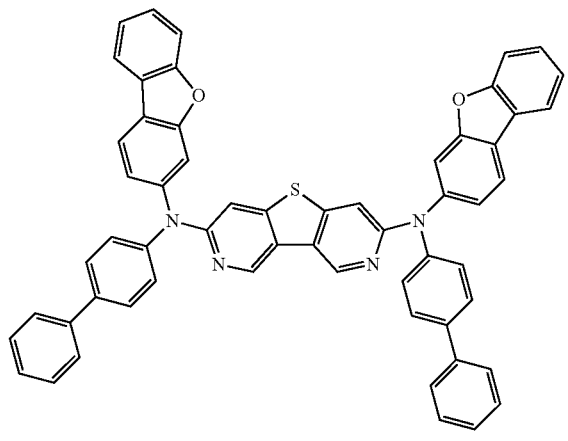
M218
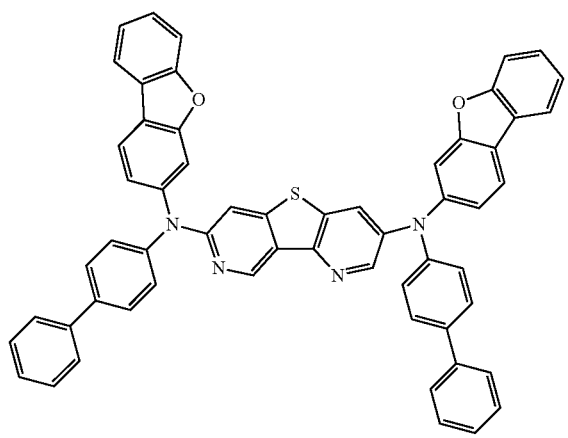
M219
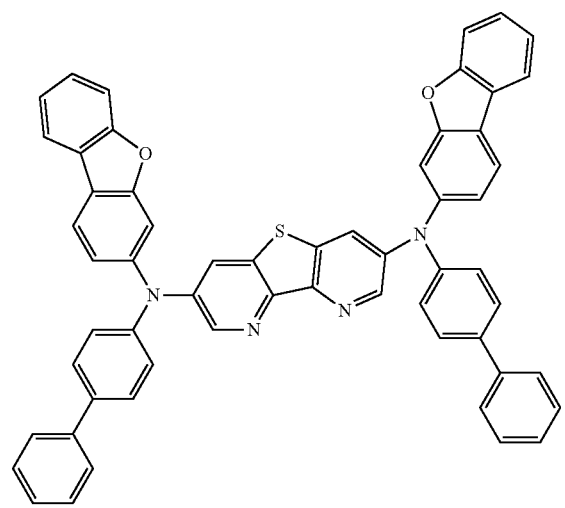

-continued
M220
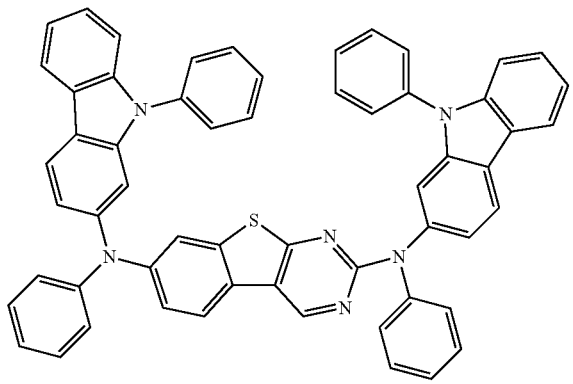
M221
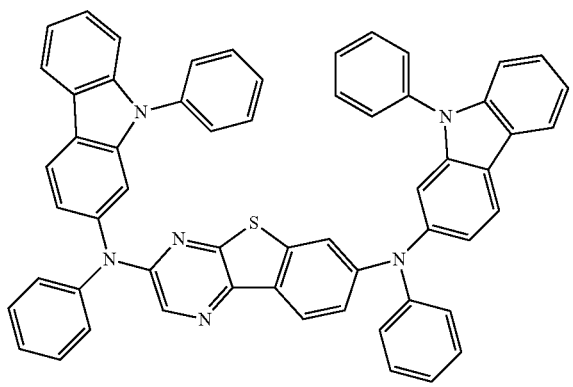
M222
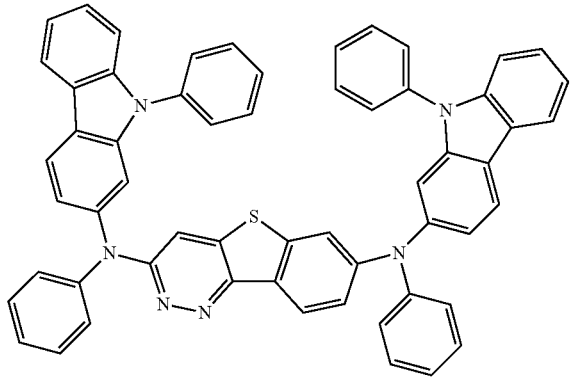
M223
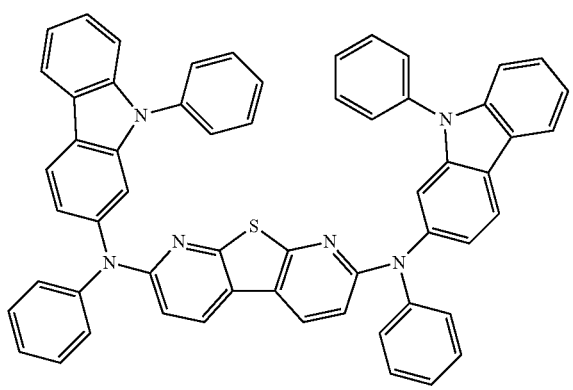
M224
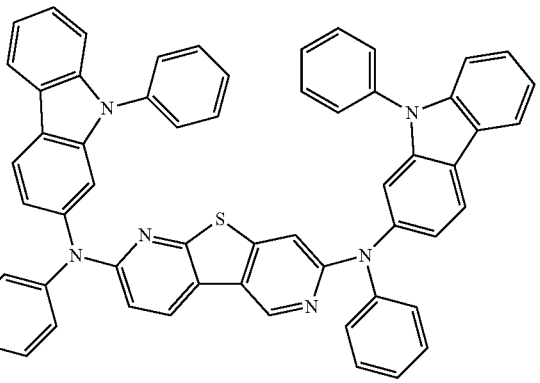
M225
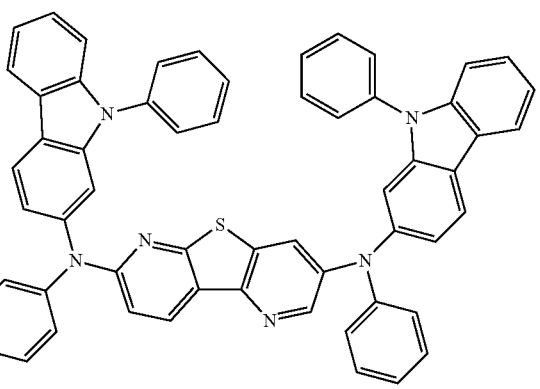
M226
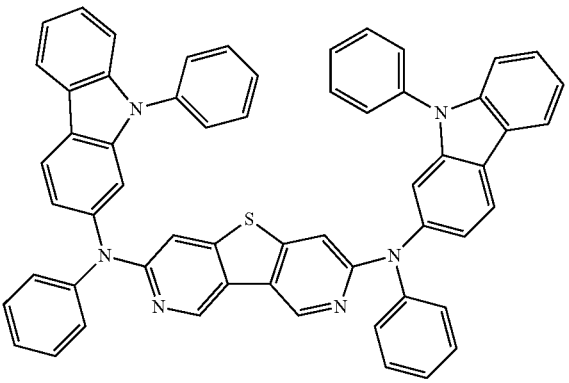
M227
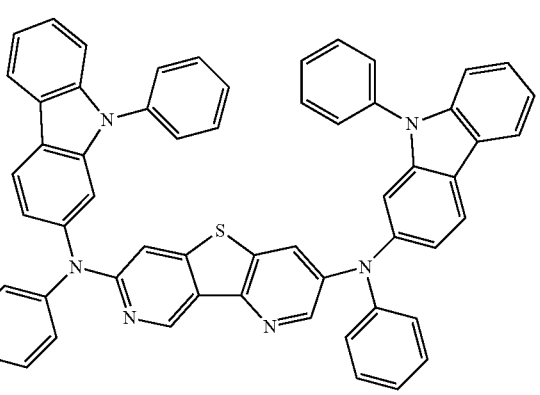

M228
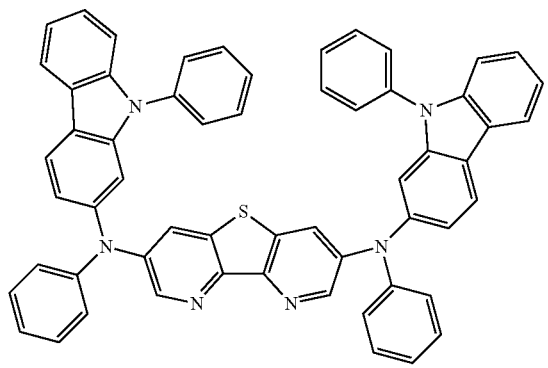
Optionally, the heterocyclic compound of the present disclosure may be any one of the following structures:
M229
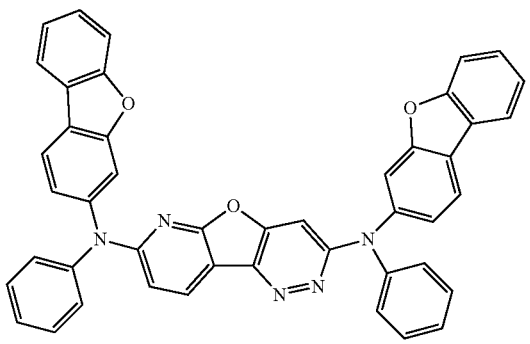
M232
M230
M233
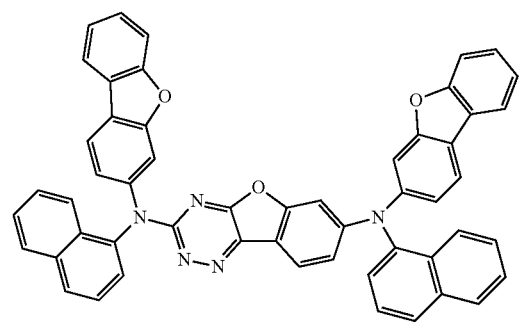
M231
M234
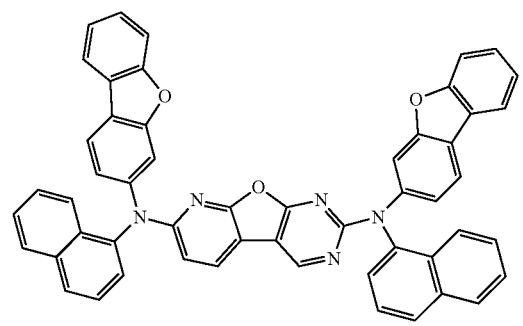
M235
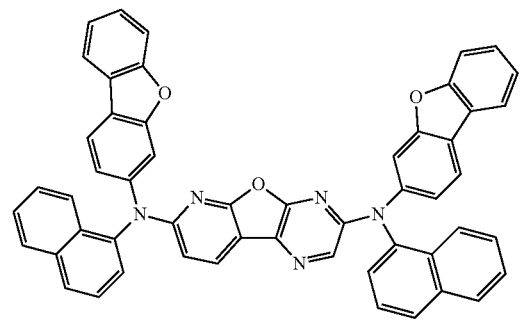

M236
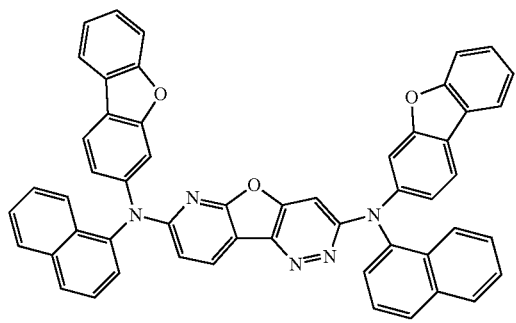
M237
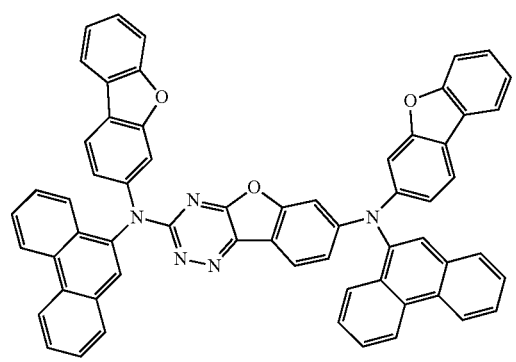
M238
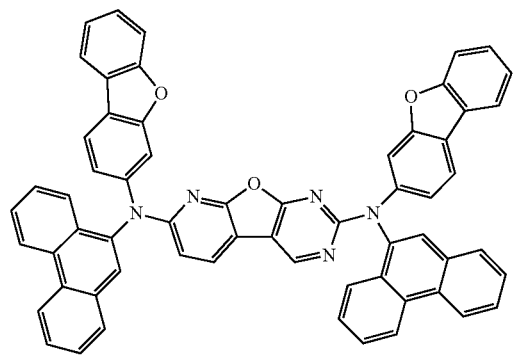
M239
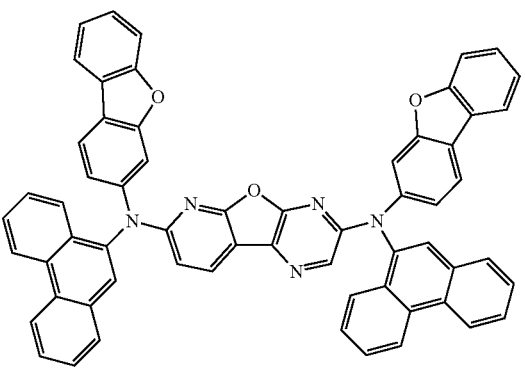
M240
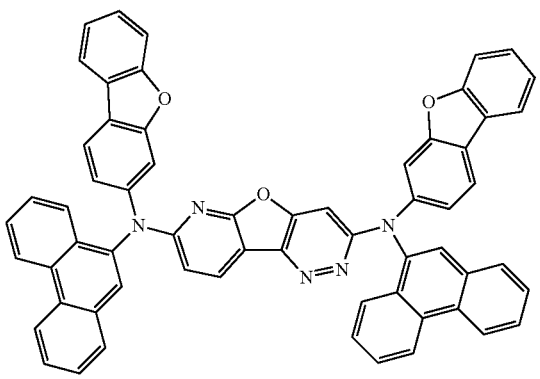
M241
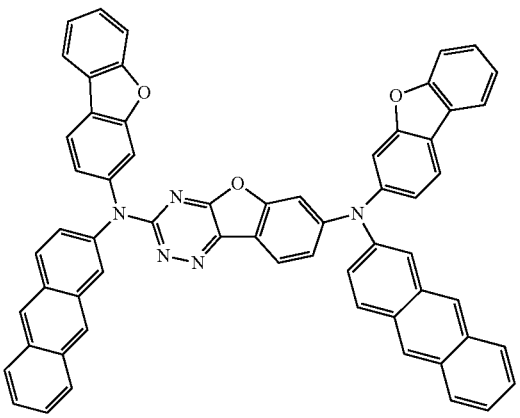
M242
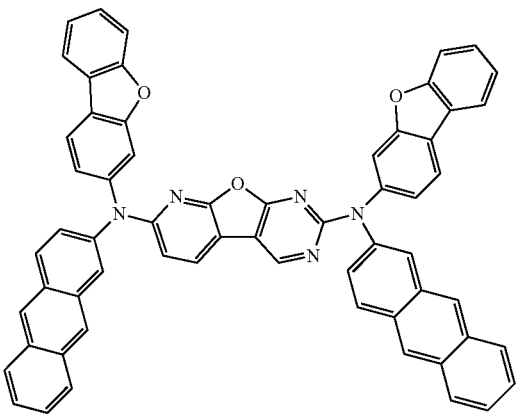

M243
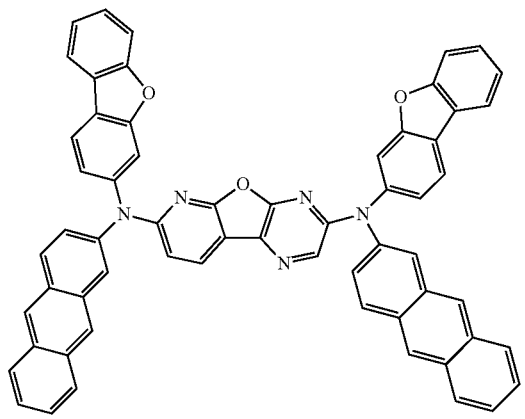
M244
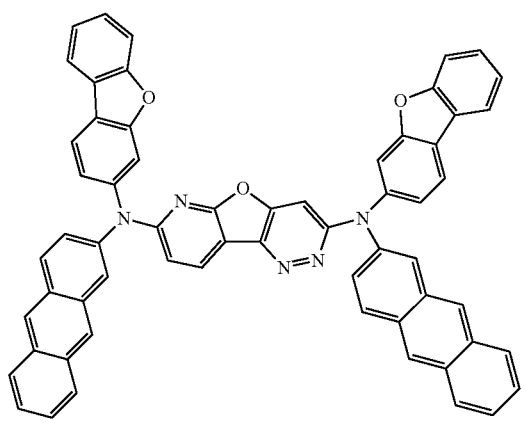
M245
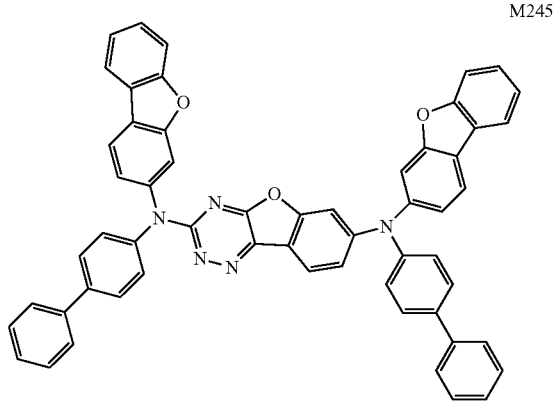
M246
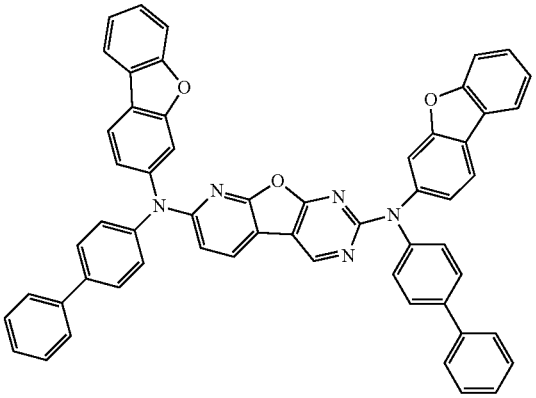
M247
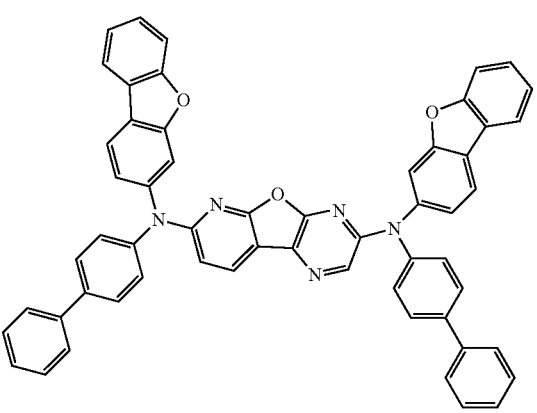
M248
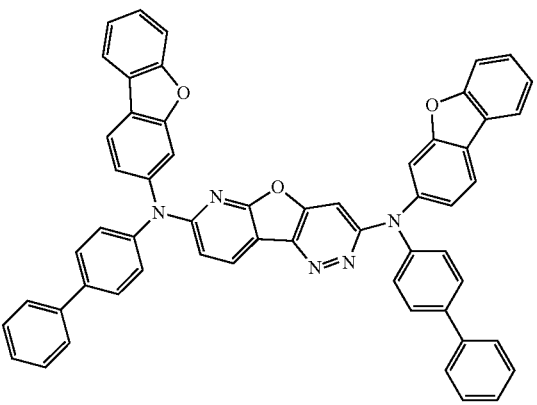
M249
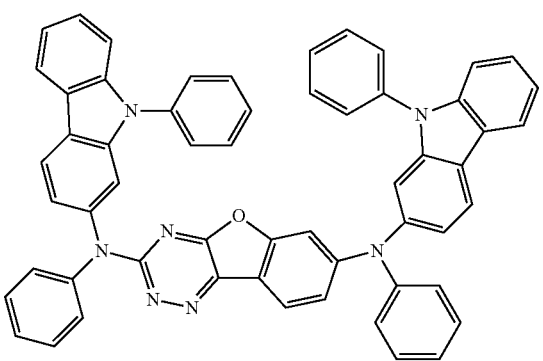

-continued
M250
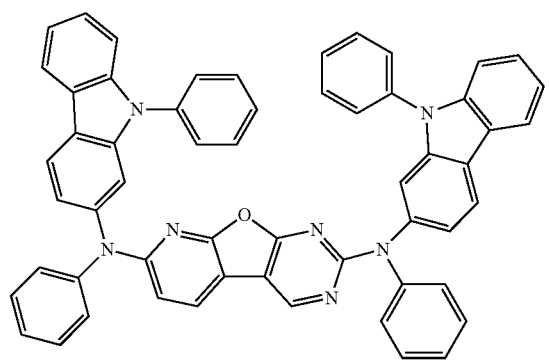
M251
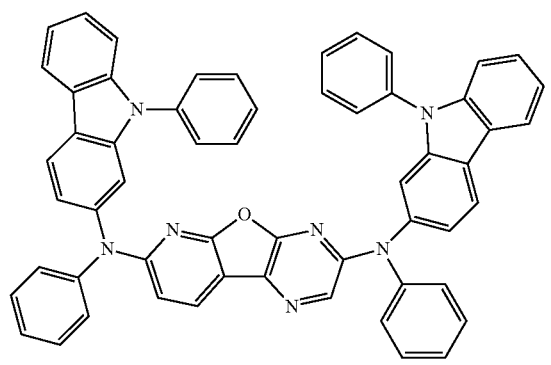
M252
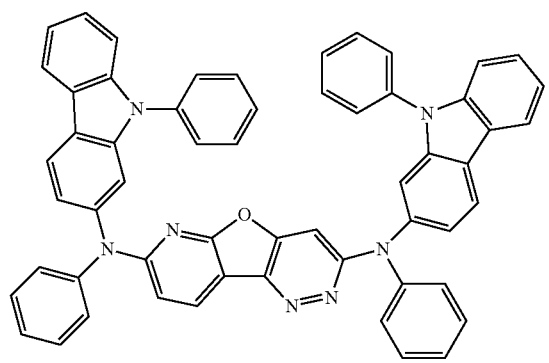
M253
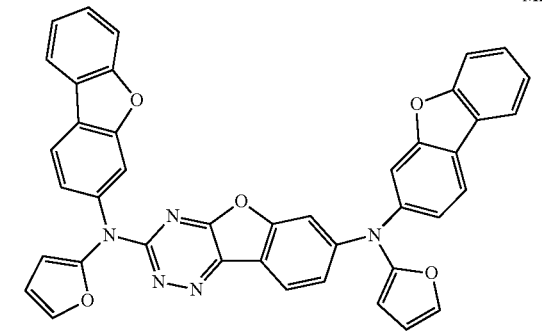
-continued
M254
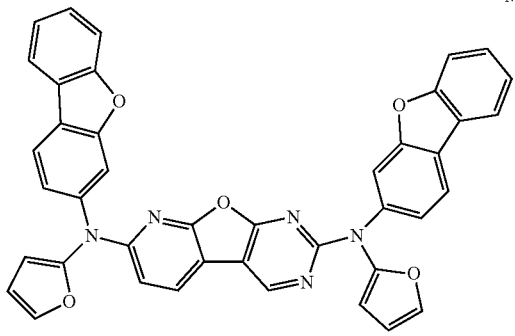
M255
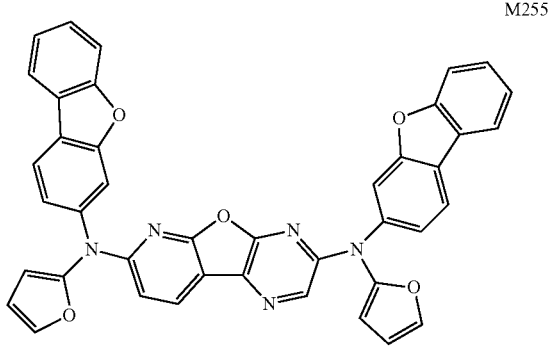
M256
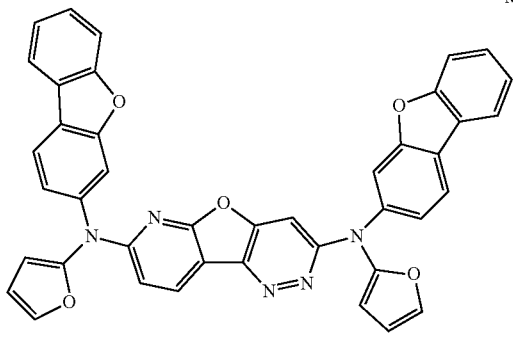
M257
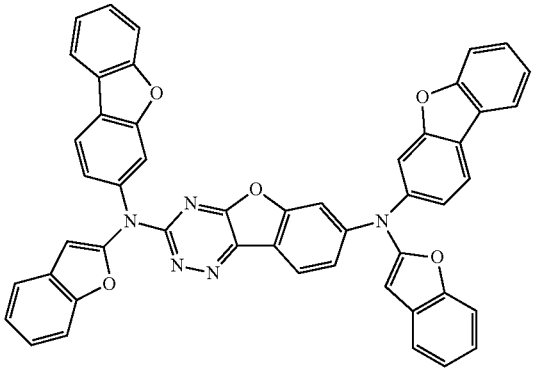

M258
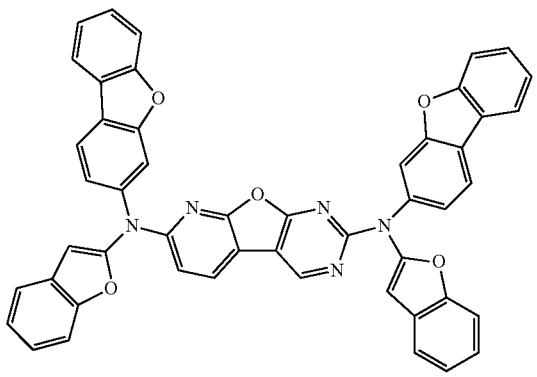
M259
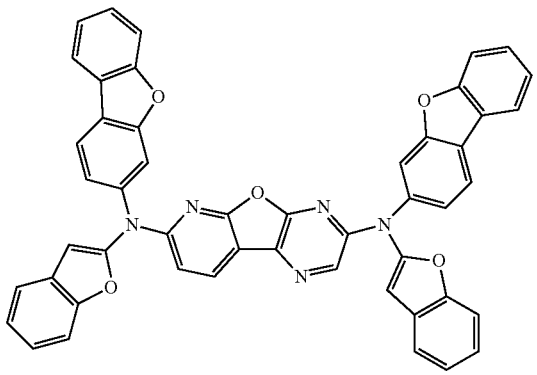
M260
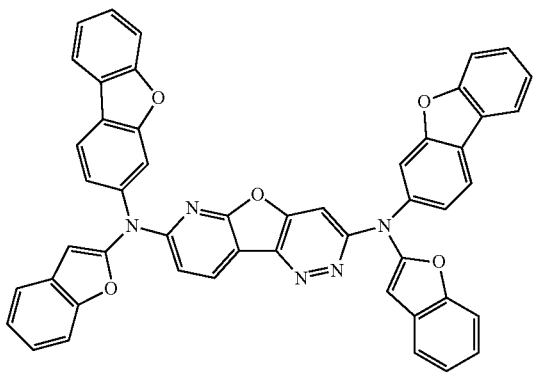
M261
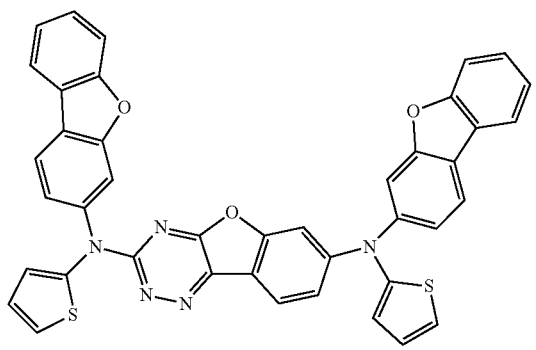
M262
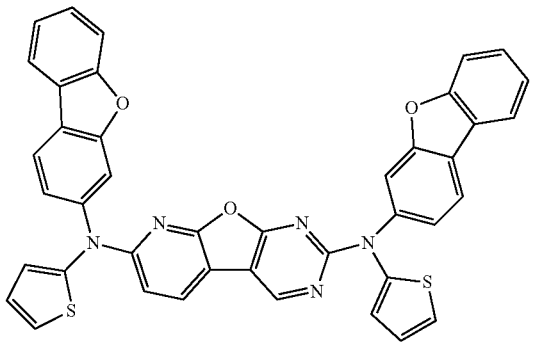
M263
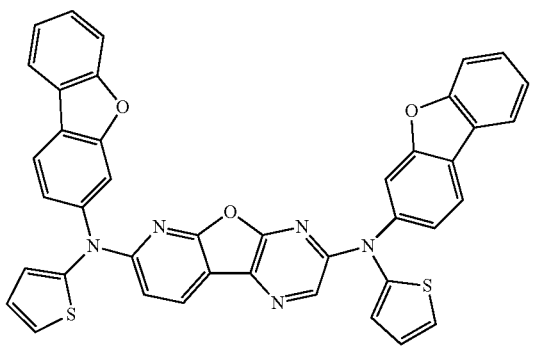
M264
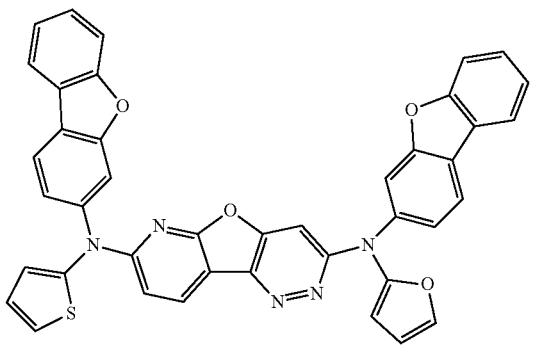
M265
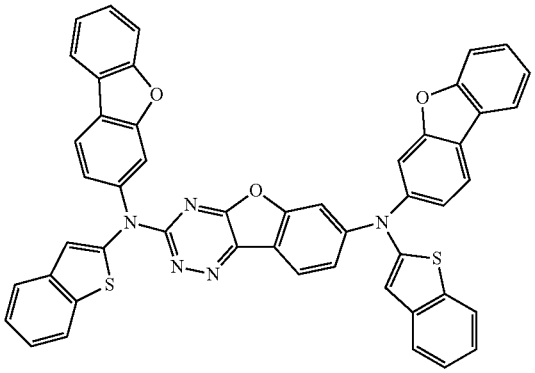

M266
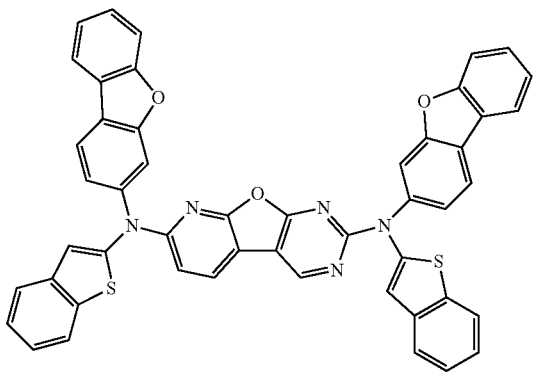
M267
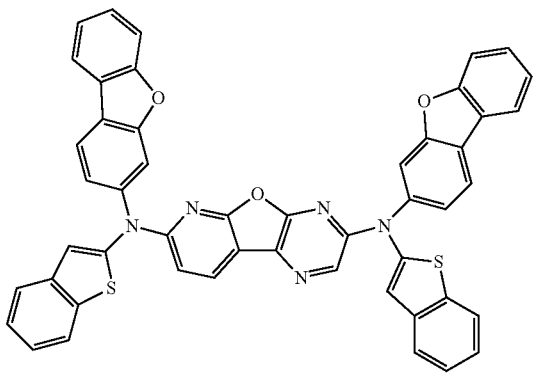
M268
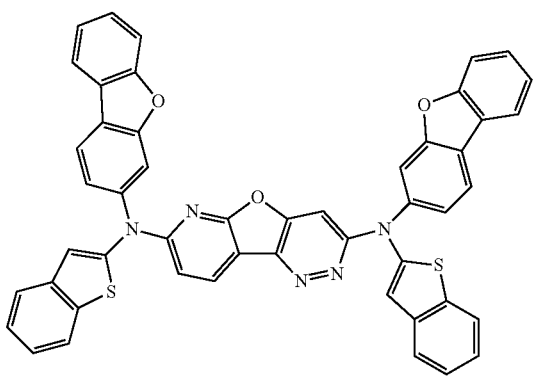
M269
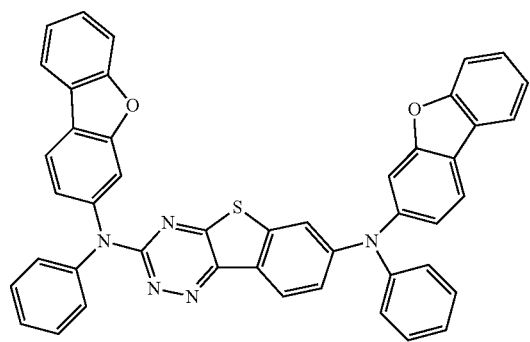
M270
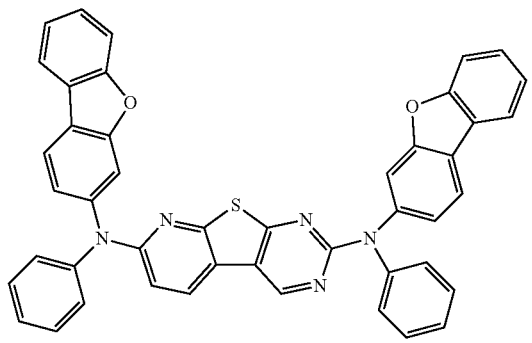
M271
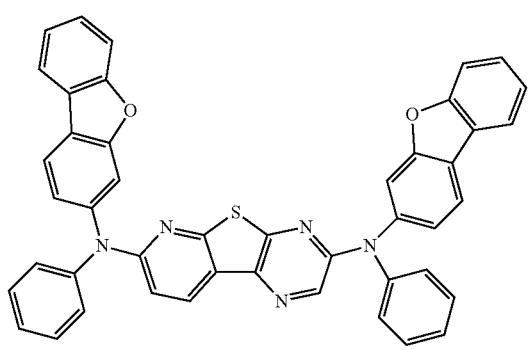
M272
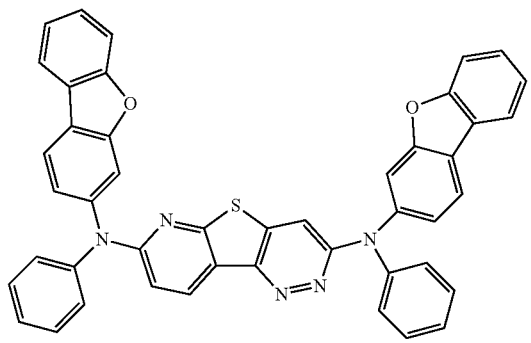
M273

M274
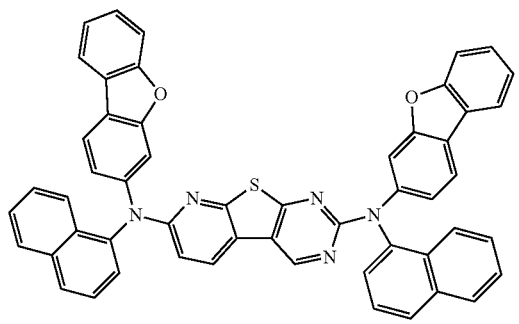
M278
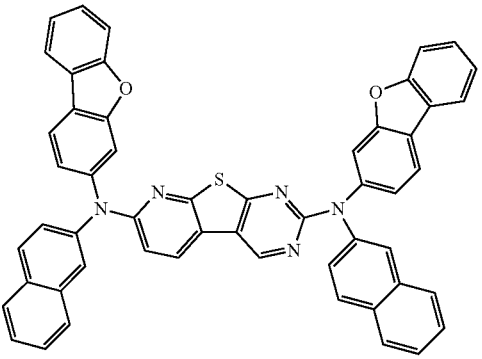
M275
M279
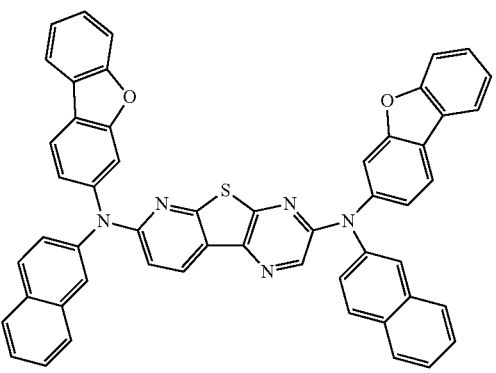
M276
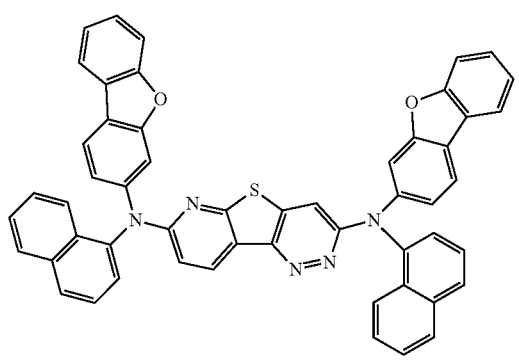
M280
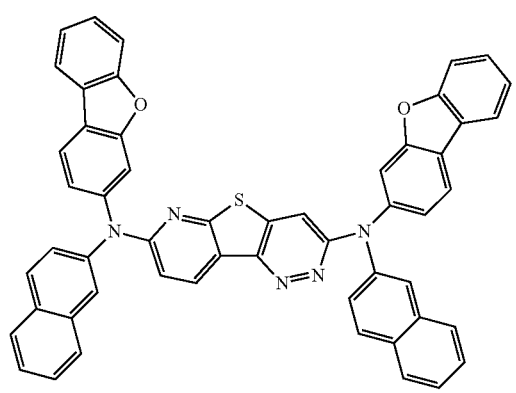
M277
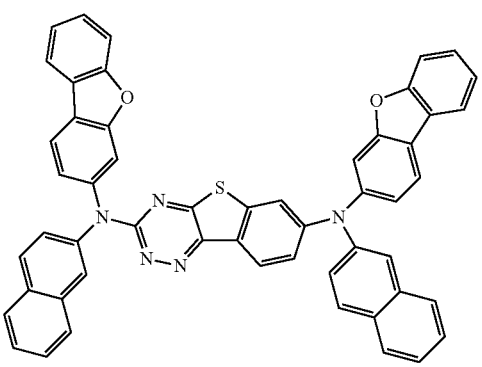
M281
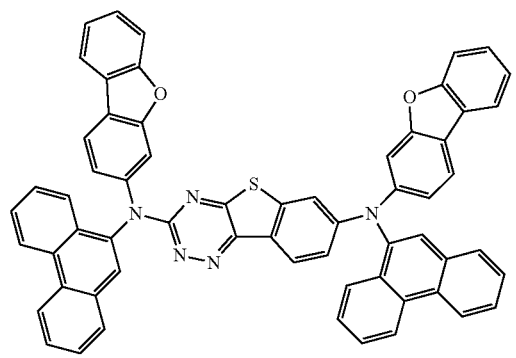

M282
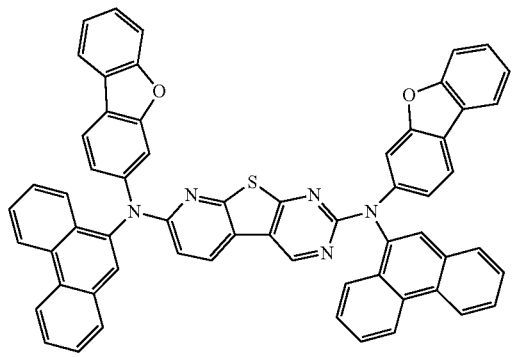
M283
M286
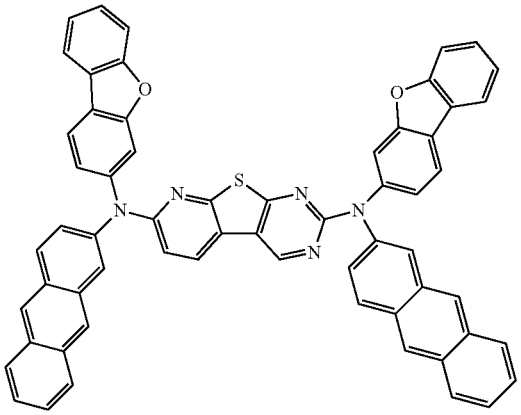
M284
M287
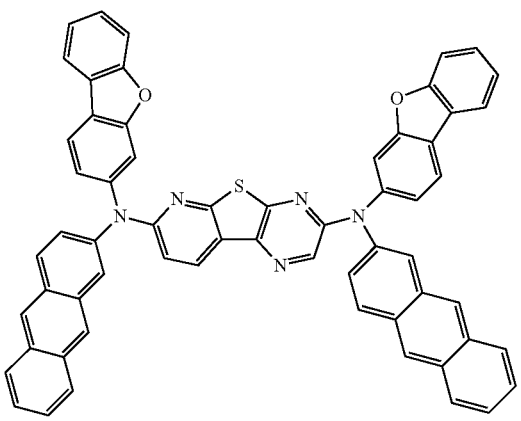
M285
M288
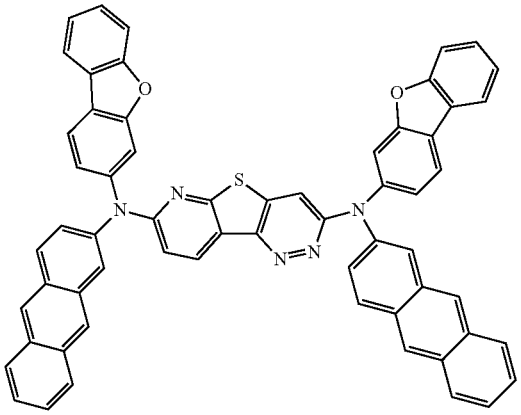

M289
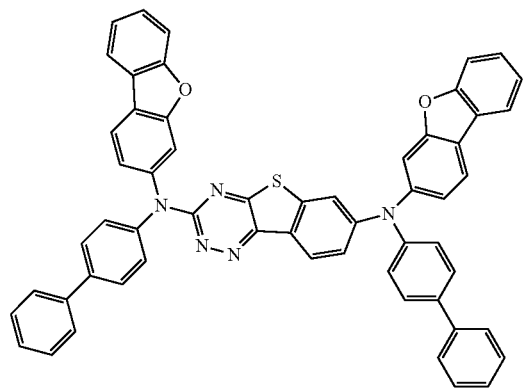
M290
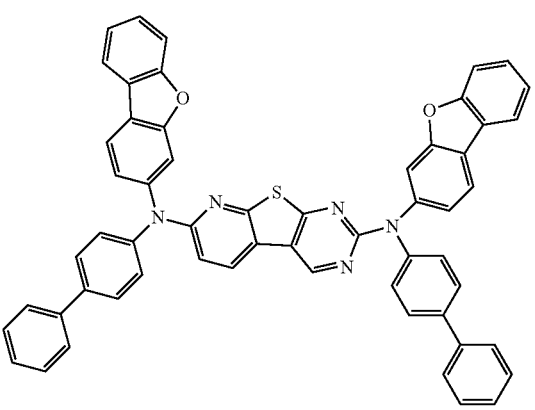
M291
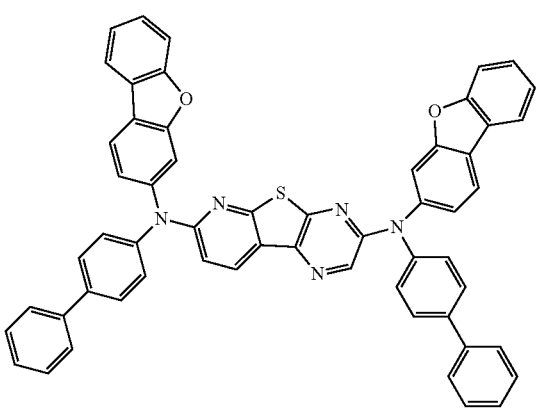
M292
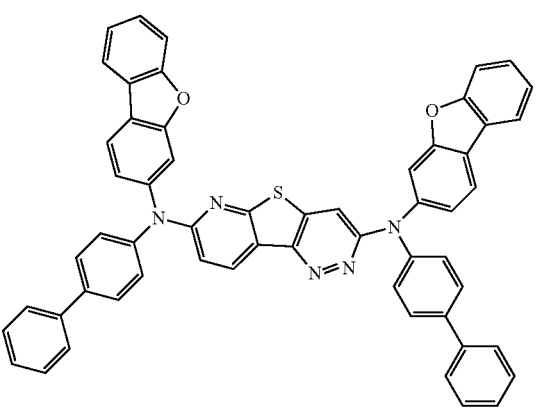
M293
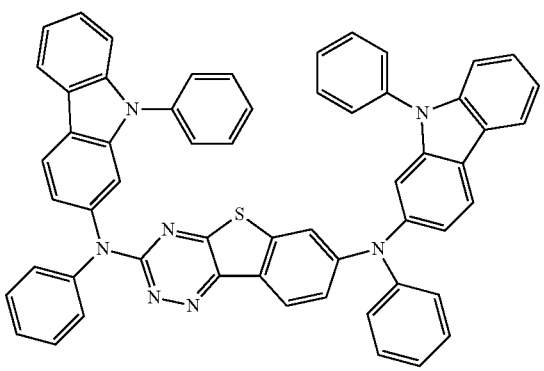
M294
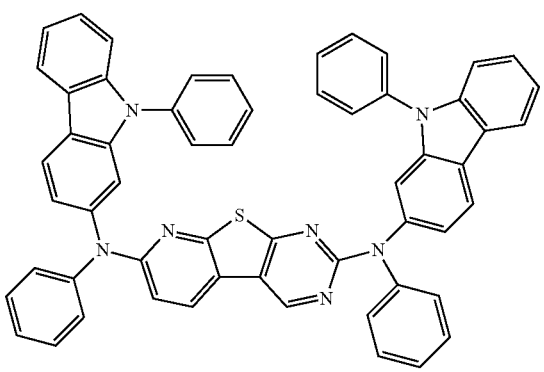
M295
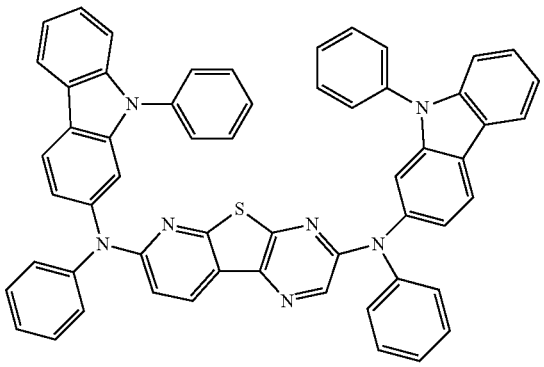

M296
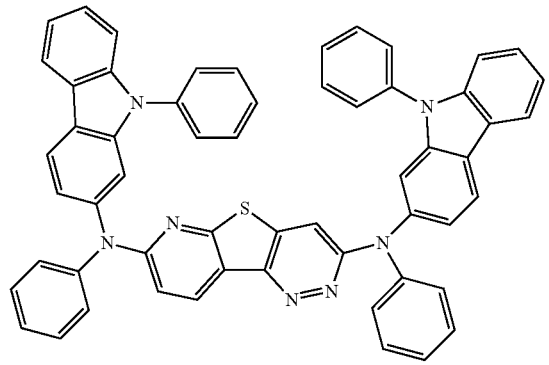
M297
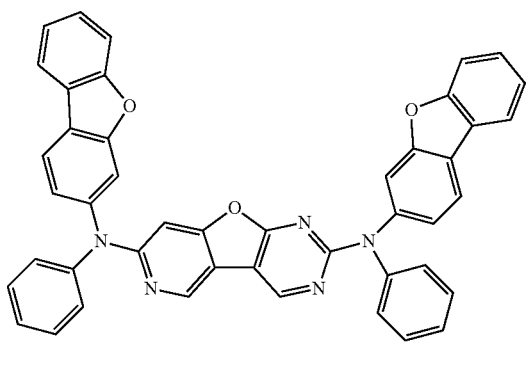
M298
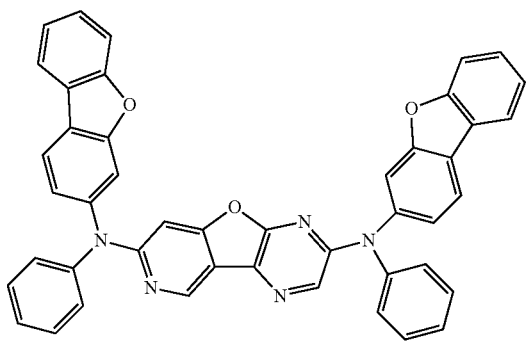
M299
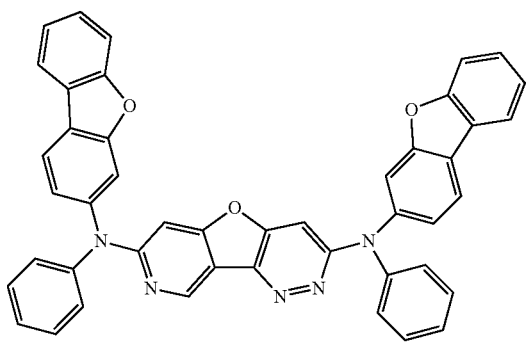
M300
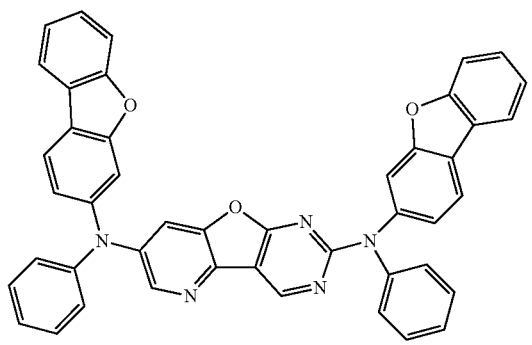
M301
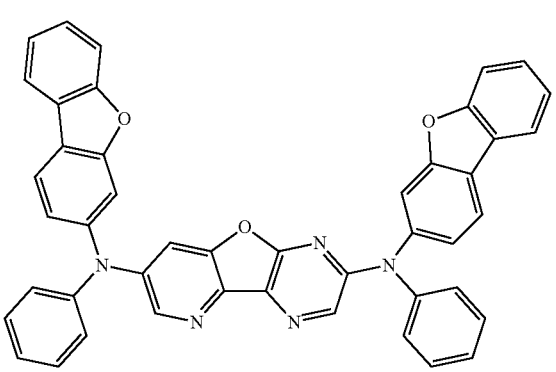
M302
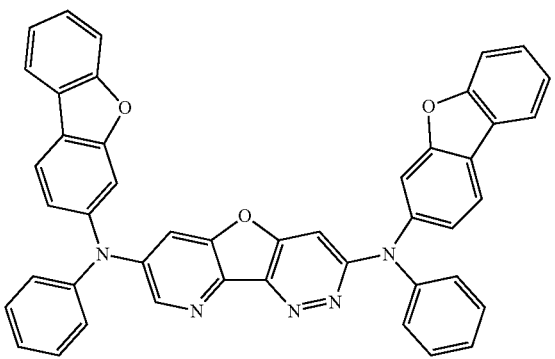
M303
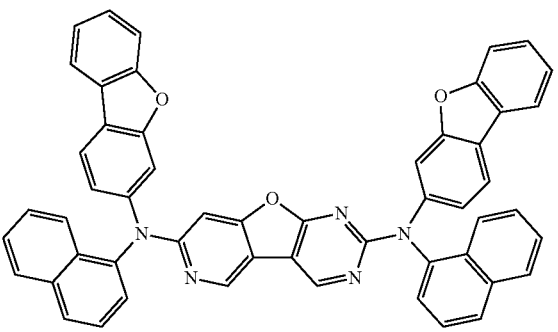

-continued
M304
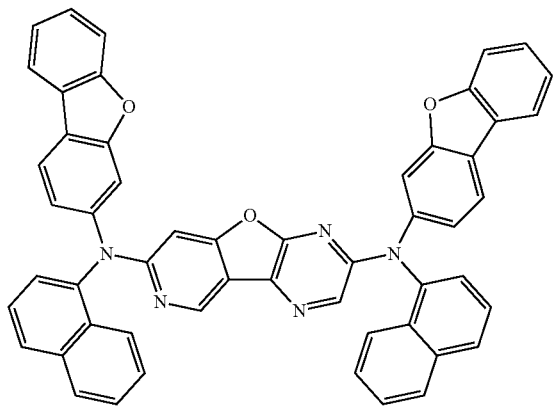
M305
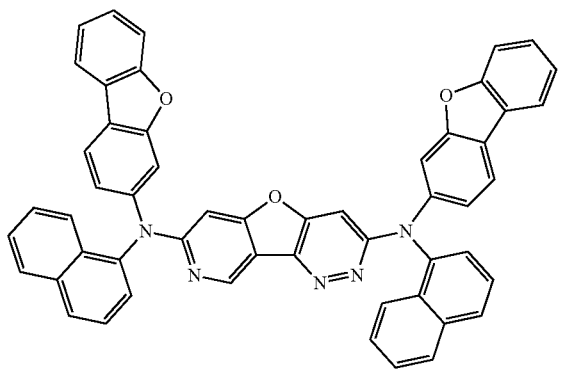
M306
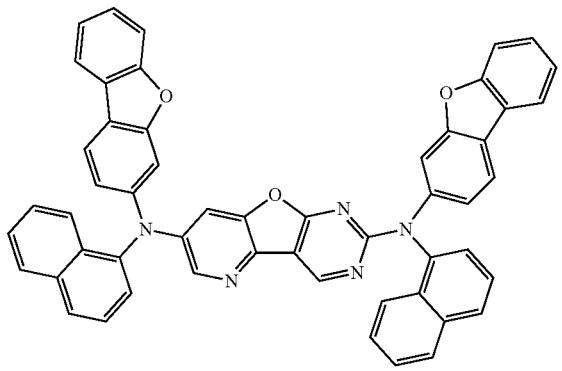
M307
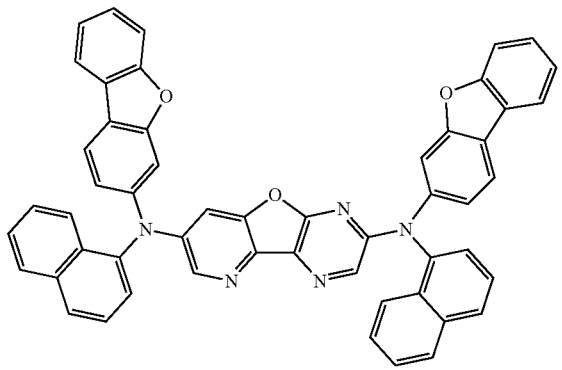
-continued
M308
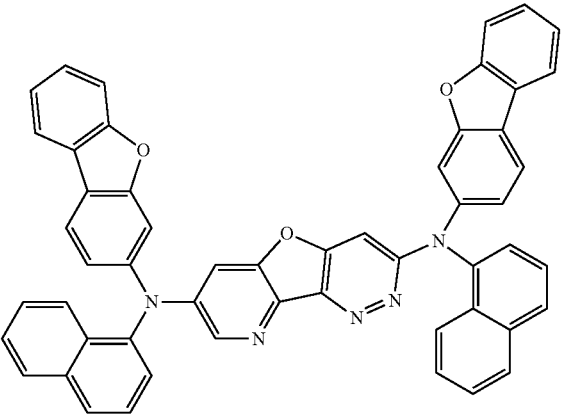
M309
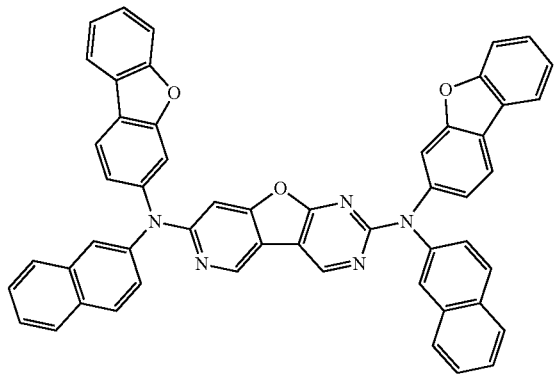
M310
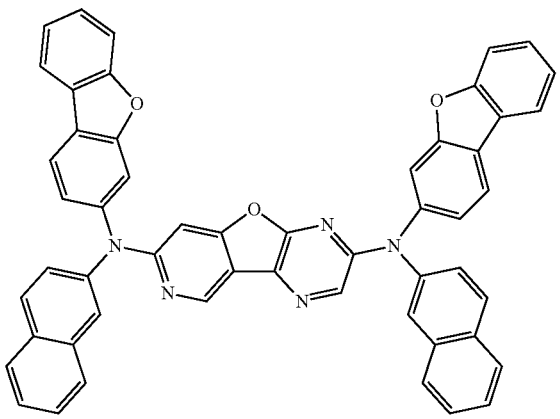

M311
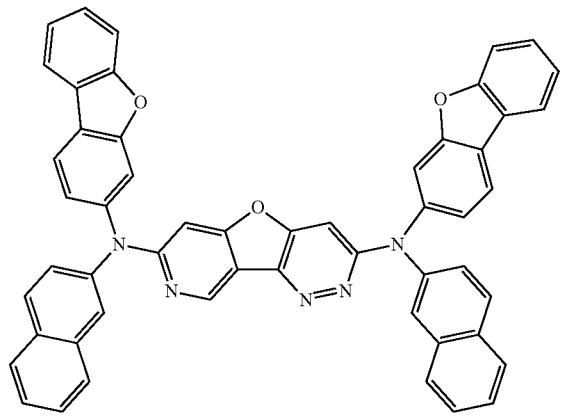
M315
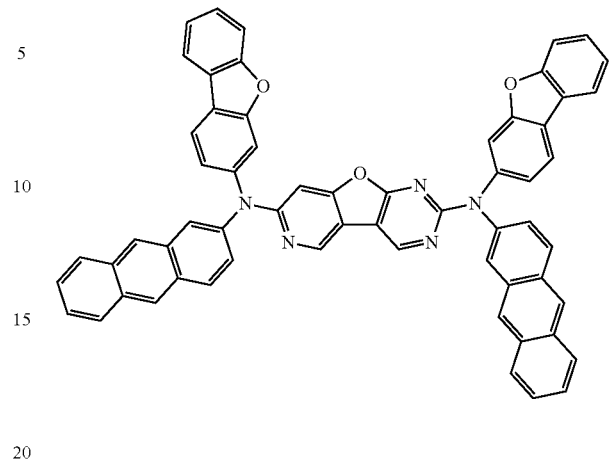
M312
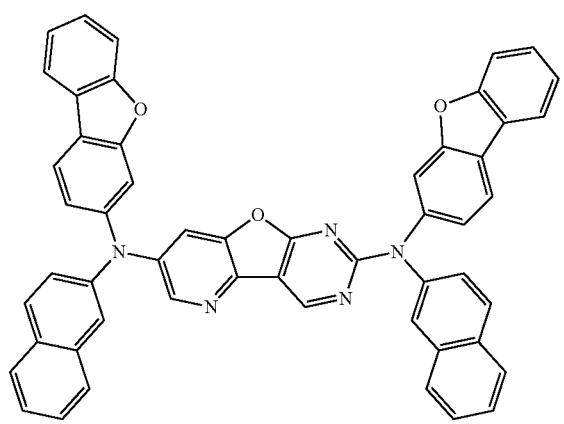
M316
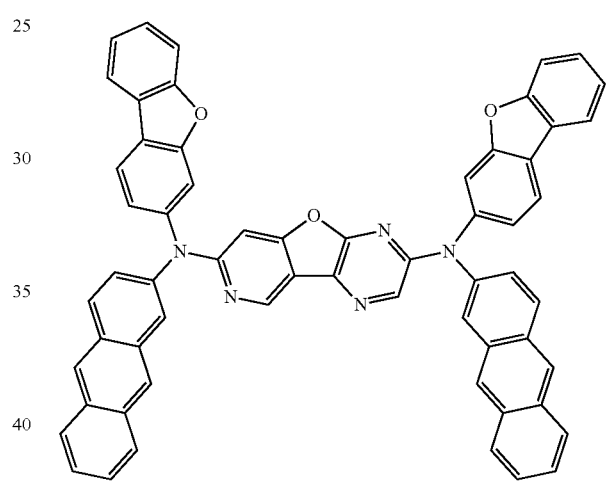
M314
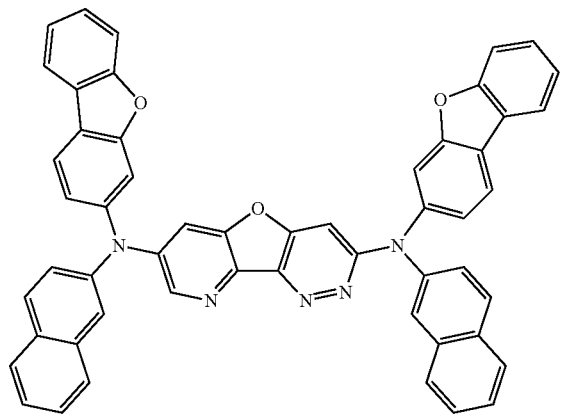
M318
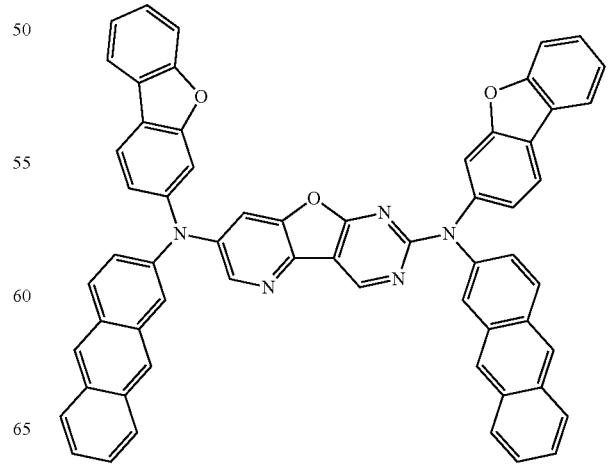

M319
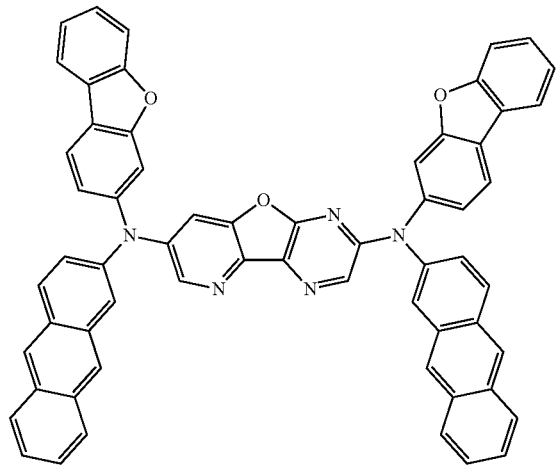
M320
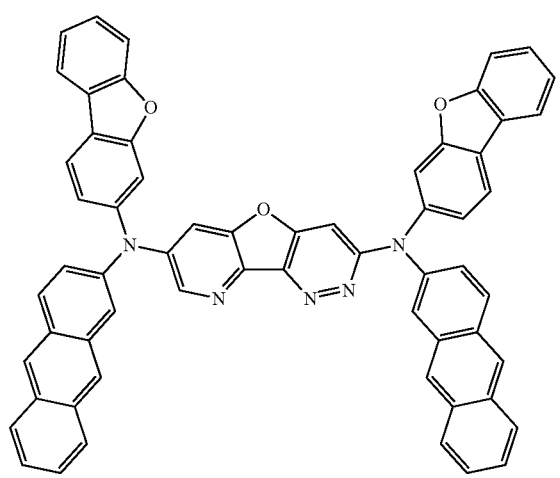
M322
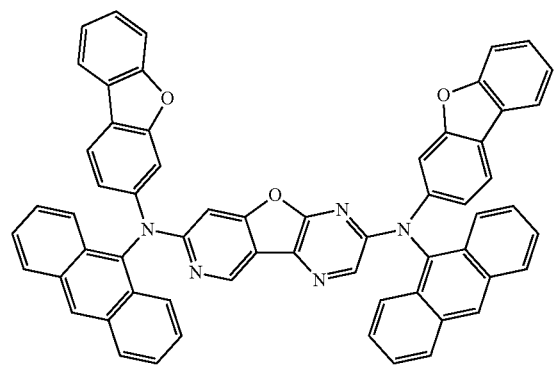
M323
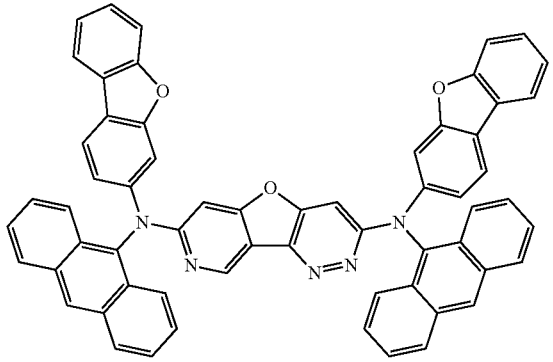
M324
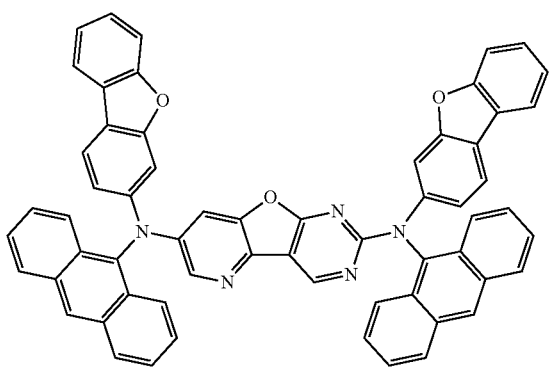
M325
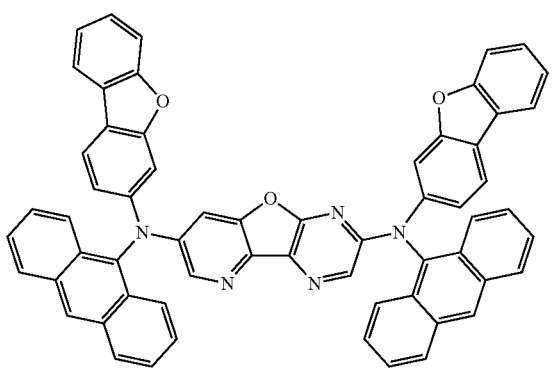
M326
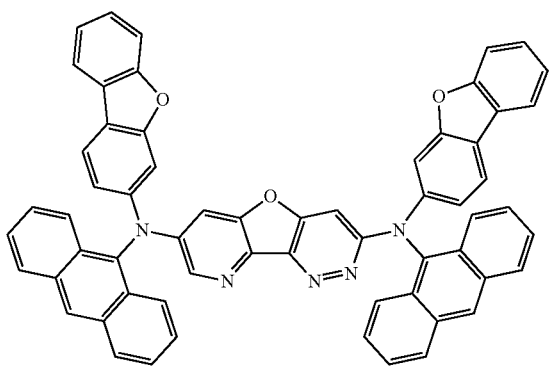

M327
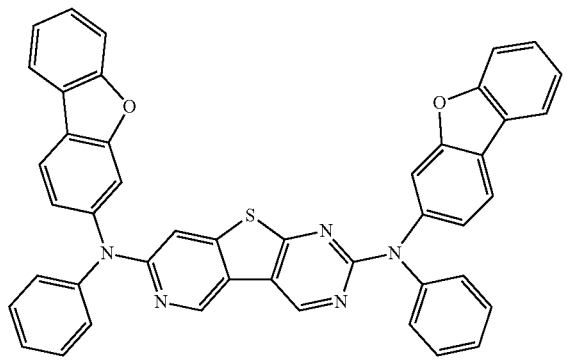
M331
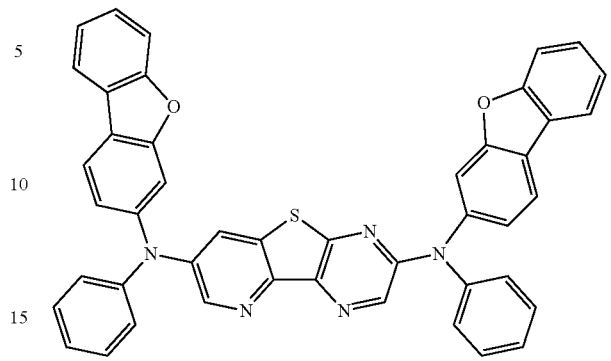
M328
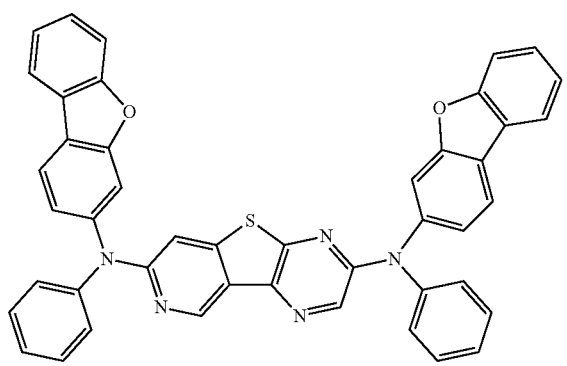
M332
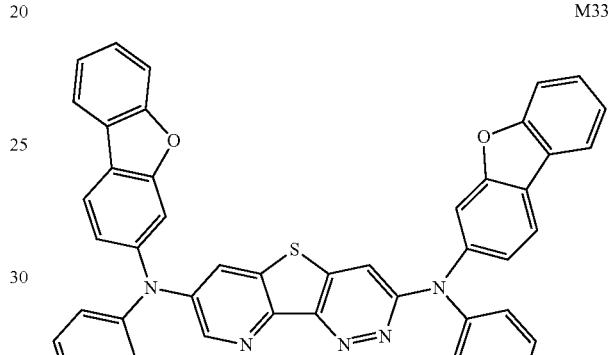
M329
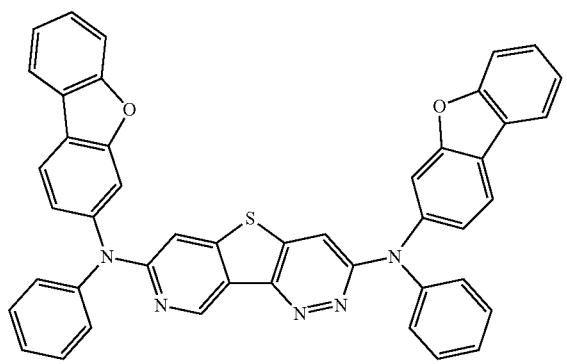
M333
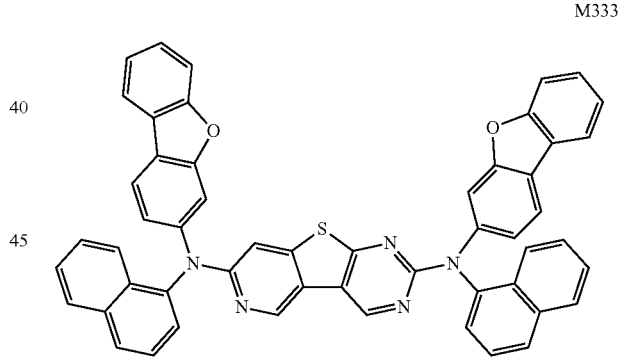
M330
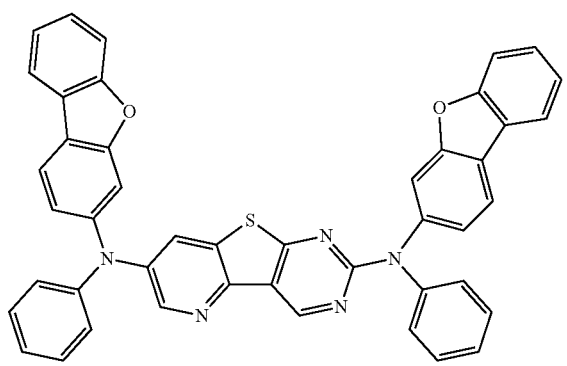
M334
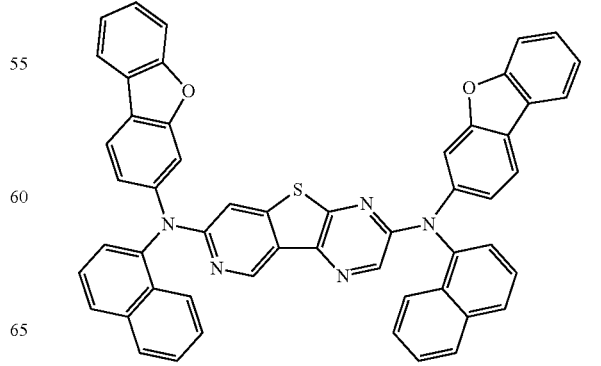

M335
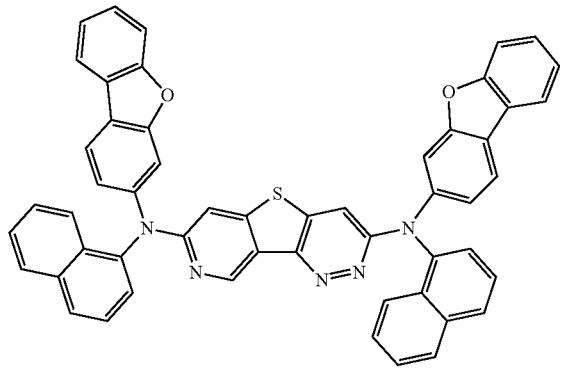
M336
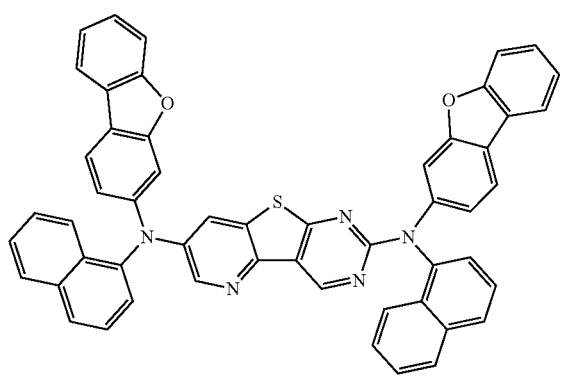
M337
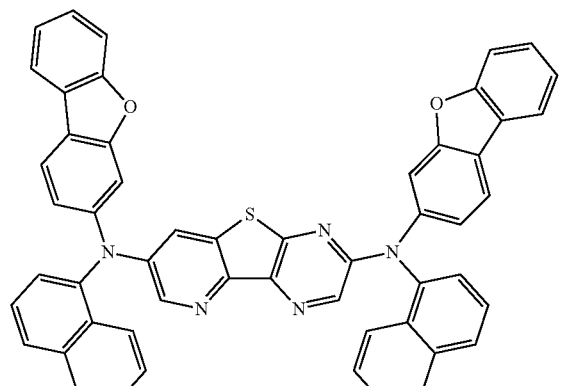
M338
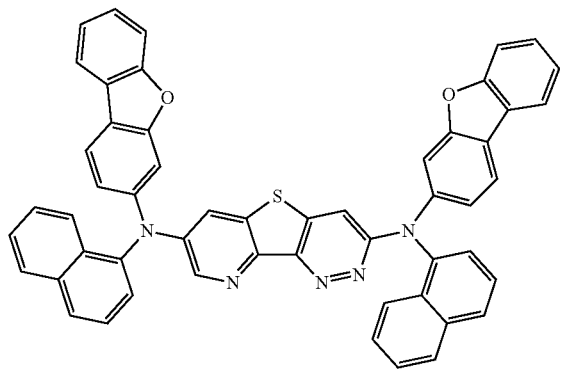
M339
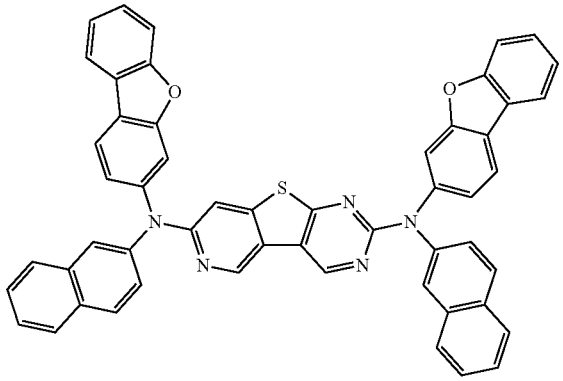
M340
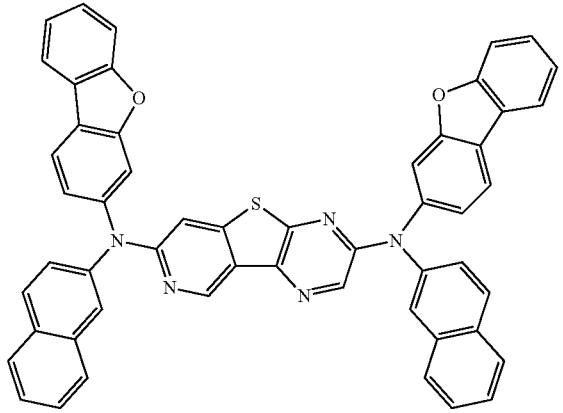
M341
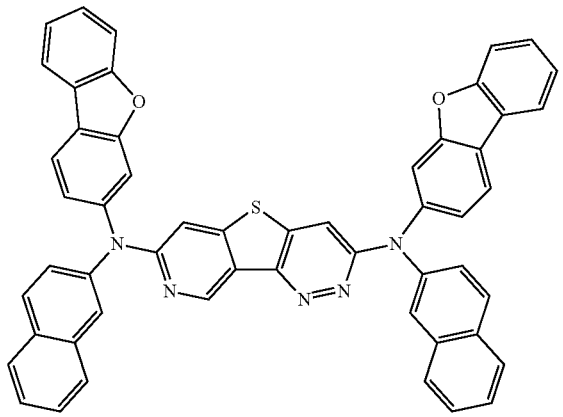

-continued
M342
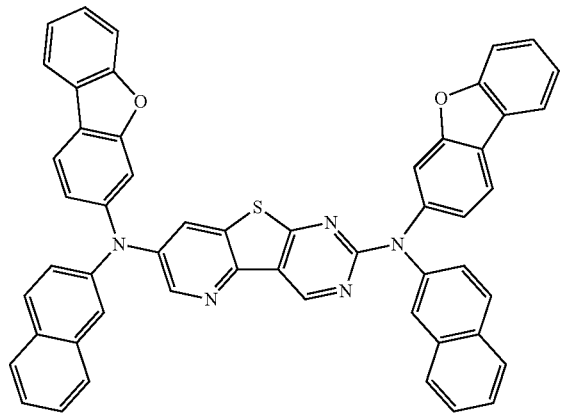
M343
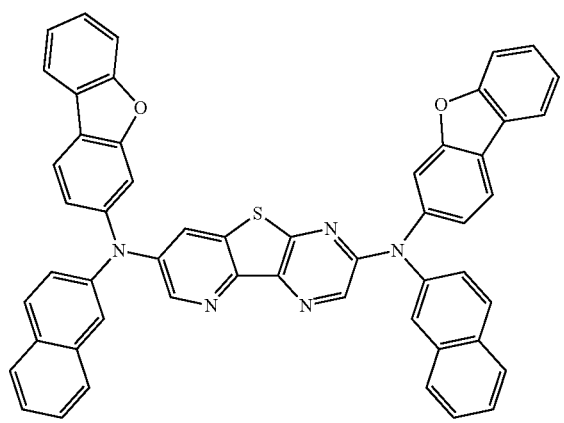
M344
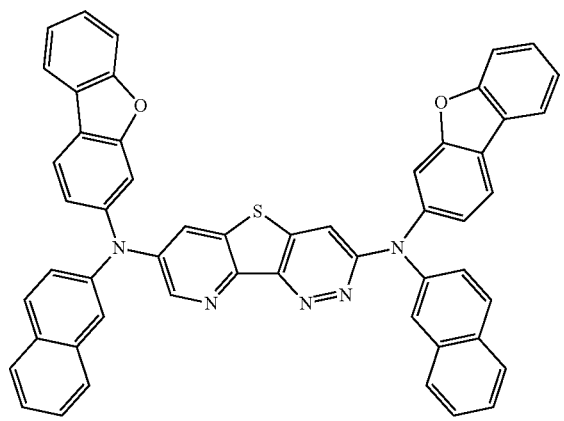
M345
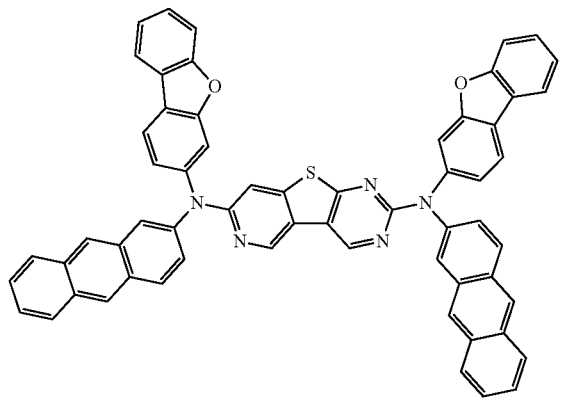
M346
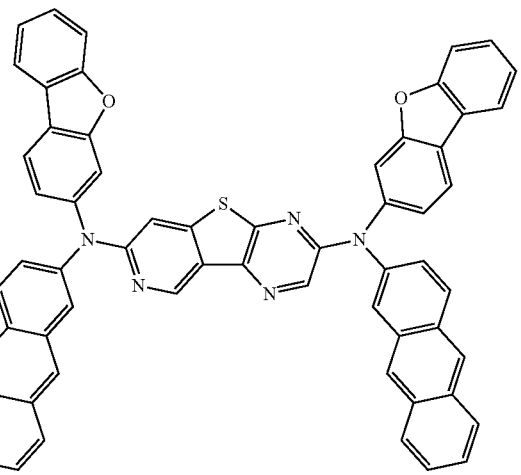
M347
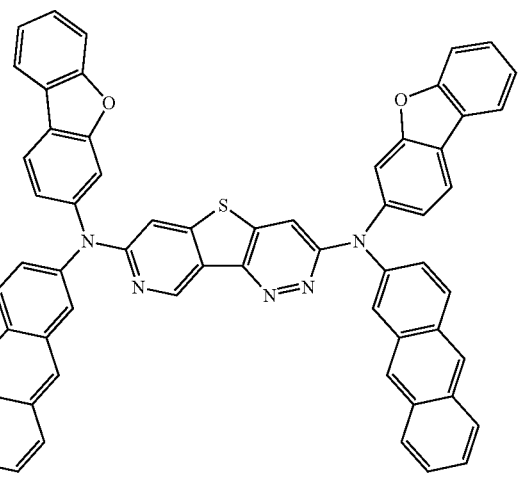

M348
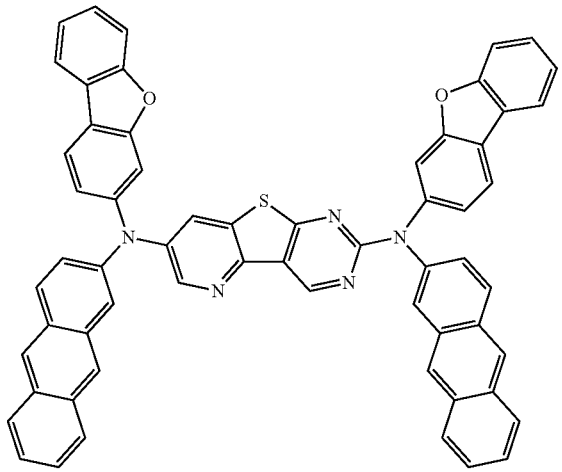
M349
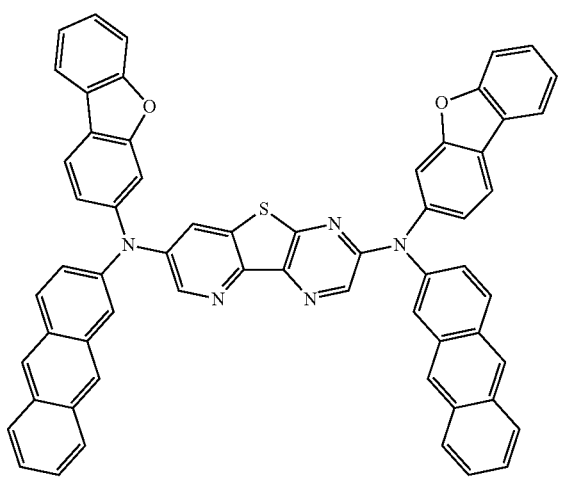
M350
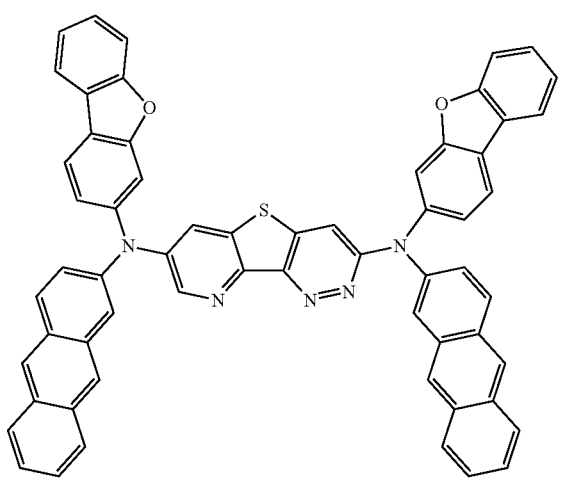
M351
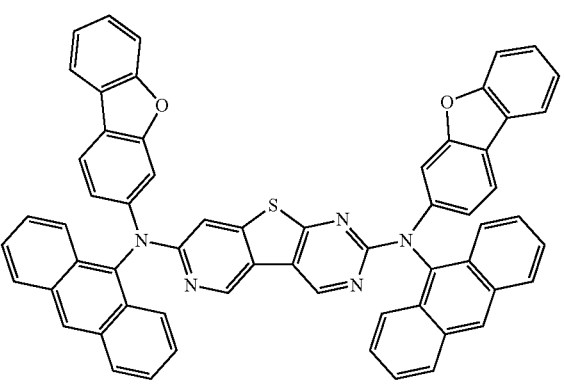
M352
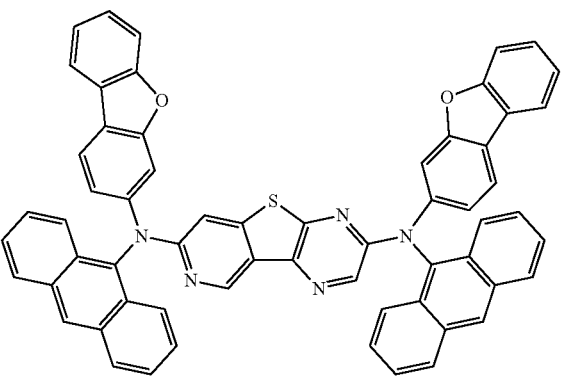
M353
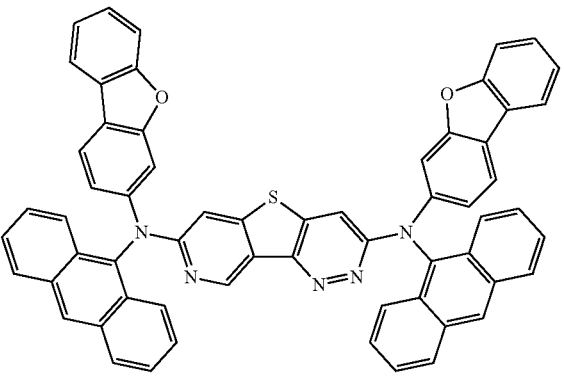
M354
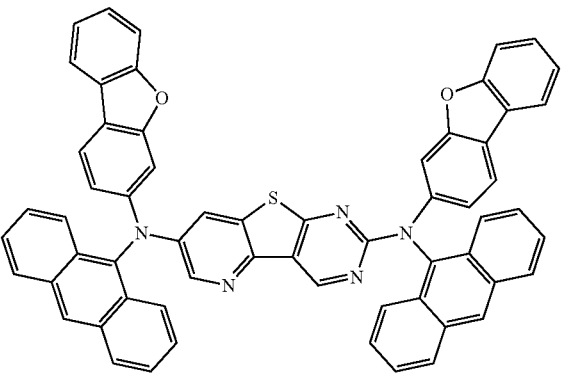

M355
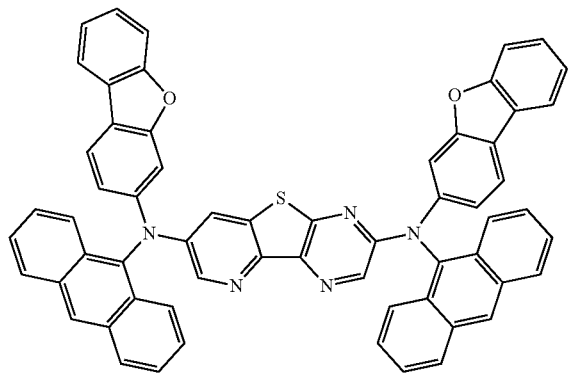
M356
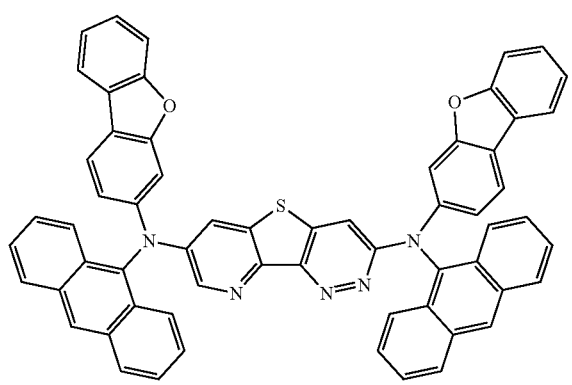
M357
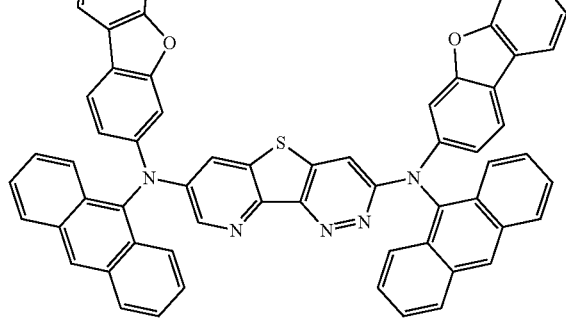
M358

M359

M360
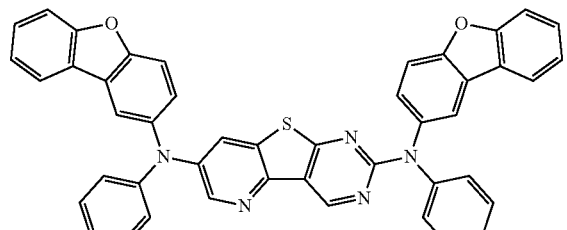
M361
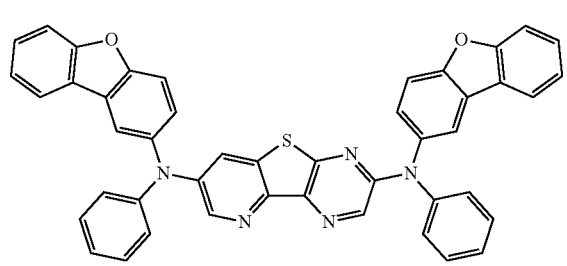
M362
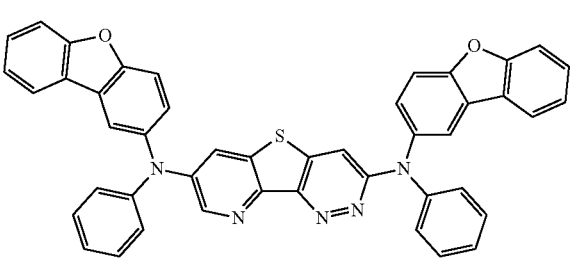
M363
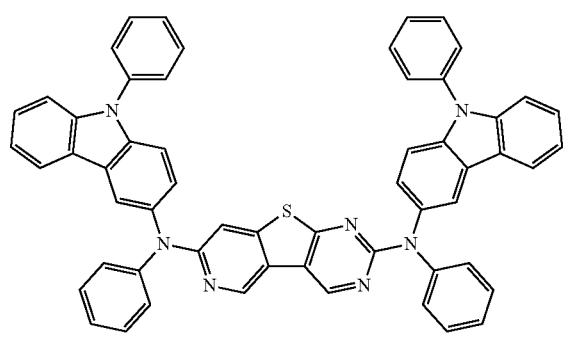
M364
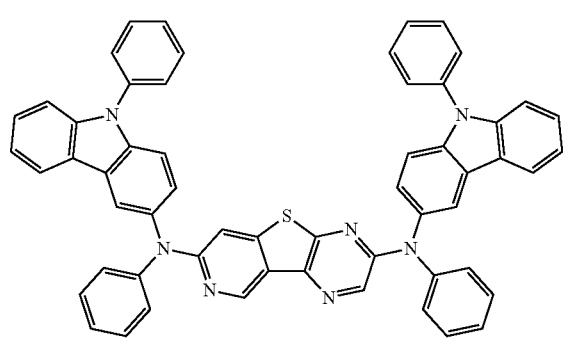

M365
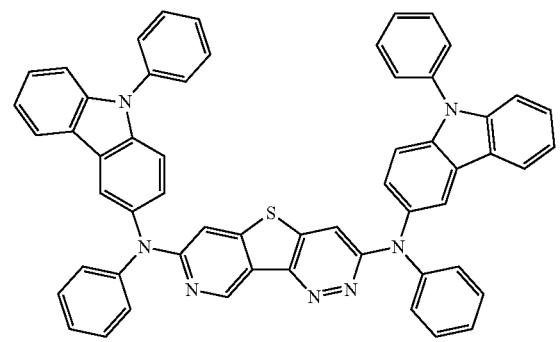
M369
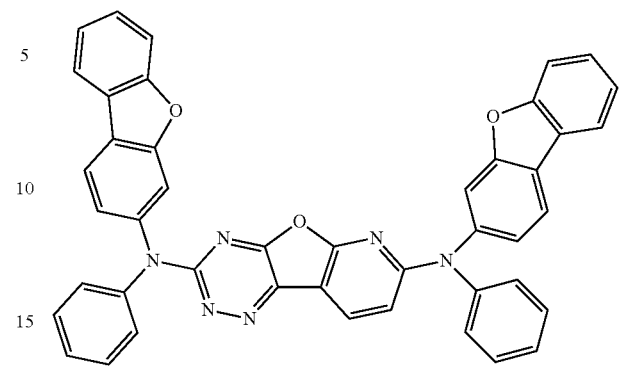
M366
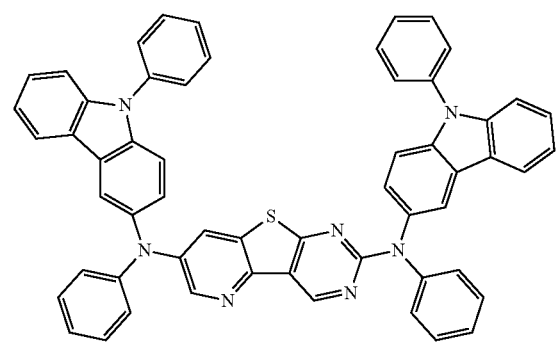
M370
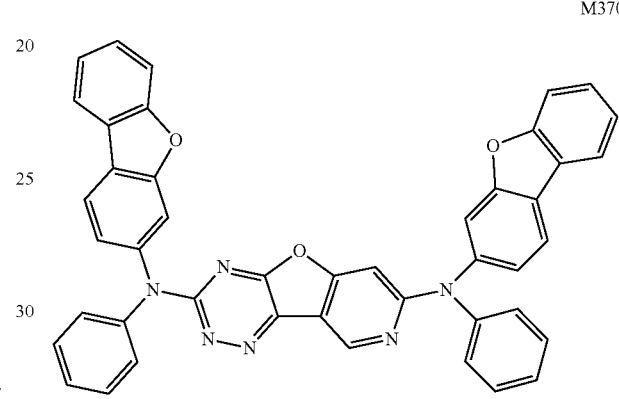
M367
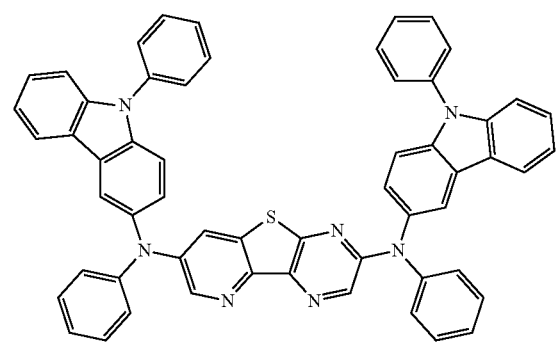
M371
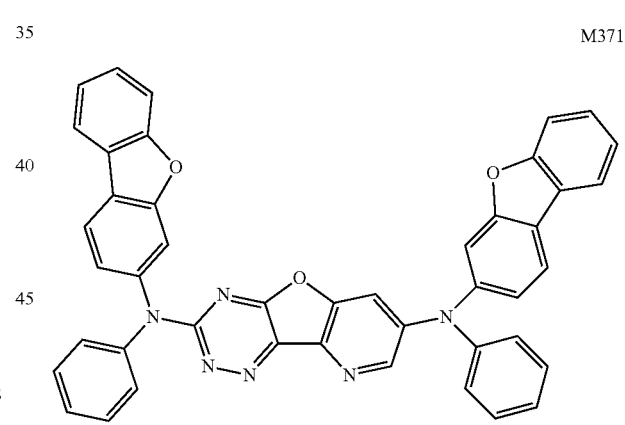
M368
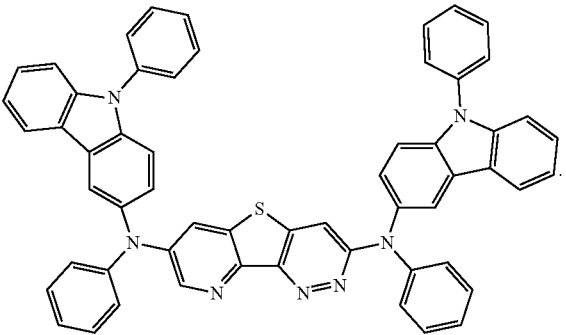
M372
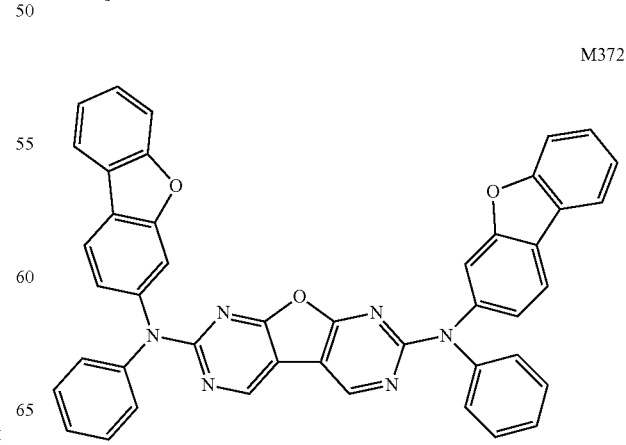
Optionally, the heterocyclic compound of the present disclosure may be any one of the following structures:

M373
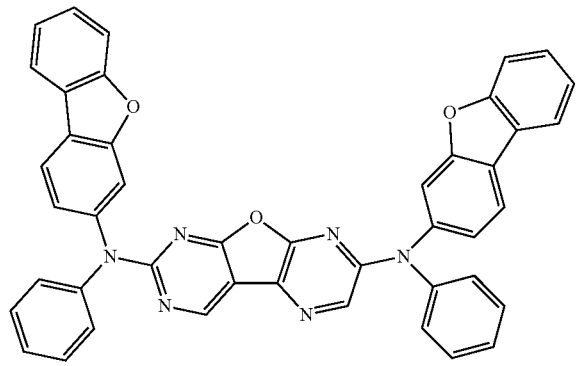
M377
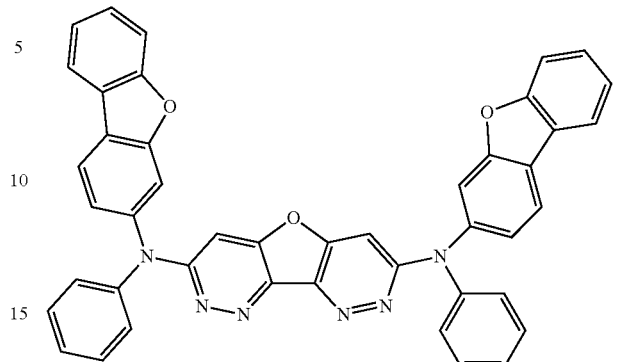
M374
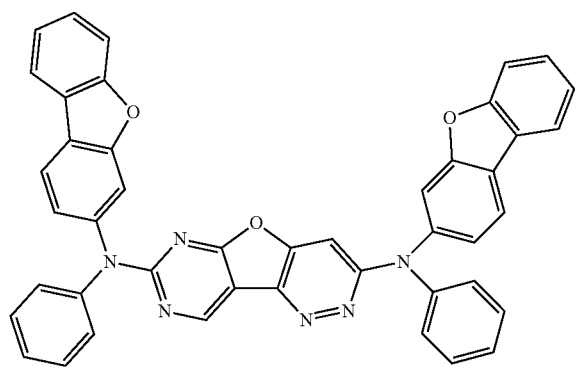
M378
M375
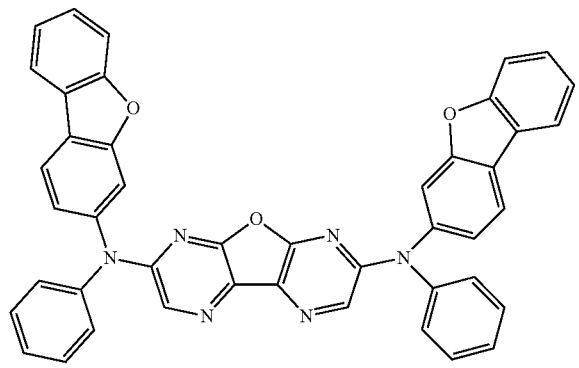
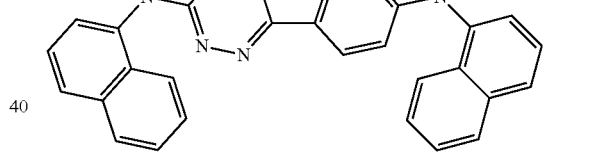
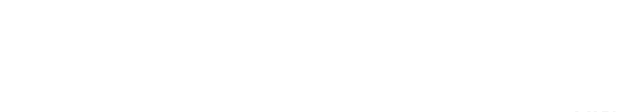
M376
M379
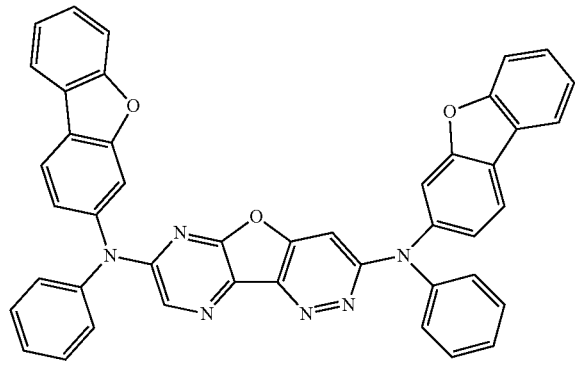
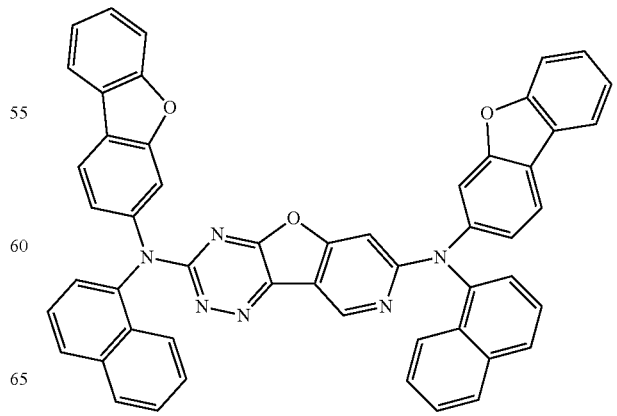

M380
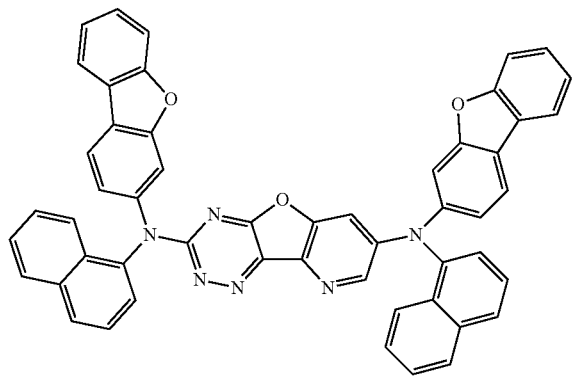
M384
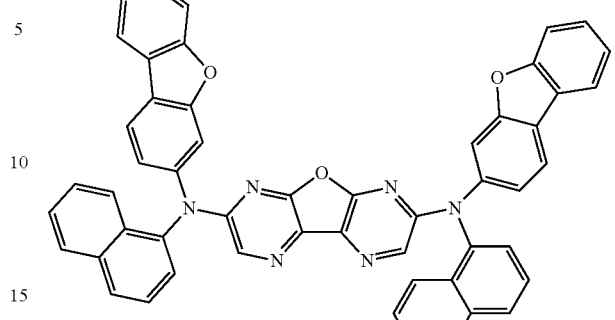
M381
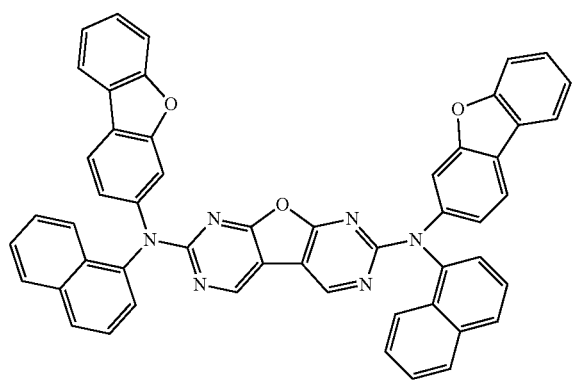
M385
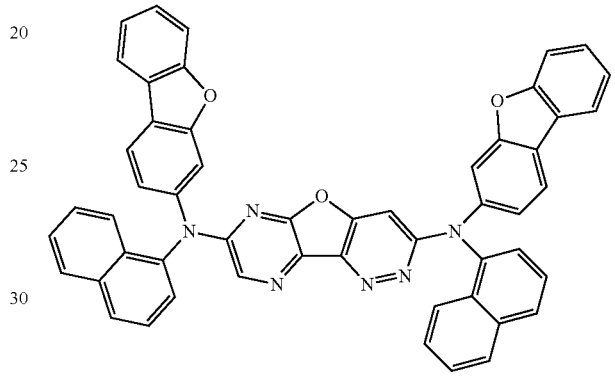
M382
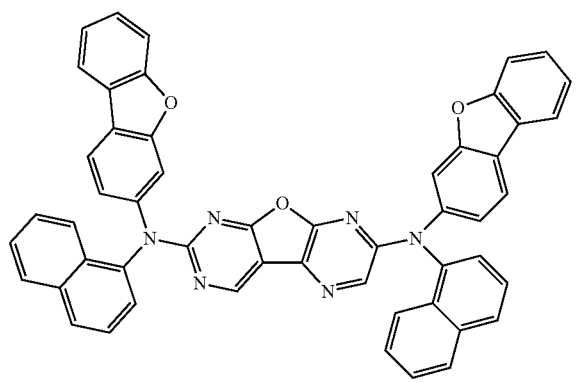
M386
M383
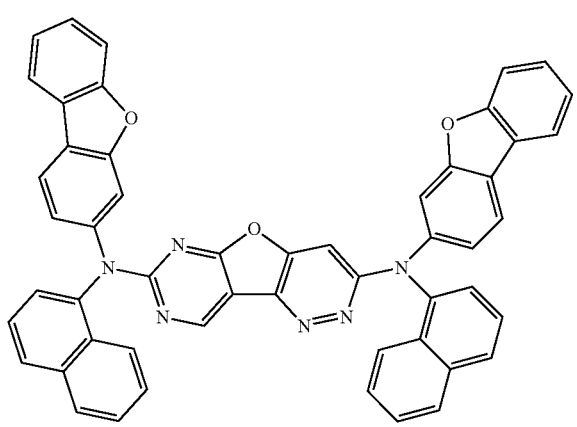
M387
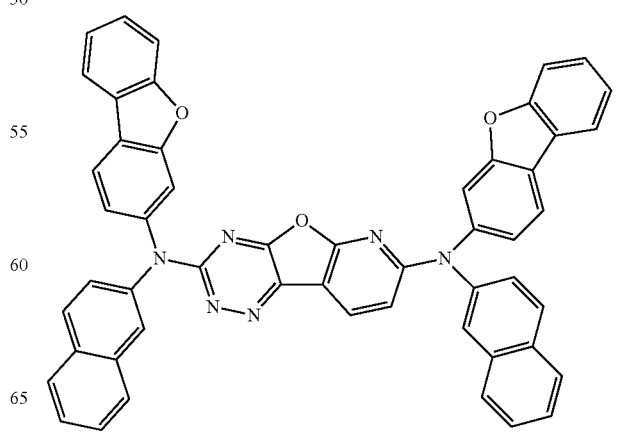

-continued
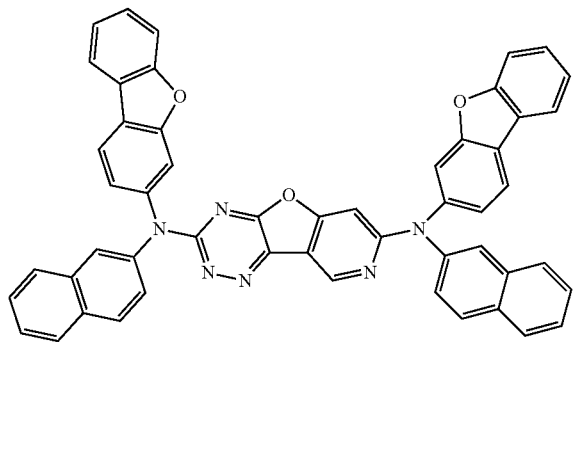
M388
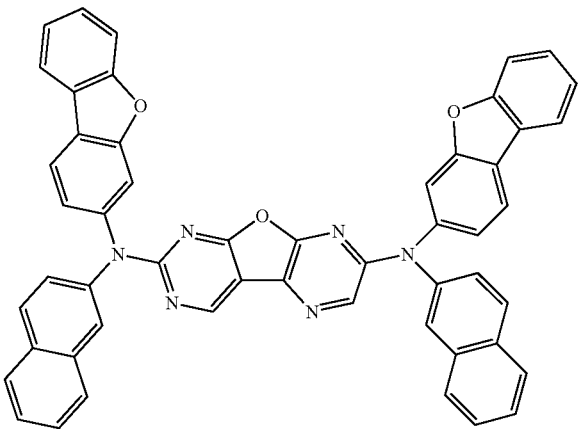
M391
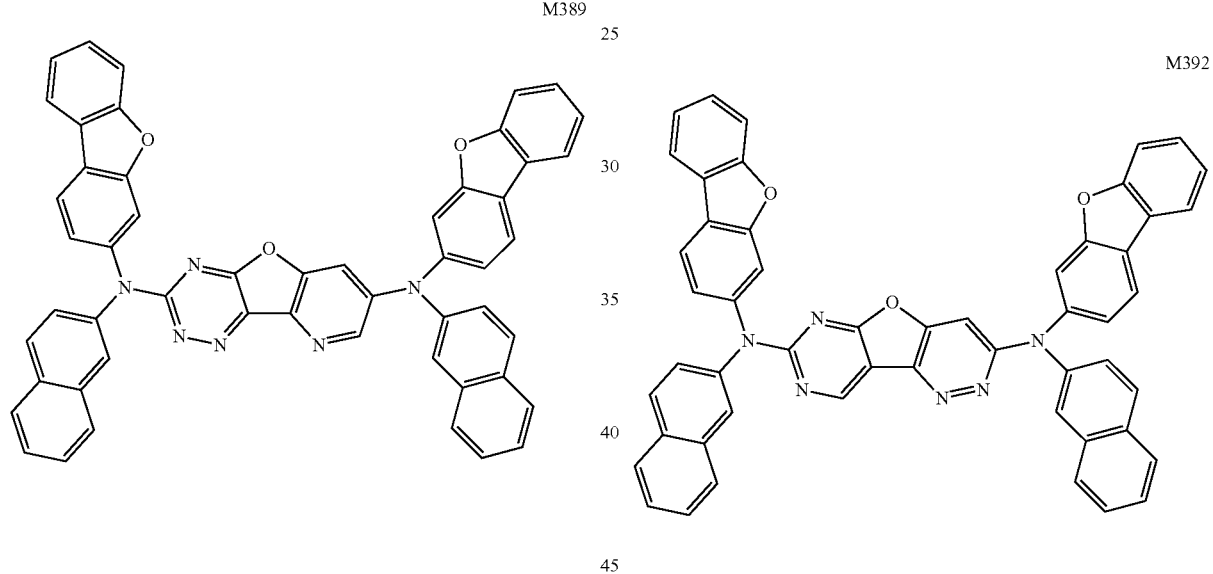
M389
M392
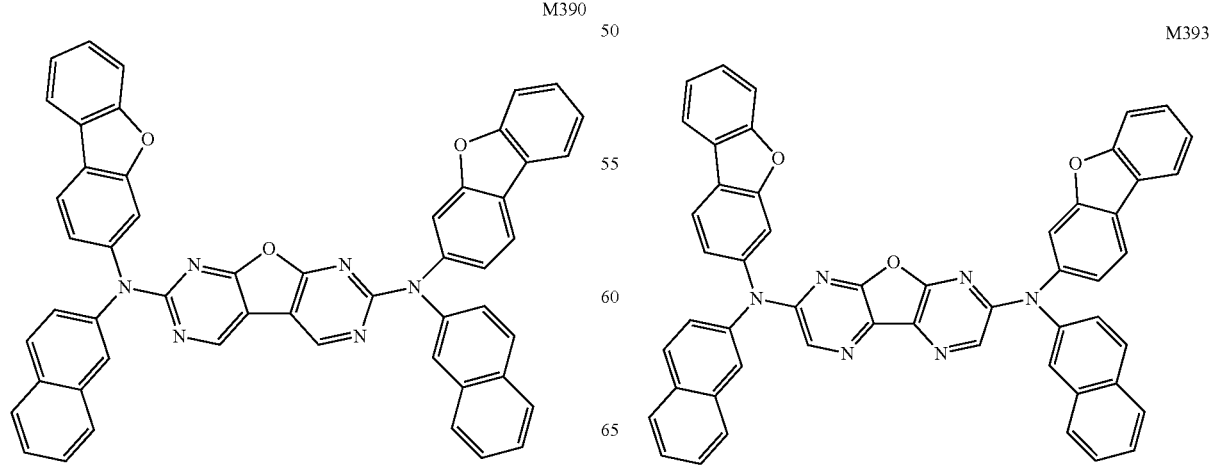
M390
M393

M394
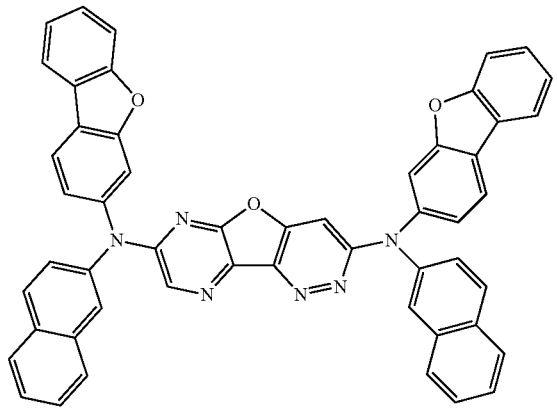
M397
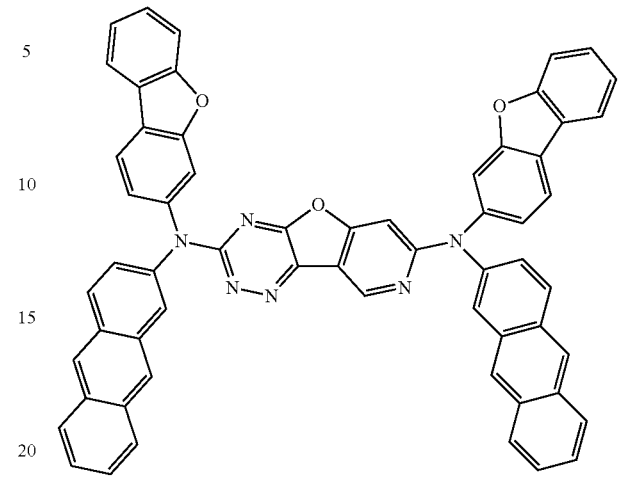
M395
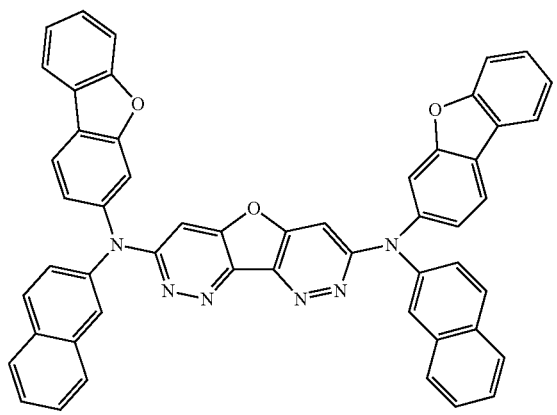
M398
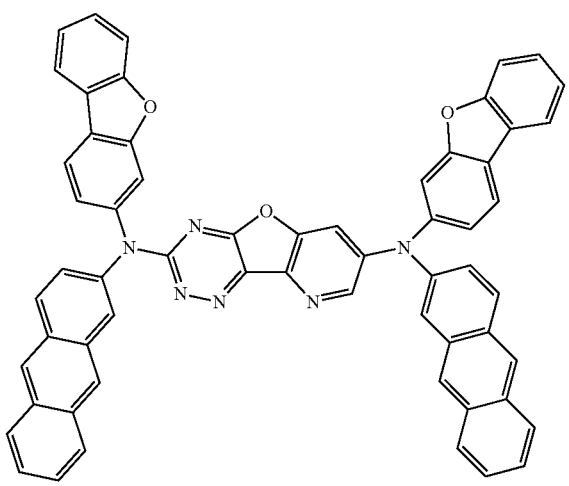
M396
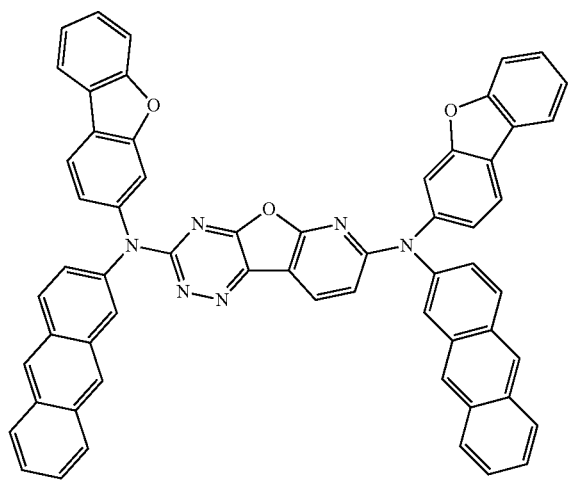
M399
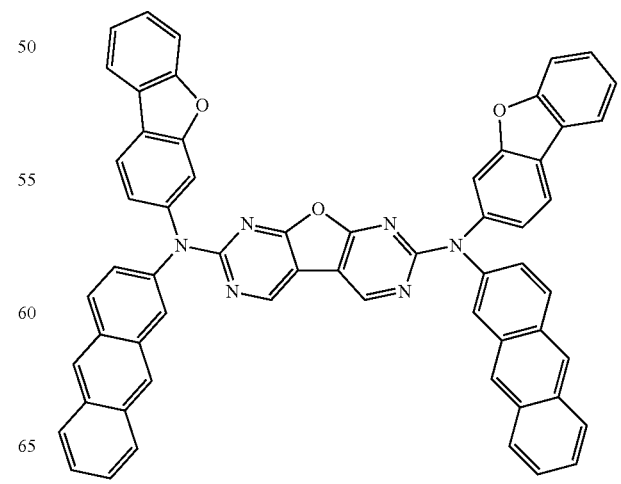

-continued
M400
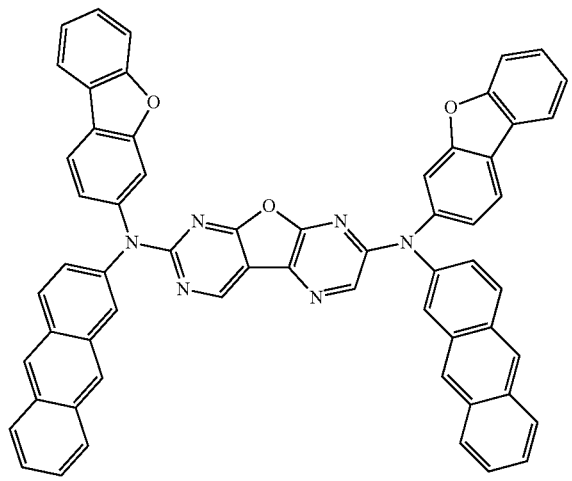
M401
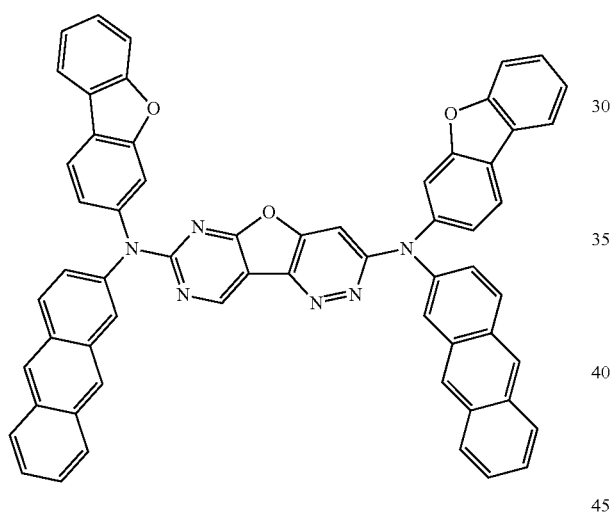
M402
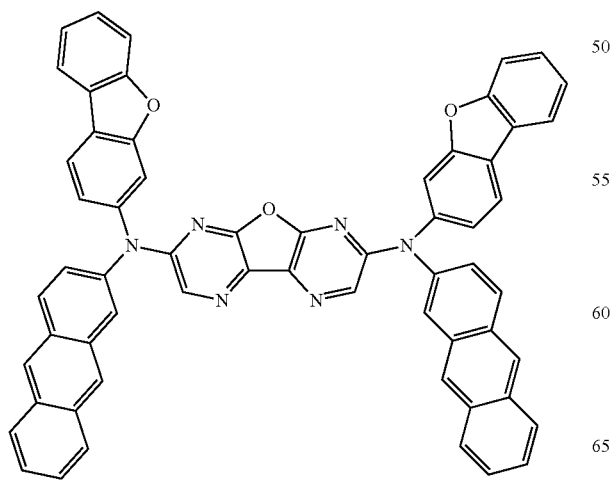
-continued
M403
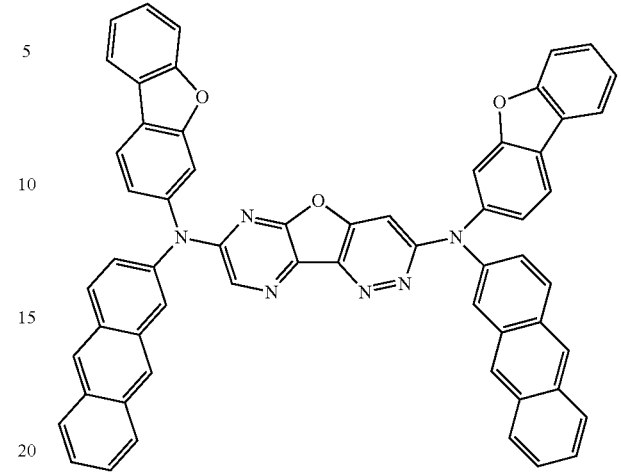
M404
M405

M406
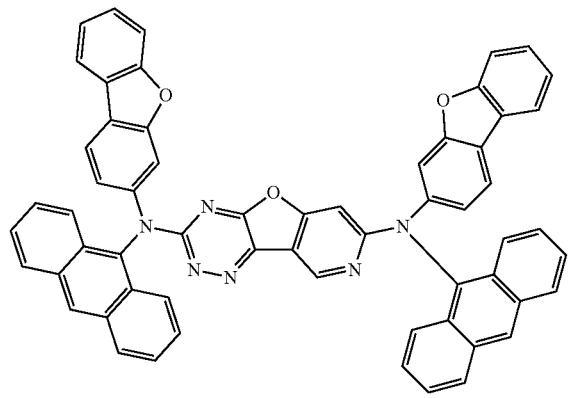
M409
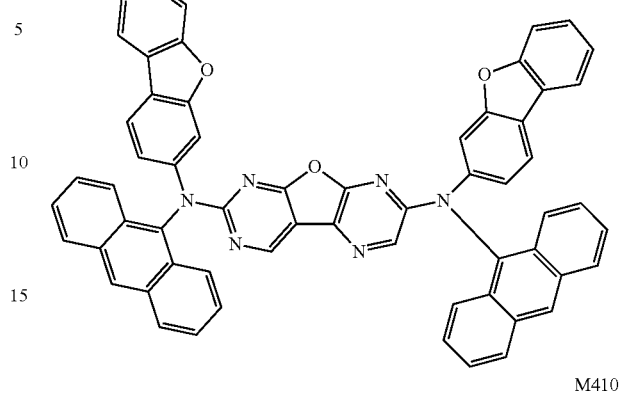
M407
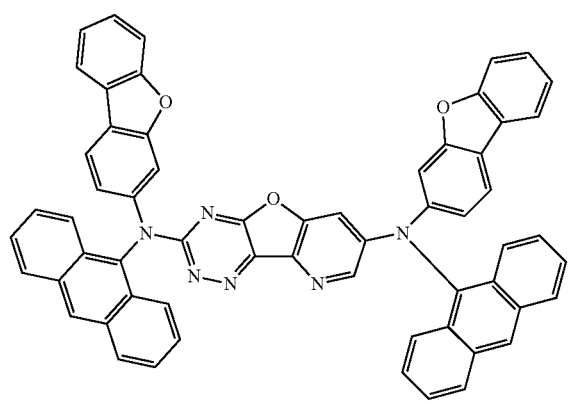
M410
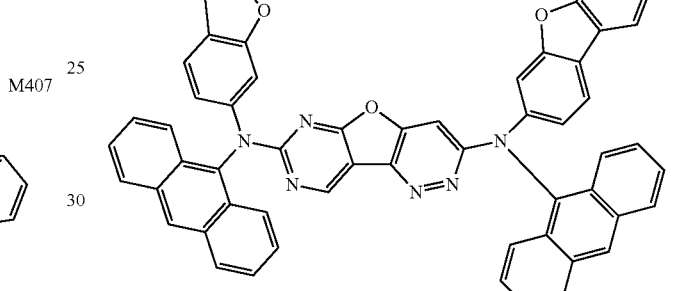
M411
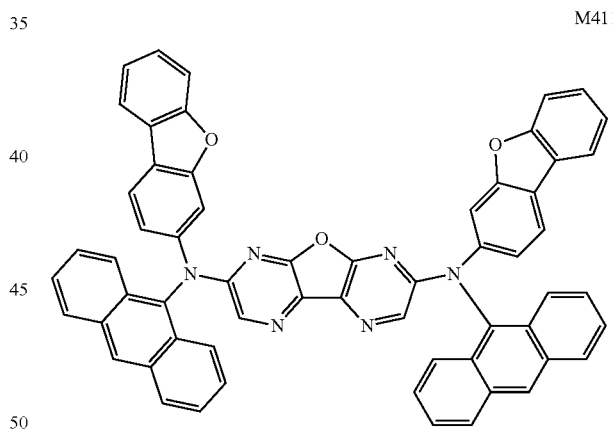
M408
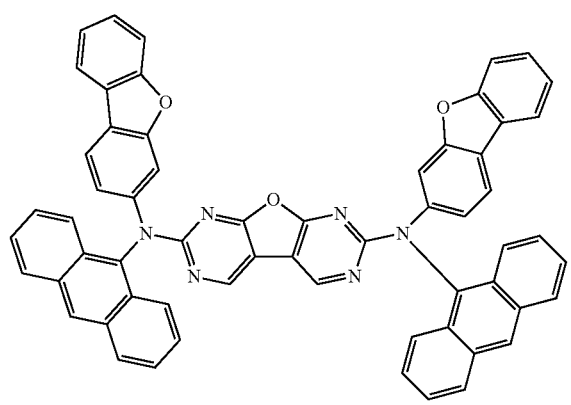
M412
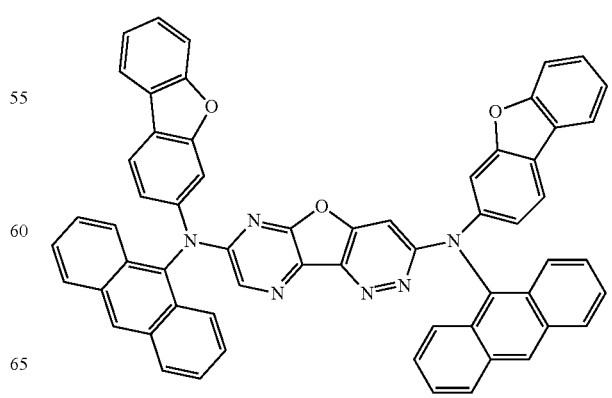

-continued
M413
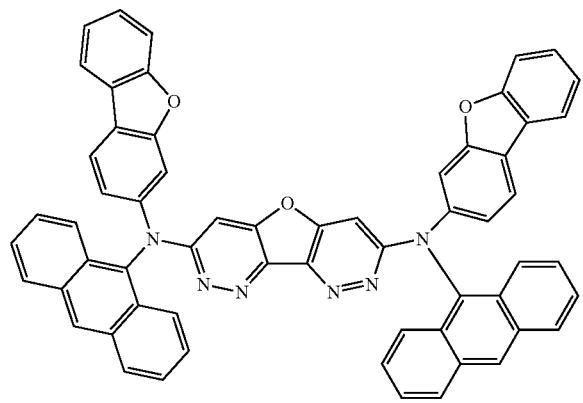
M417
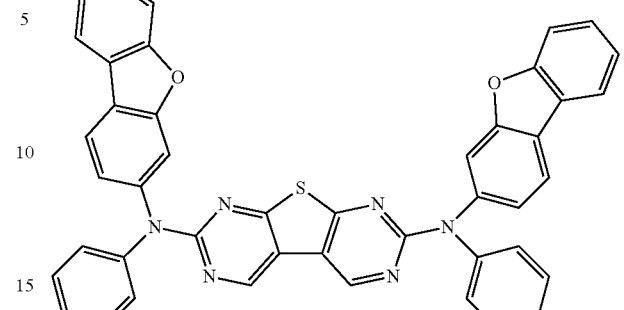
M414
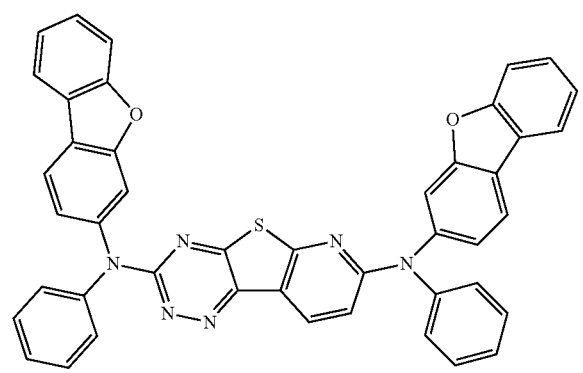
M418
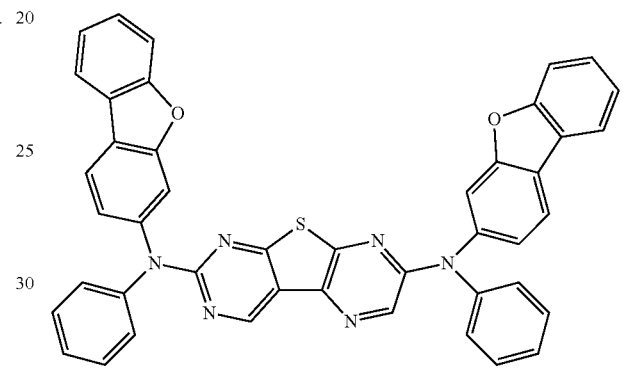
M415
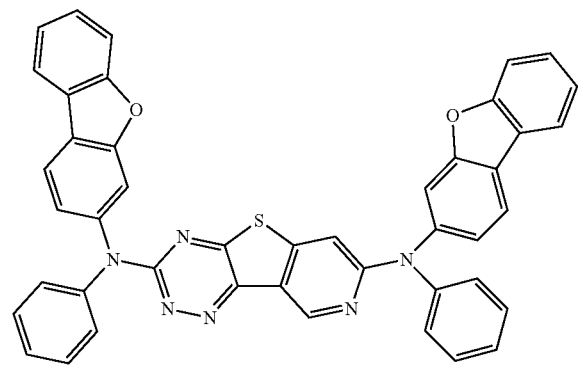
M419
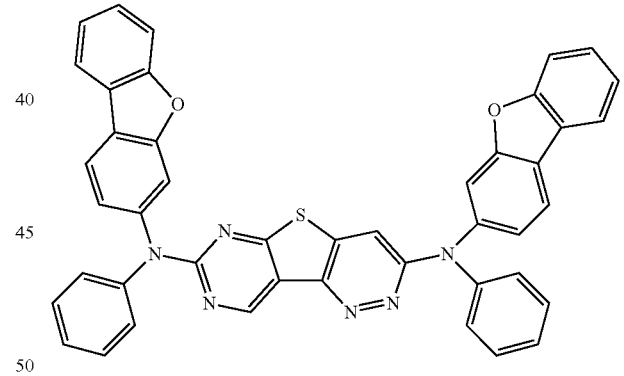
M416
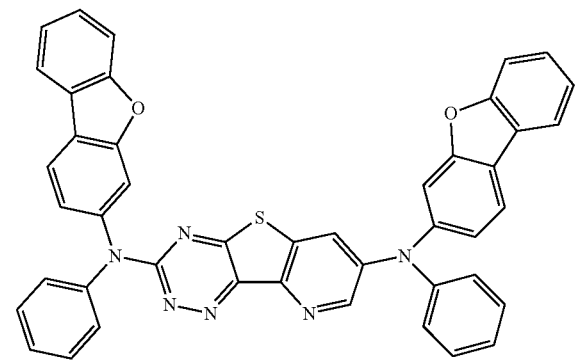
M420
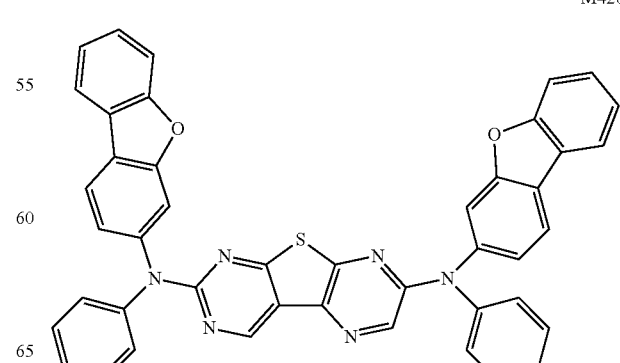

M421
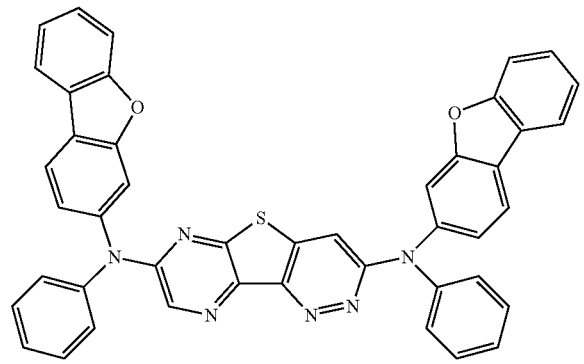
M422
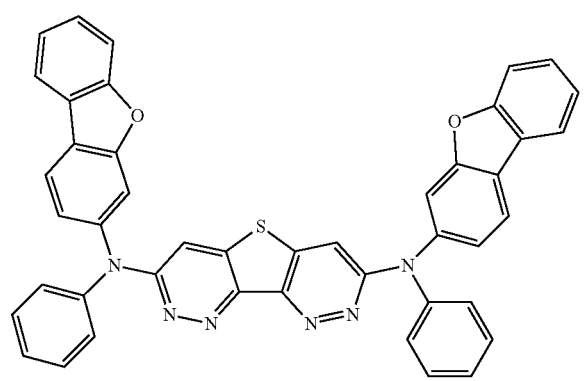
M423
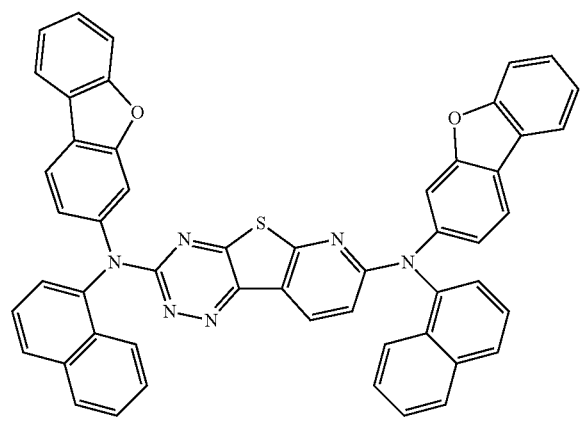
M424
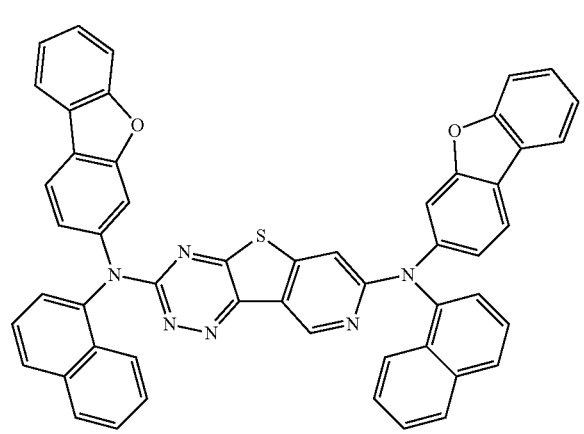
M425
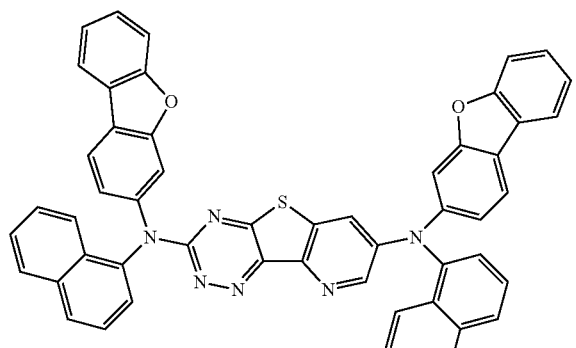
M426
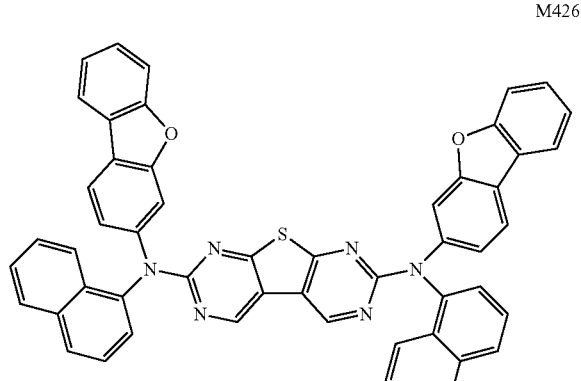
M427
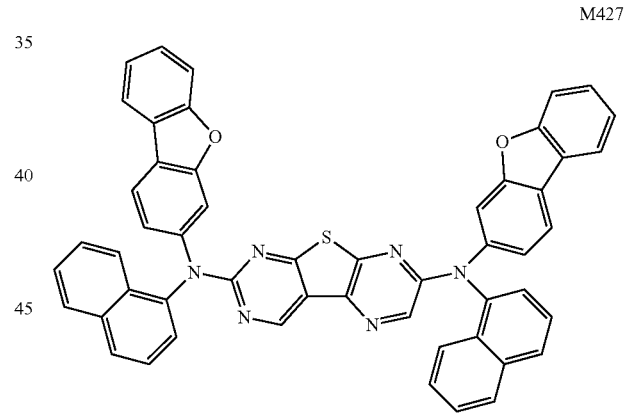
M428
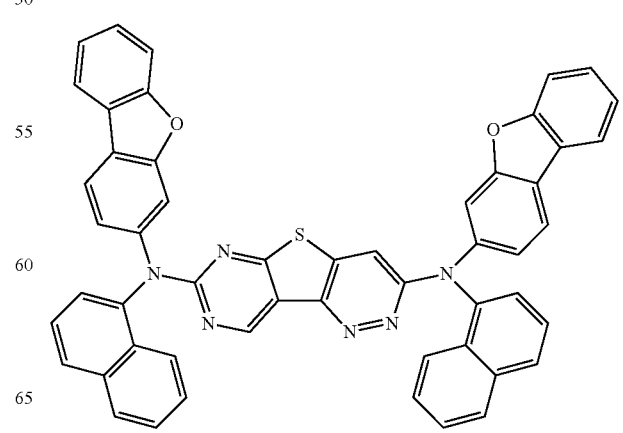

M429
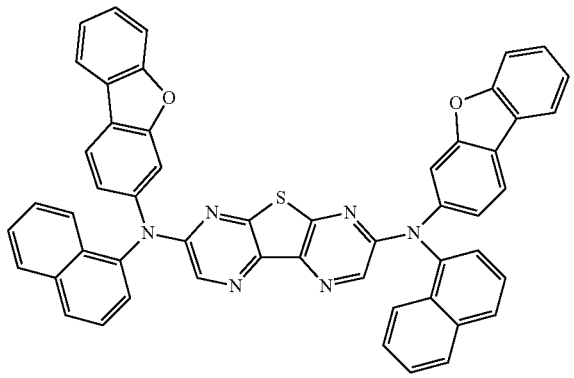
M430
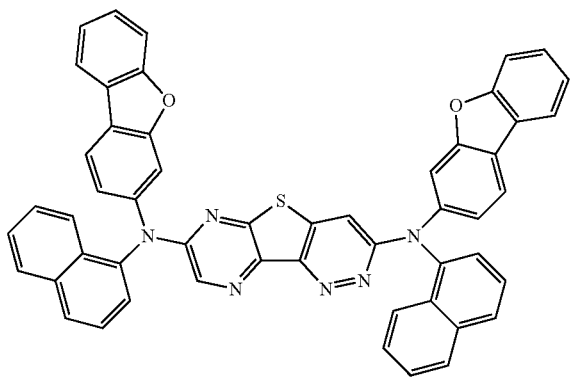
M431
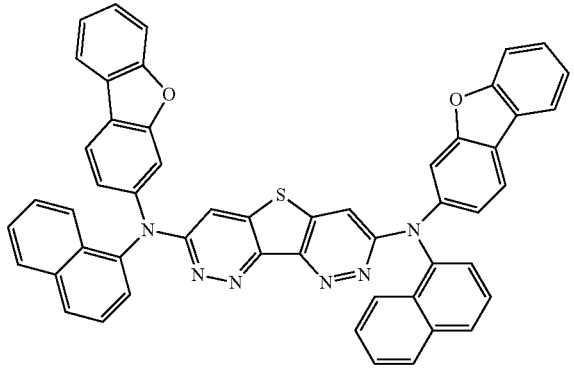
M432
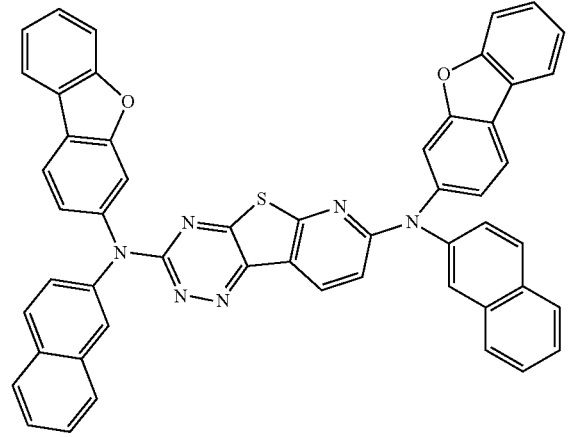
M433
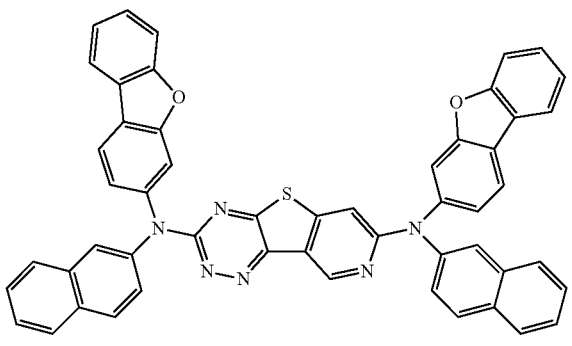
M434
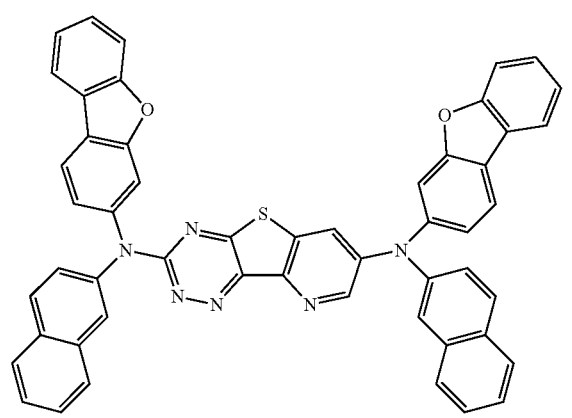
M435
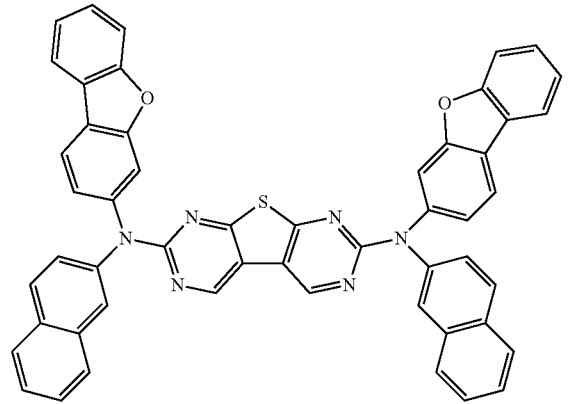
M436
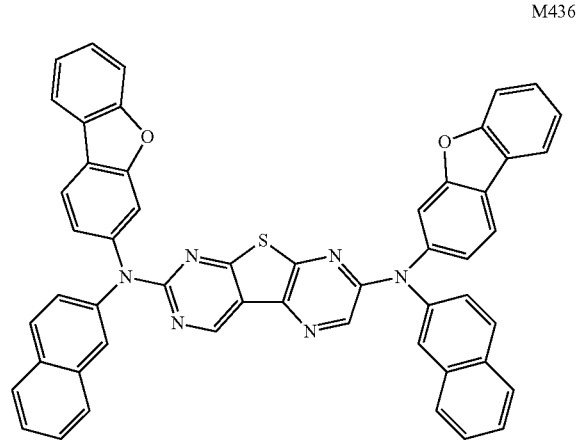

M437
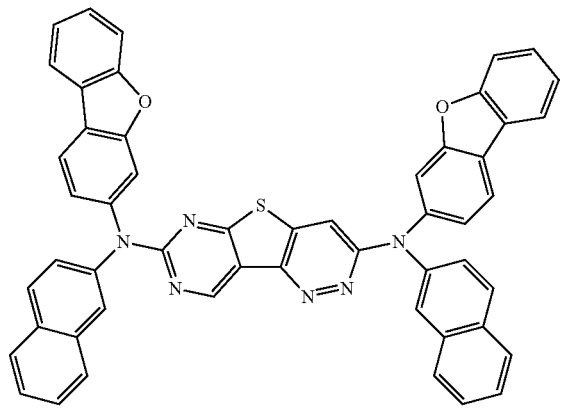
M440
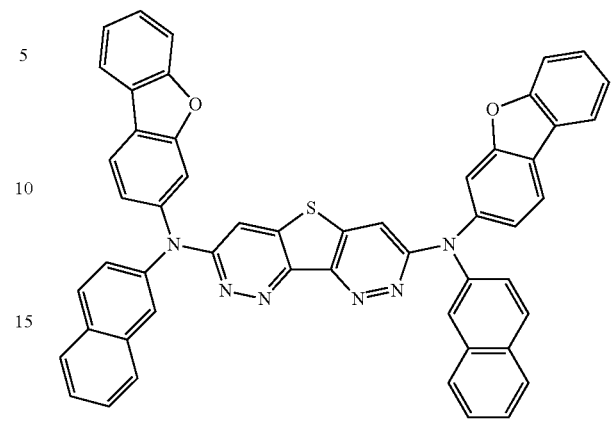
M438
M441
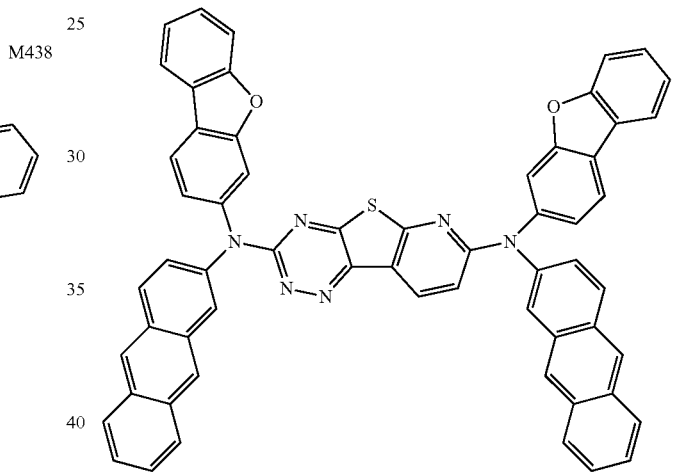
M439
M442
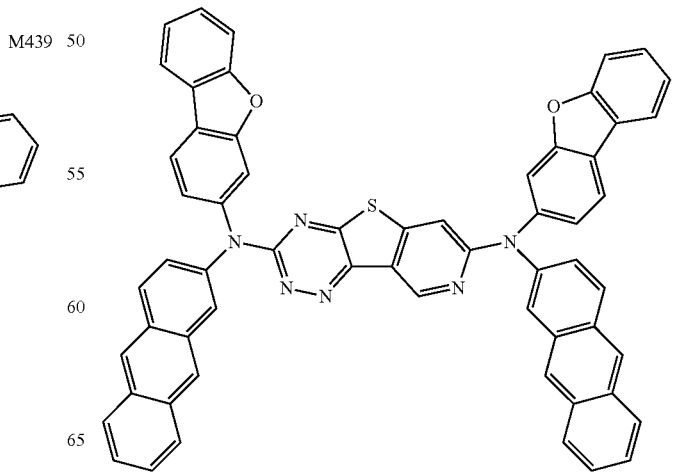

M443
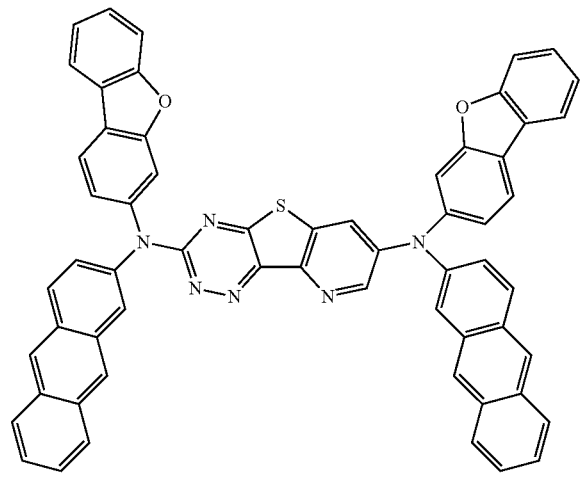
M446
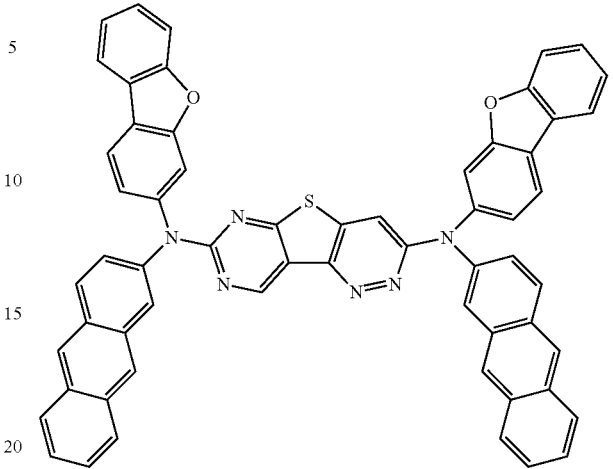
M444
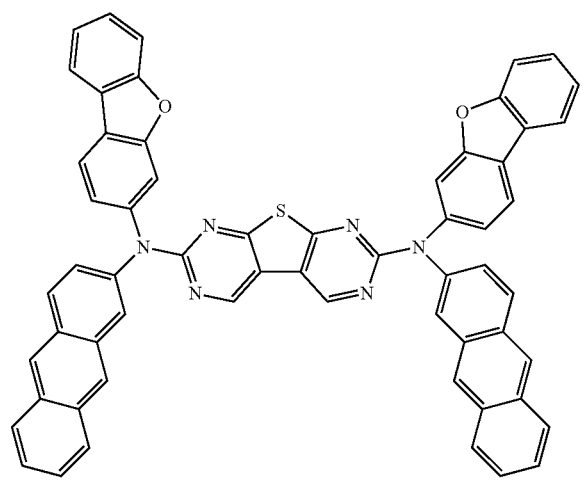
M447
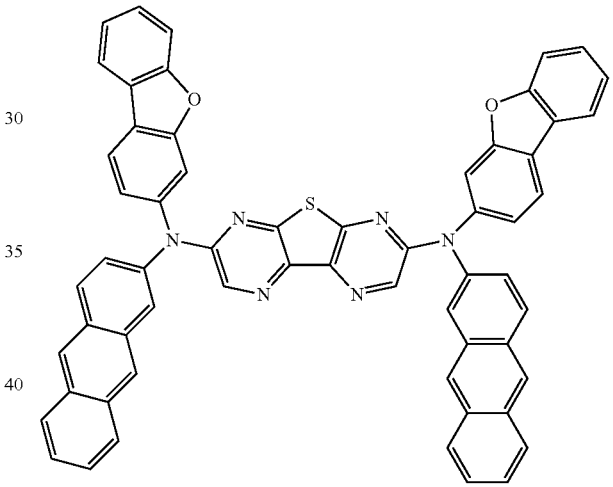
M445
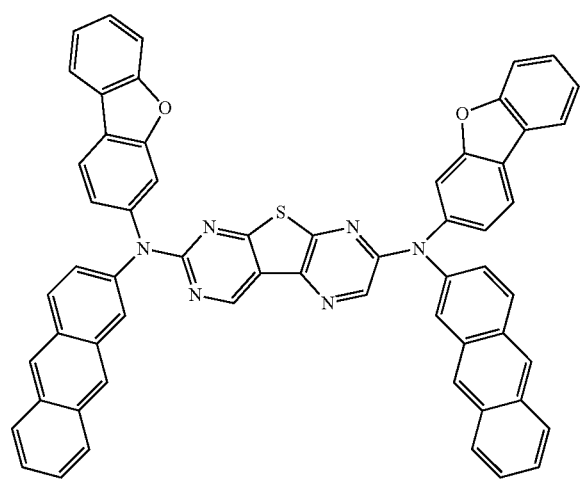
M448
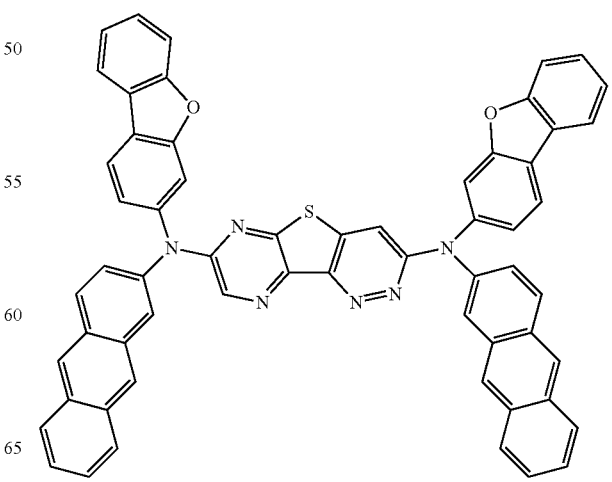

M449
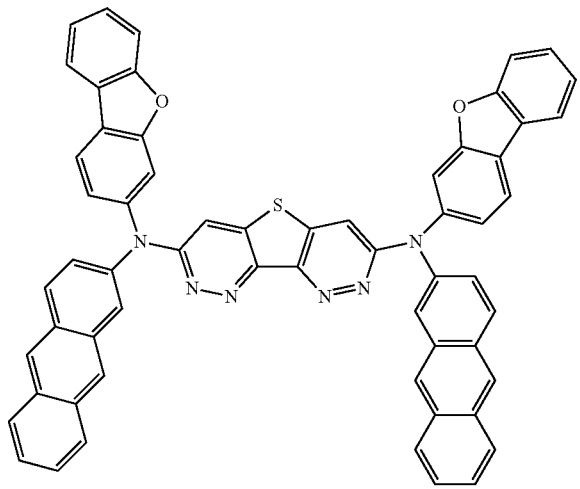
M450
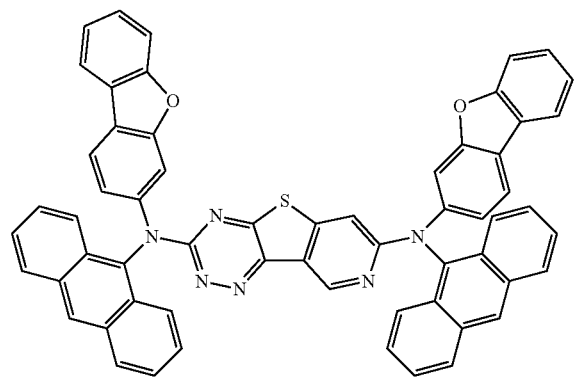
M451
M452
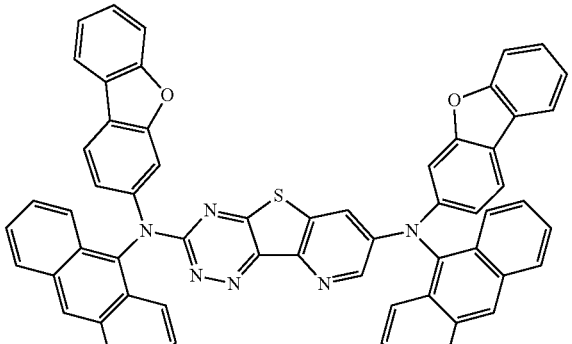
M453
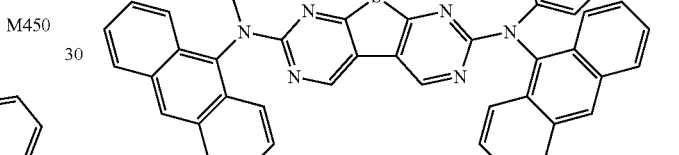
M454
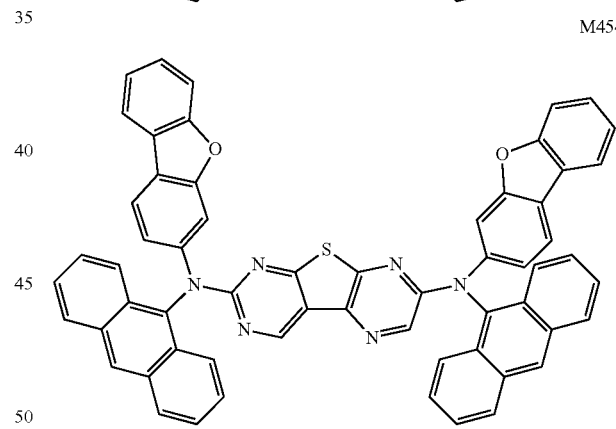
M455
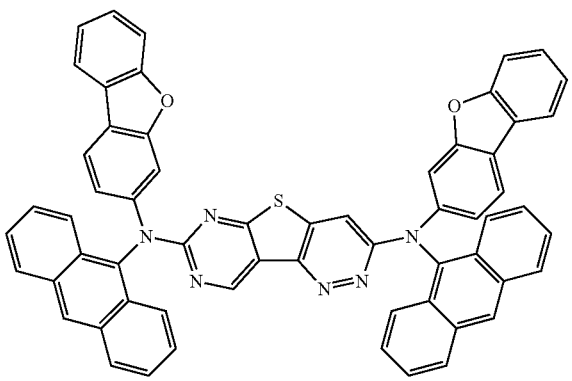

M456
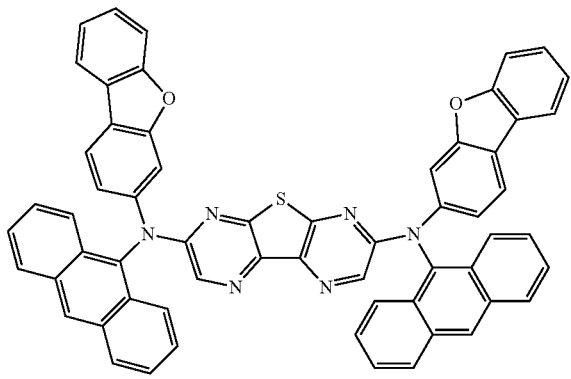
M457
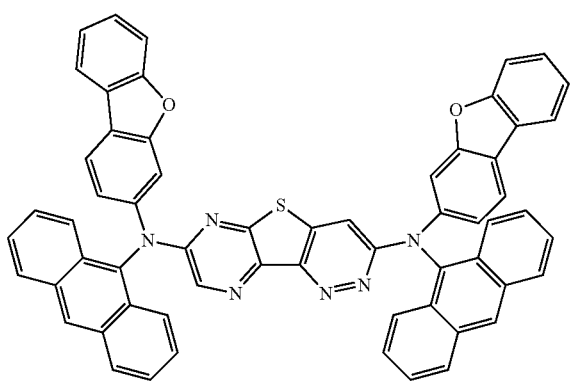
M458
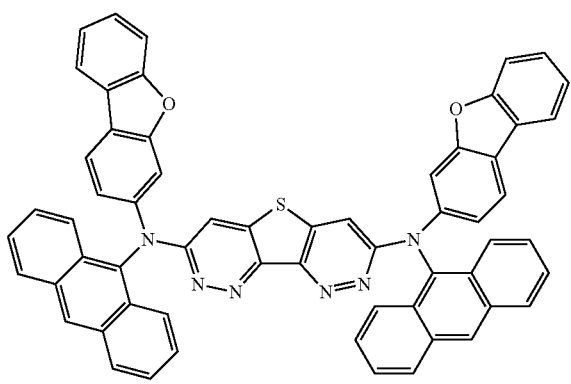
M459
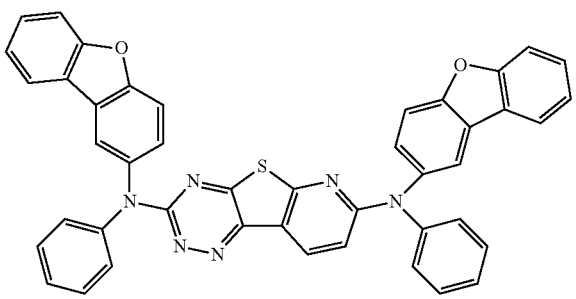
M460
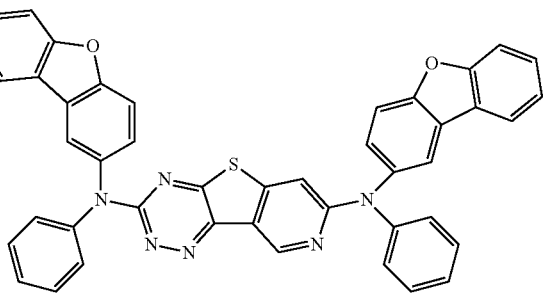
M461
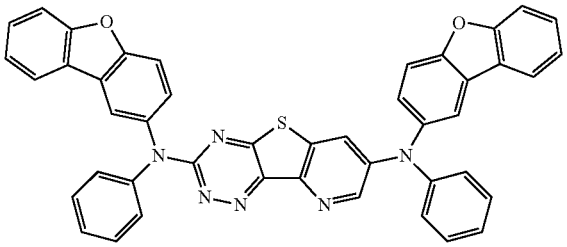
M462
M463
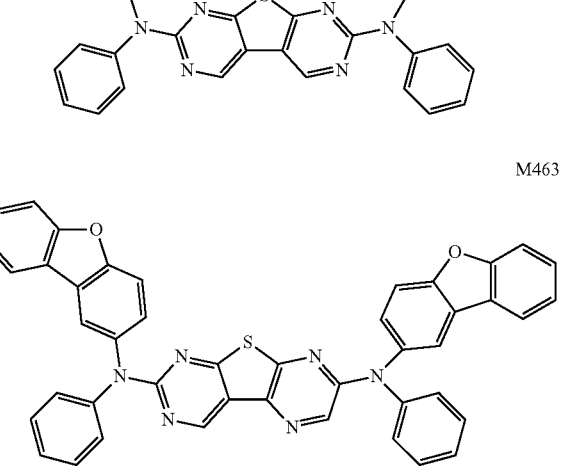
M464
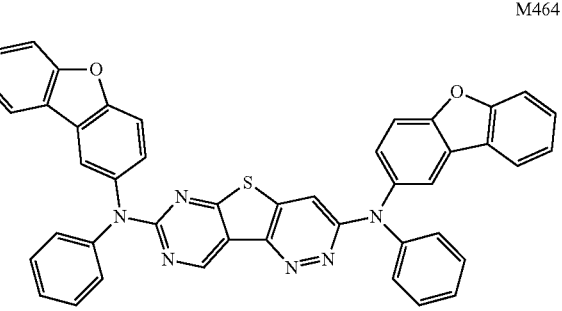

-continued
M465
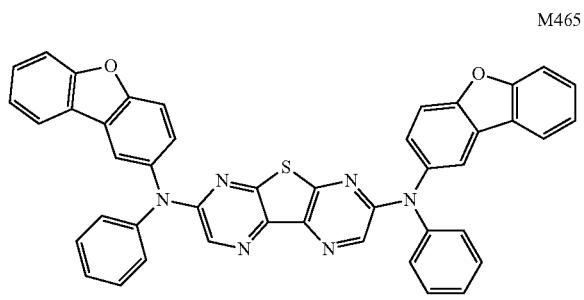
M466
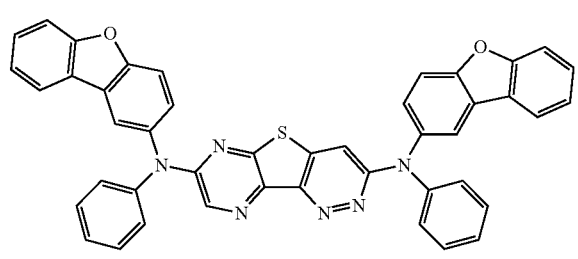
M467
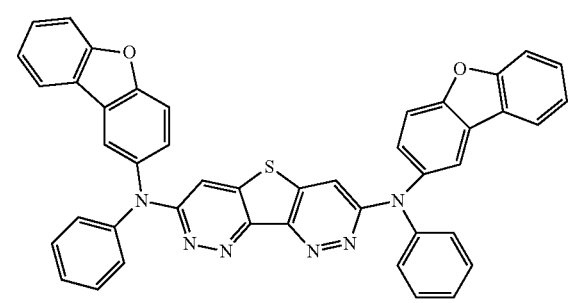
M468
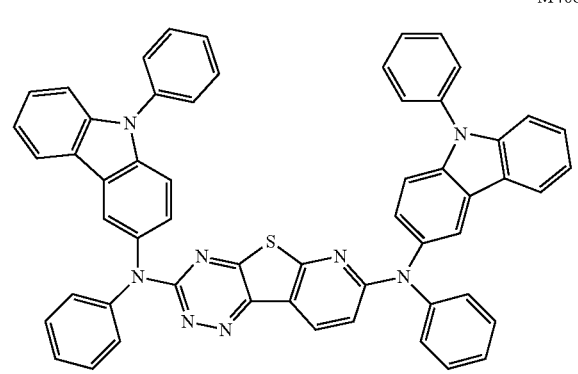
M469
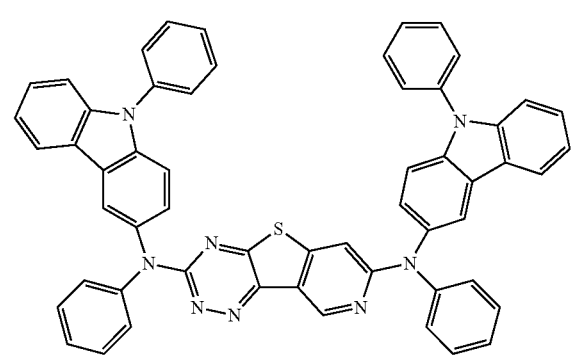
-continued
M470
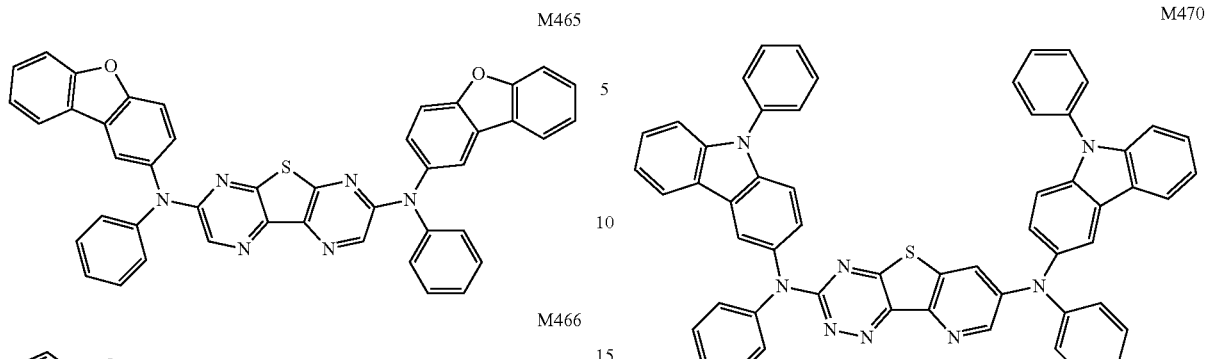
M471
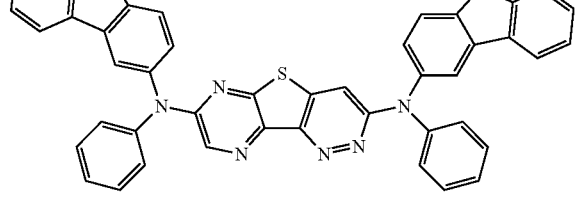
M472
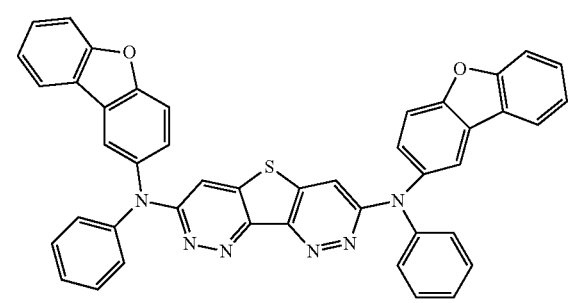
M473
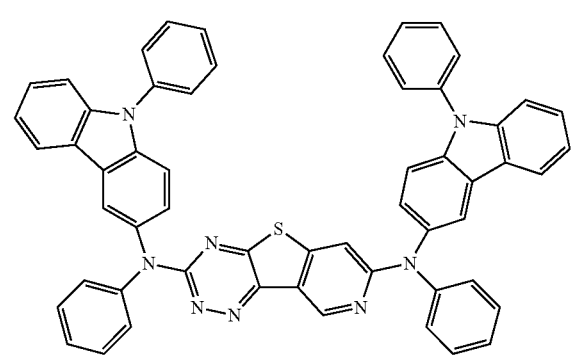

M474
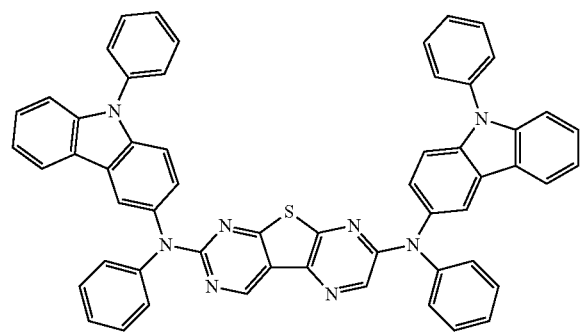
M475
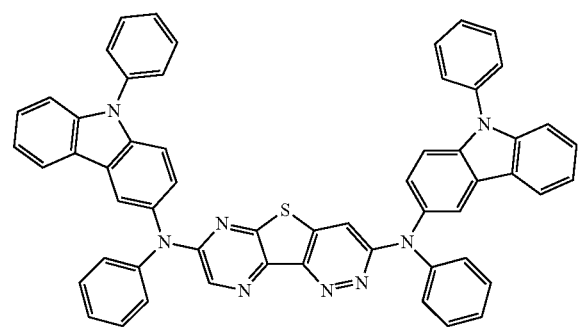
M476
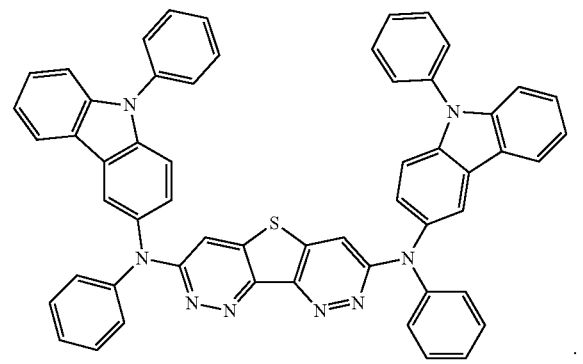
Optionally, the heterocyclic compound of the present disclosure may be any one of the following structures:
M477
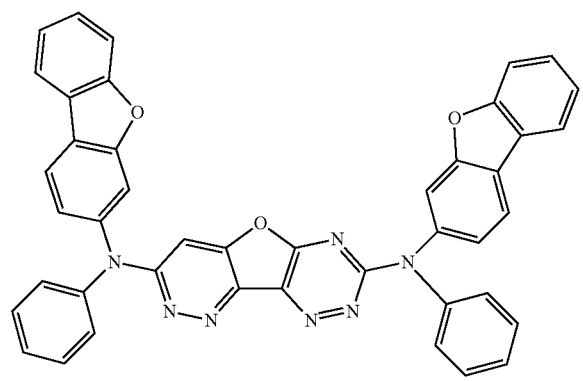
M478
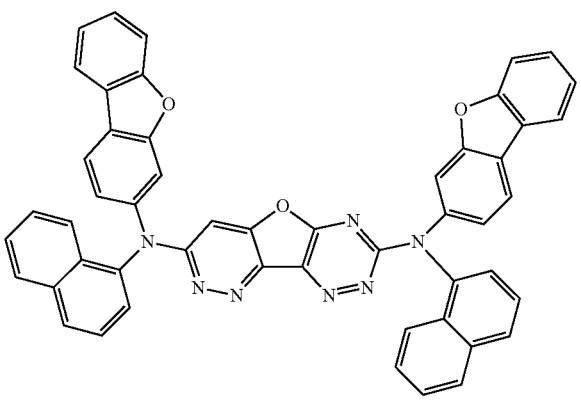
M479
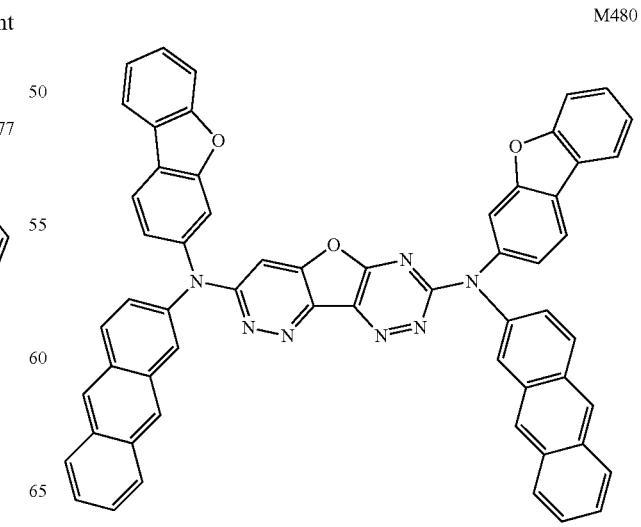
M480

M481
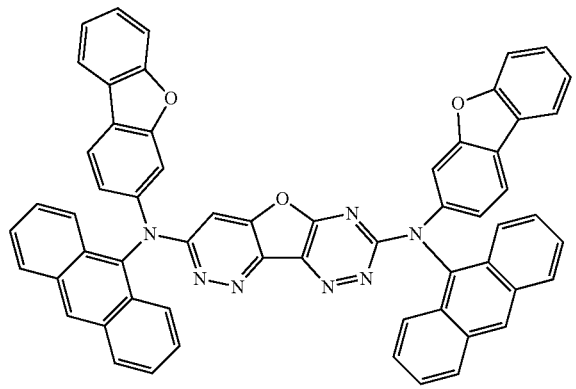
M482
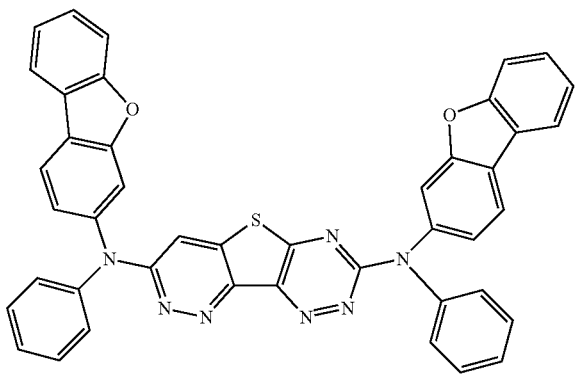
M483
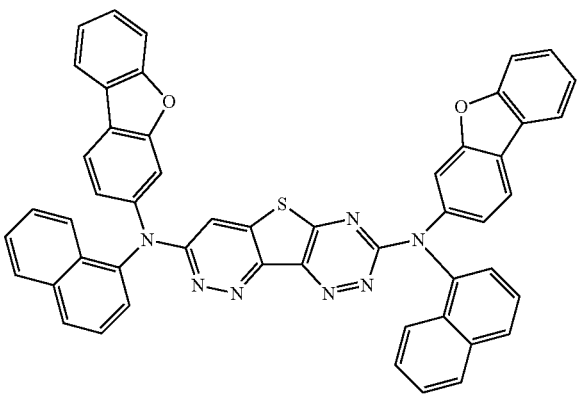
M484
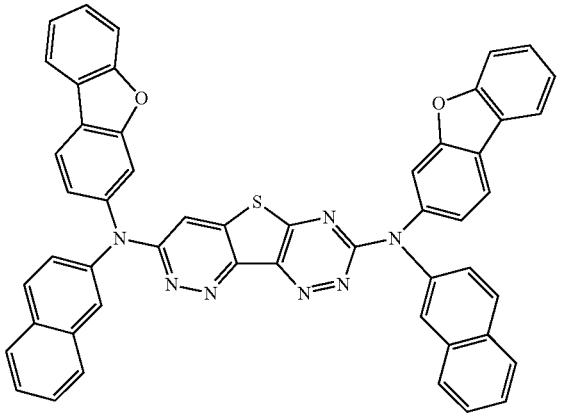
M485
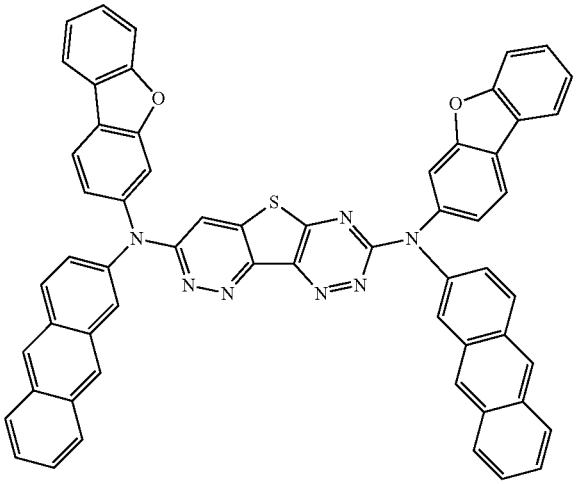
M486
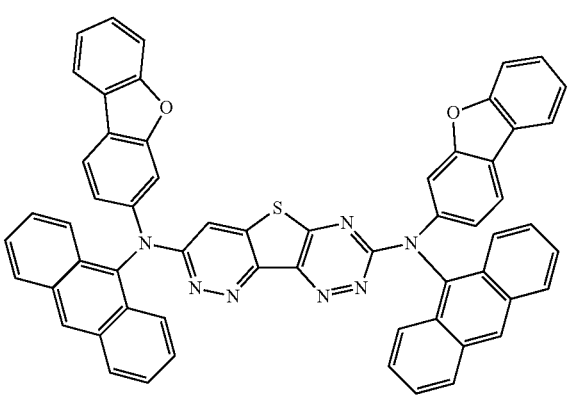

M487
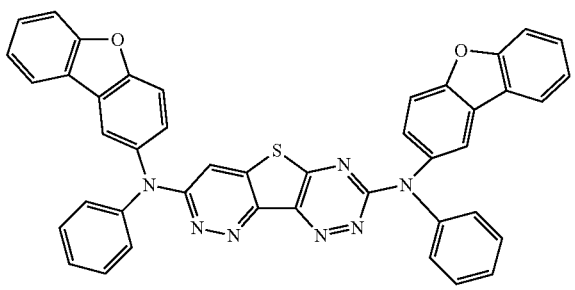
M488
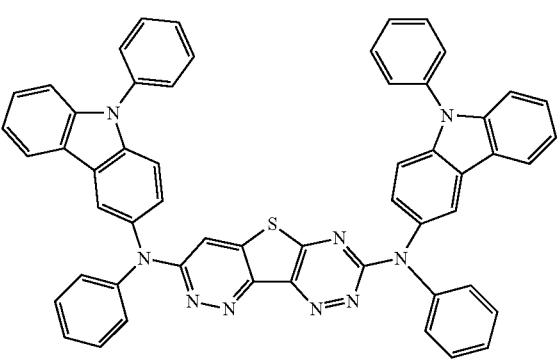
Optionally, the heterocyclic compound of the present disclosure may be any one of the following structures:
M489
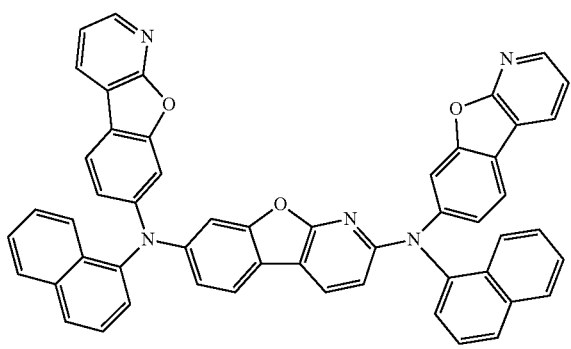
M490
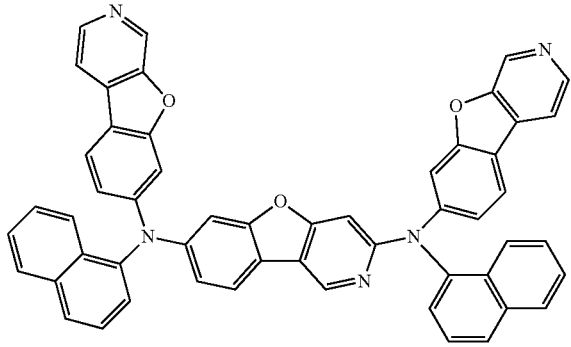
M491
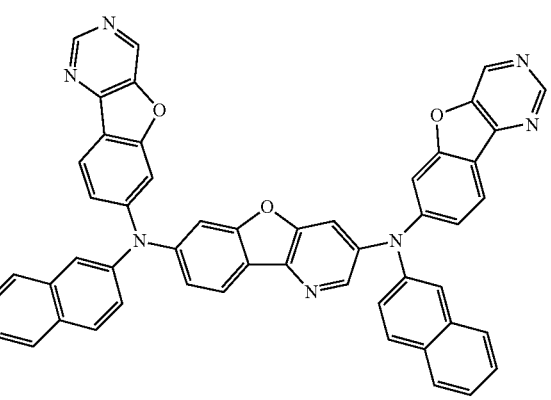
M492
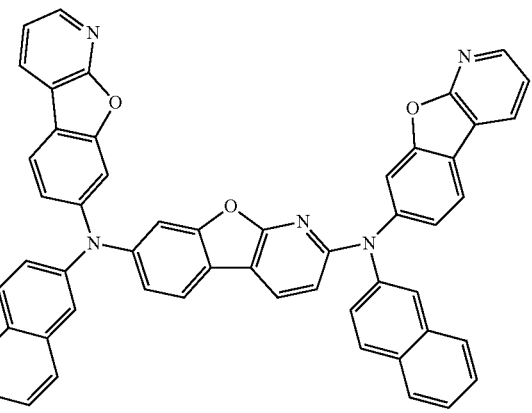
M493
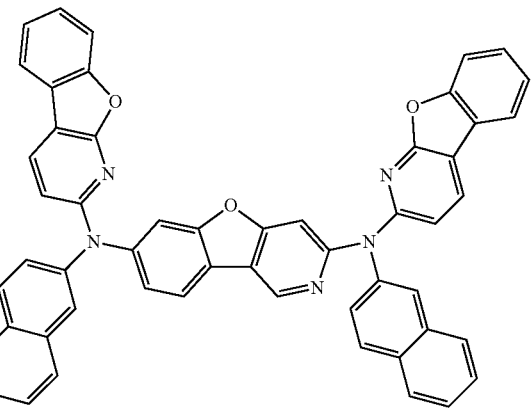

M494
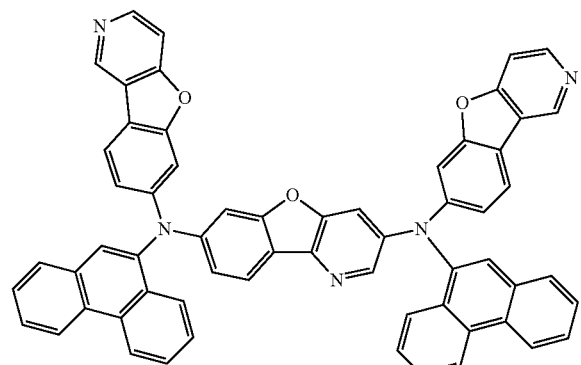
M495
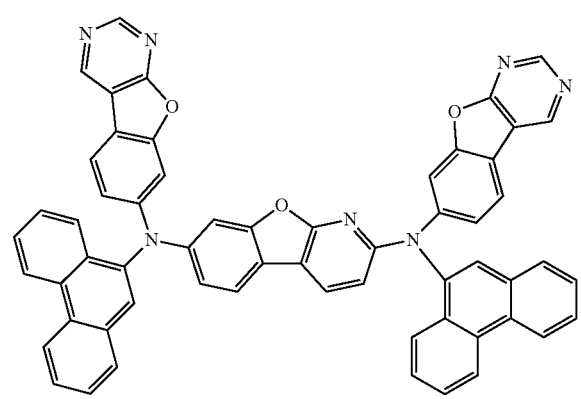
M496
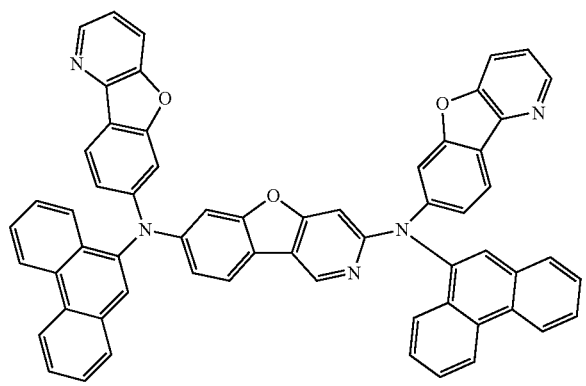
M497
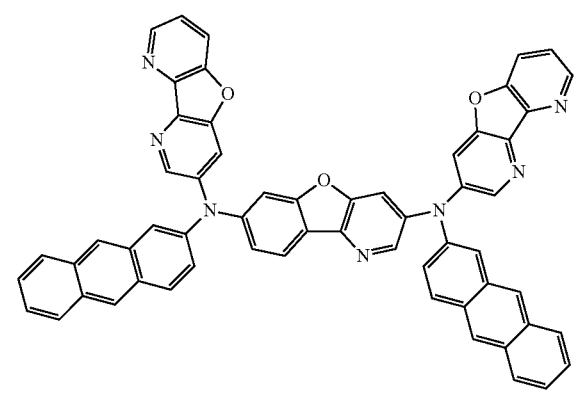
M498
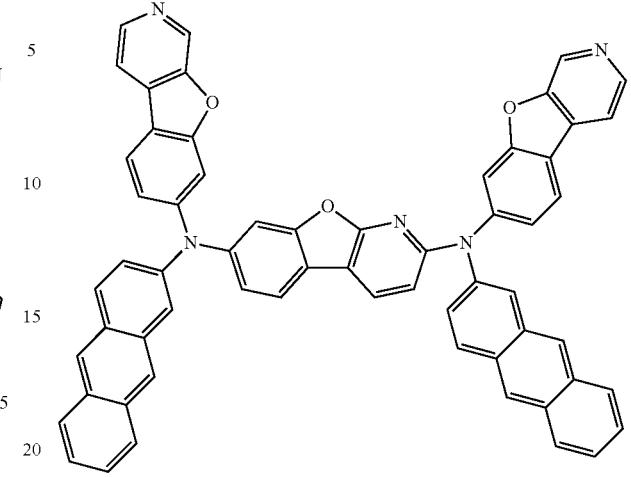
M499
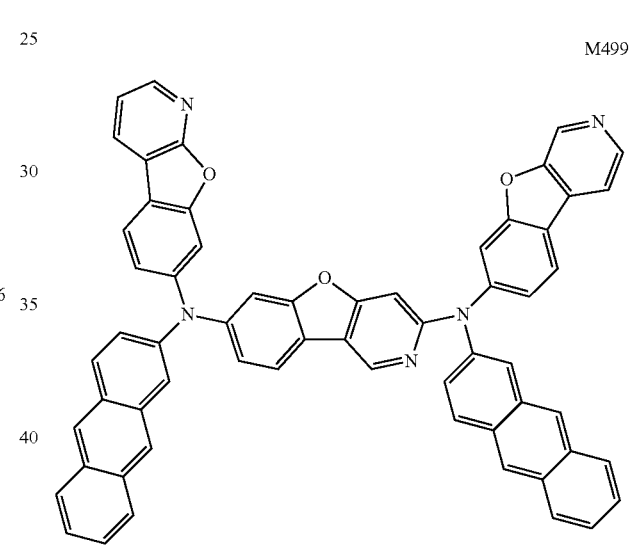
M500
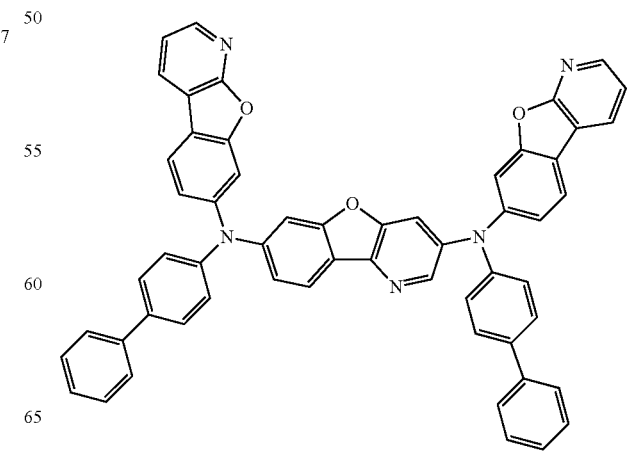

155
-continued

M501

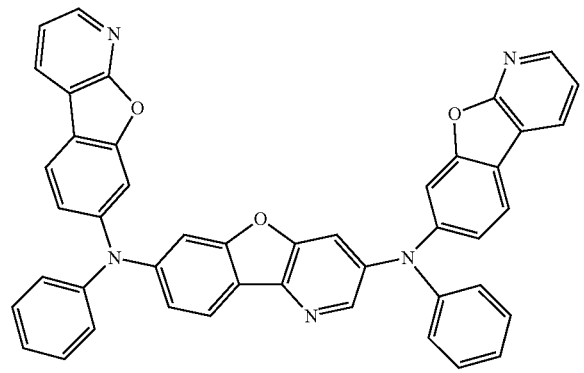

M502

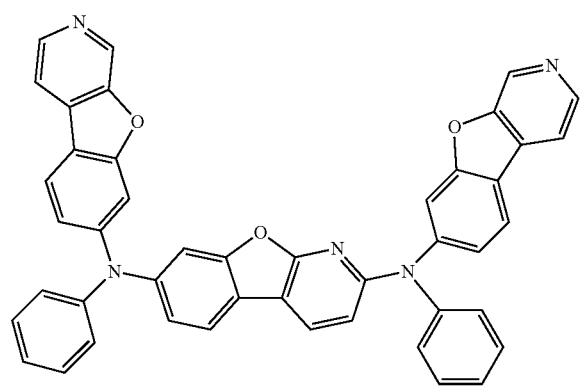

M503

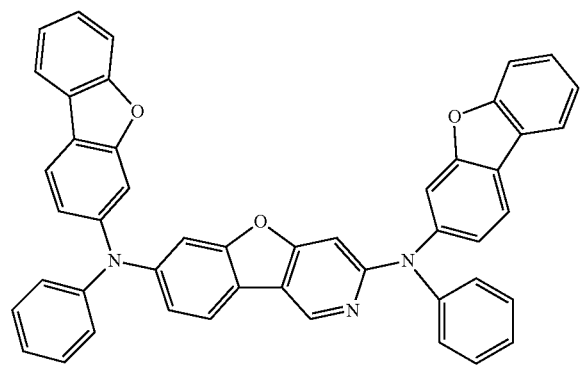

156
-continued

M504

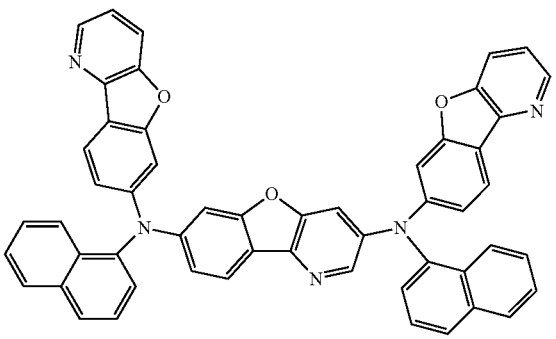

The present disclosure provides a preparation method of the above-mentioned heterocyclic compound containing heteroatom substituted fluorene, where the structures represented by formula A and formula B are subjected to a condensation reaction.

formula A

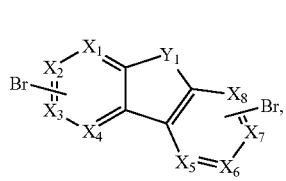

formula B

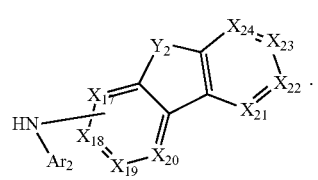

At this point, the molar ratio of the compound of formula A and the compound of formula B is controlled to be about 1:2 to prepare a compound of formula A with the same left and right substituent groups, that is, the structure represented by formula I-a:

formula I-a

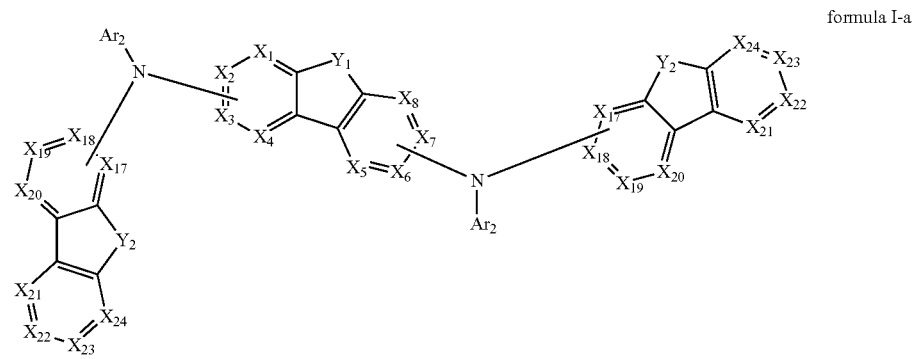

When preparing the compound of formula A with different left and right substituent groups, that is, the compound represented by formula I, the compound represented by formula A may react with the compounds represented by formula B and formula C sequentially. Optionally, the addition amount of the compound represented by formula B and the compound represented by formula C may be controlled to be about 1 equivalent.

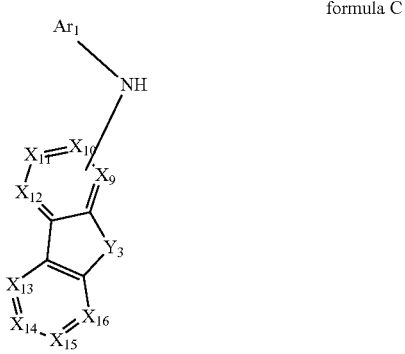

formula C

In the present disclosure, the addition order of formula B and formula C may not be limited according to various embodiments of the present disclosure.

Optionally, in the present disclosure, an acid binding agent may be added to the reaction system during the condensation reaction.

Optionally, in the present disclosure, the acid binding agent is NaH.

The heterocyclic compound containing heteroatom substituted fluorene provided by the present disclosure may be used in a CPL layer, a hole transport layer, an electron transport layer or an optical auxiliary layer of an organic optoelectronic device.

The present disclosure provides a display panel including an organic light-emitting device. The organic light-emitting device includes an anode, a cathode, and an organic thin film layer located between the anode and the cathode. The cathode is covered with a CPL layer, and the CPL layer contains at least one of the above-mentioned heterocyclic compounds.

The present disclosure provides a display panel including an organic light-emitting device. The organic light-emitting device includes an anode, a cathode, and an organic thin film layer located between the anode and the cathode. The organic thin film layer includes a hole transport layer; and the hole transport layer contains at least one of the above-mentioned heterocyclic compounds.

The present disclosure provides a display panel including an organic light-emitting device. The organic light-emitting device includes an anode, a cathode, and an organic thin film layer located between the anode and the cathode. The organic thin film layer includes an electron transport layer; and the electron transport layer contains at least one of the above-mentioned heterocyclic compounds.

The organic light-emitting device provided by the present disclosure may be an organic light-emitting device known to those skilled in the art. In the present disclosure, optionally, the organic light-emitting device may include a substrate, an ITO anode, a first hole transport layer, a second hole transport layer, an electron blocking layer, a light-emitting layer, a first electron transport layer, a second electron transport layer, a cathode (magnesium silver electrode, the mass ratio of magnesium to silver is about 1:9) and a capping layer (CPL).

Optionally, in the present disclosure, the anode material of the organic light-emitting device may be selected from metals including copper, gold, silver, iron, chromium, nickel, manganese, palladium, platinum, alloys thereof, metal oxides such as indium oxide, zinc oxide, indium tin oxide (ITO), indium zinc oxide (IZO) and the like, conductive polymers such as polyaniline, polypyrrole, poly(3-methylthiophene) and the like, and/or any other suitable material(s). In addition to the above-mentioned hole injection materials and combinations thereof, the anode material may also include known suitable anode materials.

Optionally, in the present disclosure, the cathode material of the organic light-emitting device may be selected from metals including aluminum, magnesium, silver, indium, tin, titanium and the like, and alloys thereof including multilayer metal materials-LiF/Al, LiO2/Al, BaF2/Al, and the like. In addition to the above-mentioned hole injection materials and combinations thereof, the cathode material may also include known suitable cathode materials.

Optionally, in the present disclosure, an organic photoelectric device, such as an organic thin film layer in the organic light-emitting device, may have at least one light-emitting layer (EML), and also contain other functional layers, including one or more of a hole injection layer (HIL), a hole transport layer (HTL), an electron blocking layer (EBL), a hole blocking layer (HBL), an electron transport layer (ETL), an electron injection layer (EIL) and an optical auxiliary layer.

Optionally, in the present disclosure, the organic light-emitting device may be prepared according to the following method:

forming an anode on a transparent or opaque smooth substrate, forming an organic thin layer on the anode, and forming a cathode on the organic thin layer.

Optionally, in the present disclosure, available film forming methods such as evaporation, sputtering, spin coating, dipping, and ion plating may be used to form the organic thin layer.

The present disclosure also provides a display device including the above-mentioned display panel.

In the present disclosure, the organic light-emitting device (OLED device) may be used in a display device, where the organic light-emitting display device may be one of a mobile phone display, a computer display, a TV display, a smart watch display, a smart car display panel, a VR or AR helmet display, displays of various smart devices, and the like.

In order to clearly illustrate the technical solutions in the embodiments of the present disclosure, the accompanying drawings, which are required to be used in the description of disclosed embodiments, are briefly described hereinafter. Obviously, the accompanying drawings in the following description are merely certain embodiments of the present disclosure. Other accompanying drawings derived from such accompanying drawings may be acquired by those skilled in the art without creative work.

Exemplary Embodiment One

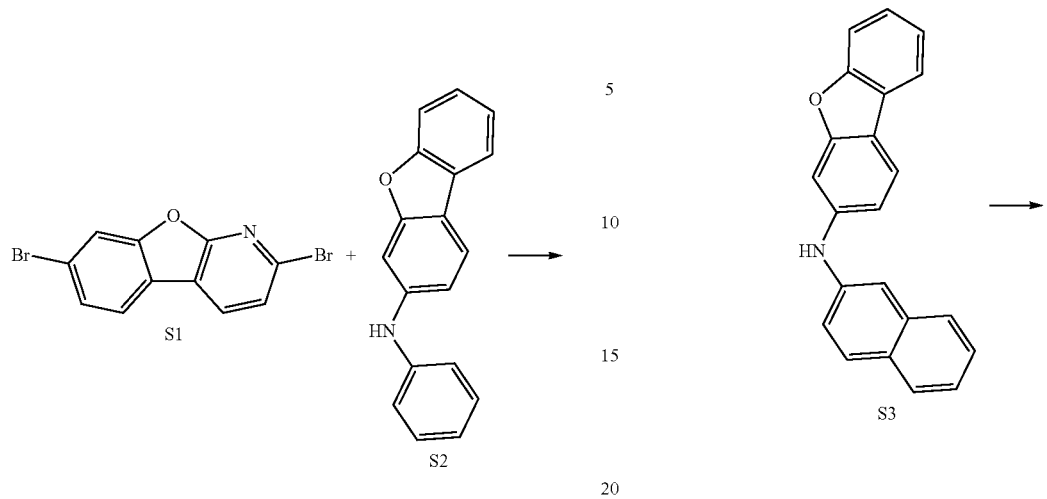

S2 (7 mmol), S1 (3.5 mmol), NaH (17.5 mmol) and dimethylformamide (100 mL) are mixed in a 250 ml round bottom flask. Next, the mixture is stirred at room temperature for 12 hours under a nitrogen stream. Then, a reduced-pressure distillation is performed on the mixture to remove organic solvents, and column chromatography is performed to separate the mixture and obtain a solid M002 (2.45 mmol and yield 76%).

MALDI-TOF MS: $C_{47}H_{29}N_3O_3$, m/z calculated value: 683.2; and measured value: 683.5.

Elemental analysis calculated values: C, 82.56; H, 4.28; N, 6.15; O, 7.02; and test values: C, 82.60; H, 4.30; N, 6.12; O, 6.99.

Exemplary Embodiment Two

Referring to exemplary embodiment one, a compound M008 is synthesized.

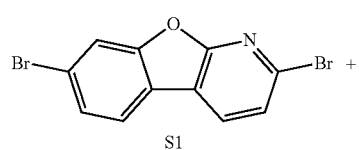

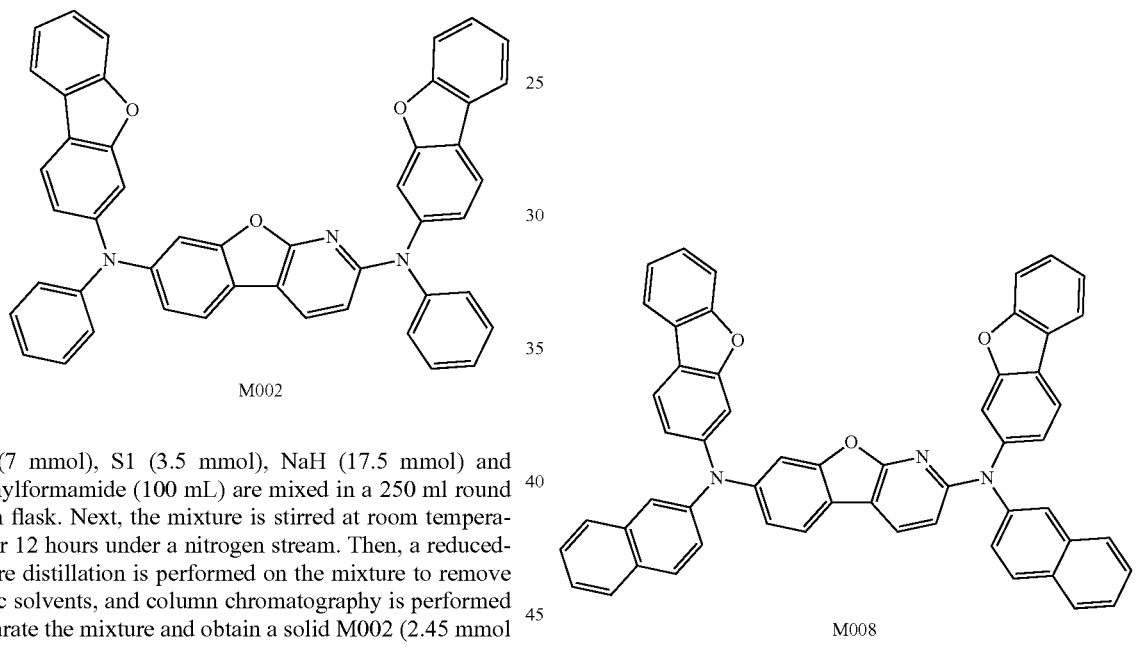

MALDI-TOF MS: $C_{55}H_{33}N_3O_3$, m/z calculated value: 783.2; and measured value: 783.6.

Elemental analysis calculated values: C, 84.27; H, 4.24; N, 5.36; O, 6.12; and test values: C, 84.32; H, 4.25; N, 5.33; O, 6.09.

Exemplary Embodiment Three

Referring to exemplary embodiment one, a compound M018 is synthesized.

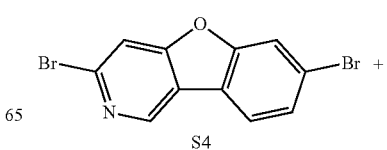

-continued

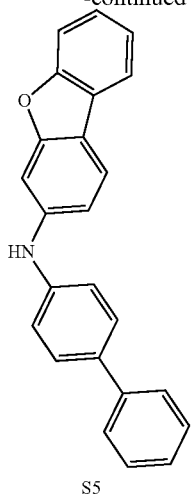

S5

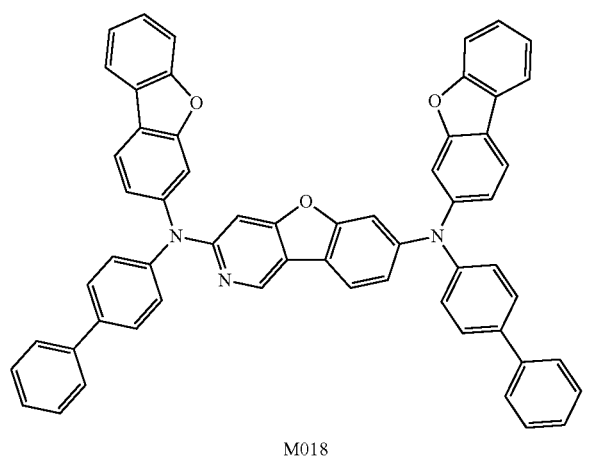

M018

MALDI-TOF MS: C$_{59}$H$_{37}$N$_3$O$_3$, m/z calculated value: 835.3; and test value: 835.6.

Elemental analysis calculated values: C, 84.77; H, 4.46; N, 5.03; O, 5.74; and test values: C, 84.80; H, 4.48; N, 5.00; O, 5.72.

Exemplary Embodiment Four

Referring to exemplary embodiment one, a compound M075 is synthesized.

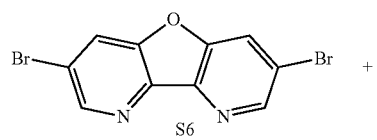

S6

-continued

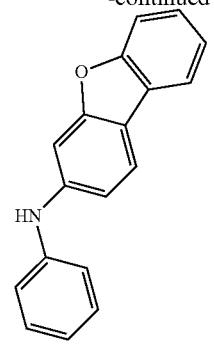

S2

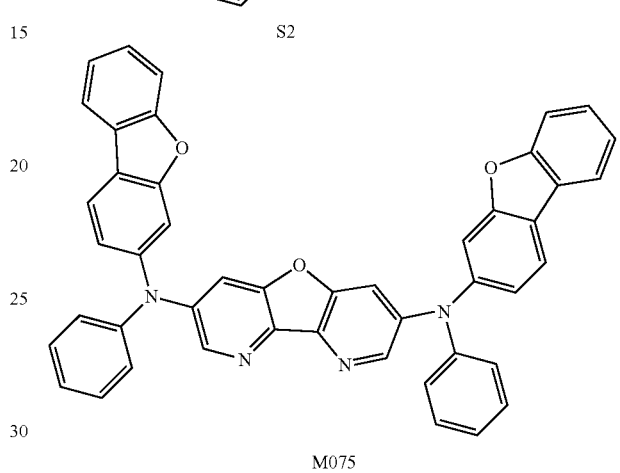

M075

MALDI-TOF MS: C$_{46}$H$_{28}$N$_4$O$_3$, m/z calculated value: 684.2; and measured value: 684.5.

Elemental analysis calculated values: C, 80.69; H, 4.12; N, 8.18; O, 7.01; and test values: C, 80.73; H, 4.15; N, 8.15; O, 6.97.

Exemplary Embodiment Five

Referring to exemplary embodiment one, a compound M085 is synthesized.

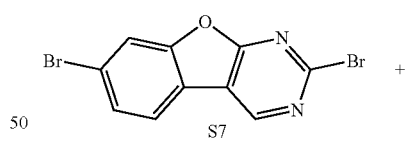

S7

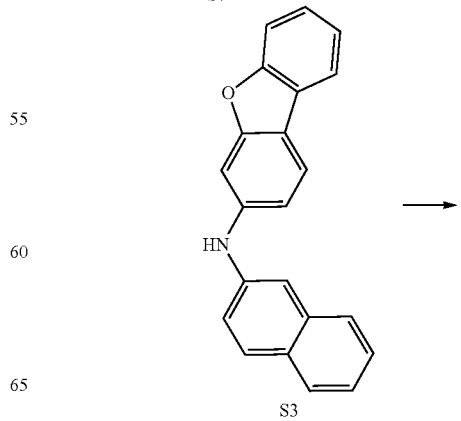

S3

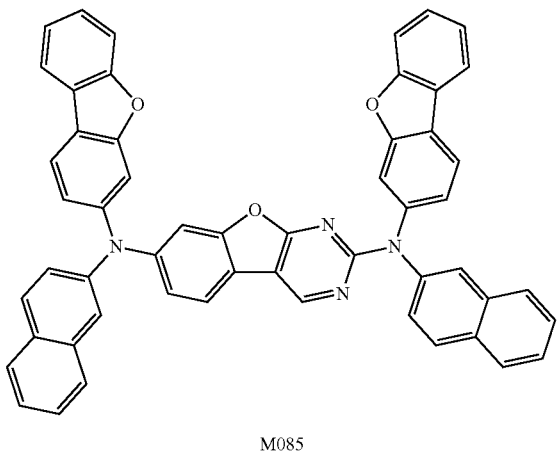

M085

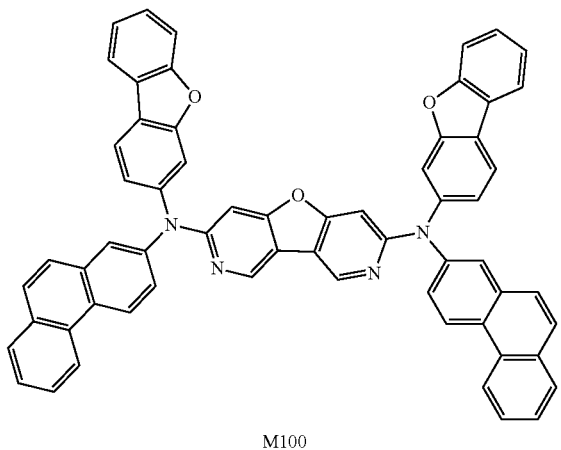

M100

MALDI-TOF MS: $C_{54}H_{32}N_4O_3$, m/z calculated value: 784.2; and measured value: 784.5.

Elemental analysis calculated values: C, 82.64; H, 4.11; N, 7.14; O, 6.12; and test values: C, 82.68; H, 4.13; N, 7.11; O, 6.09.

MALDI-TOF MS: $C_{62}H_{36}N_4O_3$, m/z calculated value: 884.3; and measured value: 884.6.

Elemental analysis calculated values: C, 84.15; H, 4.10; N, 6.33; O, 5.42; and test values: C, 84.19; H, 4.12; N, 6.30; O, 5.39.

Exemplary Embodiment Six

Referring to exemplary embodiment one, a compound M100 is synthesized.

Exemplary Embodiment Seven

Referring to exemplary embodiment one, a compound M106 is synthesized.

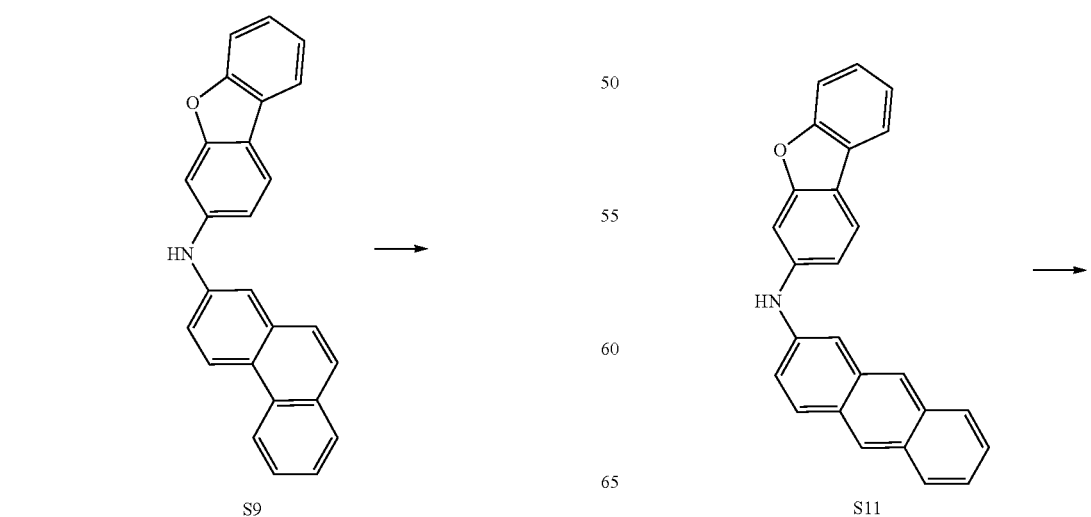

-continued

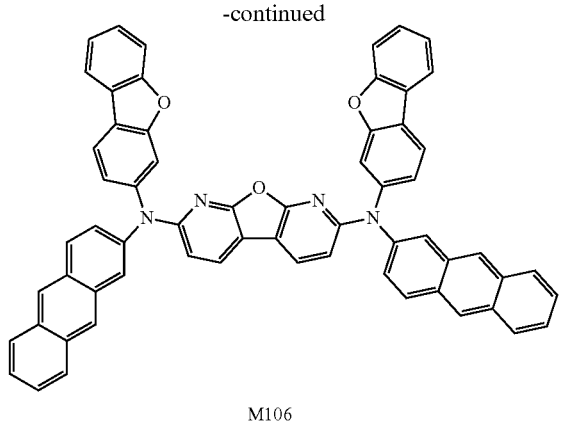

M106

MALDI-TOF MS: $C_{62}H_{36}N_4O_3$, m/z calculated value: 884.3; and measured value: 884.7.

Elemental analysis calculated values: C, 84.15; H, 4.10; N, 6.33; O, 5.42; and test values: C, 84.18; H, 4.13; N, 6.30; O, 5.39.

Exemplary Embodiment Eight

Referring to exemplary embodiment one, a compound M327 is synthesized.

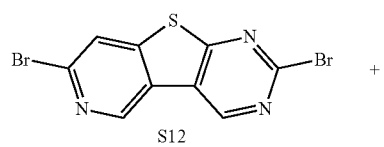

S12

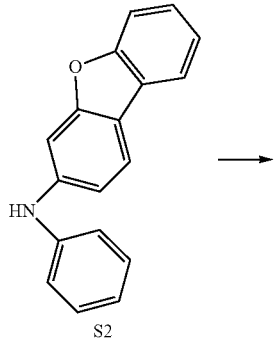

S2

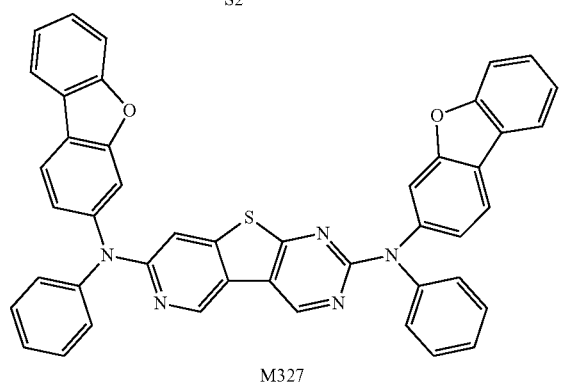

M327

MALDI-TOF MS: $C_{45}H_{27}N_5O_2S$, m/z calculated value: 701.2; and test value: 701.5.

Elemental analysis calculated values: C, 77.02; H, 3.88; N, 9.98; O, 4.56; S, 4.57; and test values: C, 77.05; H, 3.91; N, 9.96; O, 4.54; S, 4.55.

Exemplary Embodiment Nine

Referring to exemplary embodiment one, a compound M393 is synthesized.

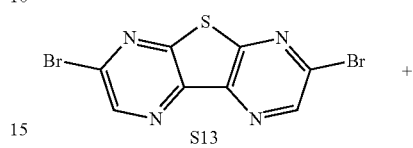

S13

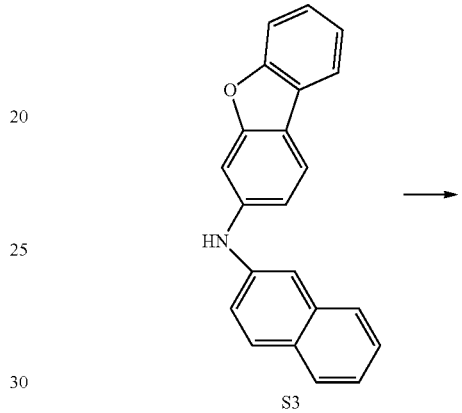

S3

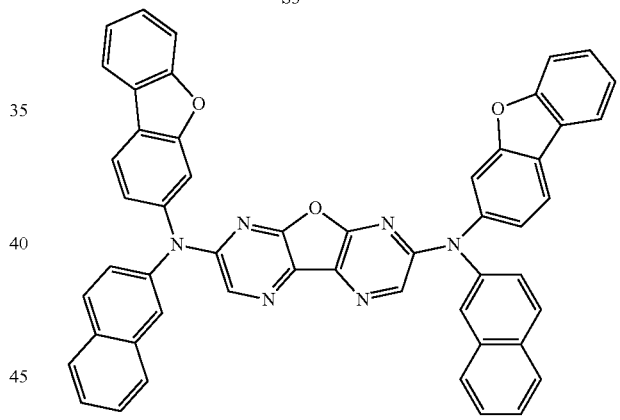

M393

MALDI-TOF MS: $C_{52}H_{30}N_6O_3$, m/z calculated value: 786.2; and test value: 786.4.

Elemental analysis calculated values: C, 79.38; H, 3.84; N, 10.68; O, 6.10; and test values: C, 79.42; H, 3.86; N, 10.65; O, 6.07.

Exemplary Embodiment Ten

Referring to exemplary embodiment one, a compound M479 is synthesized.

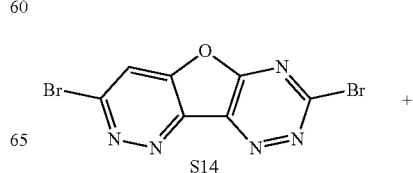

S14

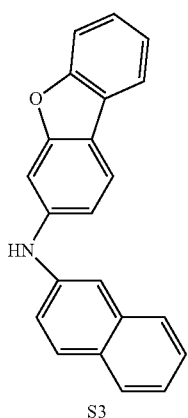

S3

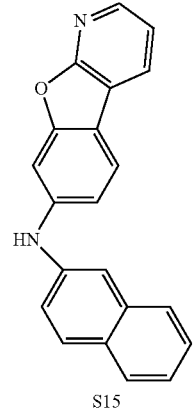

S15

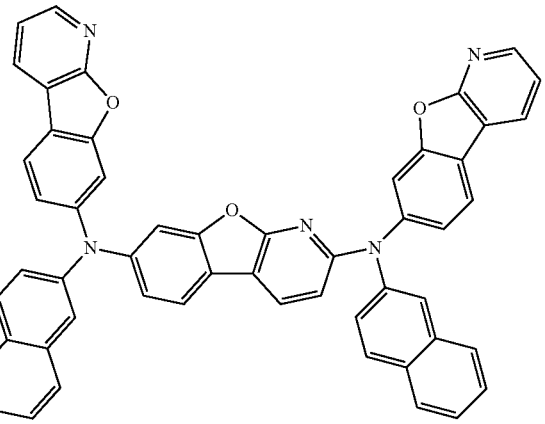

M479

MALDI-TOF MS: $C_{53}H_{31}N_5O_3$, m/z calculated value: 785.2; and test value: 785.3.

Elemental analysis calculated values: C, 81.00; H, 3.98; N, 8.91; O, 6.11; and test values: C, 81.03; H, 4.01; N, 8.88; O, 6.08.

Application Example 1

The present application example provides an OLED device, which may sequentially include a glass substrate, an ITO anode of 15 nm, a hole injection layer of 5 nm, a first hole transport layer of 100 nm, a second hole transport layer of 5 nm, a light-emitting layer of 30 nm, an electron transport layer of 30 nm, an electron injection layer of 5 nm, a cathode of 15 nm (magnesium silver electrode, the mass ratio of magnesium to silver is about 1:9), and a capping layer (CPL) of 100 nm.

The OLED device may be prepared as the following steps.

1) The glass substrate is cut into a size of 50 mm×50 mm×0.7 mm, which is ultrasonically treated in isopropanol and deionized water (respectively) for 30 min and then exposed to ozone cleaning for 10 min; and the obtained glass substrate with the ITO anode is installed on a vacuum deposition device;

2) on an ITO anode layer 101, a hole injection layer material compound 1 is evaporated by a vacuum evaporation manner, with a thickness of about 5 nm, and such layer is used as a hole injection layer 102;

3) a hole transport layer material compound 2 is vacuum evaporated on the hole injection layer 102, with a thickness of about 100 nm, and such layer is used as a first hole transport layer 103;

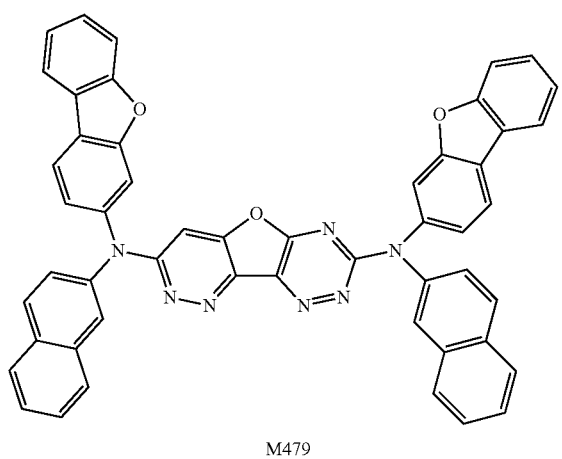

M479

MALDI-TOF MS: $C_{51}H_{29}N_7O_3$, m/z calculated value: 787.2; and measured value: 787.5.

Elemental analysis calculated values: C, 77.75; H, 3.71; N, 12.45; O, 6.09; and test values: C, 77.79; H, 3.73; N, 12.42; O, 6.06.

Exemplary Embodiment Eleven

Referring to exemplary embodiment one, a compound M492 is synthesized.

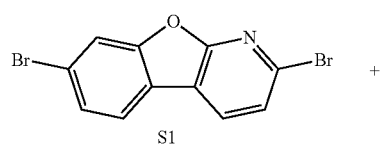

S1

4) a hole transport material compound 3 is vacuum evaporated on the first hole-transport layer 103, with a thickness of about 5 nm, and such layer is used as a second hole transport layer 104;

5) a light-emitting layer 105 is vacuum evaporated on the second hole transport layer 104, where a compound 4 is used as the host material and a compound 5 is used as the doping material, the doping ratio is about 3% (mass ratio), and the thickness of the light-emitting layer is about 30 nm;

6) an electron transport material compound 6 is vacuum evaporated on the light-emitting layer 105, with a thickness of about 30 nm, and such layer is used as an electron transport layer 106;

7) an electron transport material compound 7 is vacuum evaporated on the electron transport layer 106, with a thickness of about 5 nm, and such layer is used as an electron injection layer 107;

8) a magnesium-silver electrode is vacuum evaporated on the electron injection layer 107, where the magnesium to silver ratio is about 1:9, the thickness is about 15 nm, the magnesium-silver electrode is used as a cathode 108; and 9) a compound M002 is vacuum evaporated on the cathode 108, with a thickness of about 100 nm, and such layer is used as a capping layer CPL.

The compound structures used in the OLED device are as follows:

Compound 1

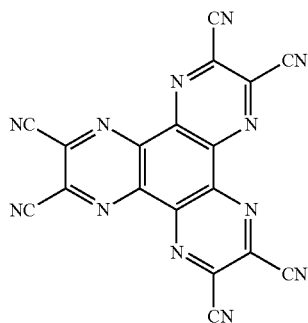

Compound 2

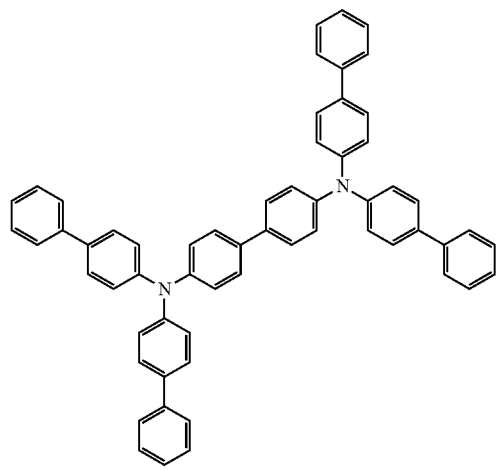

Compound 3

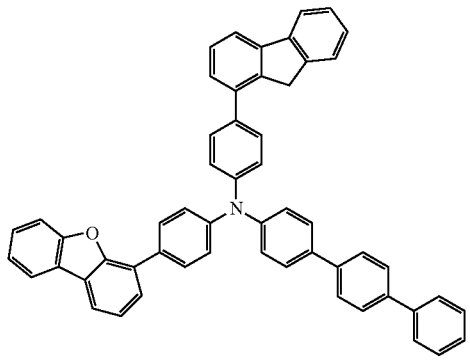

Compound 4

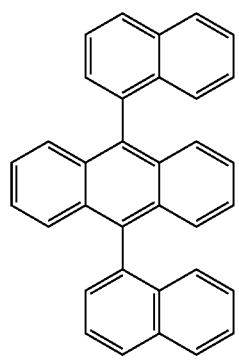

Compound 5

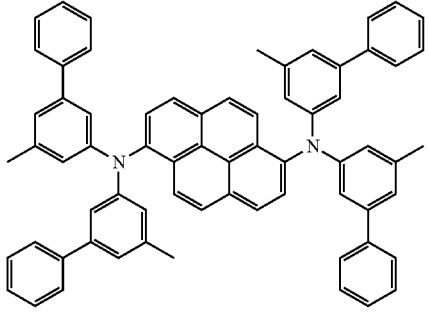

Compound 6

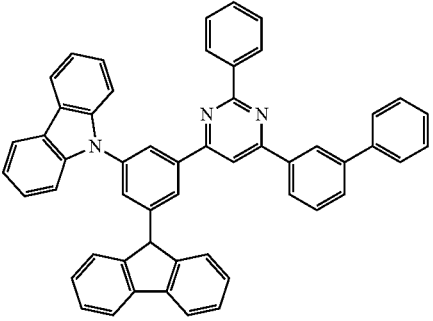

Compound 7

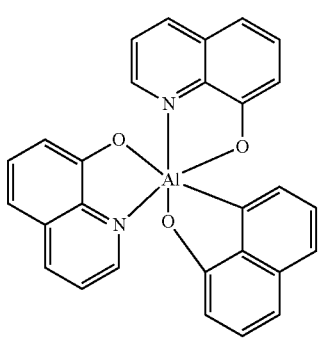

Application Example 2

The organic compound M002 in step (9) in application example 1 is replaced with an equivalent amount of compound M008; and other preparation steps are same.

Application Example 3

The organic compound M002 in step (9) in application example 1 is replaced with an equivalent amount of compound M017; and other preparation steps are same.

Application Example 4

The organic compound M002 in step (9) in application example 1 is replaced with an equivalent amount of compound M018; and other preparation steps are same.

Application Example 5

The organic compound M002 in step (9) in application example 1 is replaced with an equivalent amount of compound M075; and other preparation steps are same.

Application Example 6

The organic compound M002 in step (9) in application example 1 is replaced with an equivalent amount of compound M091; and other preparation steps are same.

Application Example 7

The organic compound M002 in step (9) in application example 1 is replaced with an equivalent amount of compound M093; and other preparation steps are same.

Application Example 8

The organic compound M002 in step (9) in application example 1 is replaced with an equivalent amount of compound M106; and other preparation steps are same.

Application Example 9

The organic compound M002 in step (9) in application example 1 is replaced with an equivalent amount of compound M109; and other preparation steps are same.

Application Example 10

The organic compound M002 in step (9) in application example 1 is replaced with an equivalent amount of compound M111; and other preparation steps are same.

Application Example 11

The organic compound M002 in step (9) in application example 1 is replaced with an equivalent amount of compound M120; and other preparation steps are same.

Application Example 12

The organic compound M002 in step (9) in application example 1 is replaced with an equivalent amount of compound M327; and other preparation steps are same.

Application Example 13

The organic compound M002 in step (9) in application example 1 is replaced with an equivalent amount of compound M393; and other preparation steps are same.

Application Example 14

The organic compound M002 in step (9) in application example 1 is replaced with an equivalent amount of compound M479; and other preparation steps are same.

Application Example 15

The organic compound M002 in step (9) in application example 1 is replaced with an equivalent amount of compound M492; and other preparation steps are same.

Application Example 16

The organic compound M002 in step (9) in application example 1 is replaced with an equivalent amount of compound M142; and other preparation steps are same.

Application Example 17

The organic compound M002 in step (9) in application example 1 is replaced with an equivalent amount of compound M165; and other preparation steps are same.

Application Example 18

The organic compound M002 in step (9) in application example 1 is replaced with an equivalent amount of compound M263; and other preparation steps are same.

Application Example 19

The difference between the present application example and the application example 1 is only that the compound 6 in step (6) is replaced with an equivalent amount of M002, and the organic compound M002 in step (9) is replaced with an equivalent amount of a comparative compound ref 1; and the other preparation steps are same.

Application Example 20

The difference between the present application example and the application example 1 is only that the compound 6 in step (6) is replaced with an equivalent amount of M075, and the organic compound M002 in step (9) is replaced with an equivalent amount of the comparative compound ref 1; and the other preparation steps are same.

Application Example 21

The difference between the present application example and the application example 1 is only that the compound 3 in step (4) is replaced with an equivalent amount of M008, and the organic compound M002 in step (9) is replaced with an equivalent amount of the comparative compound ref 1; and the other preparation steps are same.

Application Example 22

The difference between the present application example and the application example 1 is only that the compound 3 in step (4) is replaced with an equivalent amount of M018, and the organic compound M002 in step (9) is replaced with an equivalent amount of the comparative compound ref 1; and the other preparation steps are same.

Comparative Example 1

The only difference between the present comparative example and the application example 1 is that the organic compound M002 in step (9) is replaced with an equivalent amount of the comparative compound ref 1; and other preparation steps are same.

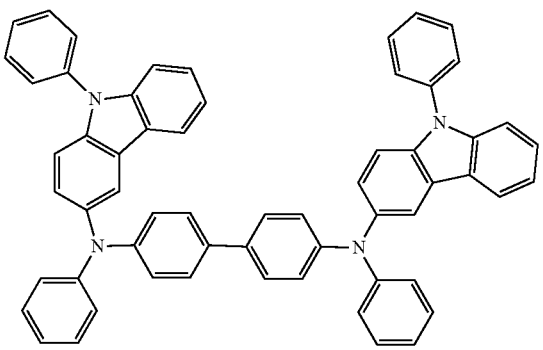

Ref 1

Comparative Example 2

The difference between the present comparative example and the application example 1 is only that the organic compound M002 in step (9) is replaced with an equivalent amount of a comparative compound ref 2; and other preparation steps are same.

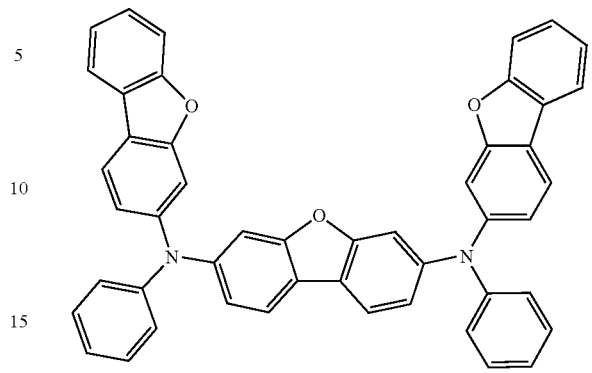

Ref 2

Compound Physical Property Parameter Test

The refractive index tests are performed on the compounds used as the capping layer in the exemplary embodiments and comparative examples are, and the results are shown in Table 1. The refractive index is measured by an ellipsometer (American J.A. Woollam Co. Model: ALPHA-SE), and the tests are performed at an atmospheric environment.

TABLE 1

| | Refractive index test values | | |
|---|---|---|---|
| Compound | Refractive index 460 nm | Refractive index 530 nm | Refractive index 620 nm |
| M002 | 2.05 | 1.94 | 1.87 |
| M008 | 2.11 | 1.95 | 1.88 |
| M017 | 2.07 | 1.93 | 1.87 |
| M018 | 2.05 | 1.94 | 1.88 |
| M075 | 2.06 | 1.95 | 1.88 |
| M091 | 2.07 | 1.97 | 1.91 |
| M093 | 2.13 | 2.01 | 1.93 |
| M106 | 2.24 | 2.09 | 2.01 |
| M109 | 2.21 | 2.08 | 2.00 |
| M111 | 2.25 | 2.10 | 2.01 |
| M120 | 2.11 | 1.95 | 1.89 |
| M327 | 2.04 | 1.94 | 1.88 |
| M393 | 2.24 | 2.06 | 1.97 |
| M479 | 2.10 | 1.98 | 1.91 |
| M492 | 2.13 | 2.01 | 1.93 |
| M142 | 2.12 | 1.96 | 1.90 |
| M165 | 2.13 | 1.97 | 1.90 |
| M263 | 2.07 | 1.94 | 1.88 |
| Ref 1 | 1.96 | 1.83 | 1.78 |
| Ref 2 | 2.02 | 1.92 | 1.86 |

It can be seen from Table 1 that, compared with the capping layer material ref 1, which is commonly used in the industry, the compounds of the present disclosure may have higher refractive indexes in the red, green, and blue regions; when used as the capping layer material in the top-emitting OLED devices, it is possible to achieve higher light extraction efficiency and improve the luminous efficiency of the OLED devices, thereby increasing the lifetime of the OLED devices.

Compared with the compound ref 2, which is not N-substituted, the compounds of the present disclosure, having the N-substituted hetero-fluorene structure, may have higher polarizability, smaller molecular volumes, and higher refractive indexes at all wavelengths; when used as the capping layer material in the top-emitting OLED devices, it is possible to achieve higher light extraction efficiency, improve the luminous efficiency of the OLED devices, and further improve the lifetime of the OLED devices, which is particularly beneficial for improving the efficiency of the blue light devices in the OLED devices and increasing the lifetime of the blue light devices to a certain extent.

Performance Evaluation of the OLED Devices

Keithley 2365A digital nanovoltmeter may be used to test the current of the OLED device under different voltages, and then the current may be divided by a light-emitting area to obtain the current density of the OLED device under different voltages; Konicaminolta CS-2000 spectroradiometer may be used to test the brightness and radiant energy density of OLED device under different voltages; according to the current density and brightness of the OLED device under different voltages, a working voltage V and a current efficiency CE (cd/A) at a same current density (10 mA/cm2) may be obtained; and the lifetime T95 may be obtained by measuring the time when the brightness of the OLED device reaches 95% of the initial brightness (under 50 mA/cm2 test condition), where the test data is shown in Table 2.

TABLE 2

Performance evaluation results of the OLED devices

| Number | CPL material | Drive voltage (V) | Current efficiency (cd/A) | Lifetime (use a first comparative device as the benchmark) |
|---|---|---|---|---|
| Application example 1 | M002 | 4.00 | 6.44 | 1.06 |
| Application example 2 | M008 | 4.02 | 6.96 | 1.04 |
| Application example 3 | M017 | 4.01 | 6.76 | 1.07 |
| Application example 4 | M018 | 4.02 | 6.50 | 1.08 |
| Application example 5 | M075 | 4.01 | 6.59 | 1.05 |
| Application example 6 | M091 | 4.03 | 6.82 | 1.06 |
| Application example 7 | M093 | 4.02 | 7.07 | 1.05 |
| Application example 8 | M106 | 4.03 | 7.26 | 1.04 |
| Application example 9 | M109 | 4.00 | 7.18 | 1.09 |
| Application example 10 | M111 | 4.02 | 7.35(131%) | 1.08(108%) |
| Application example 11 | M120 | 4.03 | 7.02 | 1.07 |
| Application example 12 | M327 | 4.02 | 6.30 | 1.04 |
| Application example 13 | M393 | 4.02 | 7.20 | 1.05 |
| Application example 14 | M479 | 4.03 | 7.12 | 1.04 |
| Application example 15 | M492 | 4.03 | 7.13 | 1.05 |
| Application example 16 | M142 | 4.02 | 7.06 | 1.06 |
| Application example 17 | M165 | 4.01 | 7.12 | 1.05 |
| Application example 18 | M263 | 4.01 | 6.82 | 1.07 |
| Comparative example 1 | Ref 1 | 4.04 | 5.60 (100%) | 1.00(100%) |
| Comparative example 2 | Ref 2 | 4.02 | 5.82 | 1.05 |

It can be seen from Table 2 that, compared with the compound ref which is not N-substituted, the compounds of the present disclosure may have higher luminous efficiency when applied to the blue light devices, where when M111 is used as the capping layer material, the luminous efficiency is increased by about 31%, and the lifetime is increased by more than 8%. It can be seen from the device performance parameters in Table 2 that when the compounds of the present disclosure are applied as the capping layer material to the top-emitting OLED devices, the light extraction efficiency may be higher, the luminous efficiency of the OLED devices may be higher, the lifetime of the OLED devices may be longer, the efficiency of the blue light devices in the OLED devices may be greatly improved and the lifetime of the blue light devices may be increased to a certain extent, which is due to that the N-substituted heterofluorene contained in the compounds of the present disclosure may have a higher refractive index, and a higher thermal stability, light stability and chemical stability.

TABLE 3

Performance evaluation results of the OLED devices

| Number | Electron transport material | Drive voltage (V) | Current efficiency (cd/A) | Lifetime (use a first comparative device as the benchmark) |
|---|---|---|---|---|
| Application example 19 | M002 | 4.02 | 5.92 | 1.09 |
| Application example 20 | M075 | 3.98 | 6.02 (107.5%) | 1.08 (108%) |
| Comparative example 1 | Compound 6 | 4.04 | 5.60 | 1.00 |

It can be seen from Table 3 that, compared with the compound 6, the compounds M002 and M075 of the present disclosure have higher luminous efficiency when applied to blue light devices, the luminous efficiency is increased by about 7.5%, and the lifetime is increased by about 8%, indicating that the compounds of the present disclosure may be used as the electron transport material in the OLED devices.

TABLE 4

Performance evaluation results of the OLED devices

| Number | Hole transport material | Drive voltage (V) | Current efficiency (cd/A) | Lifetime (use a first comparative device as the benchmark) |
|---|---|---|---|---|
| Application example 21 | M008 | 4.02 | 6.15(109.8%) | 1.05(105%) |
| Application example 22 | M018 | 4.00 | 6.12 | 1.06 |
| Comparative 1 | Compound 3 | 4.04 | 5.60 | 1.00 |

It can be seen from Table 4 that, compared with the compound 3, the compounds M008 and M018 of the present disclosure have higher luminous efficiency when applied to blue light devices, the luminous efficiency is increased by about 9.8%, and the lifetime is increased by about 5%, indicating that the compounds of the present disclosure may be used as the hole transport material in the OLED devices.

From the above-mentioned embodiments, it can be seen that the heterocyclic compound containing heteroatom substituted fluorene and the display panel provided by the present disclosure may achieve at least the following beneficial effects.

In the present disclosure, substituted fluorene containing heteroatoms may be used as a parent nucleus to prepare the heterocyclic compounds, which may have higher refractive indexes and light extraction efficiency and effectively improve the luminous efficiency of organic optoelectronic devices. The compounds of the present disclosure may have the N-substituted hetero-fluorene structure, which may have higher polarizability, smaller molecular volumes, and higher refractive indexes at all wavelengths; when used as the capping layer material in the top-emitting OLED devices, higher light extraction efficiency may be achieved, the luminous efficiency of the OLED devices may be improved, and furthermore the lifetime of the OLED devices may be increased. In particular, it is beneficial for improving the efficiency of the blue light devices in the OLED devices and increasing the lifetime of the blue light devices to a certain extent.

Meanwhile, the N-substituted hetero-fluorene contained in the compounds of the present disclosure may have higher thermal stability, light stability and chemical stability, which is beneficial for further improving the lifetime of the OLED devices.

In addition, the N-substituted hetero-fluorene contained in the compounds of the present disclosure may have a desirable interface bonding force with the silver cathode, and also have a desirable bonding force with the thin-film encapsulation layer located on the capping layer. In the flexible OLED devices, due to the strong interface bonding force, it may effectively avoid undesirable interface peeling caused by folding actions, which is beneficial for achieving a longer lifetime of the OLED devices.

The description of the above-mentioned embodiments may be merely used to help understand the method and core idea of the present disclosure. It should be understood that, for those of ordinary skill in the art, without departing from the principle of the present disclosure, certain improvements and modifications may be made to the present disclosure, and such improvements and modifications should also fall within the protection scope of the claims of the present disclosure.

What is claimed is:

1. A heterocyclic compound, having a structure shown in formula I, comprising:

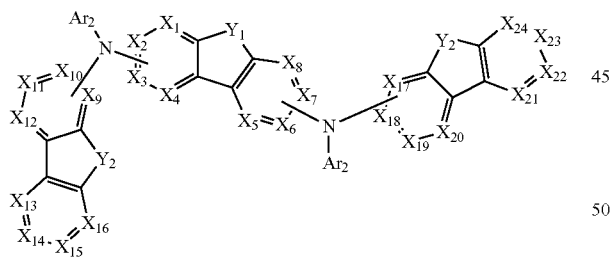

formula I wherein:
Y1 is selected from O or S;
$X_1$, $X_2$, $X_3$, $X_4$, $X_5$, $X_6$, $X_7$, and $X_8$ are independently selected from $CR_a$ or N, and at least one of $X_1$, $X_2$, $X_3$, $X_4$, $X_5$, $X_6$, $X_7$, and $X_8$ is N;
$X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, and $X_{24}$ are independently selected from $CR_1$ or N;
when there are a plurality of $CR_a$ in $X_1$-$X_8$, $R_a$ are same or different; and $R_a$ is independently selected from hydrogen, deuterium, tritium, halogen, nitrile, cyano, nitro, hydroxyl, carbonyl, ester, carboxyl, imide, amide, substituted or unsubstituted C1-C20 alkoxy, substituted or unsubstituted C1-C20 alkyl, substituted or unsubstituted C3-C20 cycloalkyl, substituted or unsubstituted C2-C20 alkenyl, substituted or unsubstituted C3-C20 cycloalkenyl, substituted or unsubstituted silyl, substituted or unsubstituted boron, substituted or unsubstituted phosphine oxide, substituted or unsubstituted phosphine, substituted or unsubstituted sulfonyl, substituted or unsubstituted amine, substituted or unsubstituted C6-C30 aryl, substituted or unsubstituted C3-C30 heteroaryl, or a ring structure formed by bonding adjacent groups;

Y2, and Y3 are independently selected from O, S or $NR_2$;
$Ar_1$ and $Ar_2$ are independently selected from substituted or unsubstituted aryl, or substituted or unsubstituted heteroaryl; and
$R_1$ and $R_2$ are independently selected from hydrogen, deuterium, substituted or unsubstituted C1-C20 alkyl, substituted or unsubstituted C6-C30 aryl, or substituted or unsubstituted C3-C30 heteroaryl.

2. The heterocyclic compound according to claim 1, wherein:
$Ar_1$ and $Ar_2$ are independently selected from phenyl, biphenyl, terphenyl, naphthyl, anthryl, phenanthryl, pyrenyl, fluoranthyl, triphenyl, pyrrolyl, pyranyl, thienyl, pyridyl, pyrimidinyl, triazinyl, benzofuranyl, benzothienyl, dibenzofuranyl, or dibenzothienyl.

3. The heterocyclic compound according to claim 2, wherein $Ar_1$ and $Ar_2$ are independently selected from any one of following structures:

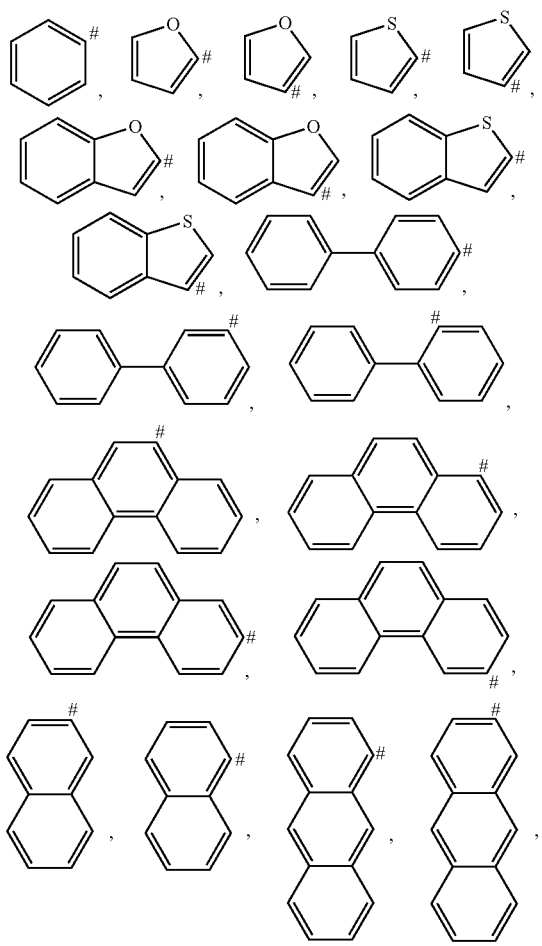

-continued

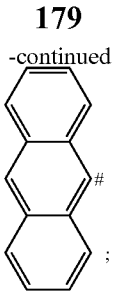

wherein # denotes a connection location.

4. The heterocyclic compound according to claim 1, wherein:
Y2 and Y3 are independently selected from O, S, or NR₂, wherein R₂ is selected from phenyl, biphenyl, terphenyl, naphthyl, anthryl, phenanthryl, pyrenyl, fluoranthyl, triphenyl, pyrrolyl, pyranyl, thienyl, pyridyl, pyrimidinyl, triazinyl, benzofuranyl, benzothienyl, dibenzofuranyl, or dibenzothienyl.

5. The heterocyclic compound according to claim 1, wherein:
in the structure

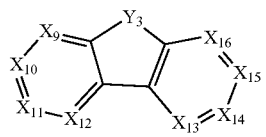

in the formula I, $X_9$, $X_{10}$, $X_{11}$, $X_{12}$, $X_{13}$, $X_{14}$, $X_{15}$, and $X_{16}$ are independently selected from $CR_1$ or N, and at least one of $X_9$, $X_{10}$, $X_{11}$, $X_{12}$, $X_{13}$, $X_{14}$, $X_{15}$, and $X_{16}$ is N; and
$R_1$ is selected from hydrogen, deuterium, substituted or unsubstituted C1-C20 alkyl, substituted or unsubstituted C6-C30 aryl, or substituted or unsubstituted C3-C30 heteroaryl.

6. The heterocyclic compound according to claim 5, wherein: the structure of

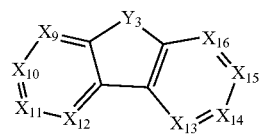

is selected from any one of following structures:

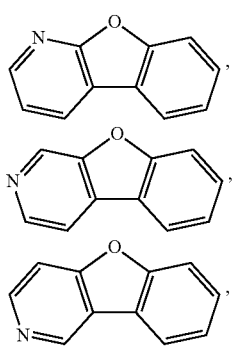

-continued

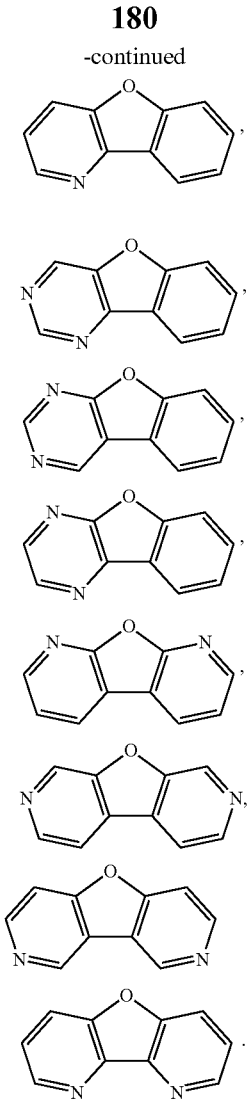

7. The heterocyclic compound according to claim 1, wherein:
the structure of is selected from:

-continued

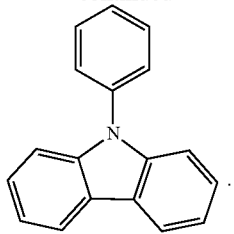

8. The heterocyclic compound according to claim 1, wherein:
in the structure

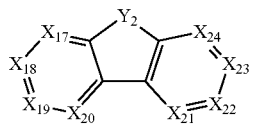

in the formula I, $X_{17}$, $X_{18}$, $X_{19}$, $X_{20}$, $X_{21}$, $X_{22}$, $X_{23}$, and $X_{24}$ are independently selected from $CR_1$ or N, and at least one of $X_{17}$, $X_{18}$, $X_{19}$, $X_{20}$, $X_{21}$, $X_{22}$, $X_{23}$, and $X_{24}$ is N; and
$R_1$ is selected from hydrogen, deuterium, substituted or unsubstituted C1-C20 alkyl, substituted or unsubstituted C6-C30 aryl, or substituted or unsubstituted C3-C30 heteroaryl.

9. The heterocyclic compound according to claim 8, wherein:
the structure of

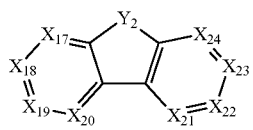

is selected from any one of following structures:

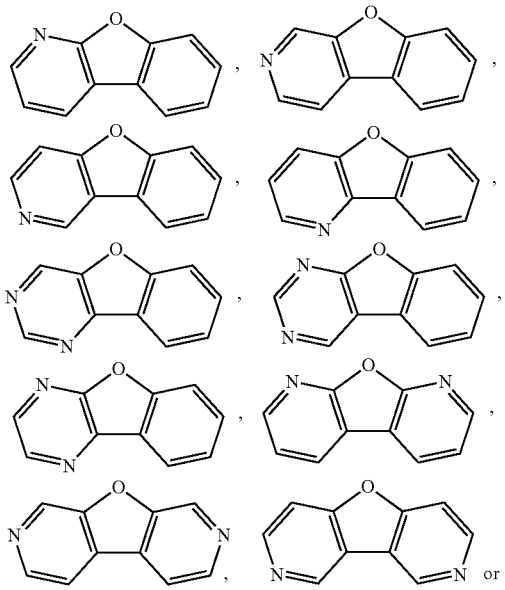

-continued

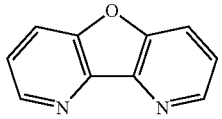

10. The heterocyclic compound according to claim 1, wherein:
the structure of

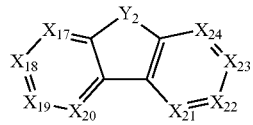

is selected from:

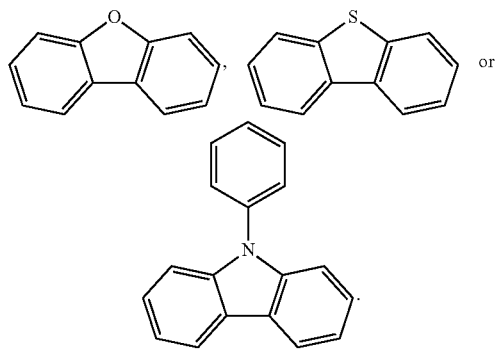

11. The heterocyclic compound according to claim 1, wherein:
any 1 to 6 of $X_1$, $X_2$, $X_3$, $X_4$, $X_5$, $X_6$, $X_7$, and $X_8$ are N.

12. The heterocyclic compound according to claim 1, wherein:
the structure of

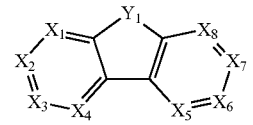

is selected from any one of following structures:

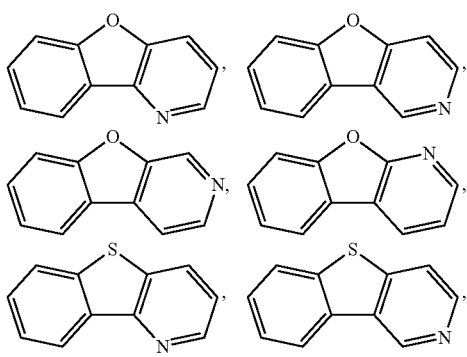

-continued
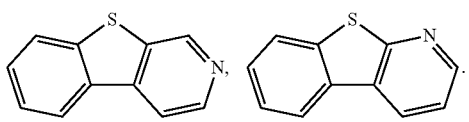
13. The heterocyclic compound according to claim 12, wherein:
the structure of
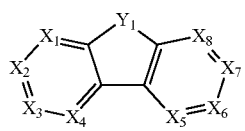
is selected from any one of following structures:
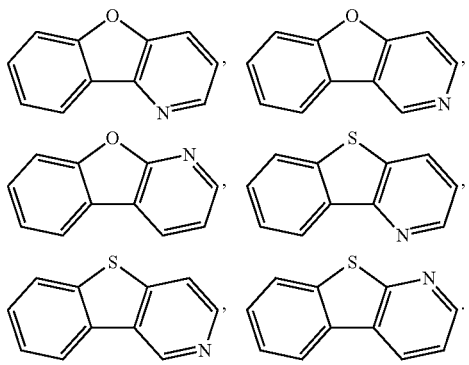
14. The heterocyclic compound according to claim 1, wherein:
the structure of
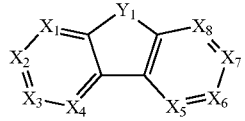
is selected from any one of following structures:
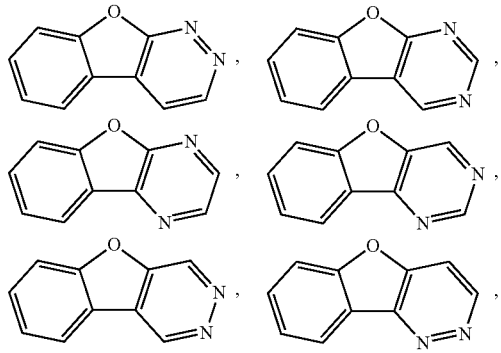
-continued
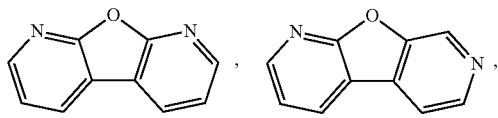
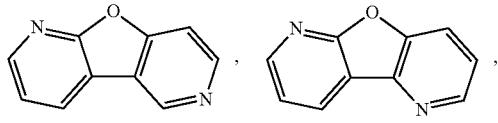
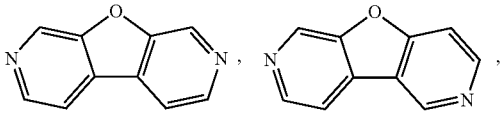
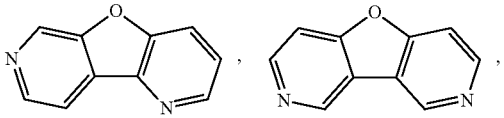
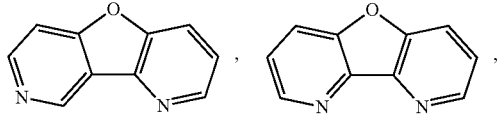
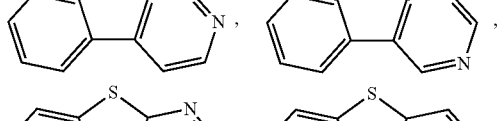
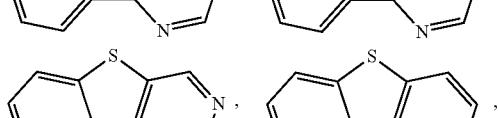
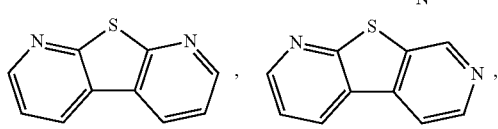
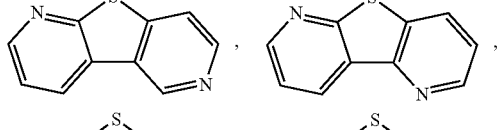
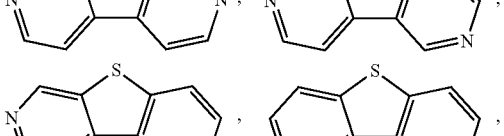
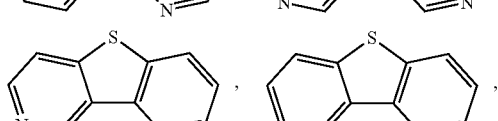

15. The heterocyclic compound according to claim 14, wherein:
the structure of
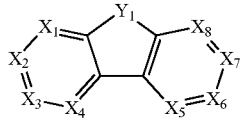
is selected from any one of following structures:
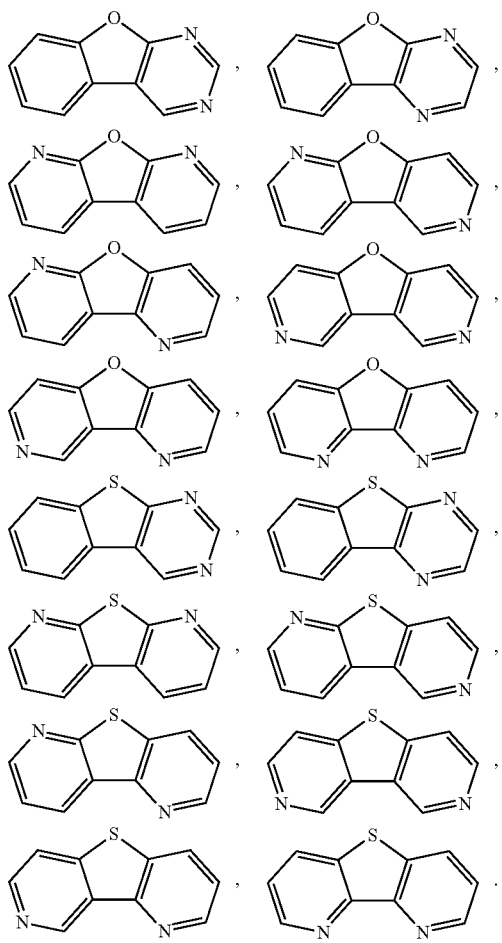
16. The heterocyclic compound according to claim 1, wherein:
the structure of
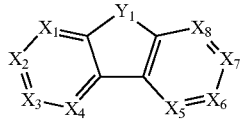
is selected from any one of following structures:
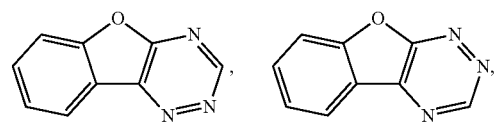
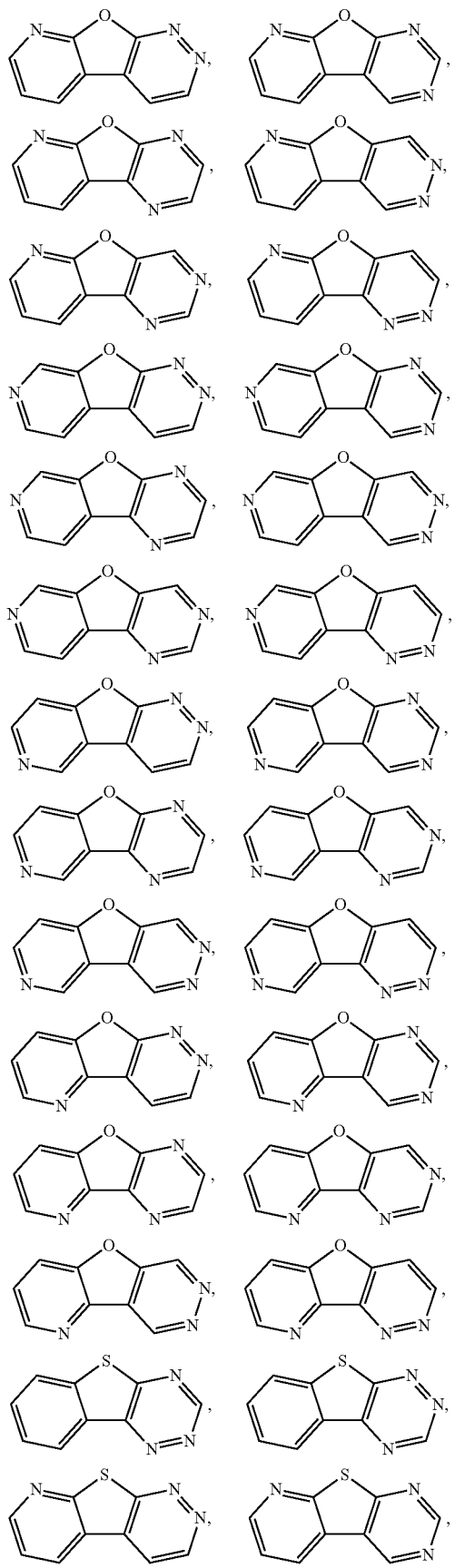

-continued
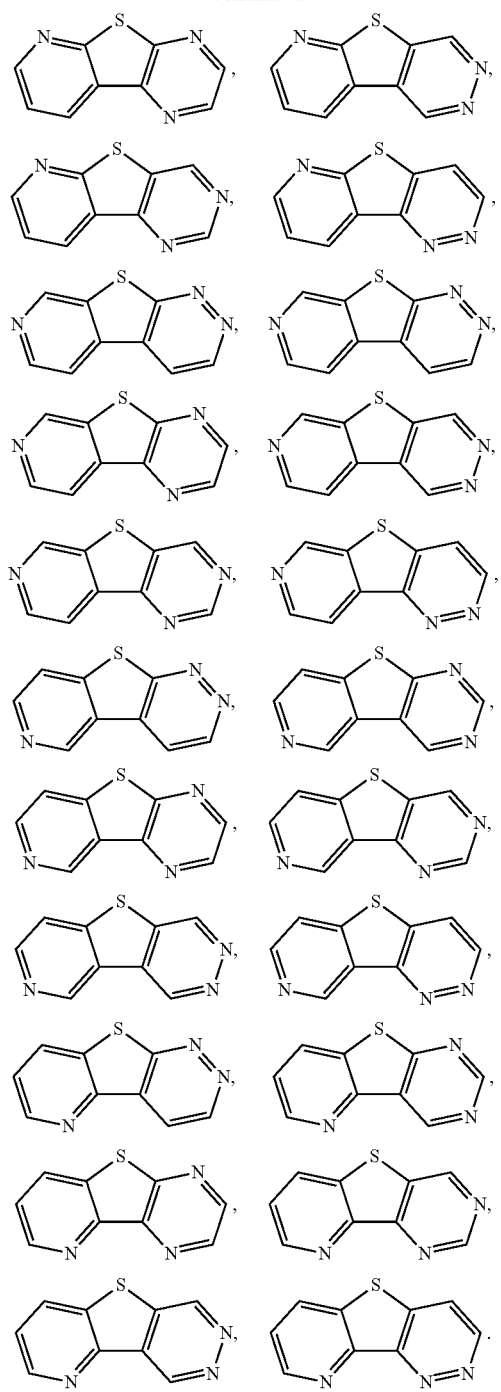
17. The heterocyclic compound according to claim 16, wherein:
the structure of
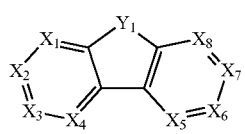
is selected from any one of following structures:
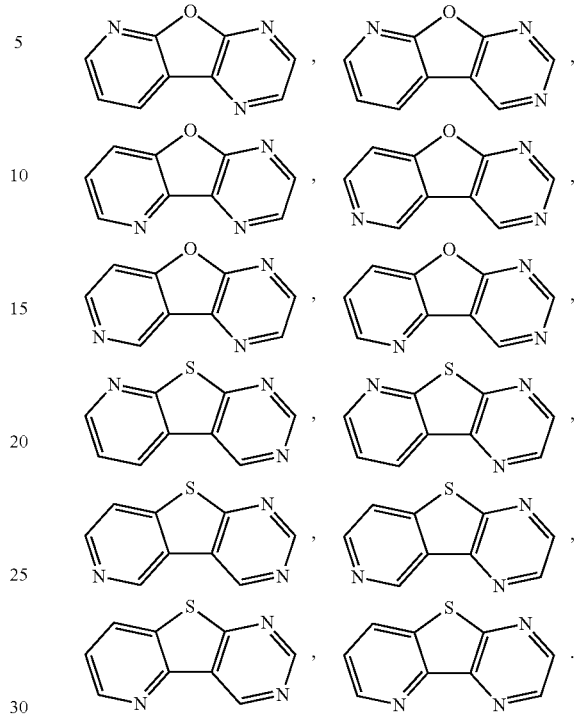
18. The heterocyclic compound according to claim 1, wherein:
the structure of
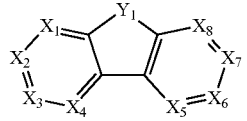
is selected from any one of following structures:
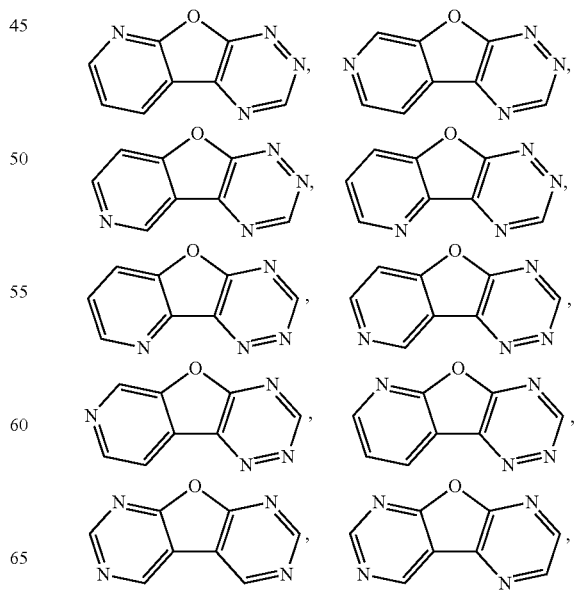

-continued
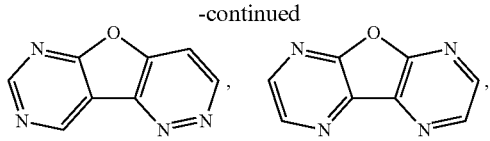
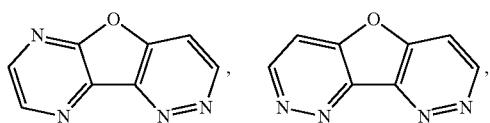
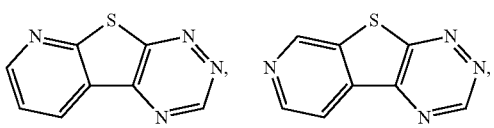
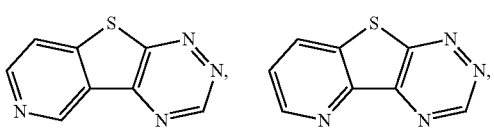
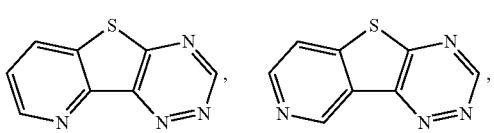
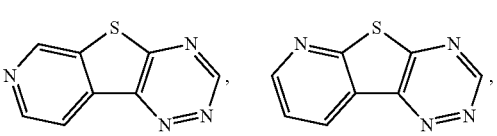
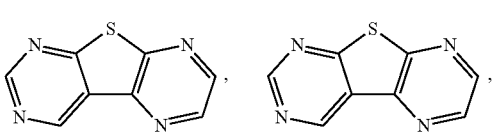
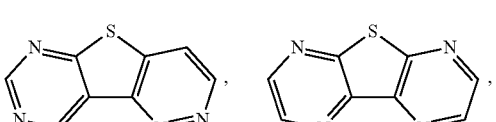
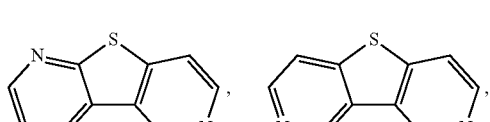
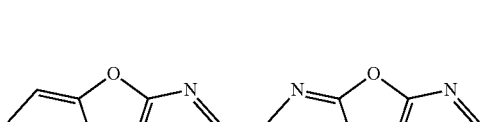
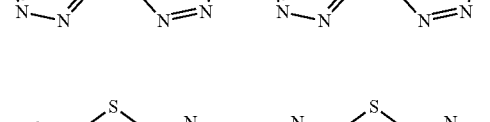
19. The heterocyclic compound according to claim 1, wherein the heterocyclic compound has any one of following structures:
M001
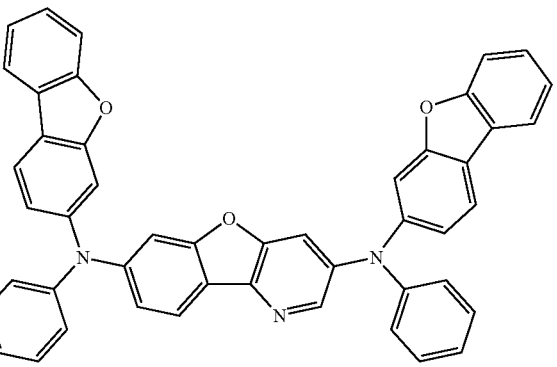
M002
M003
M004
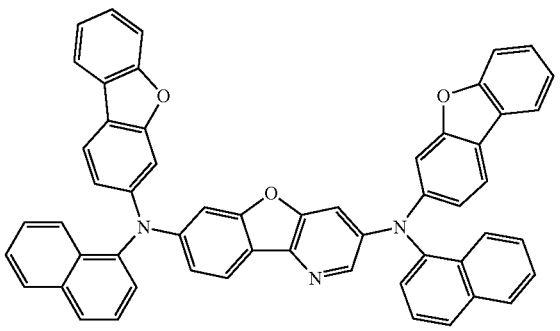

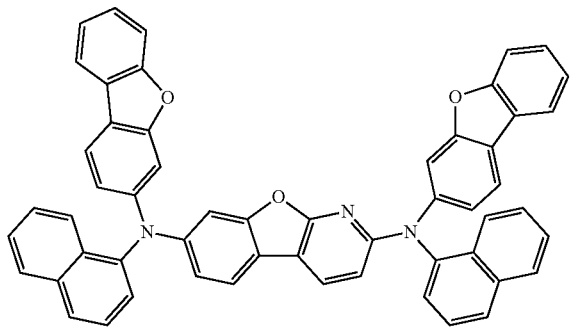
M005
M006
M007
M008
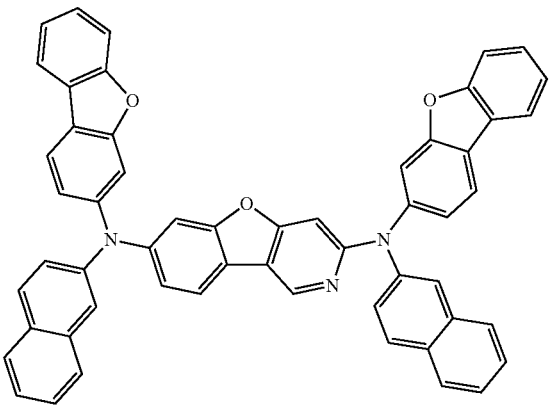
M009
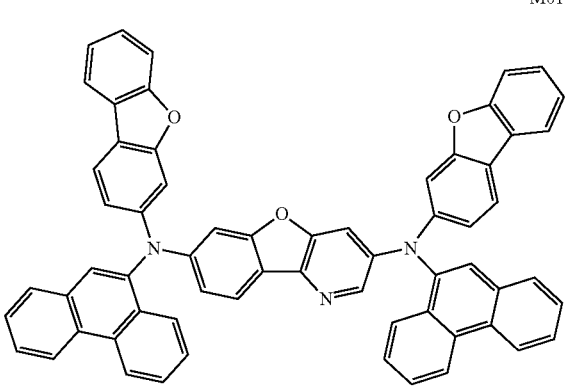
M010
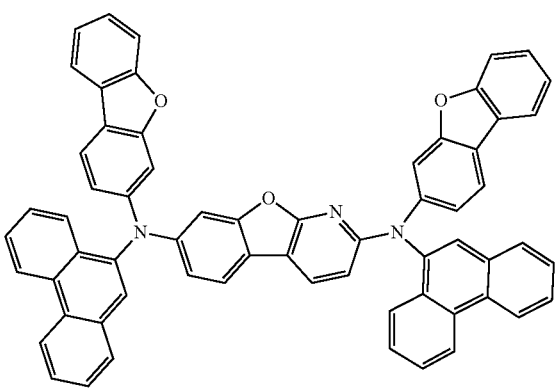
M011
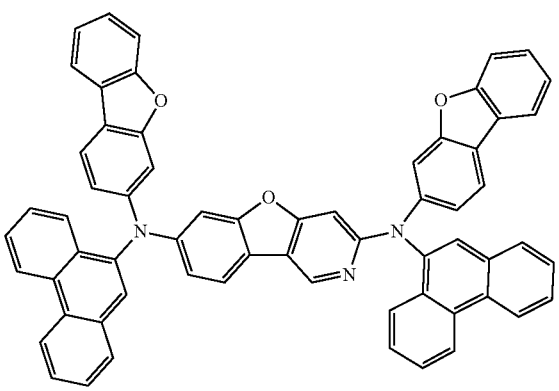
M012

M013
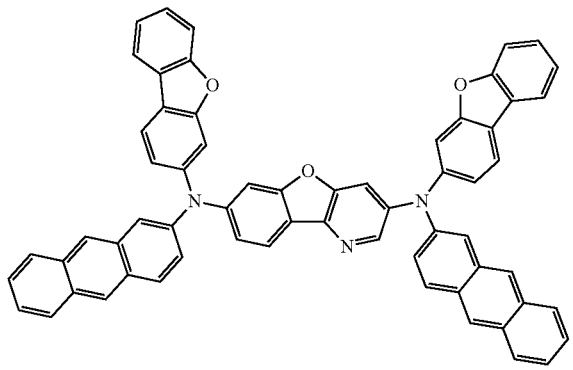
M014
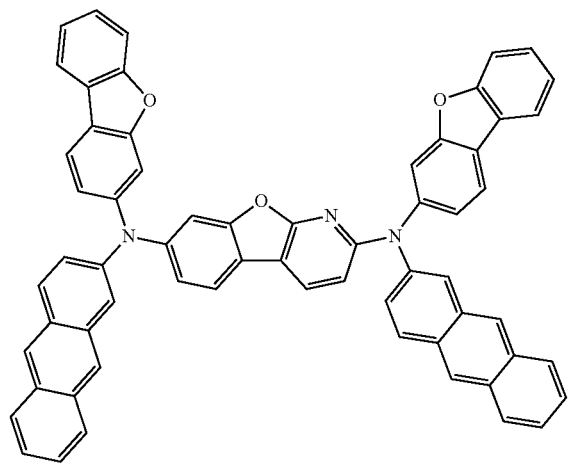
M015
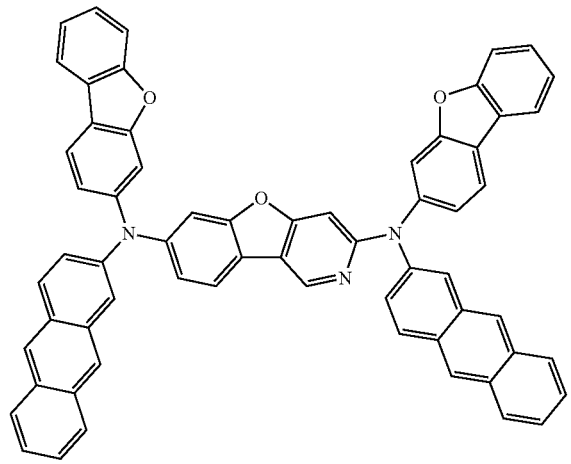
M016
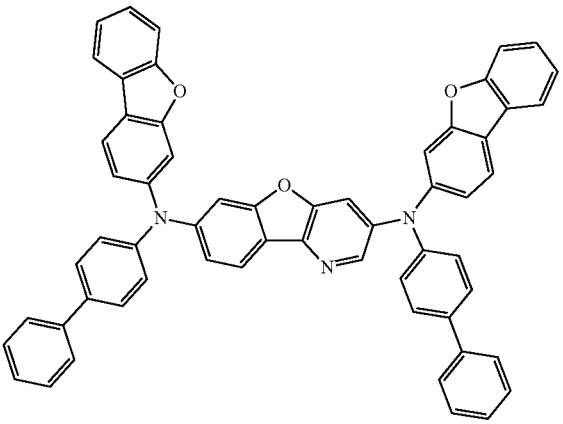
M017
M018
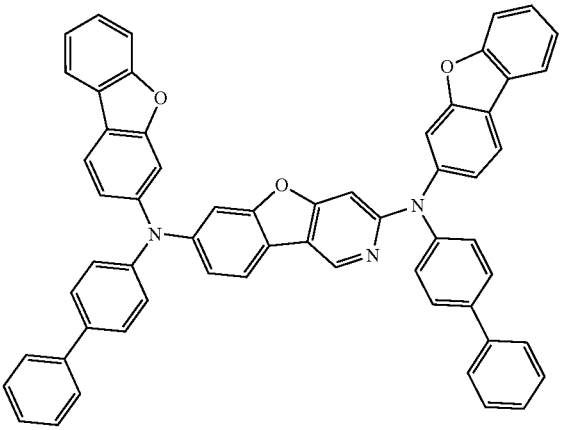

M019
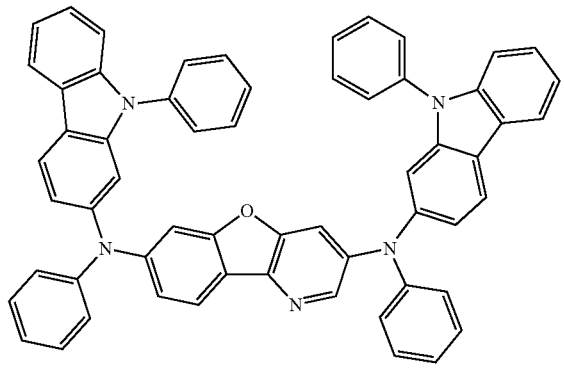
M020
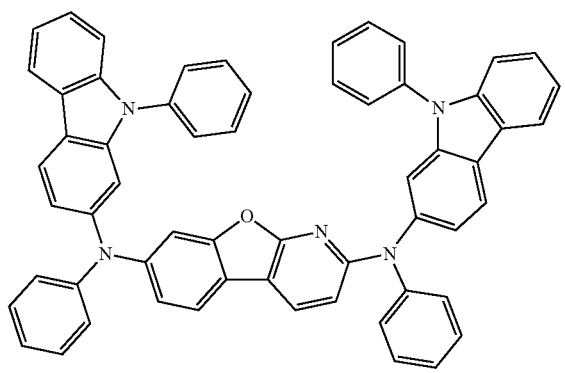
M021
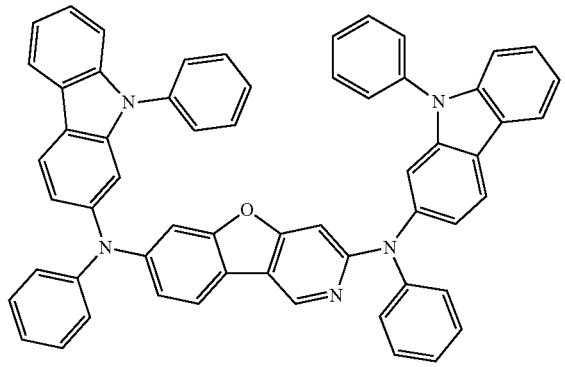
M022
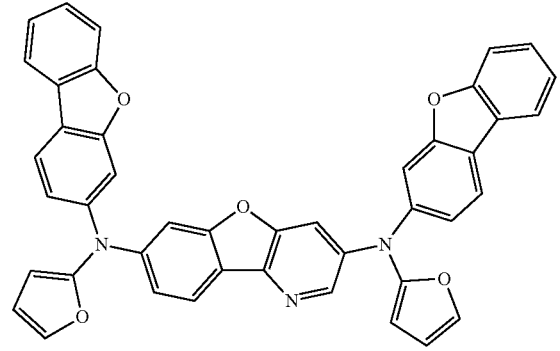
M023
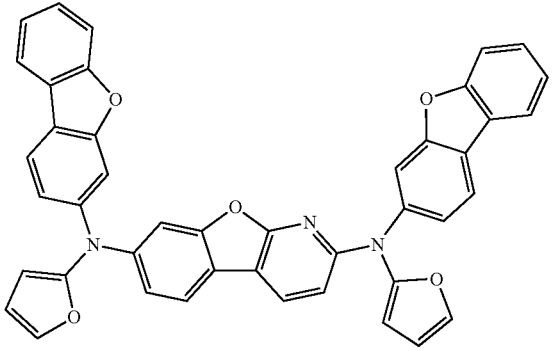
M024
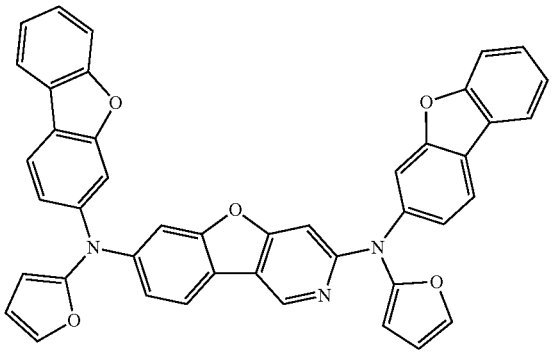
M025
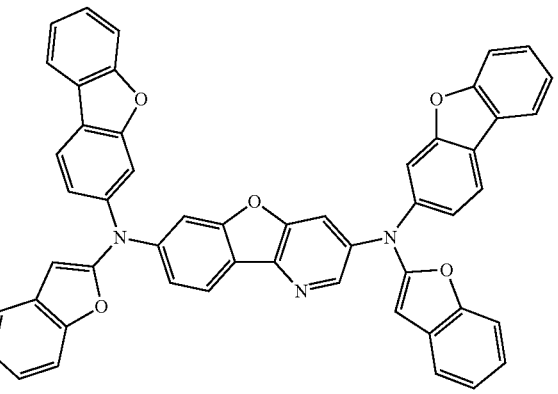
M026
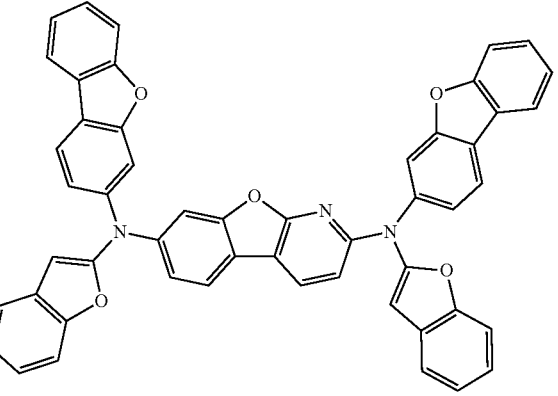

M027
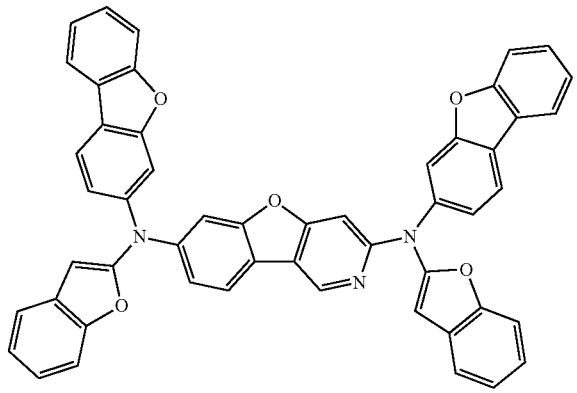
M028
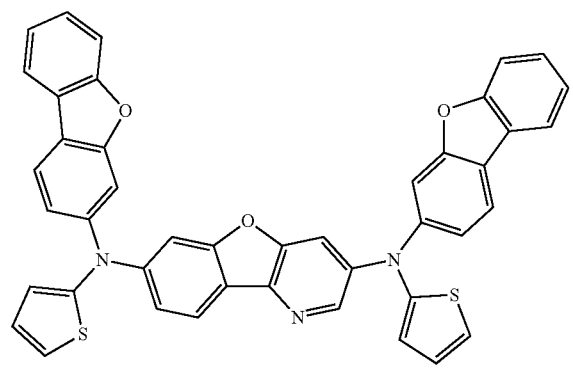
M029
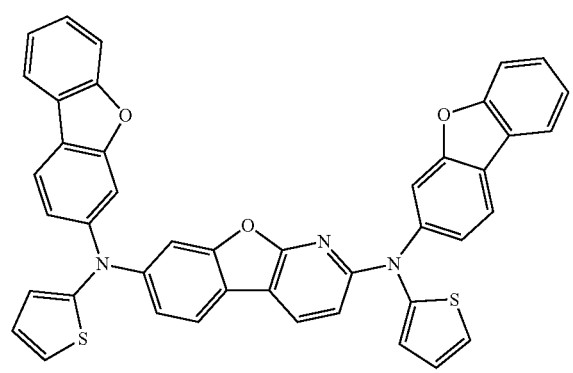
M030
M031
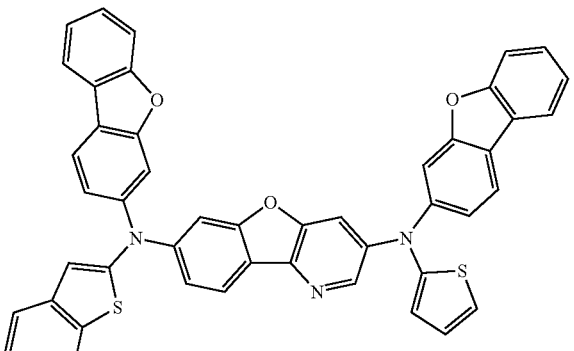
M032
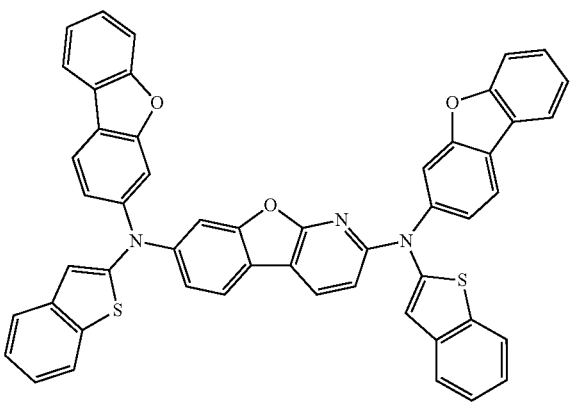
M033
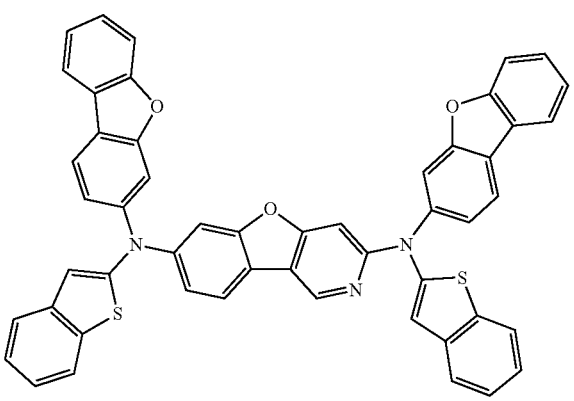
M034
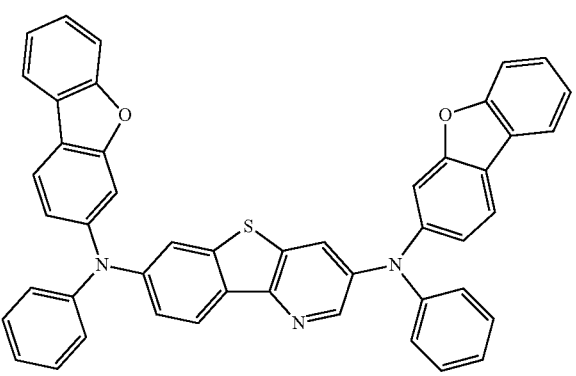

-continued
M035
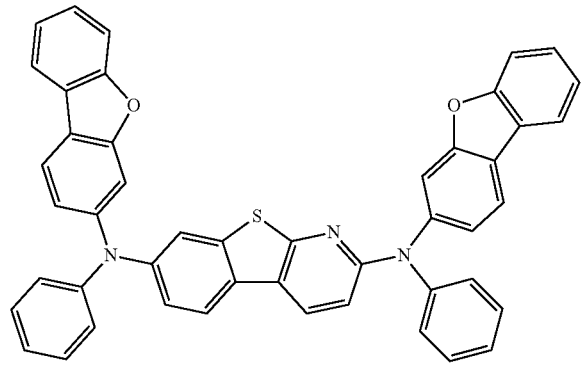
M036
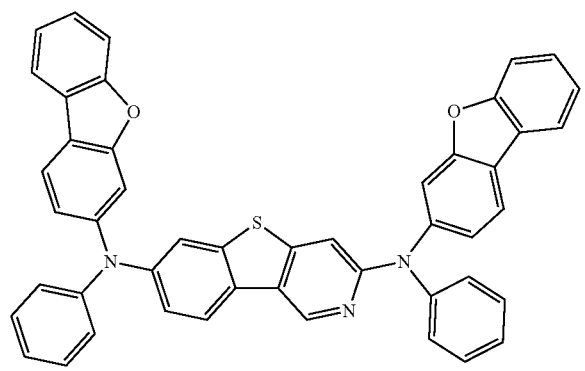
M037
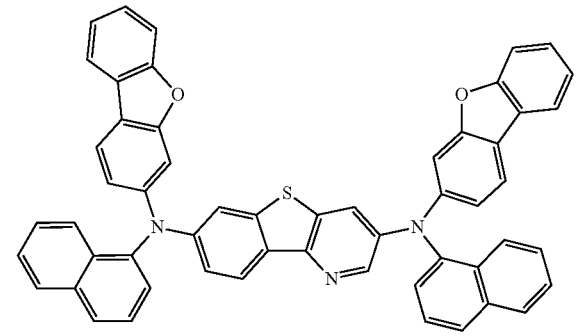
M038
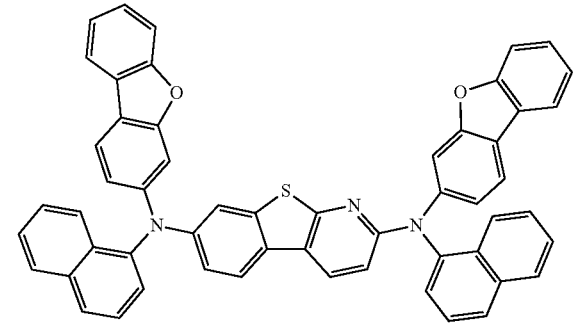
-continued
M039
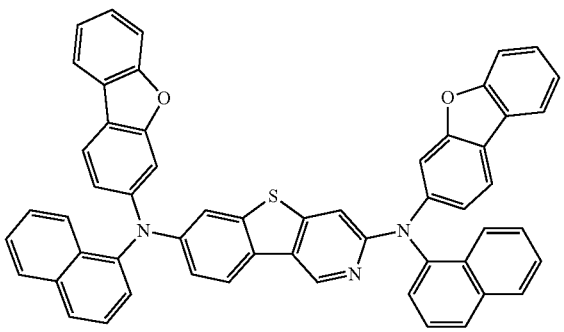
M040
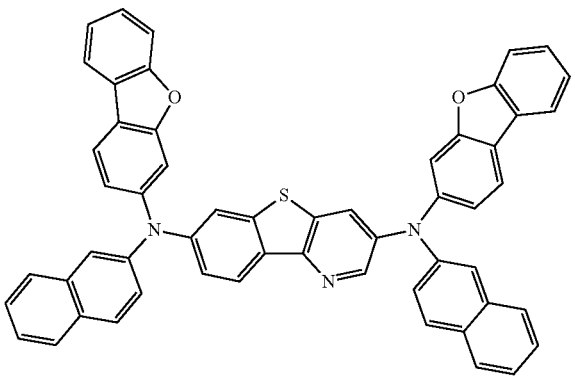
M041
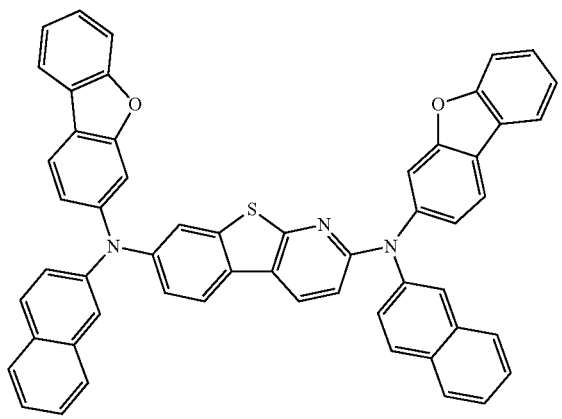
M042
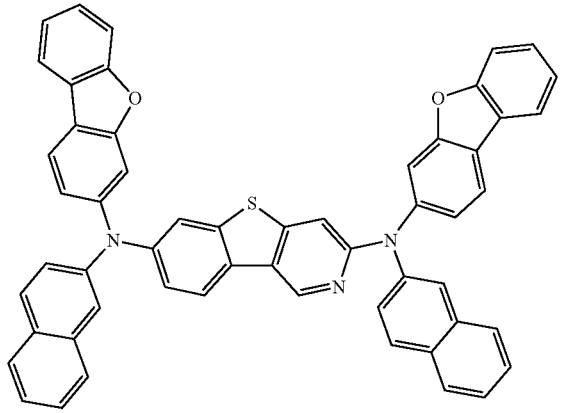

201
-continued
M043
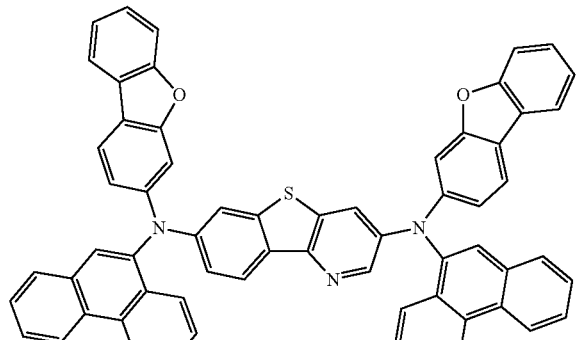
M044
M045
M046
202
-continued
M047
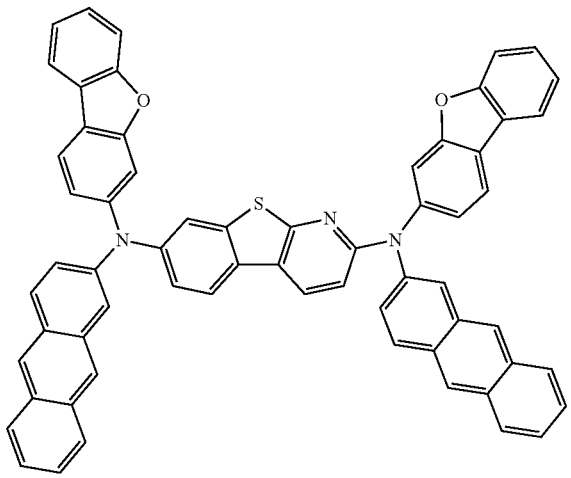
M048
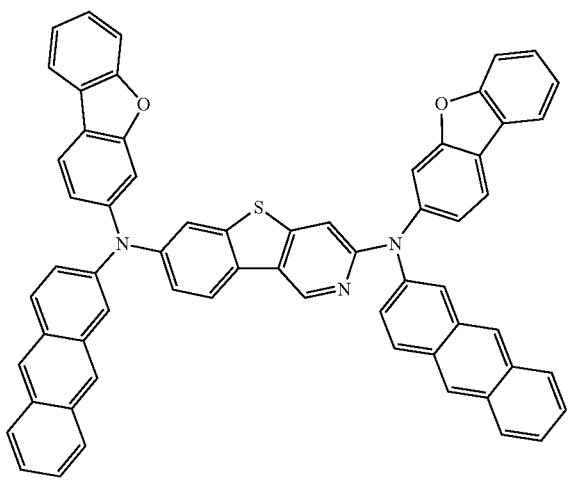
M049
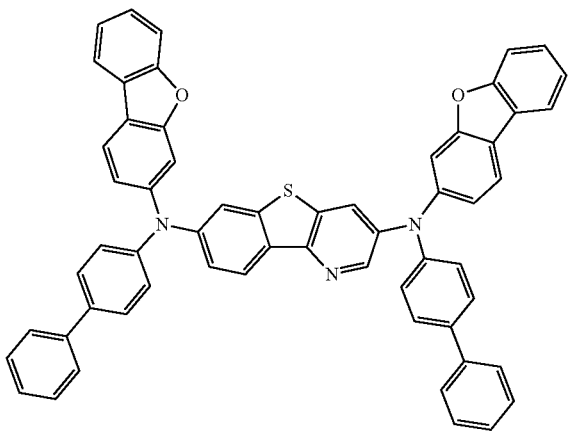

-continued
M050
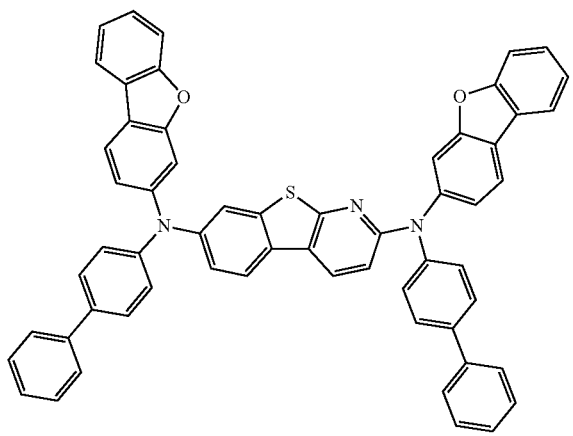
M051
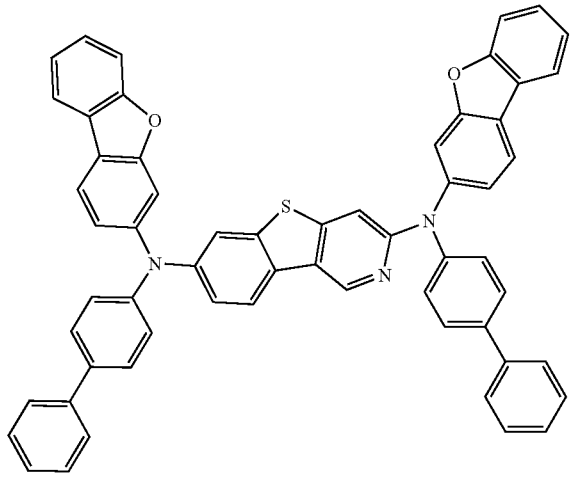
M052
-continued
M053
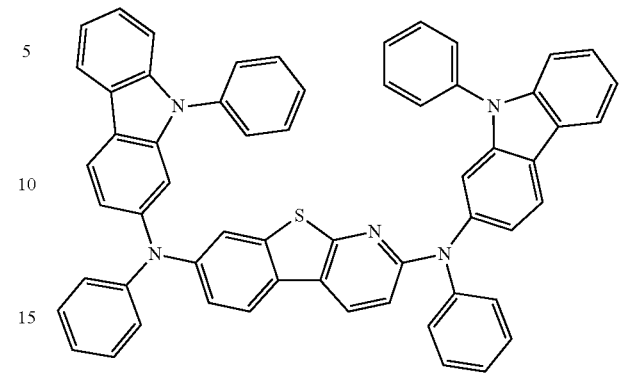
M054
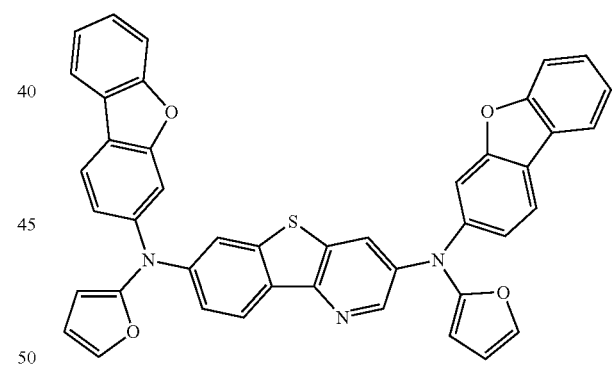
M055
M056
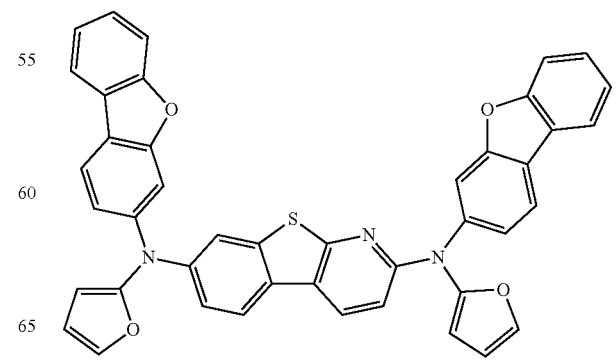

205
-continued
M057
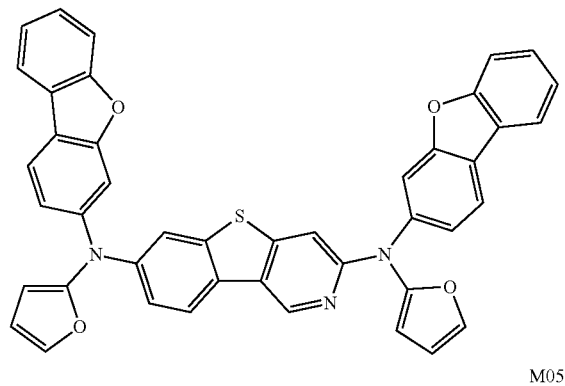
M058
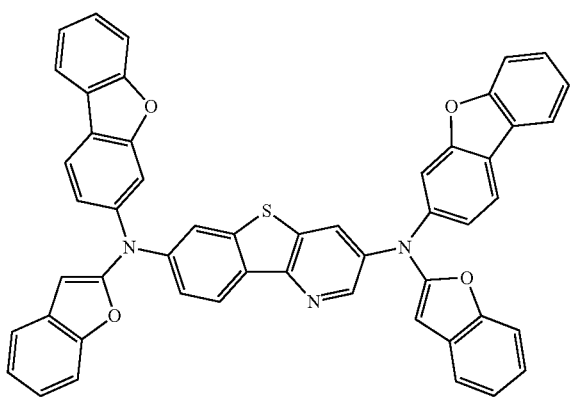
M059
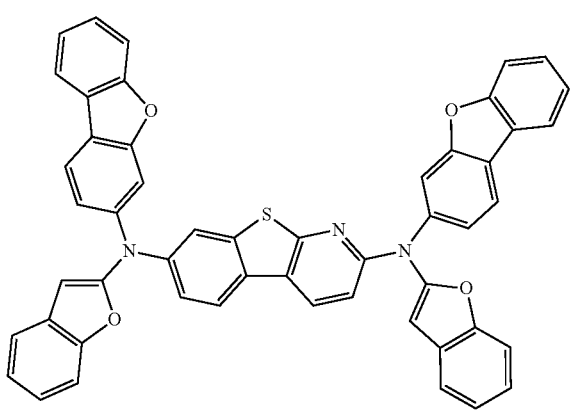
M060
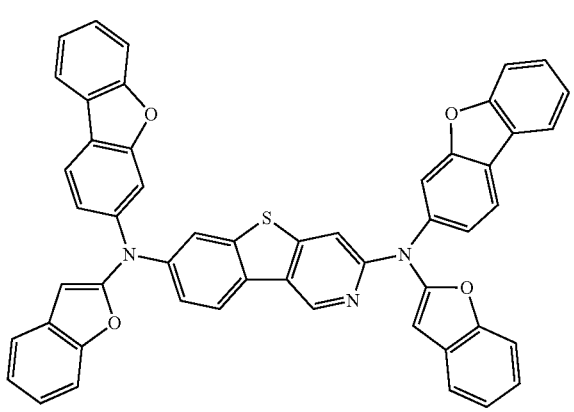
206
-continued
M061
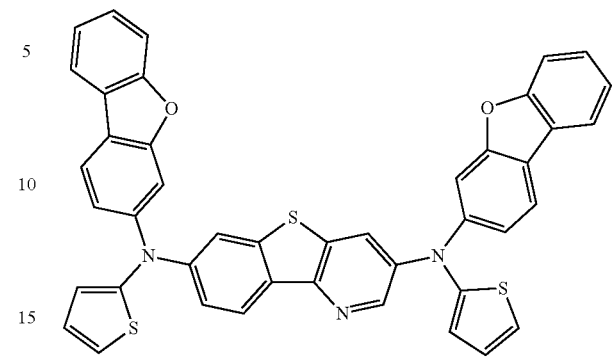
M062
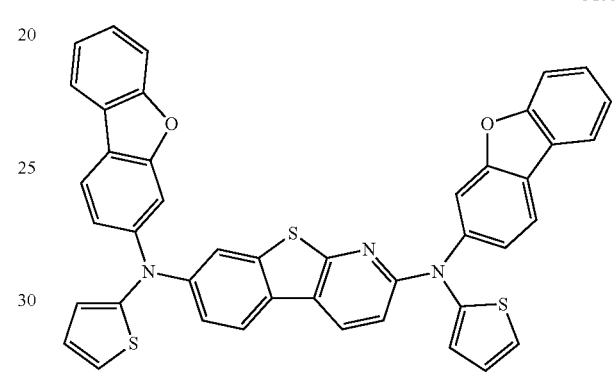
M063
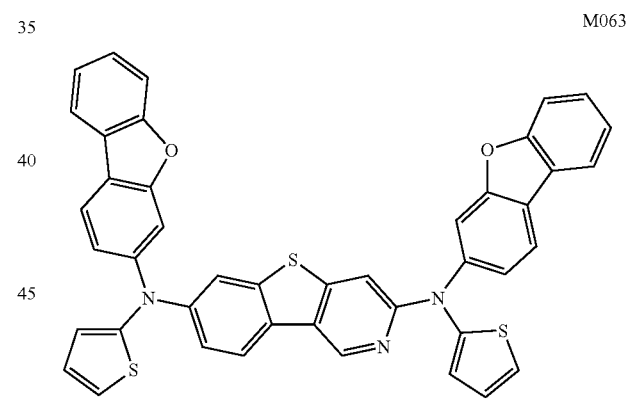
M064
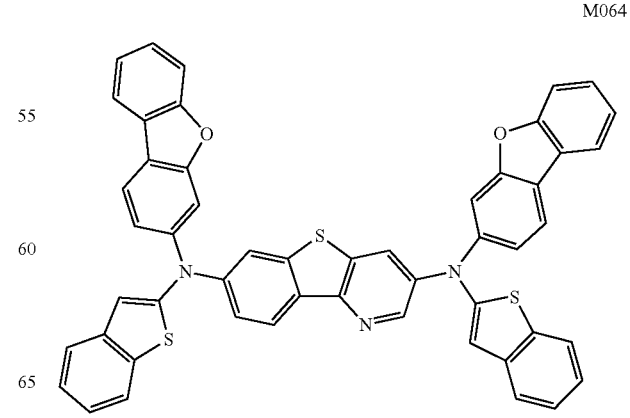

M065
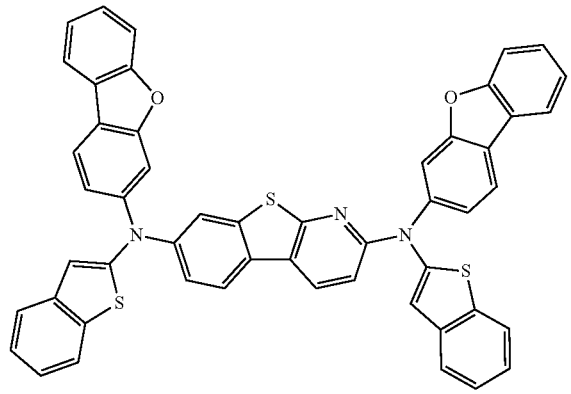
M066
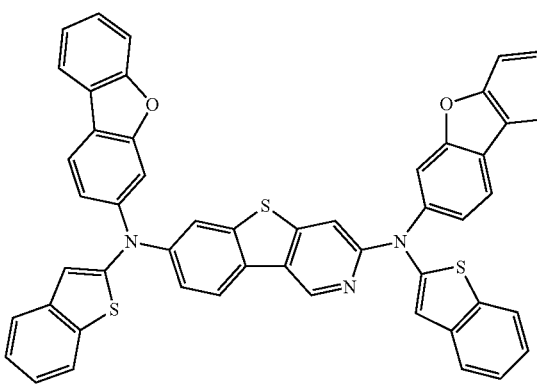
20. The heterocyclic compound according to claim 1, wherein the heterocyclic compound has any one of following structures:
M067
M068
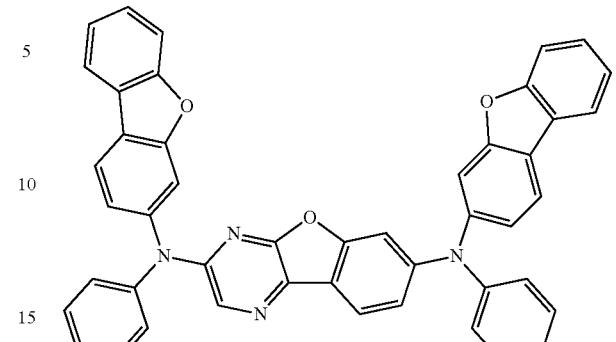
M069
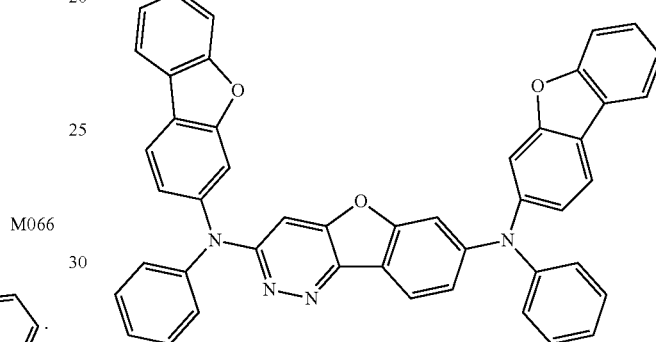
M070
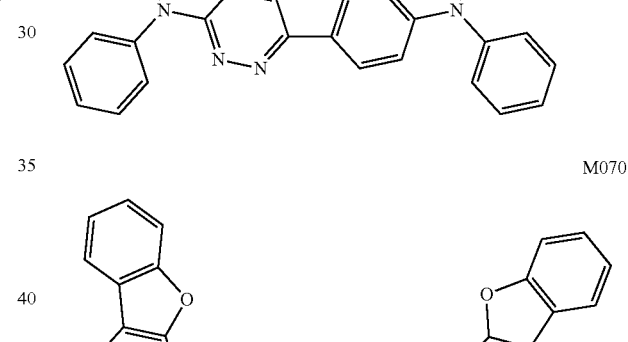
M071
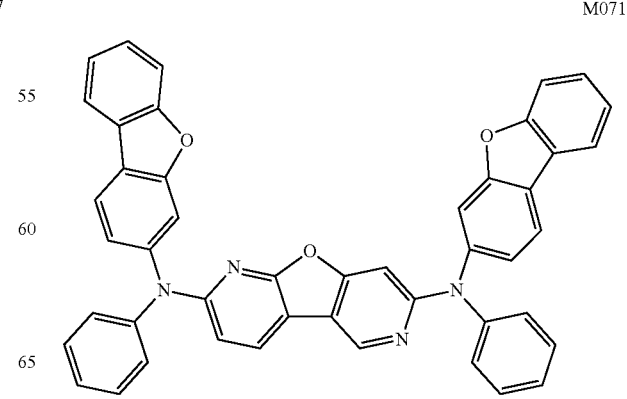

-continued
M072
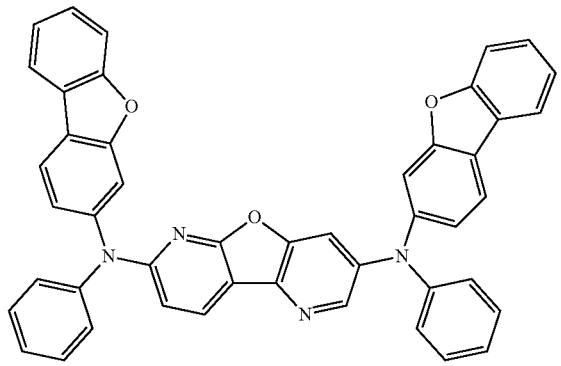
M073
M074
M075
-continued
M076
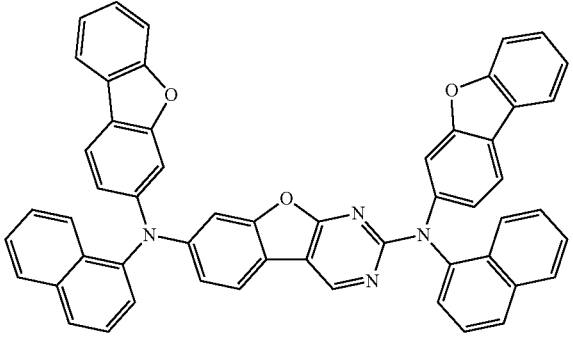
M077
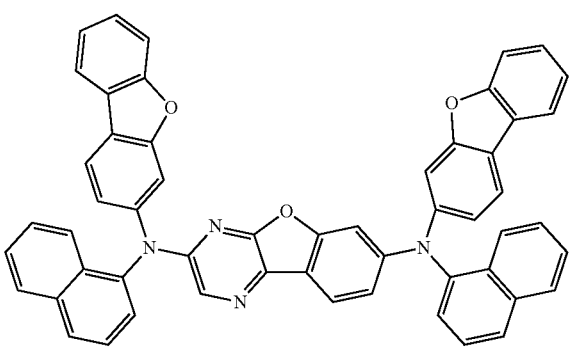
M078
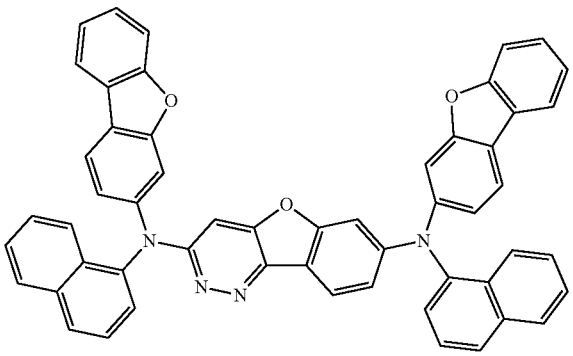
M079
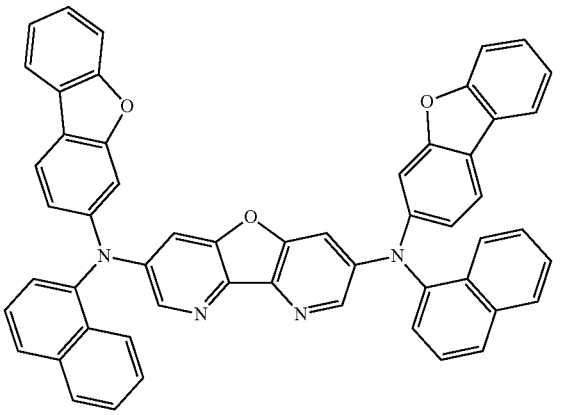

M080
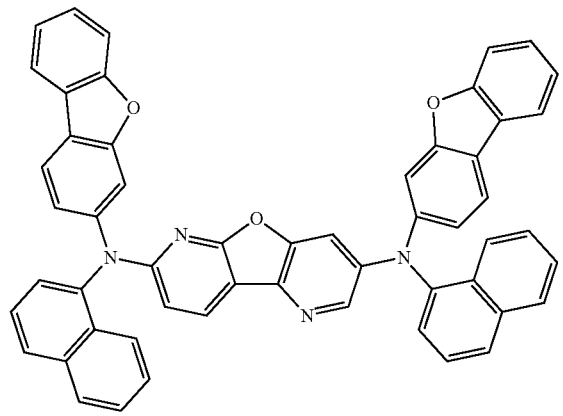
M081
M082
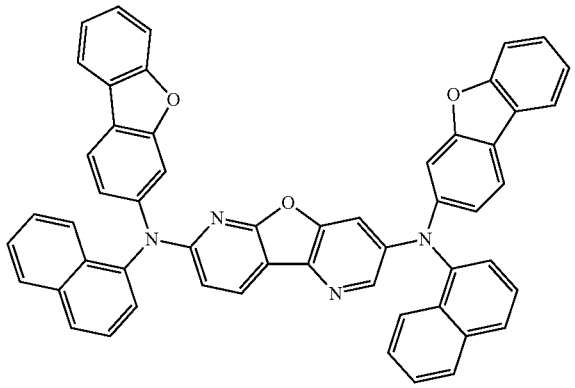
M083
M084
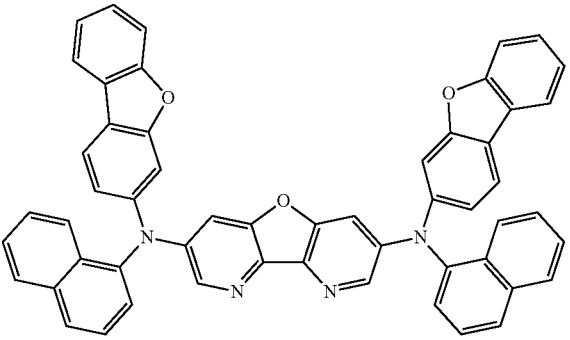
M085
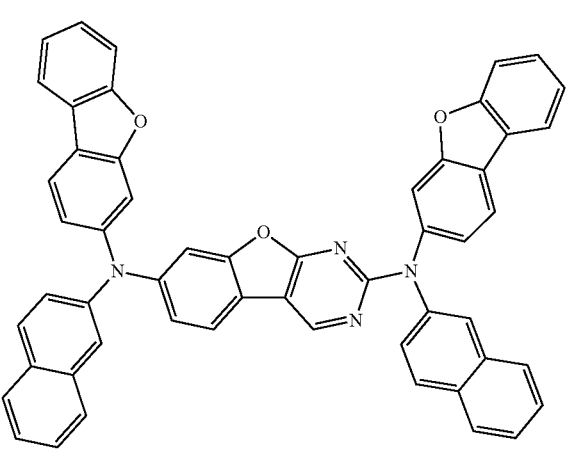
M086
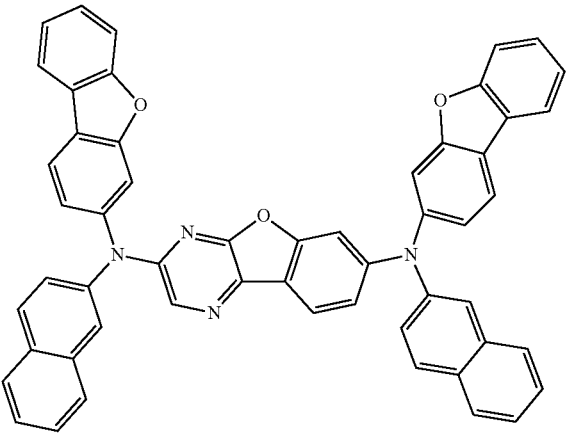

M087
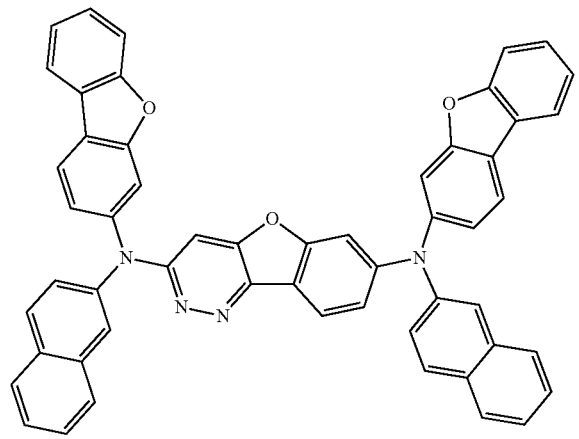
M090
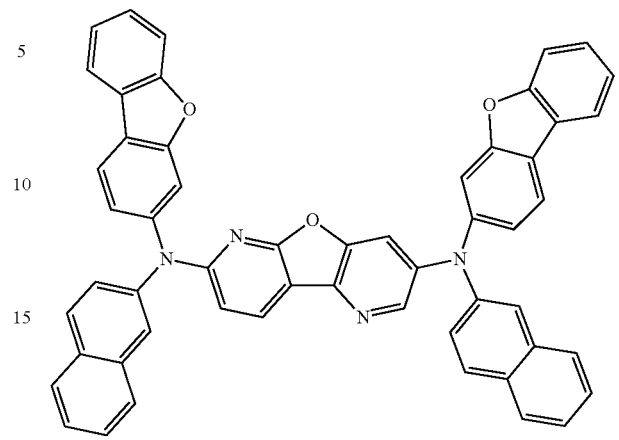
M088
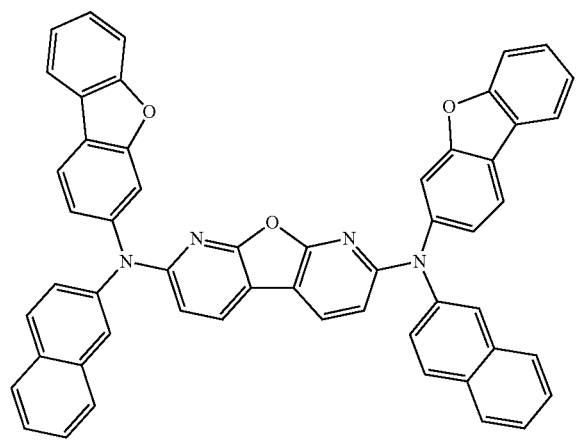
M091
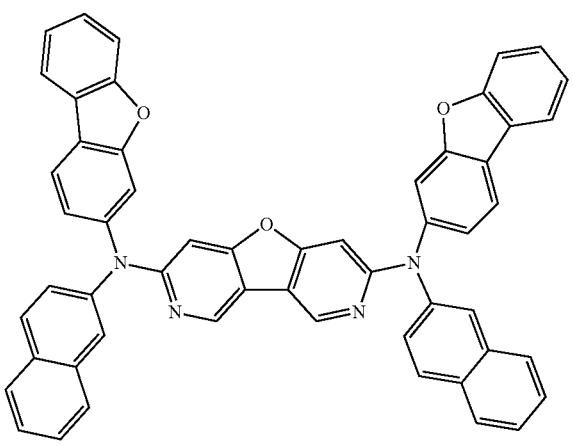
M089
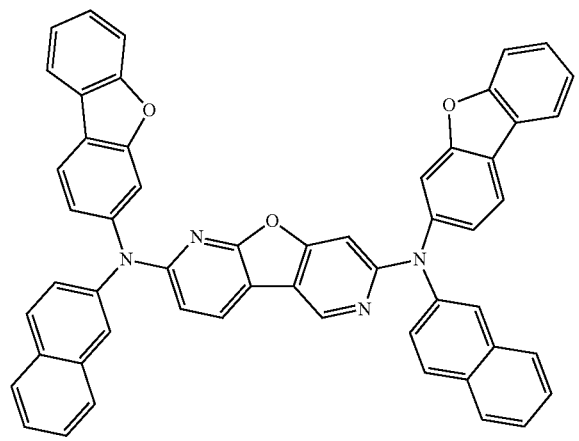
M092
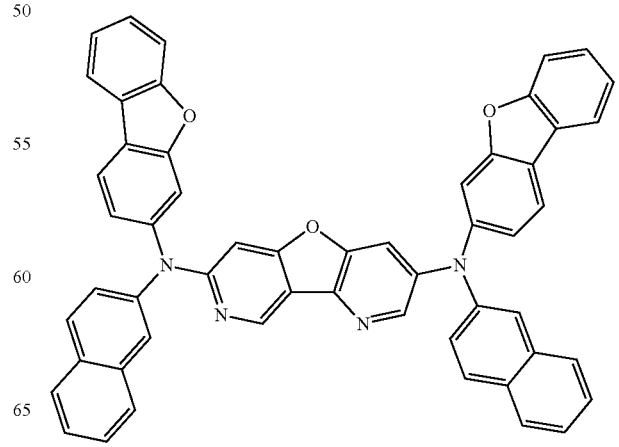

M093
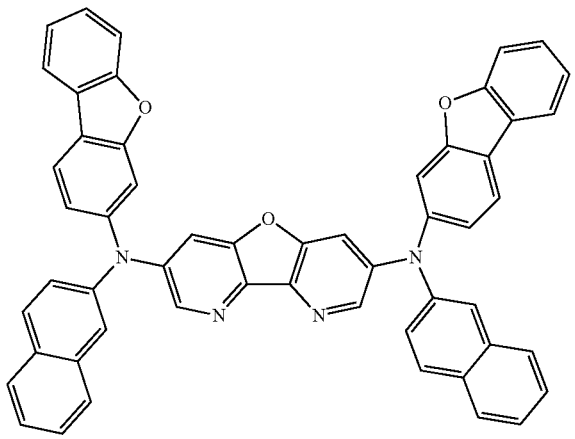
M096
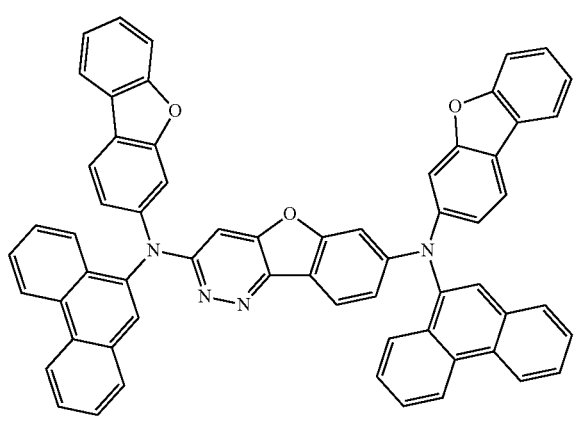
M094
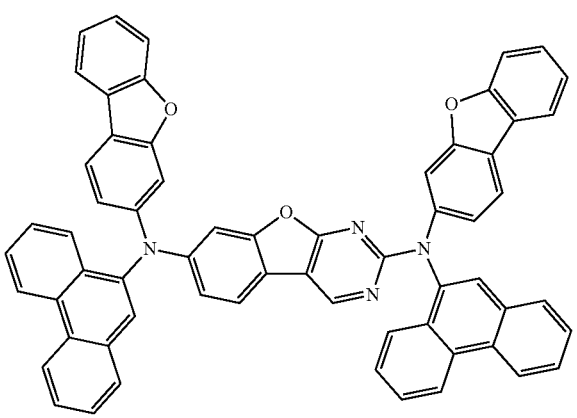
M097
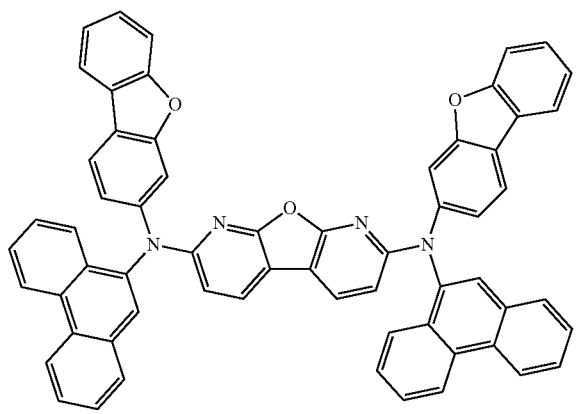
M095
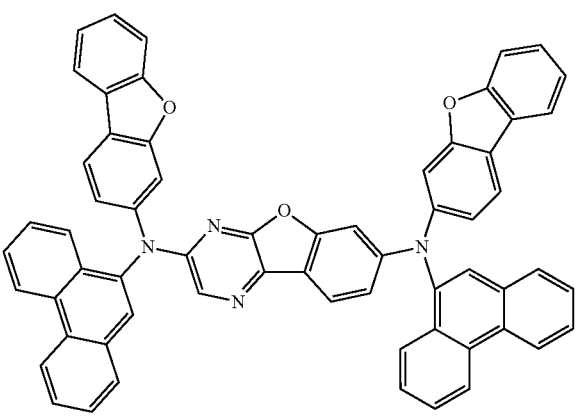
M098
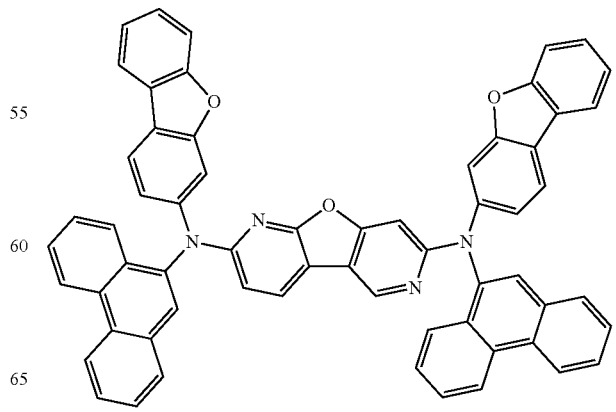

M099
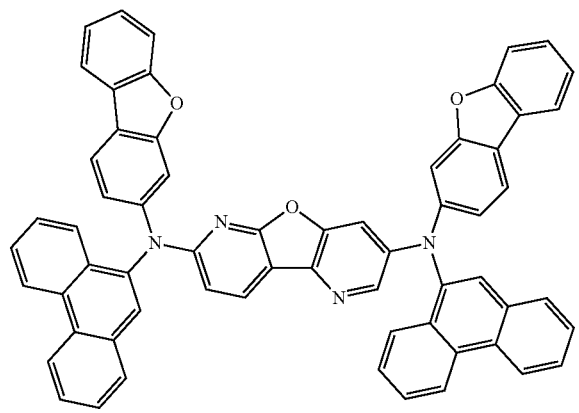
M102
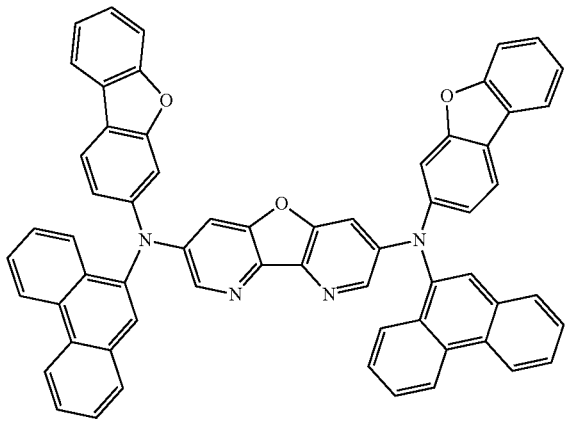
M100
M103
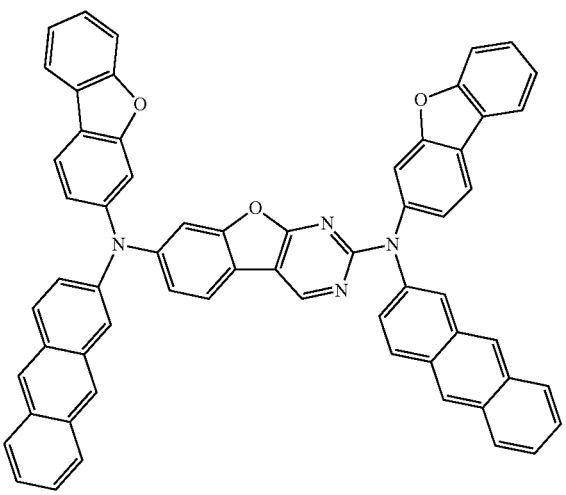
M101
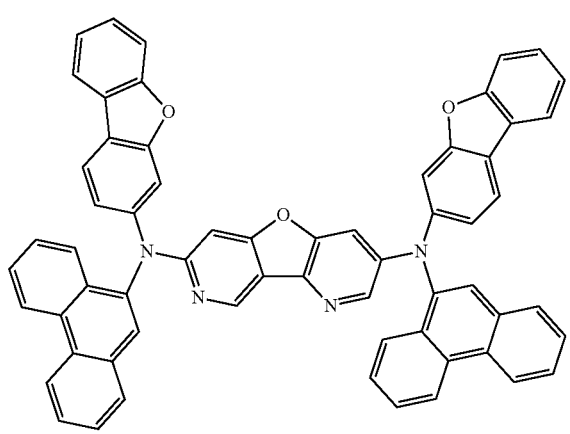
M104
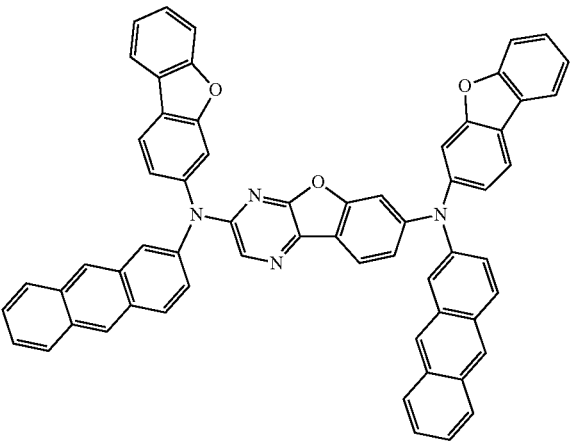

M105
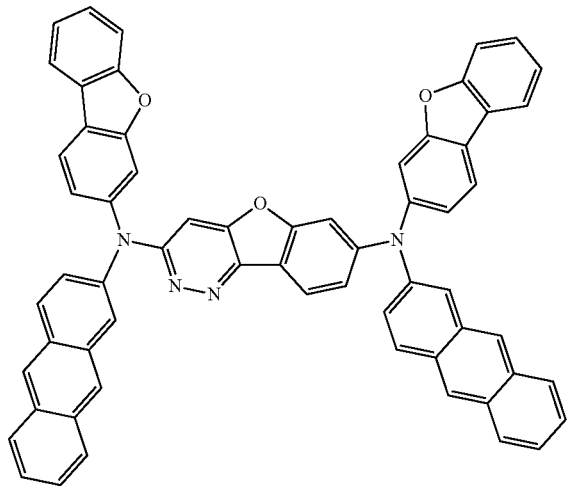
M108
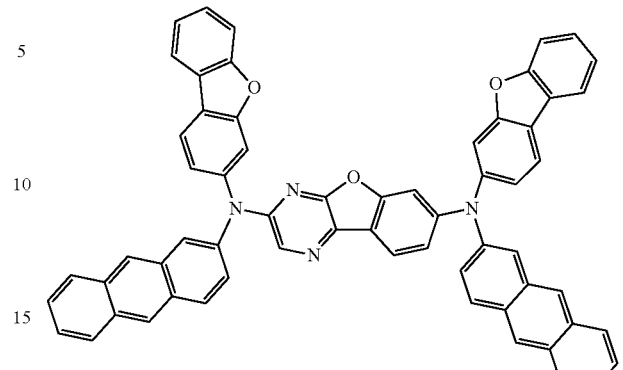
M106
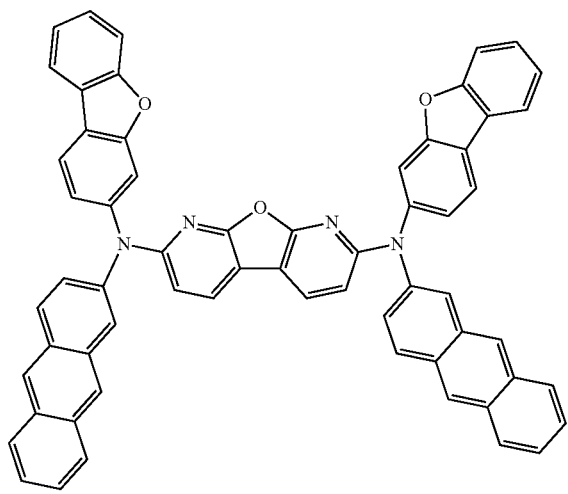
M109
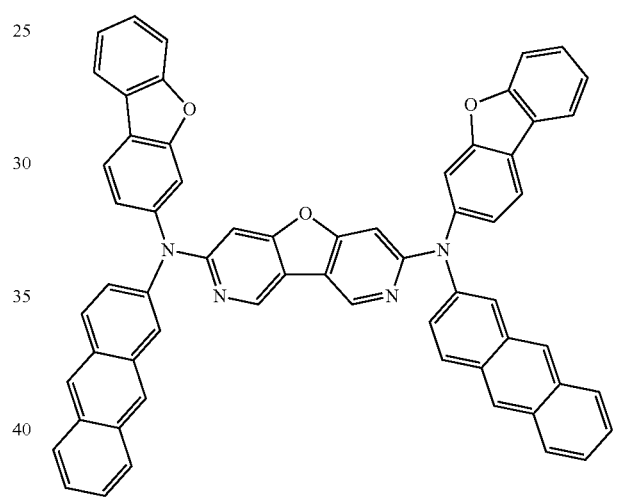
M107
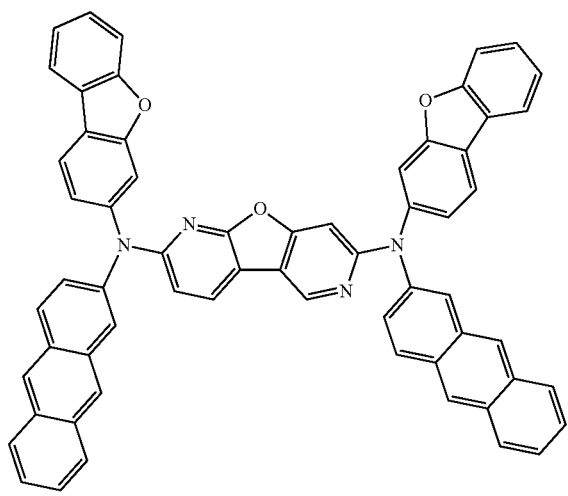
M110
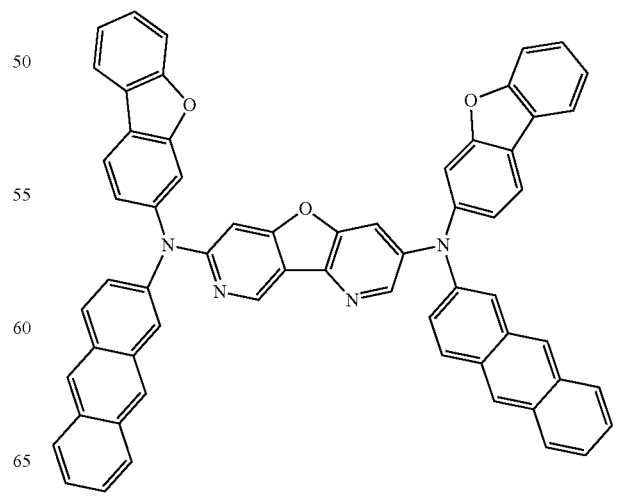

M111
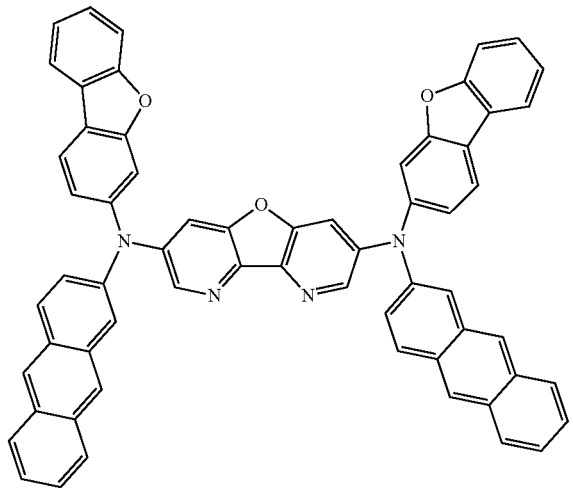
M114
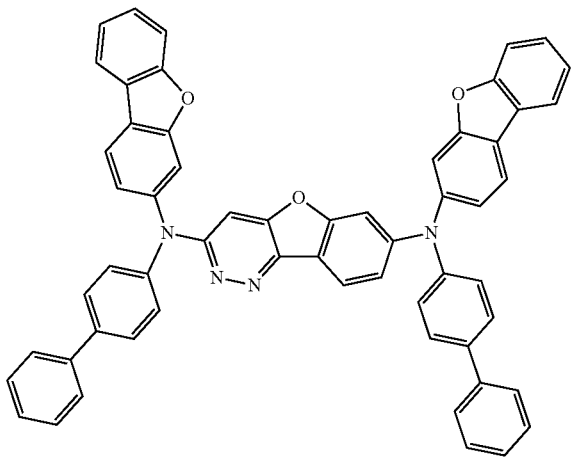
M112
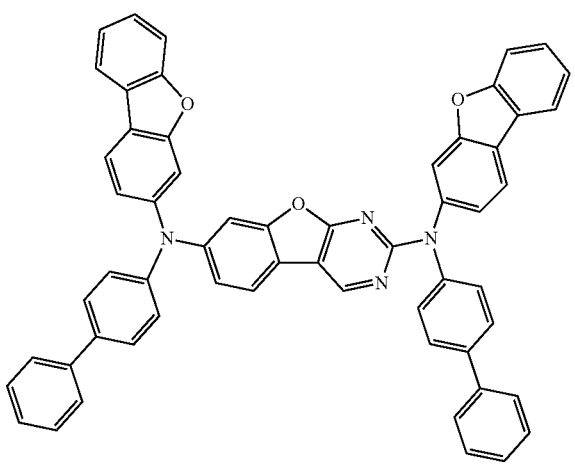
M115
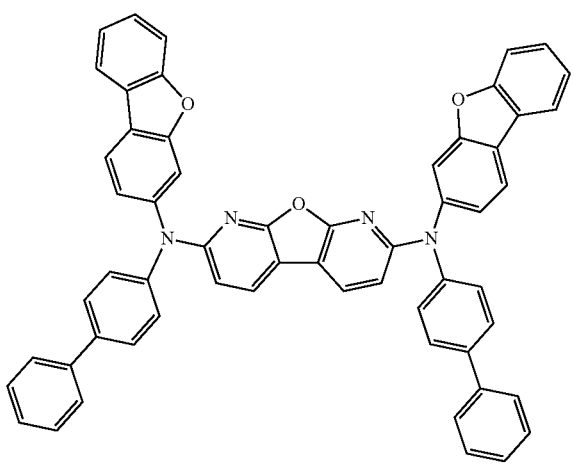
M113
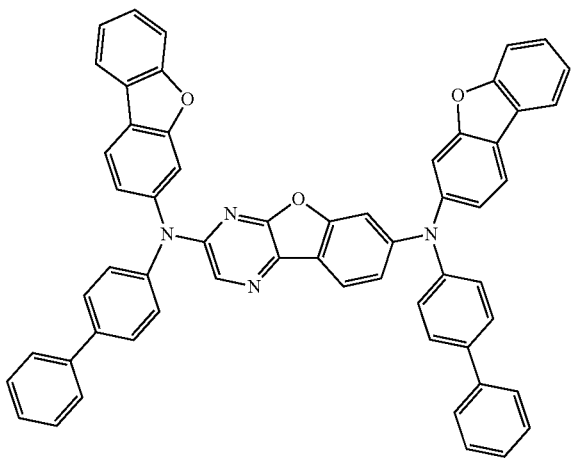
M116
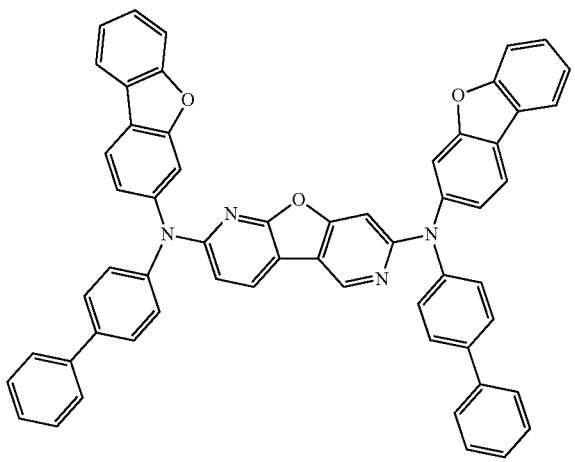

M117
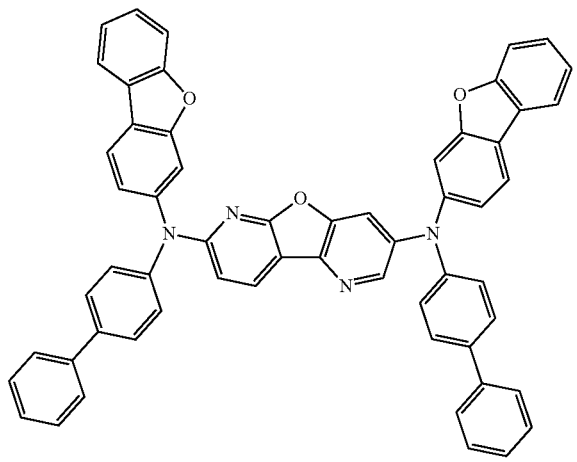
M120
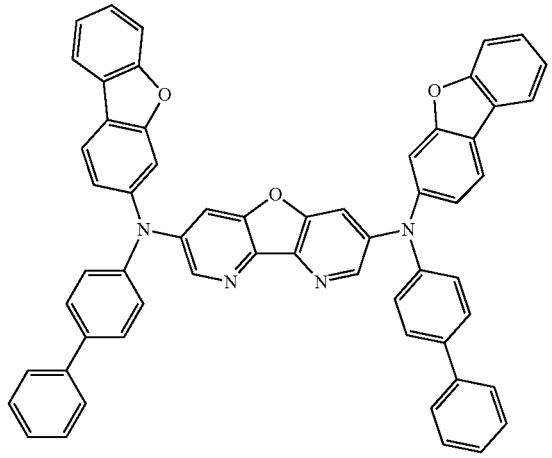
M118
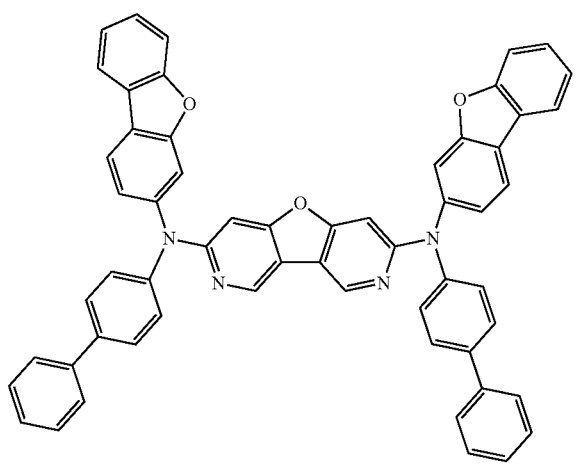
M121
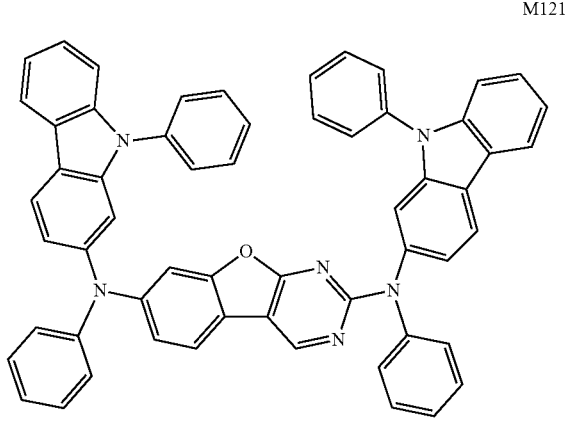
M119
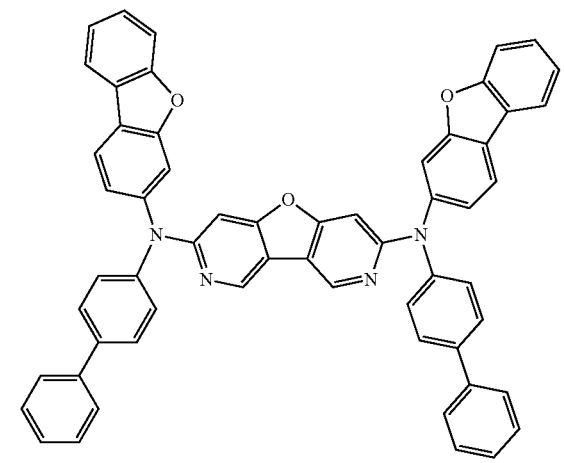
M122
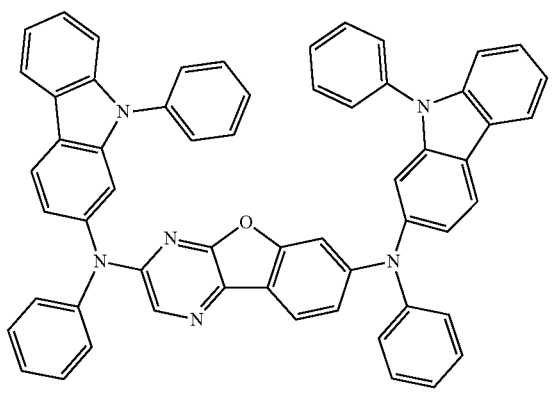

M123
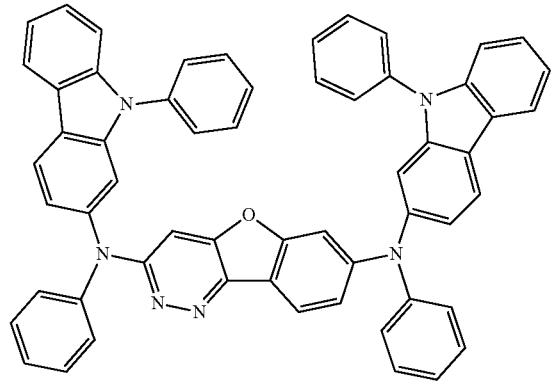
M127
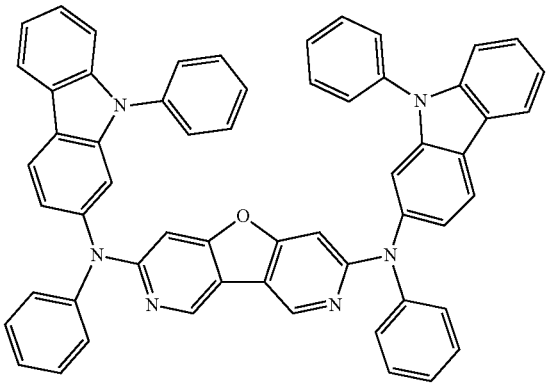
M124
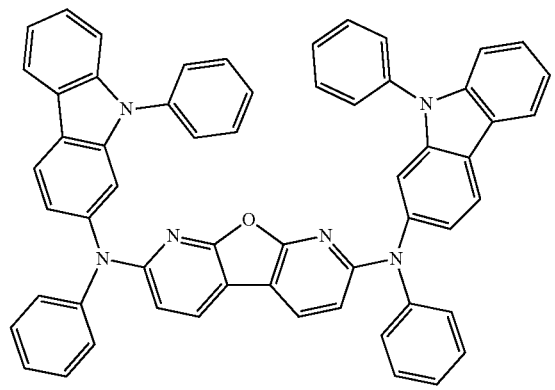
M128
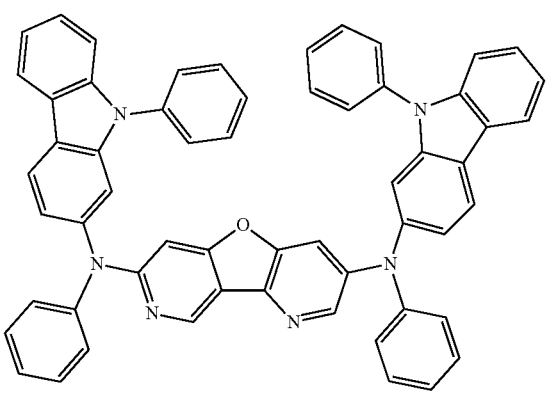
M125
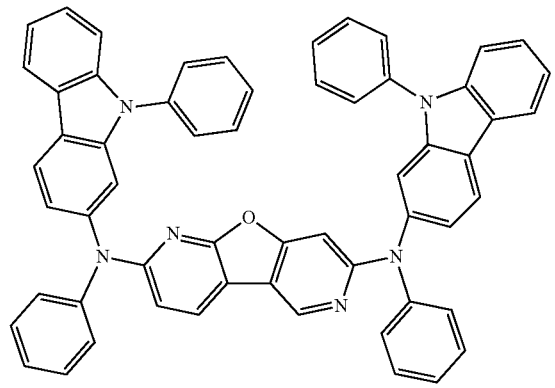
M129
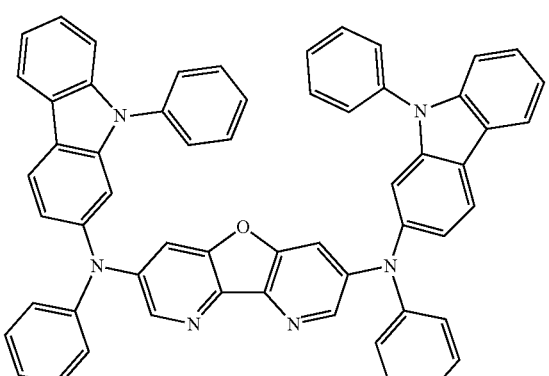
M126
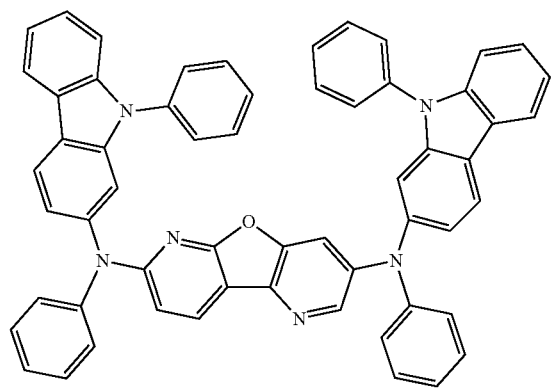
M130
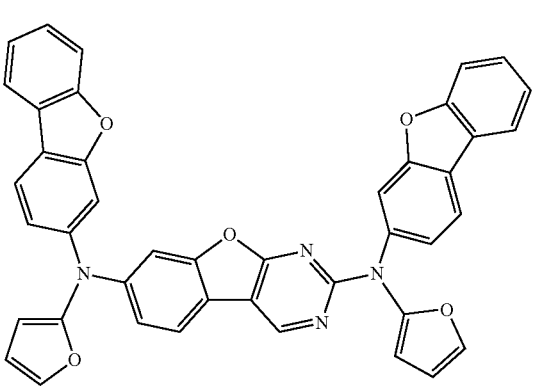

M131
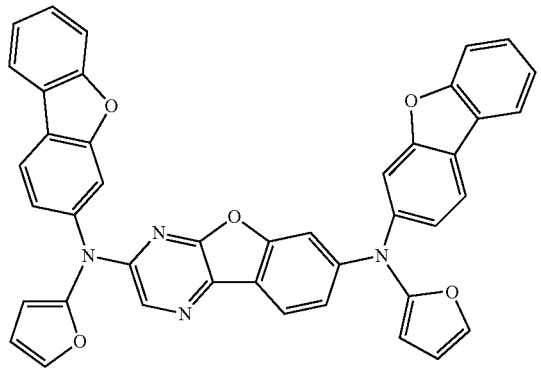
M132
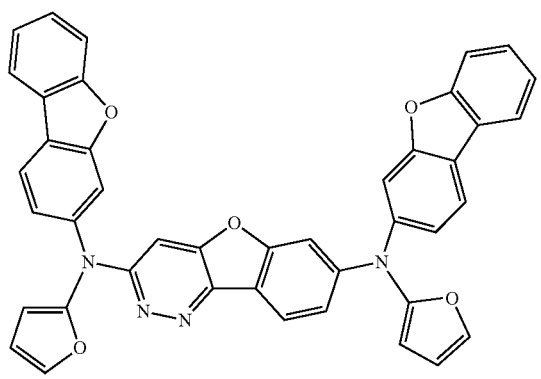
M133
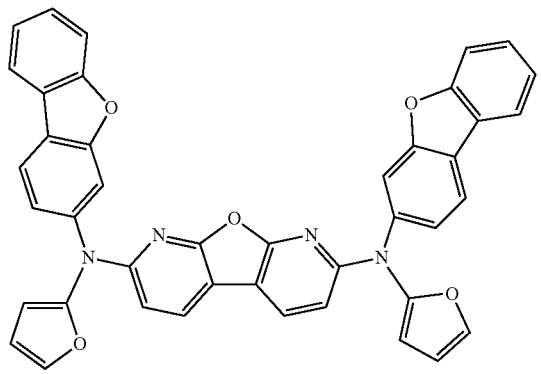
M134
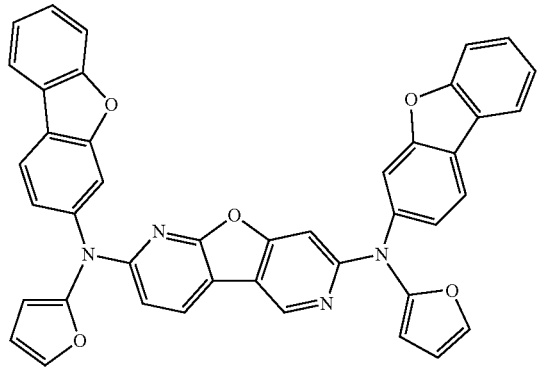
M135
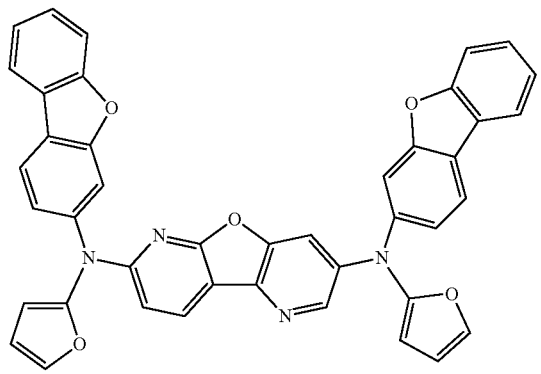
M136
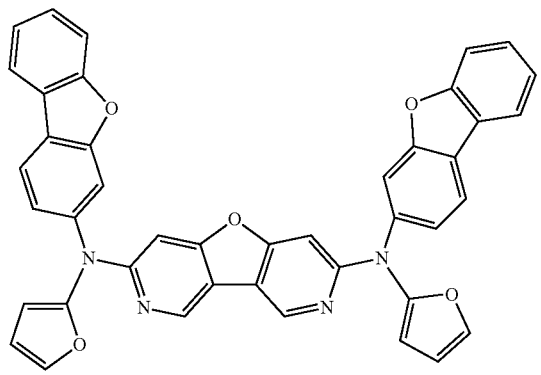
M137
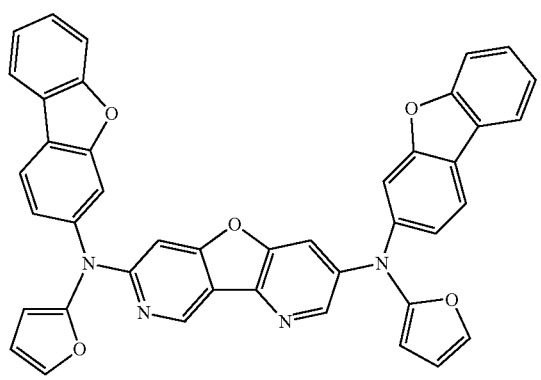
M138
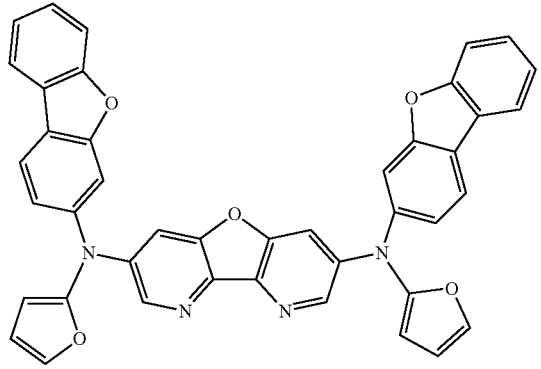

M139
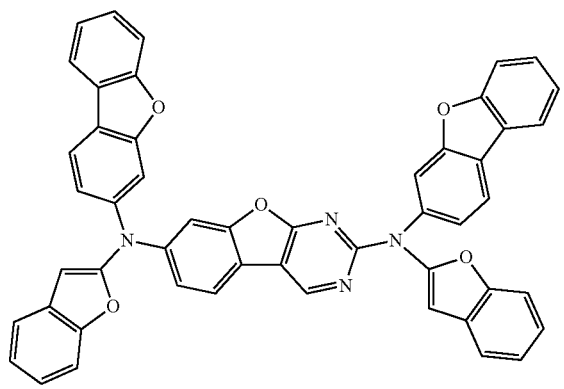
M140
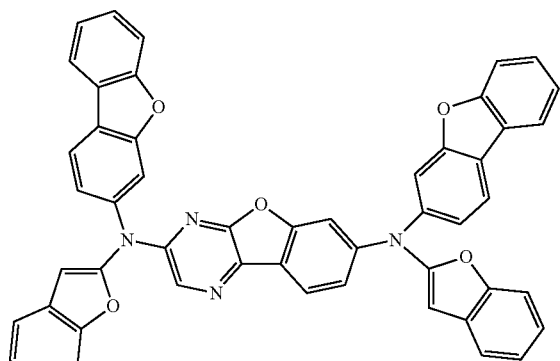
M141
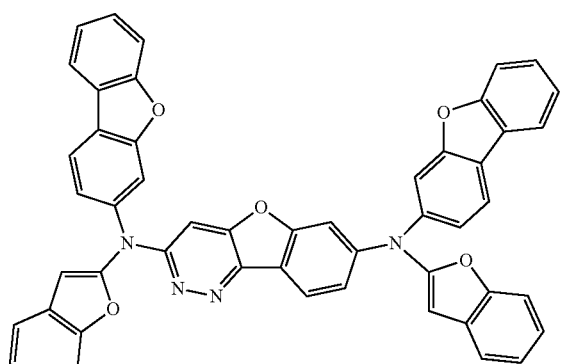
M142
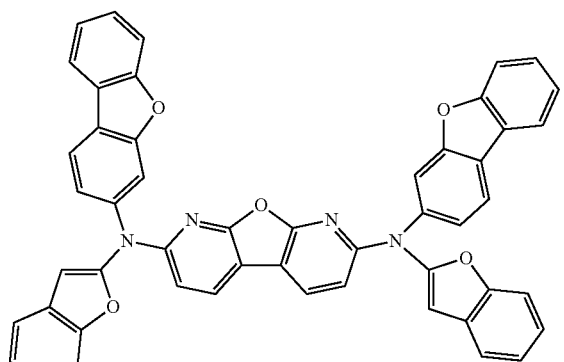
M143
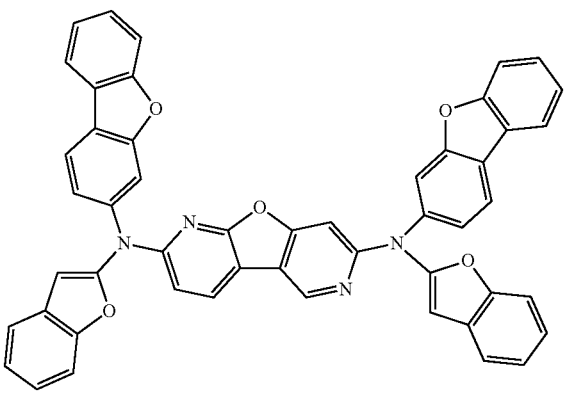
M144
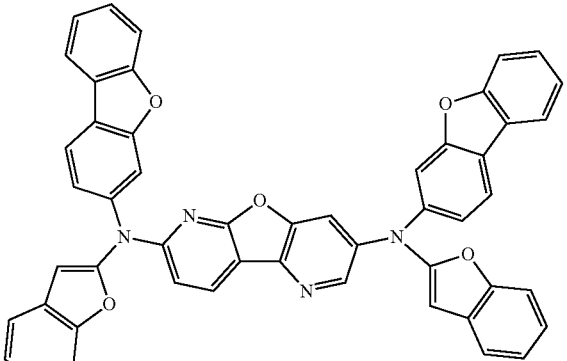
M145
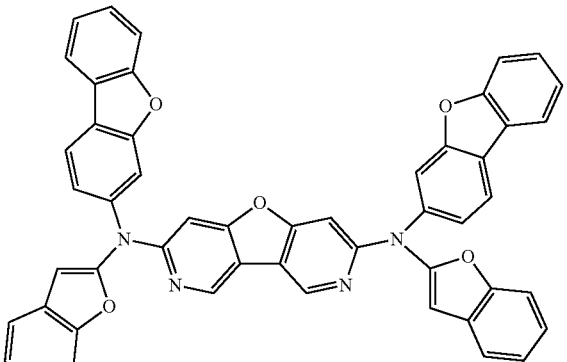
M146
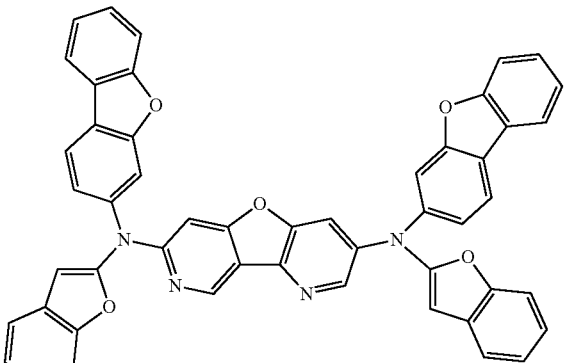

231
-continued
M147
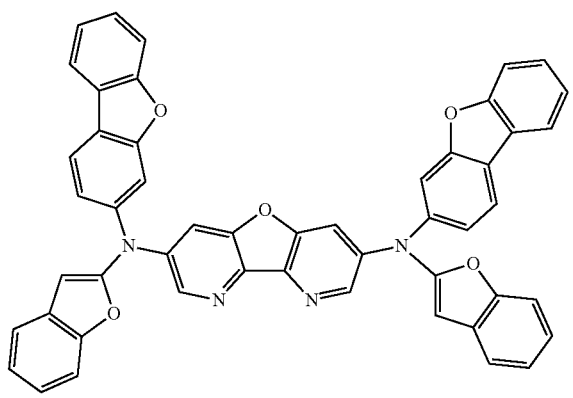
M148
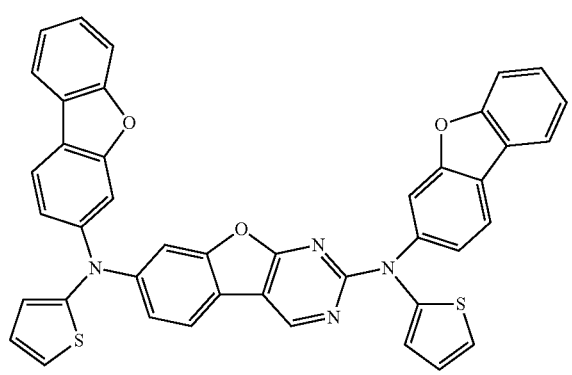
M149
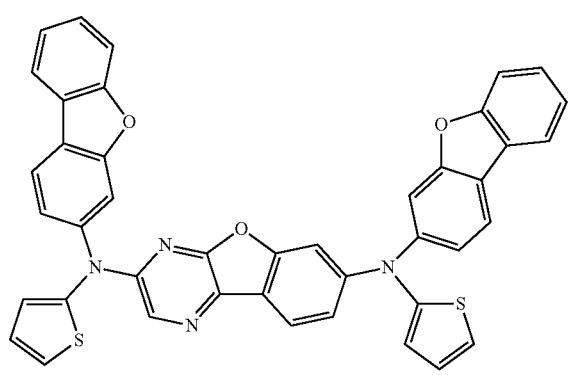
M150
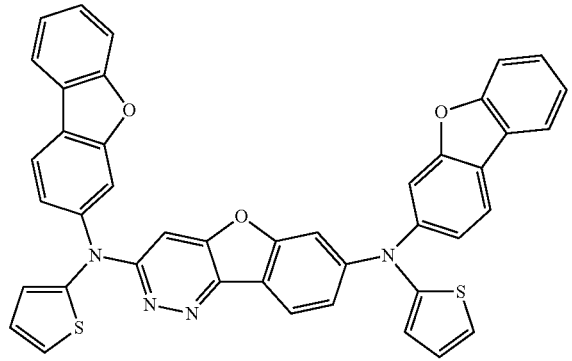
232
-continued
M151
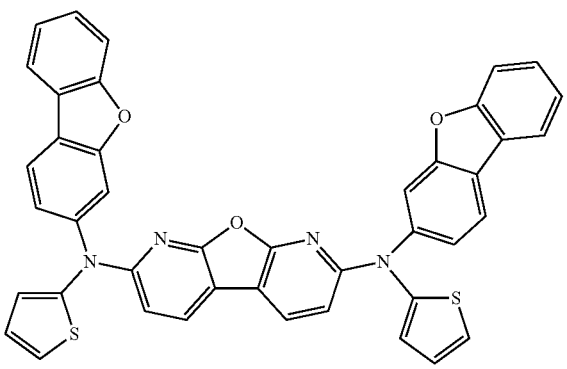
M152
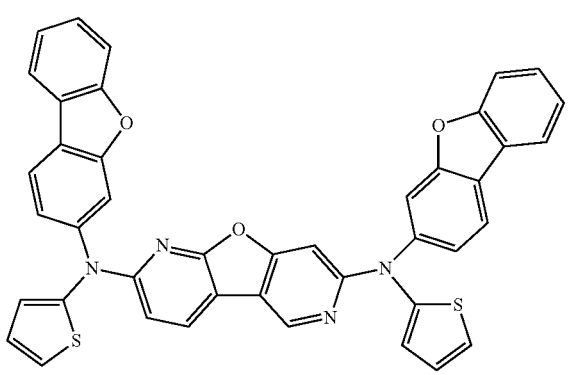
M153
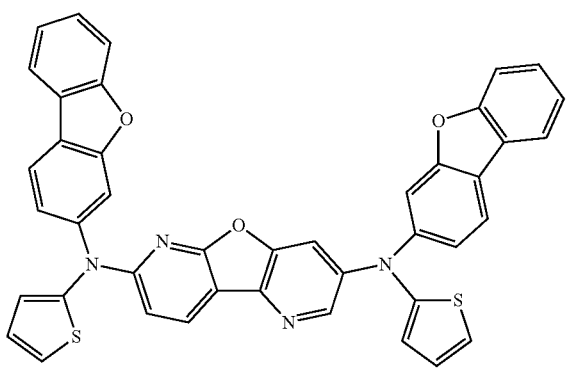
M154
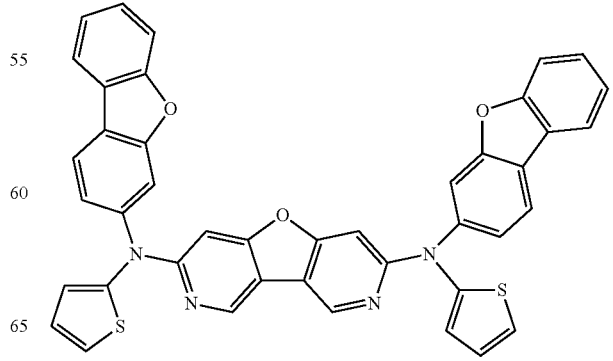

M155
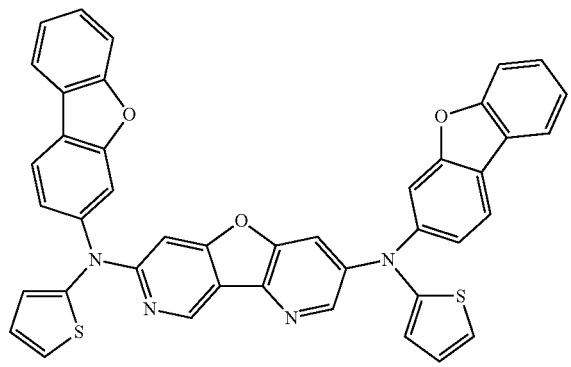
M156
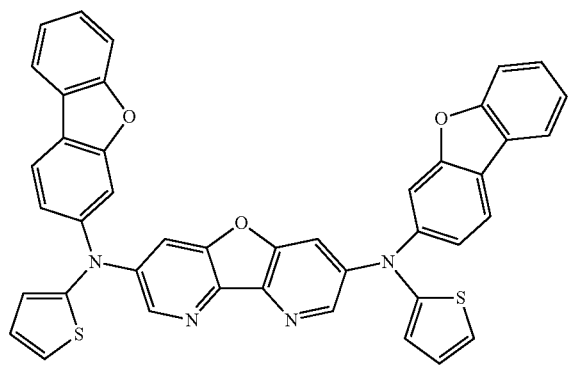
M157
M158
M159
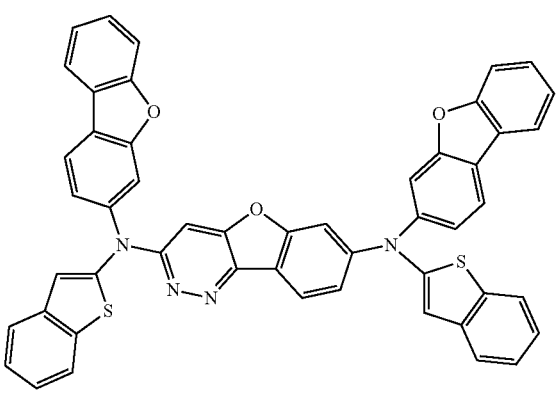
M160
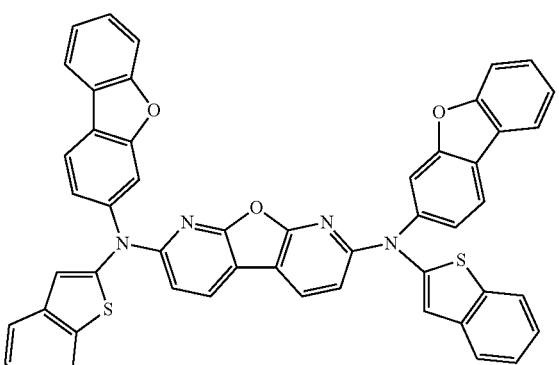
M161
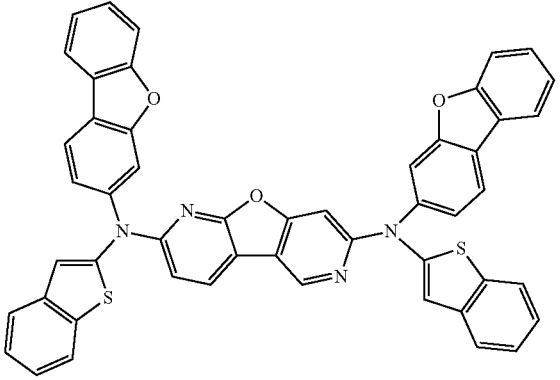
M162
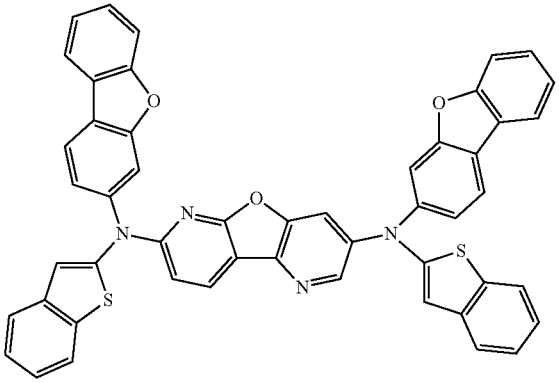

M163
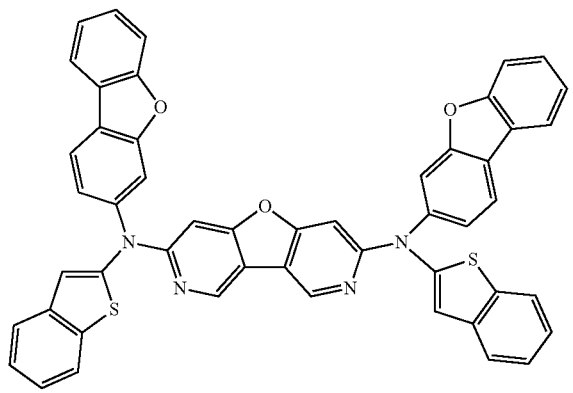
M164
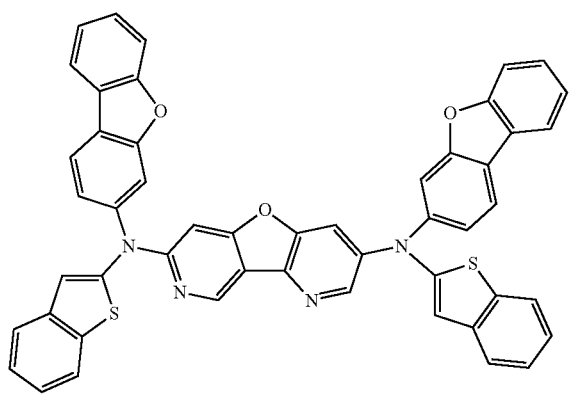
M165
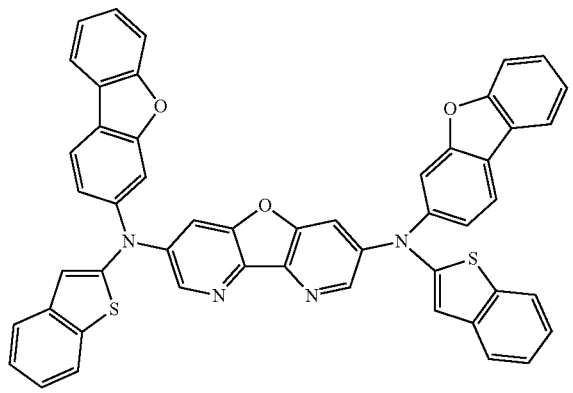
M166
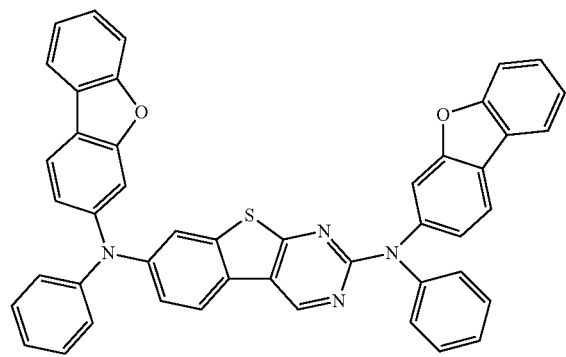
M167
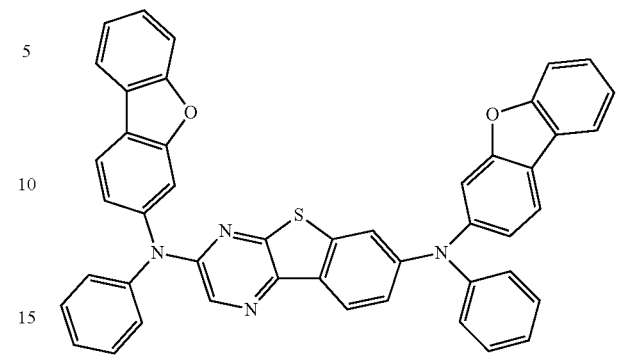
M168
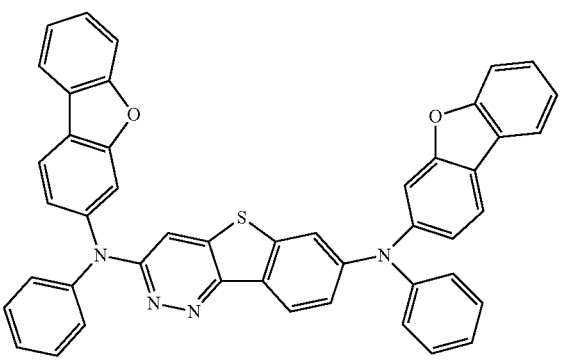
M169
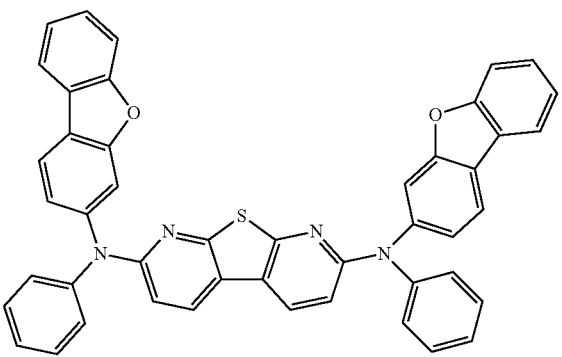
M170
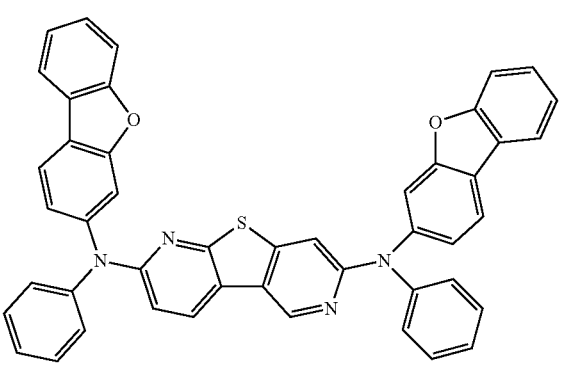

M171
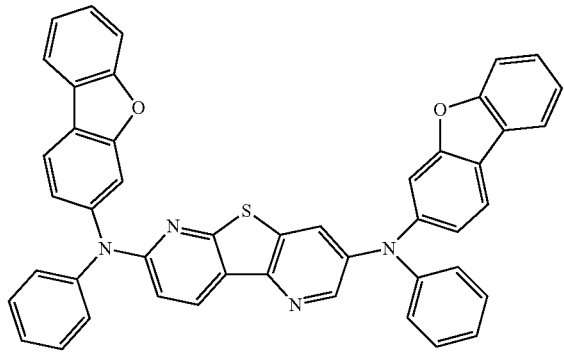
M172
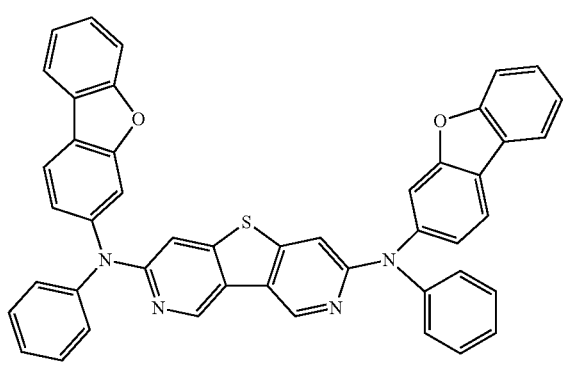
M173
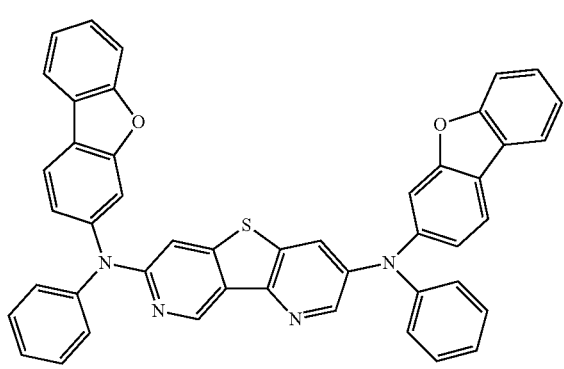
M174
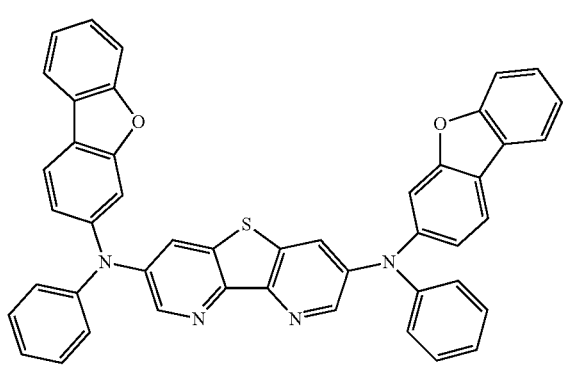
M175
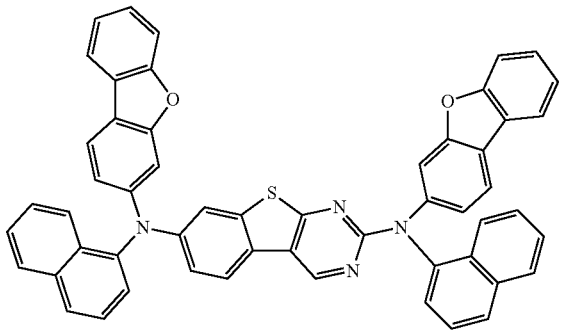
M176
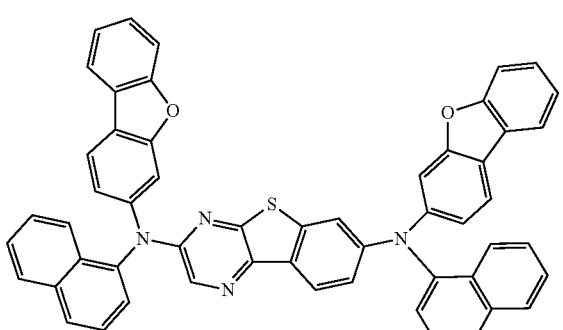
M177
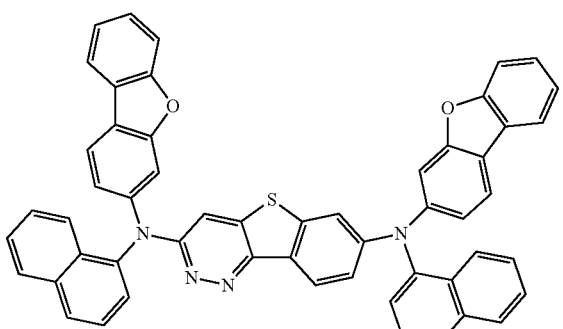
M178
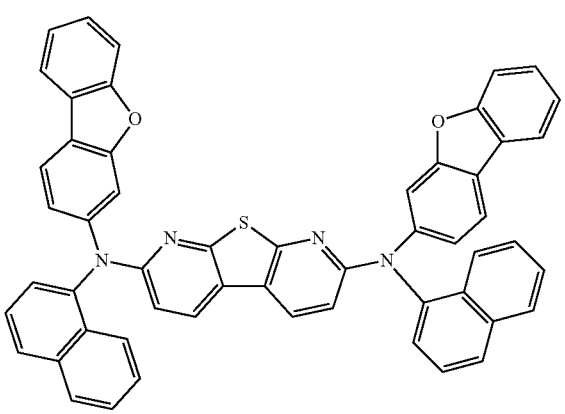

-continued
M179
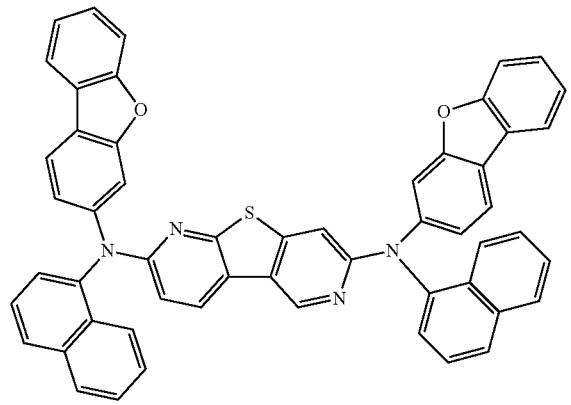
M180
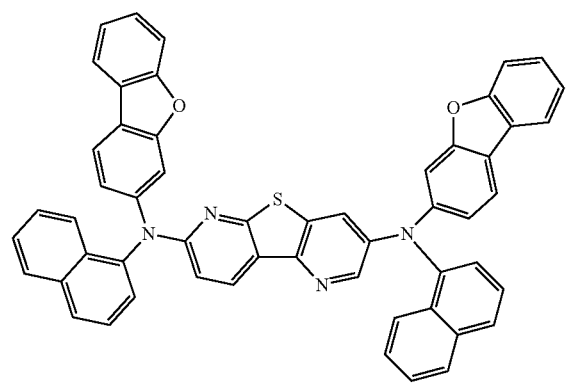
M181
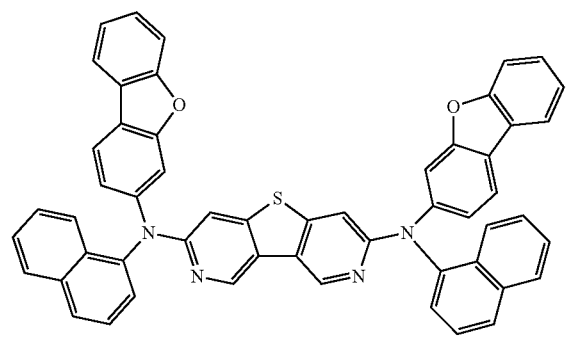
M182
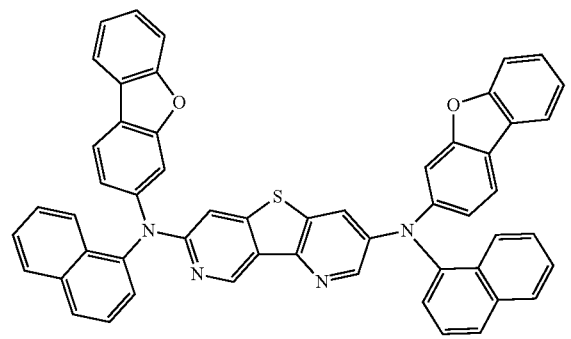
-continued
M183
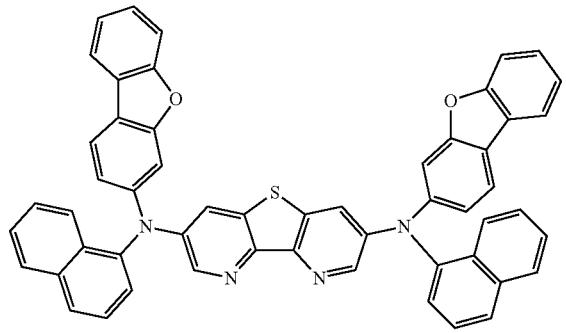
M184
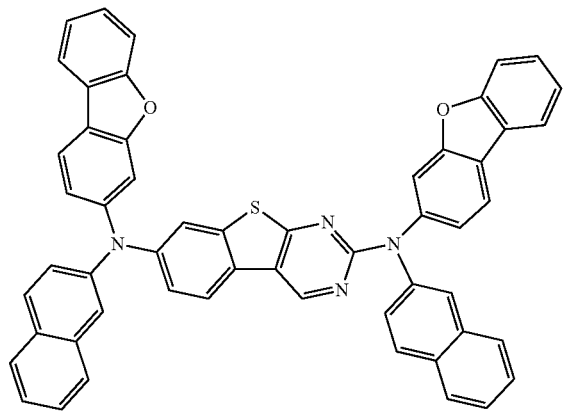
M185
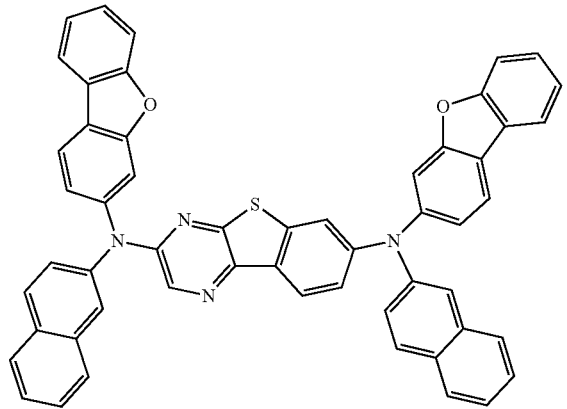
M186
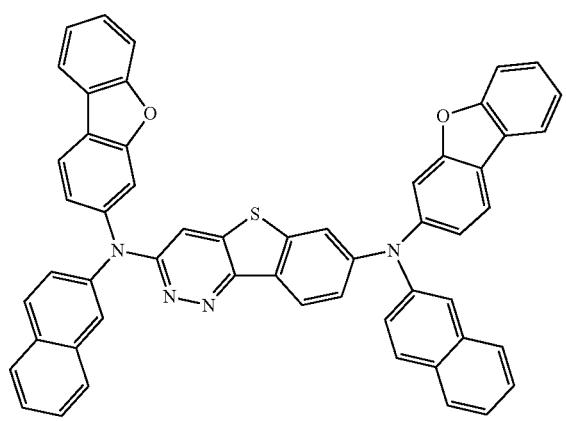

M187
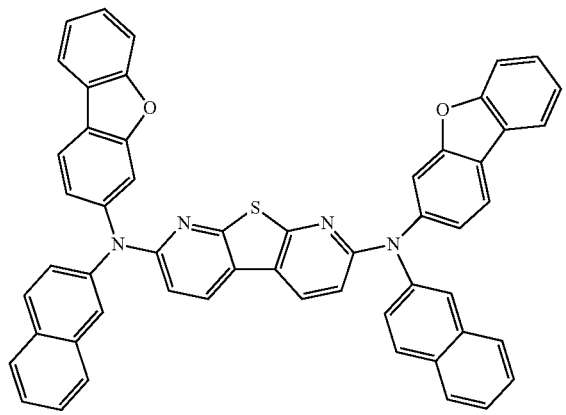
M188
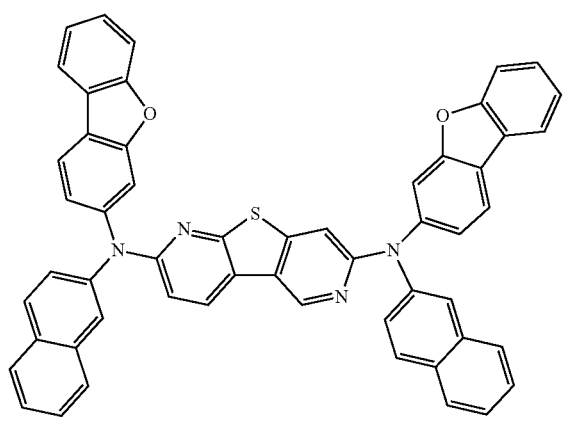
M189
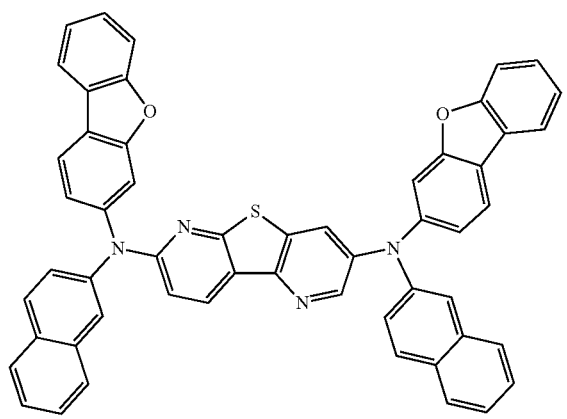
M190
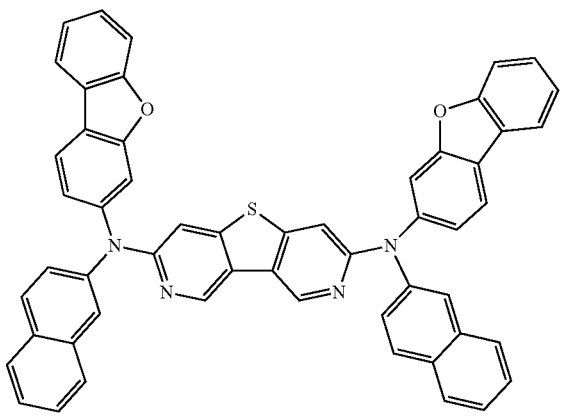
M191
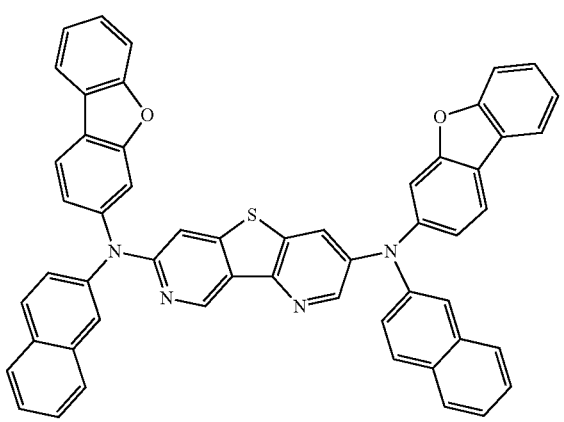
M192
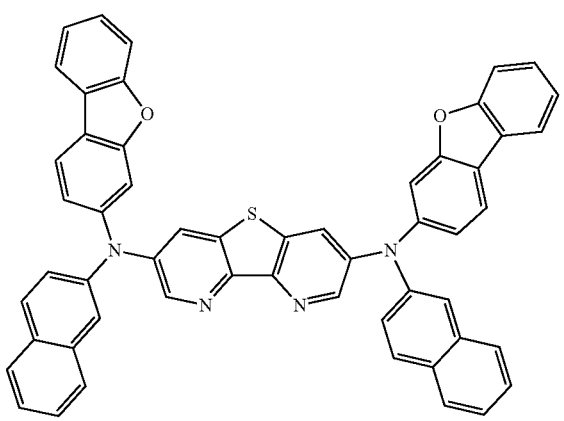

M193
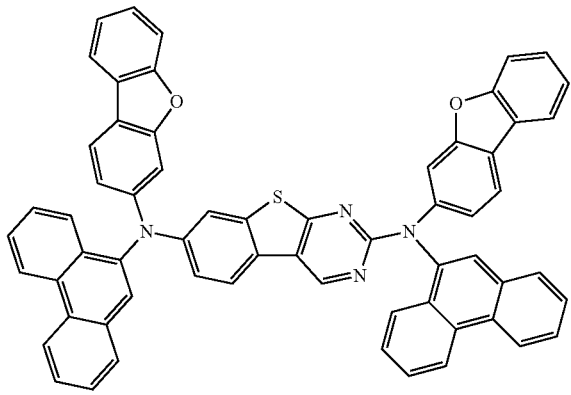
M194
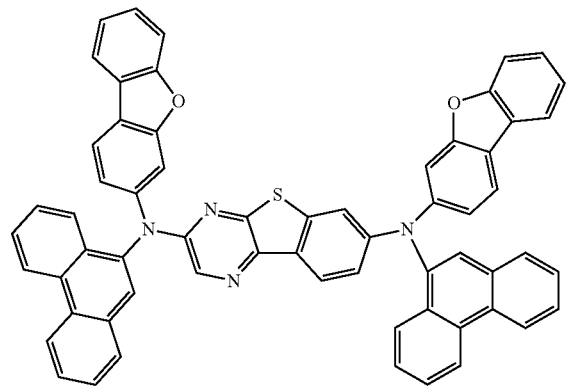
M195
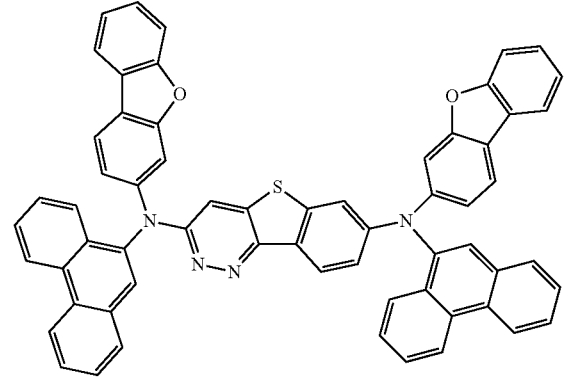
M196
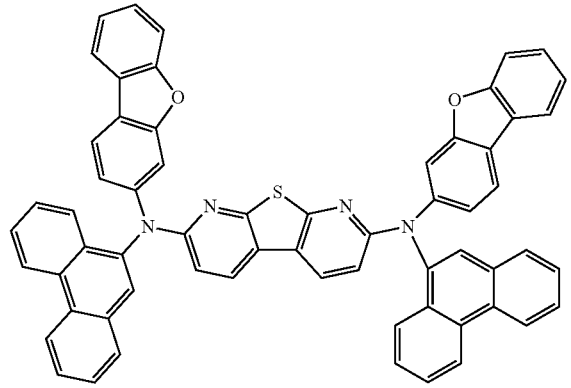
M197
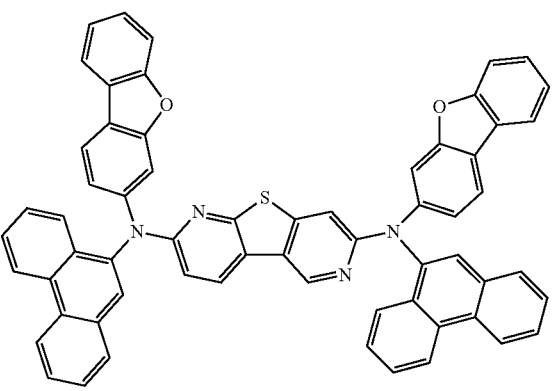
M198
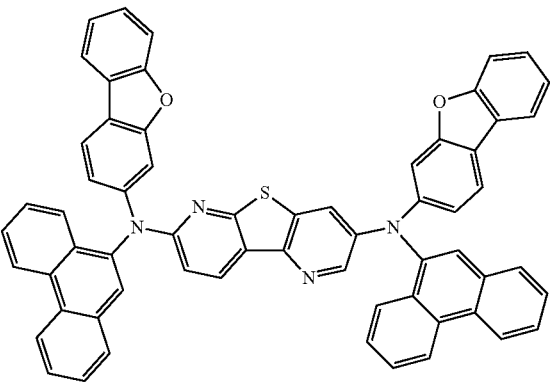
M199
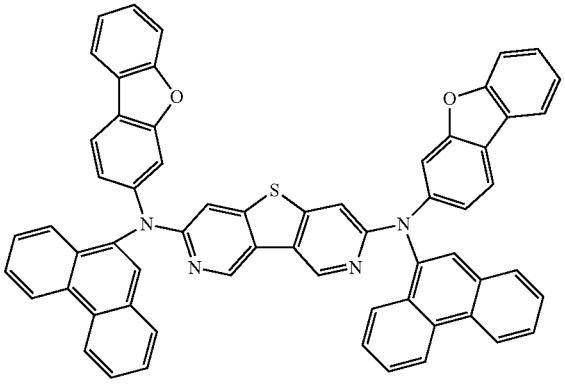
M200
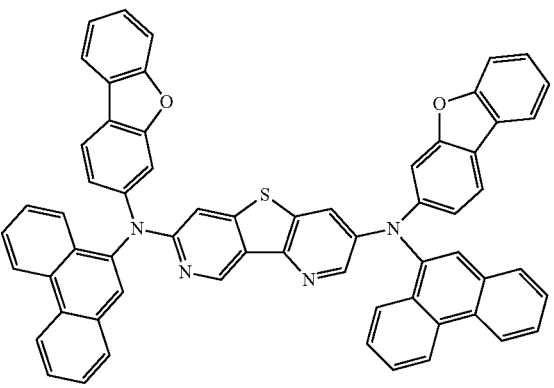

M201
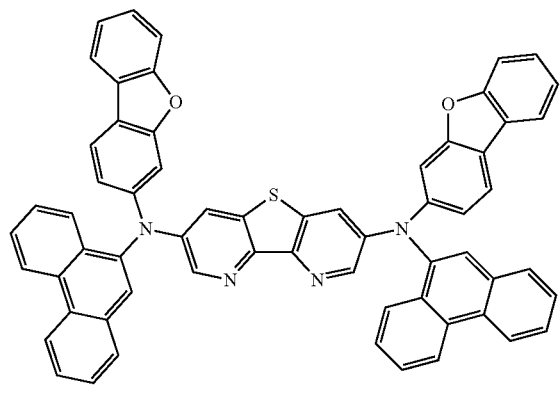
M202
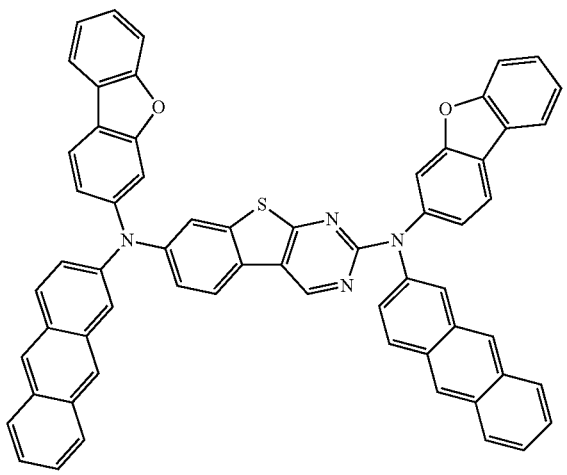
M203
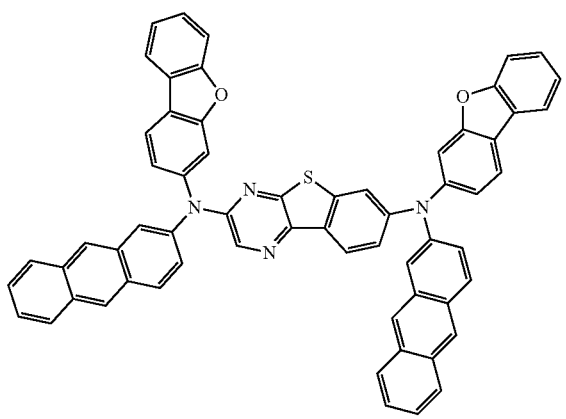
M204
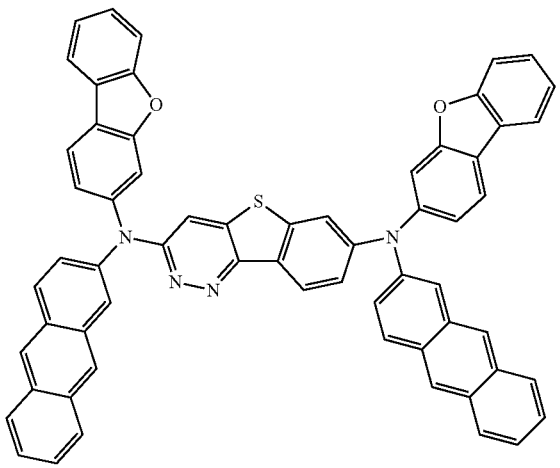
M205
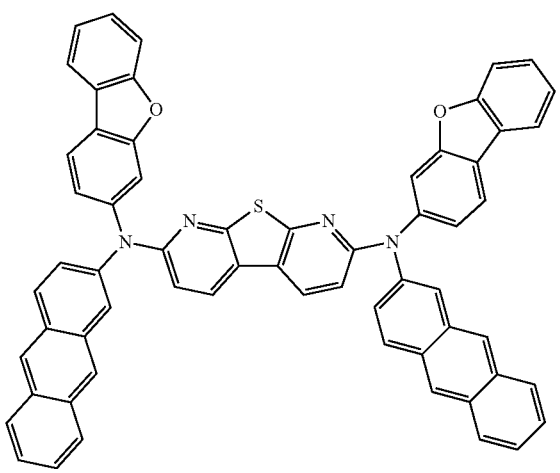
M206
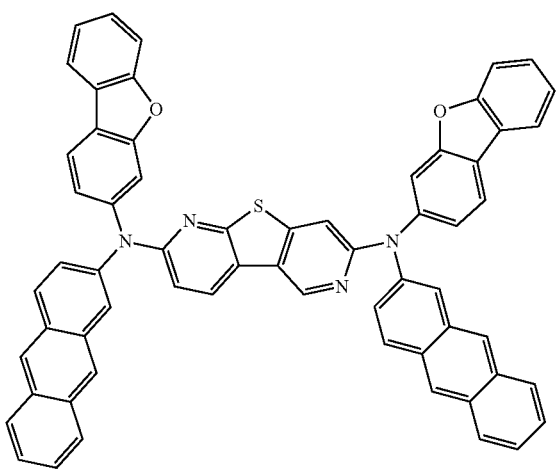

M207
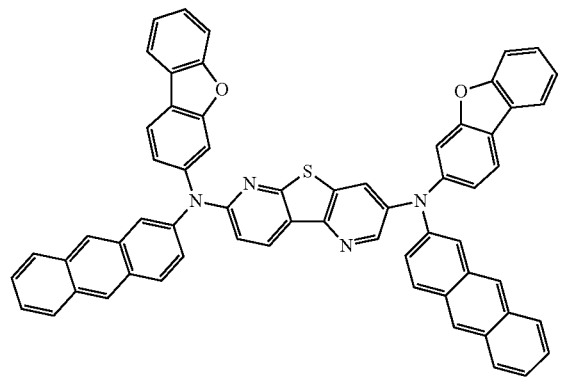
M210
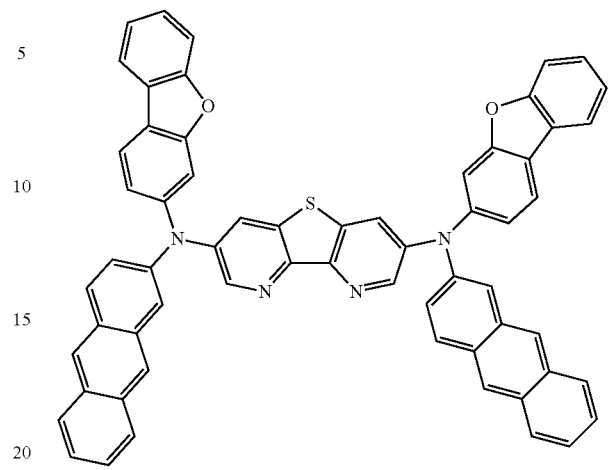
M208
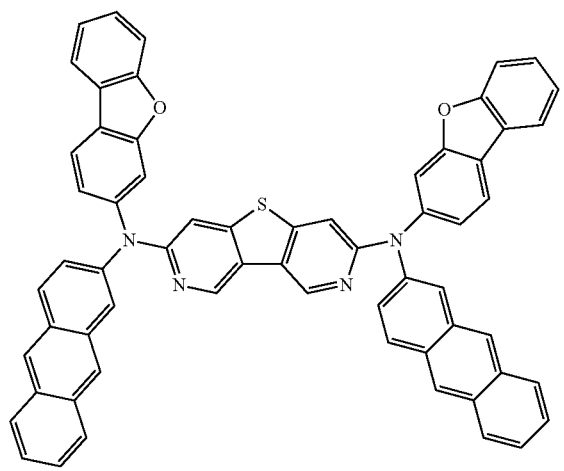
M211
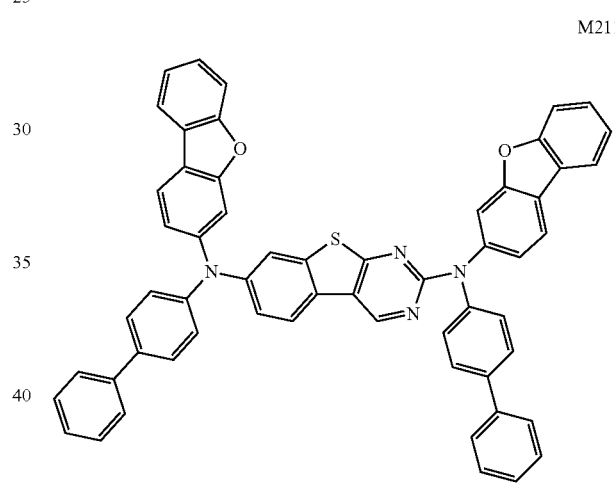
M209
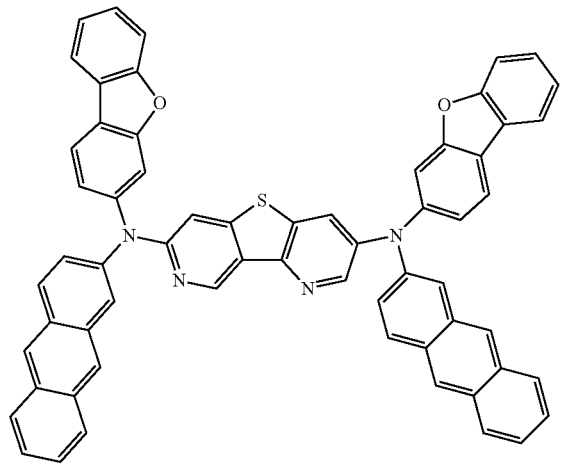
M212
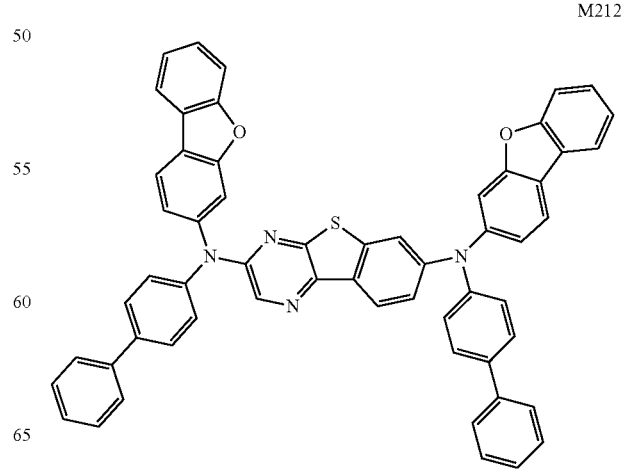

M213
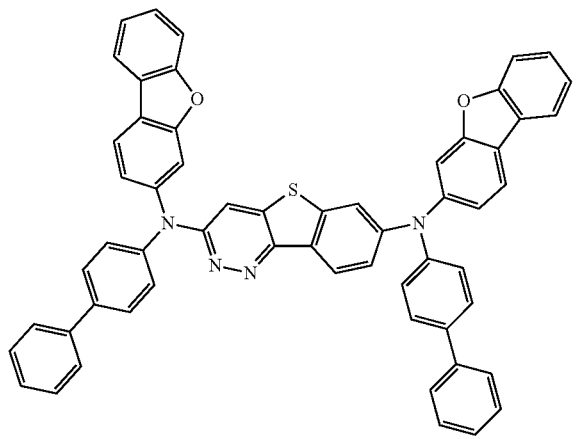
M216
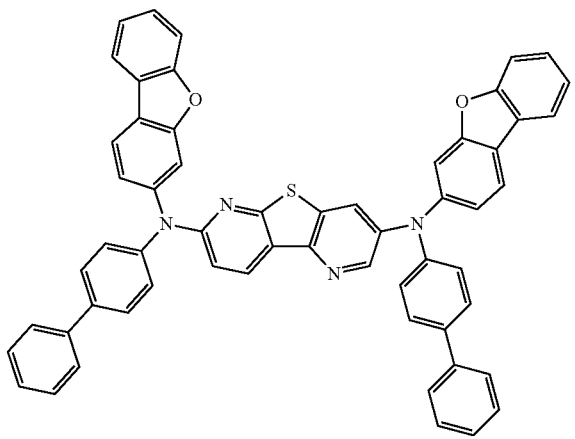
M214
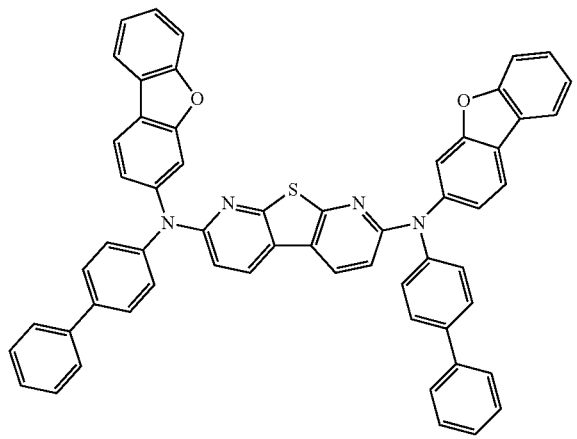
M217
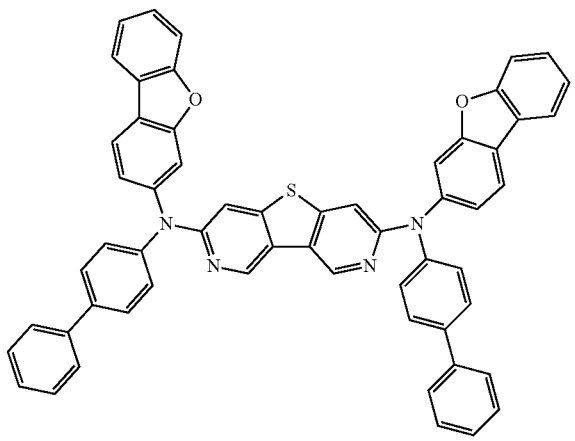
M215
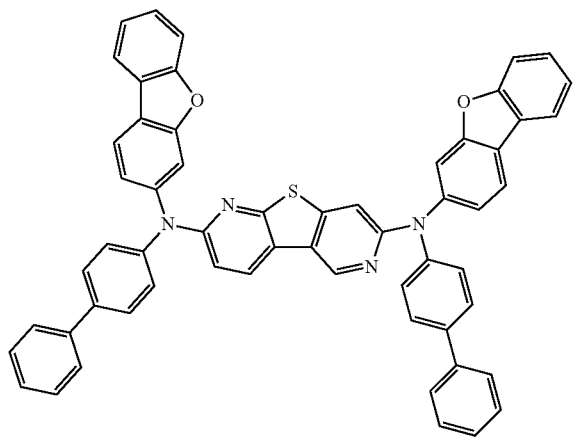
M218
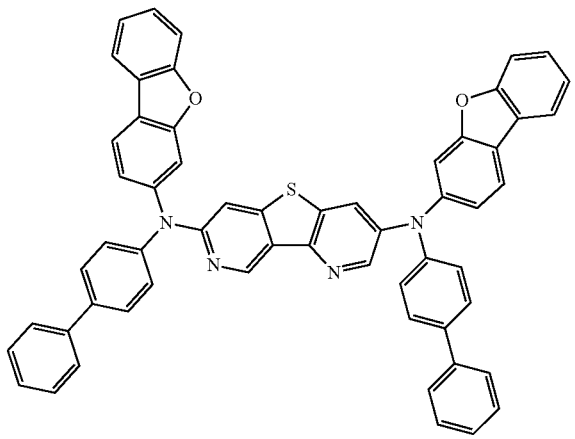

M219
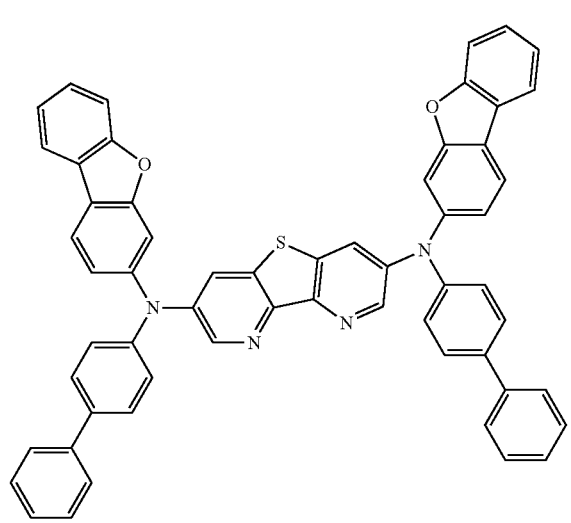
M220
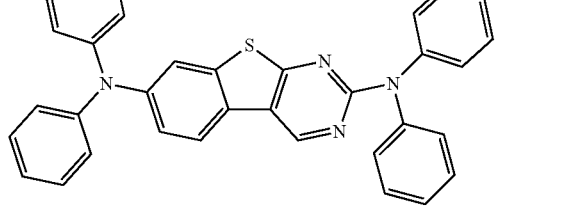
M221
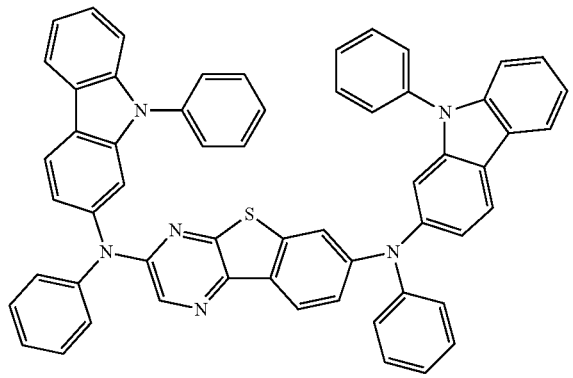
M222
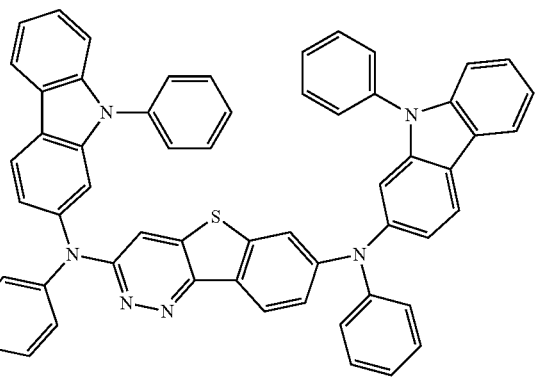
M223
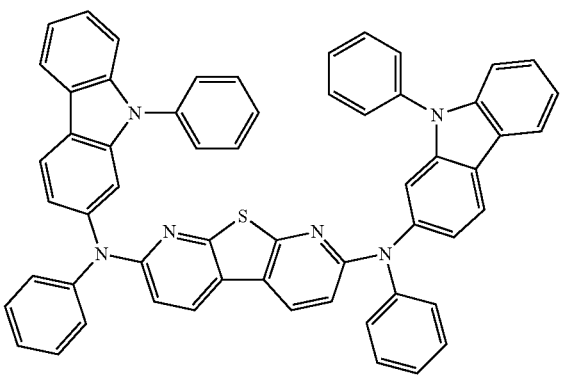
M224
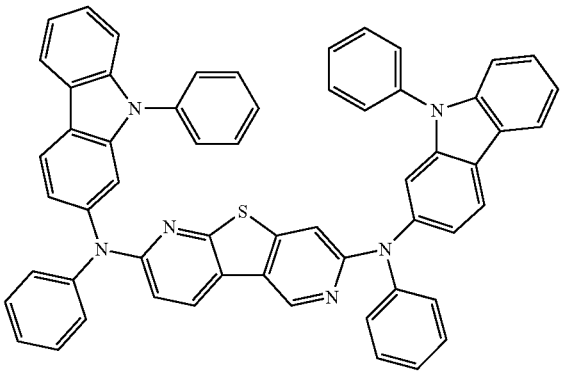
M225
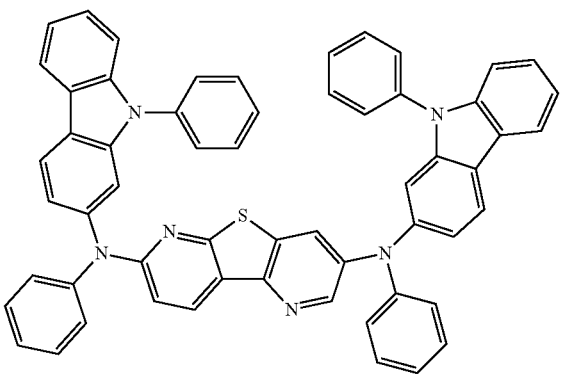

M226
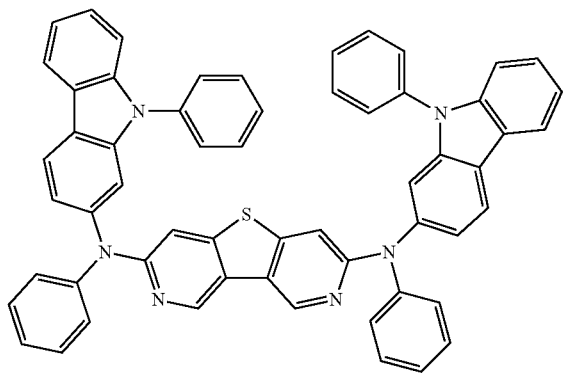
M227
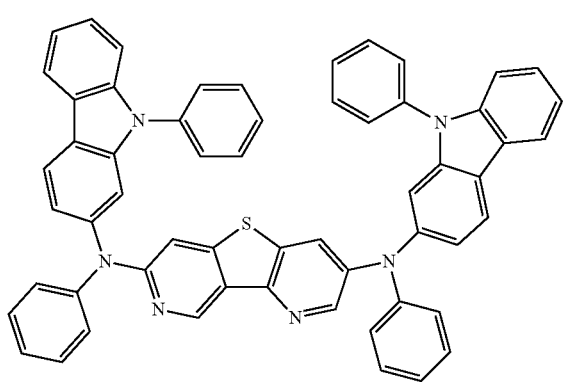
M228
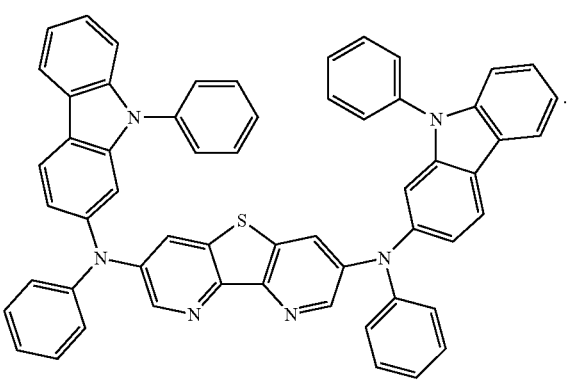
21. The heterocyclic compound according to claim 1, wherein the heterocyclic compound has any one of following structures:
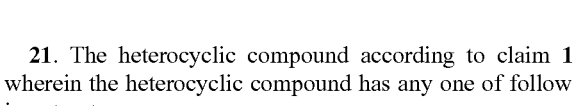
M229
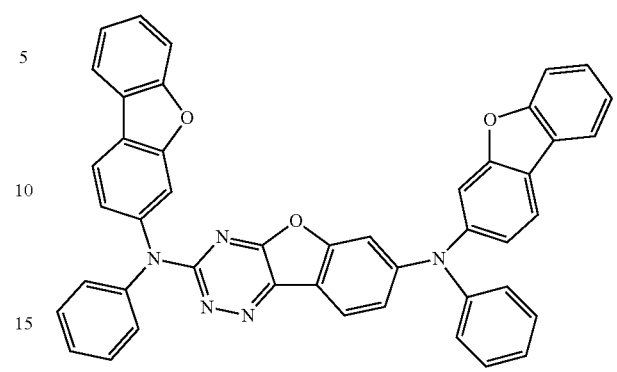
M230
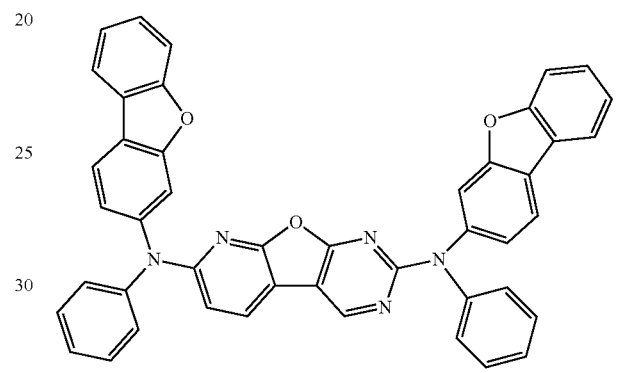
M231
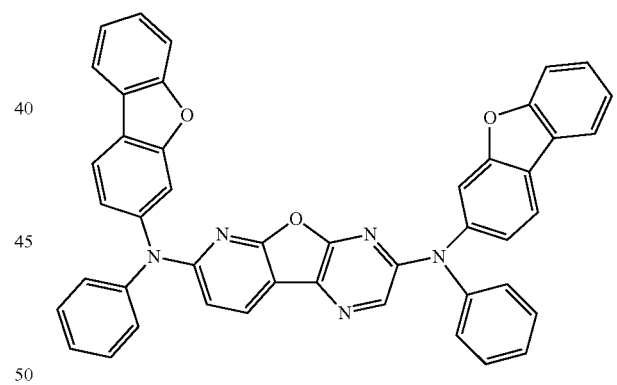
M232
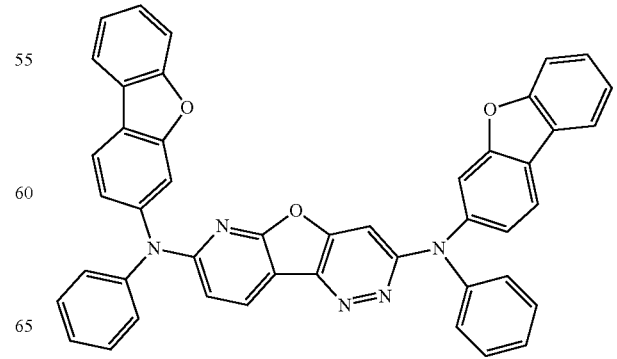

M233
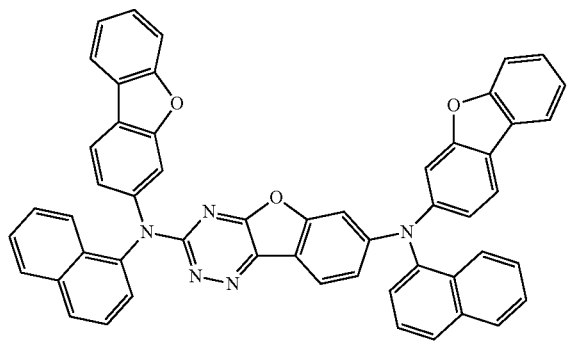
M237
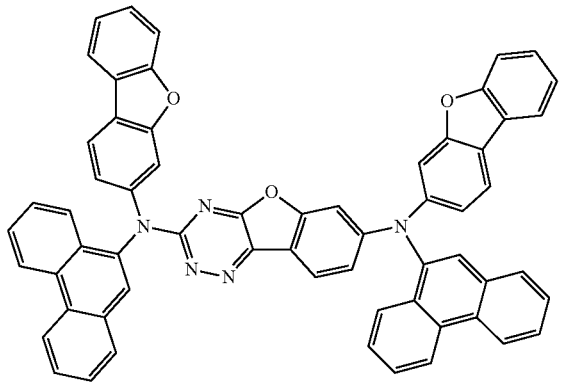
M234
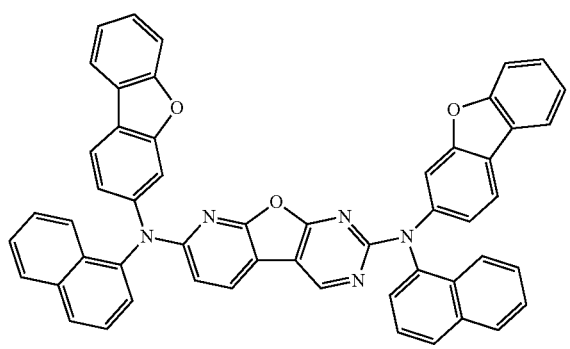
M238
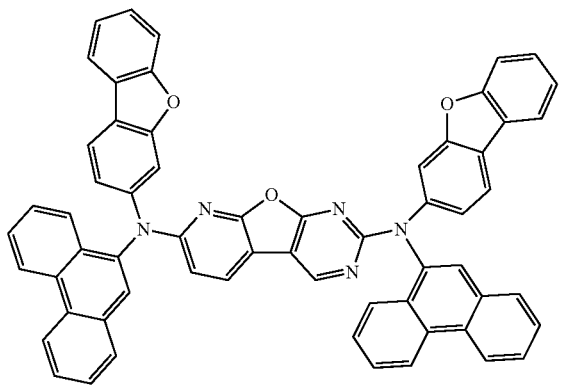
M235
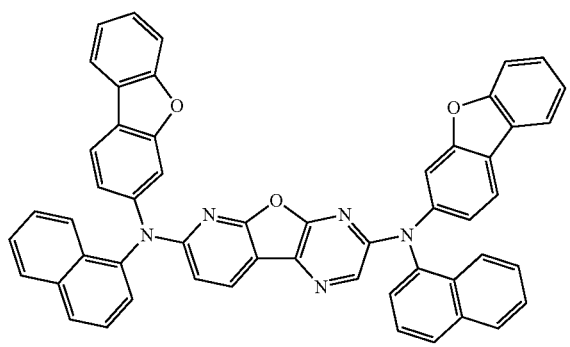
M239
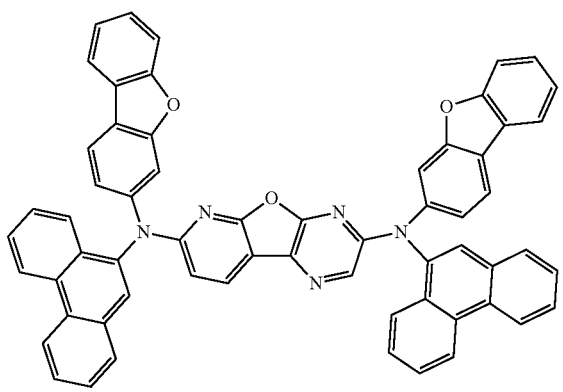
M236
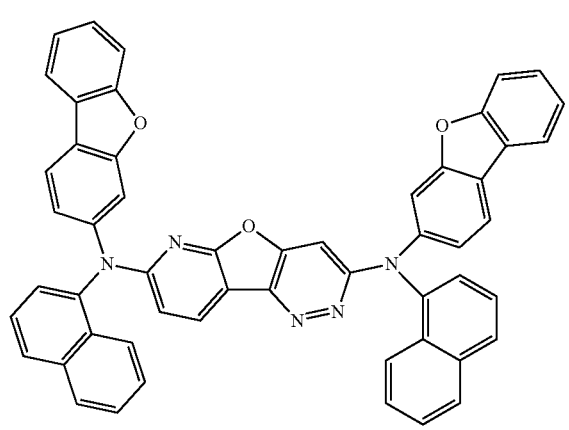
M240
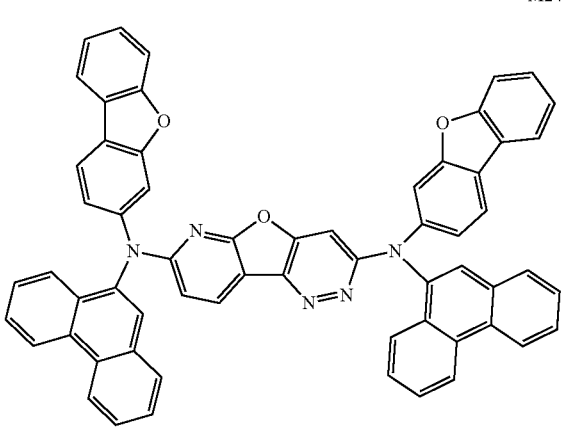

M241
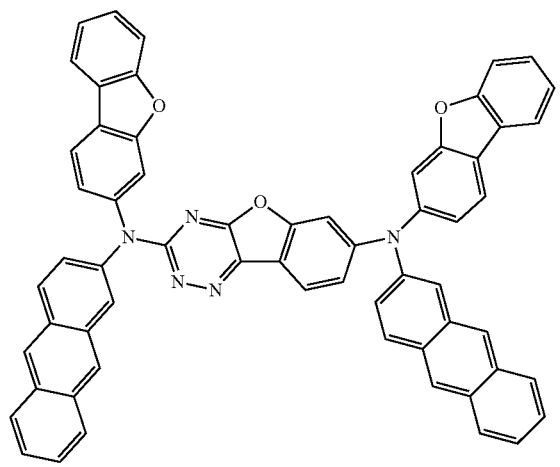
M244
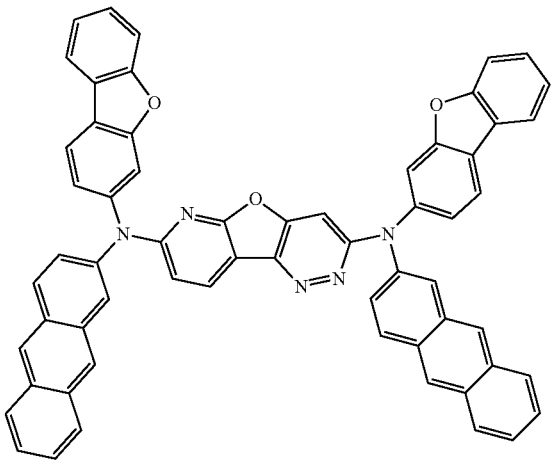
M242
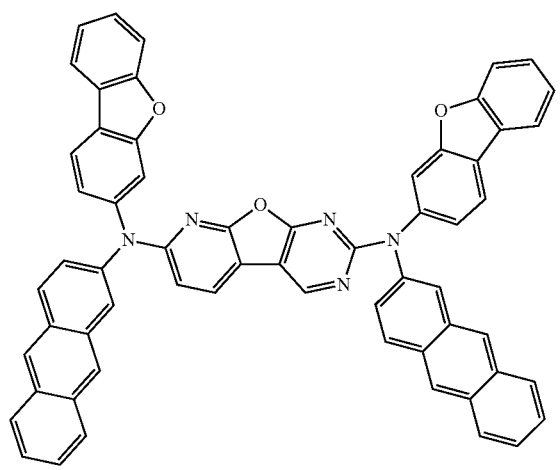
M245
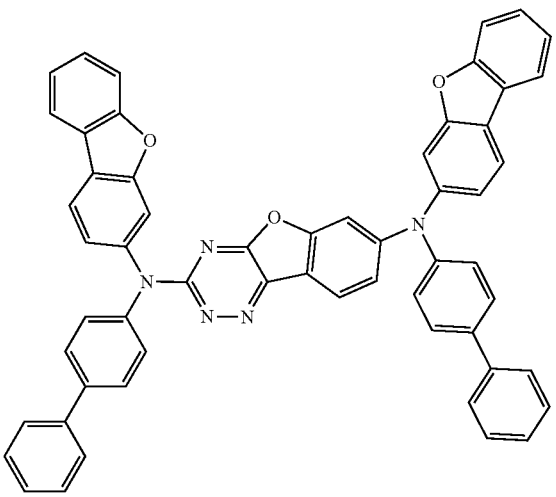
M243
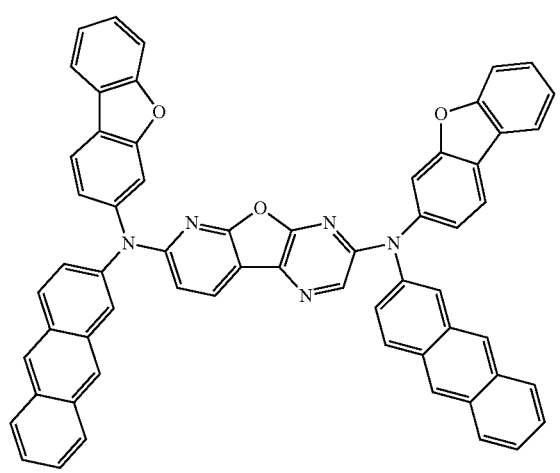
M246
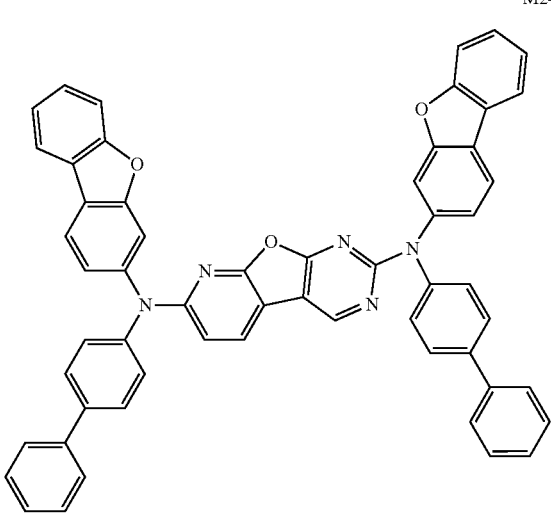

M247
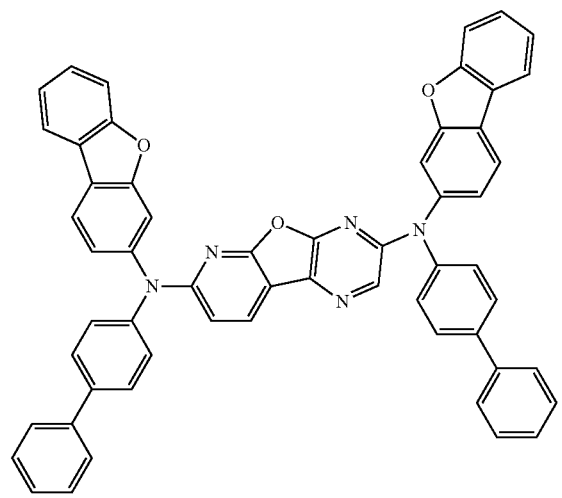
M248
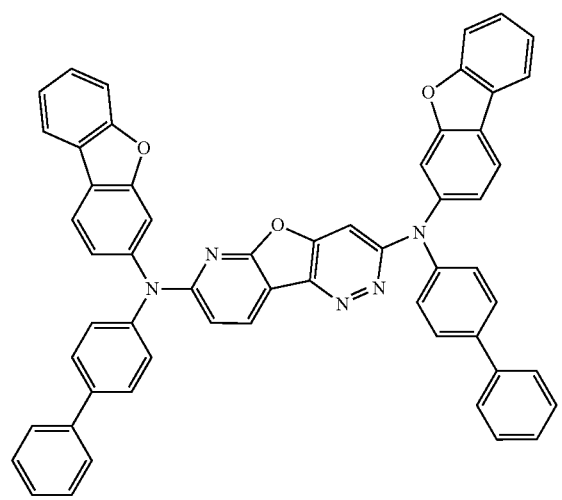
M249
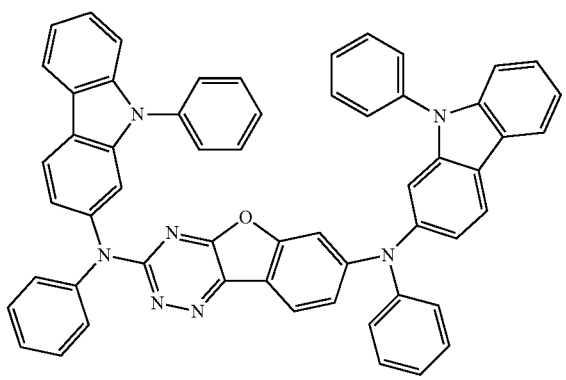
M250
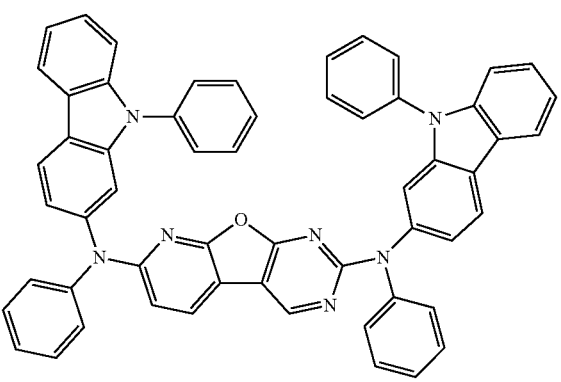
M251
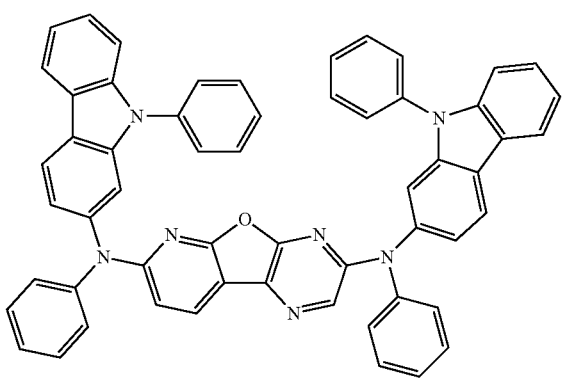
M252
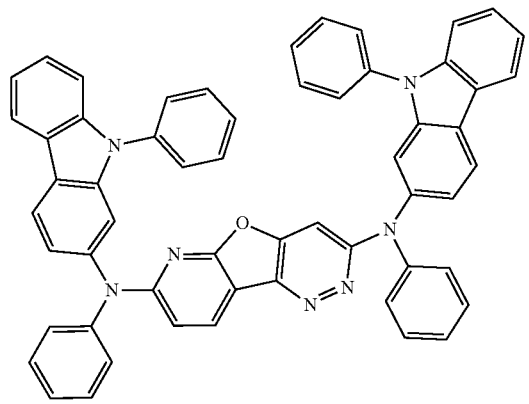
M253
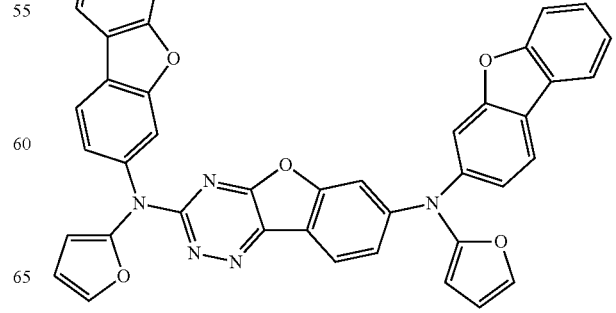

M254
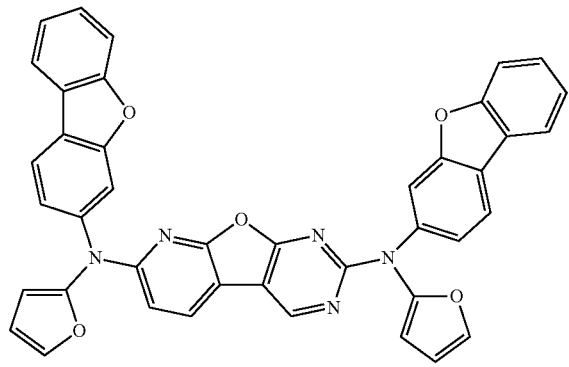
M255
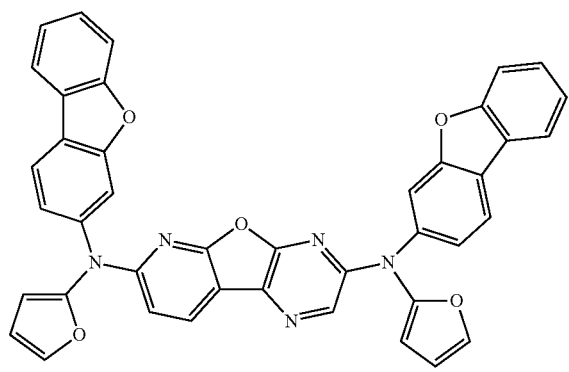
M256
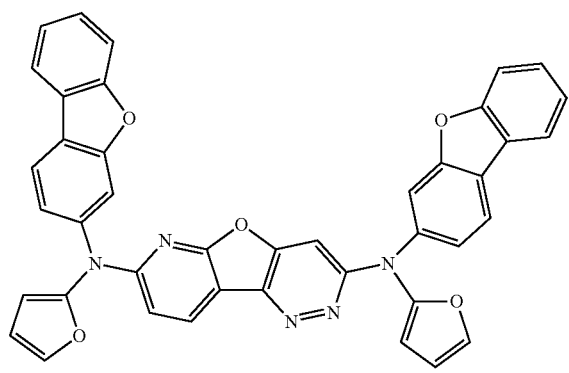
M257
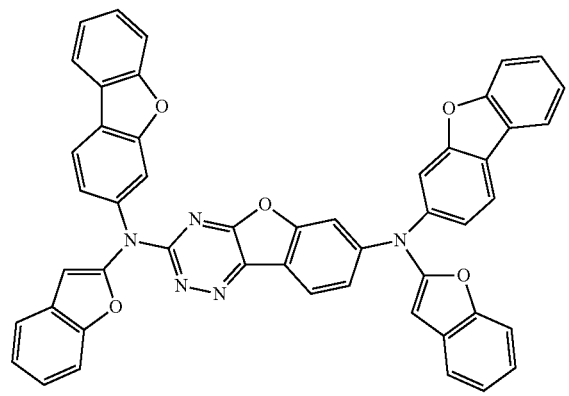
M258
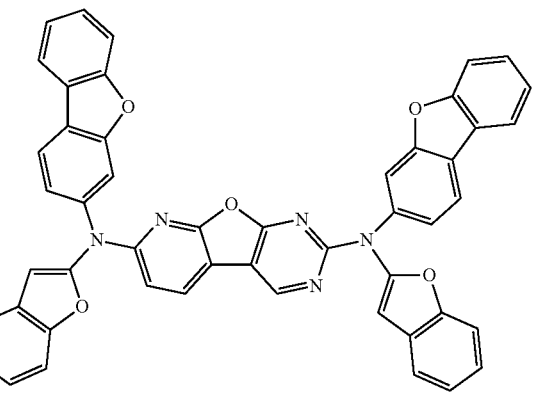
M259
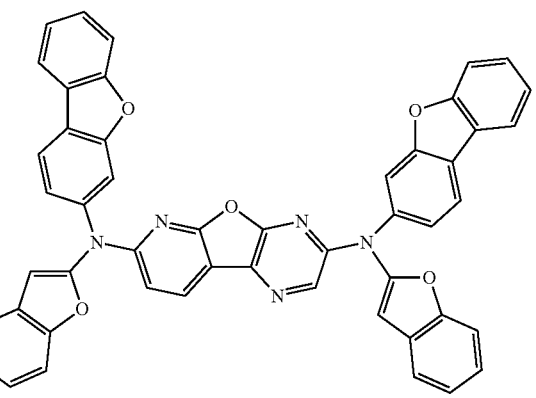
M260
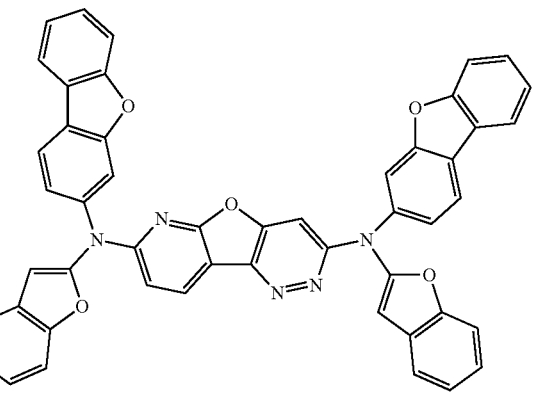
M261
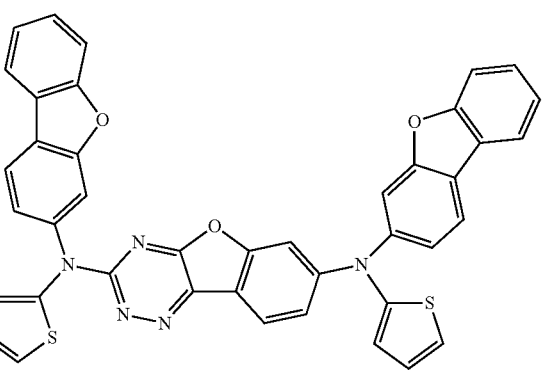

M262
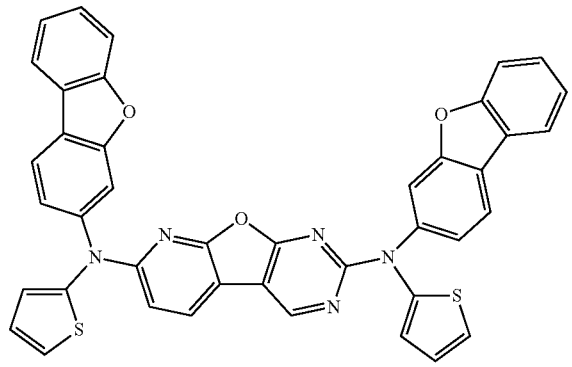
M263
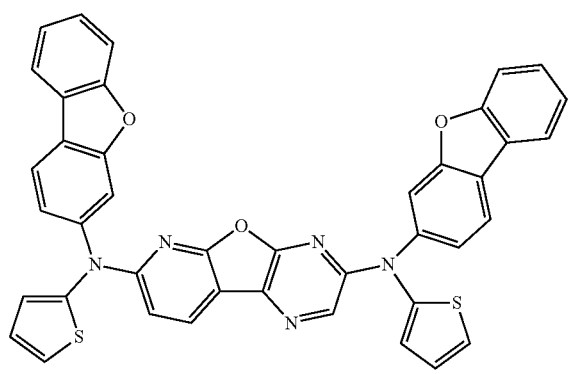
M264
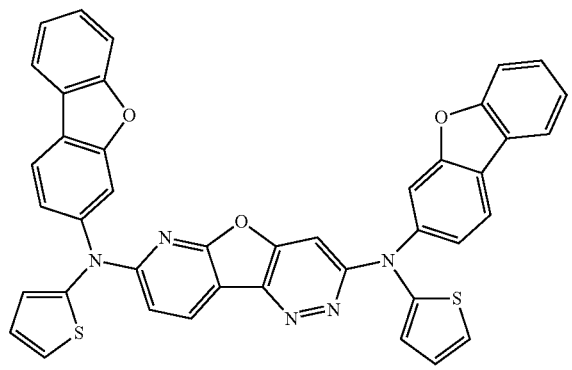
M265
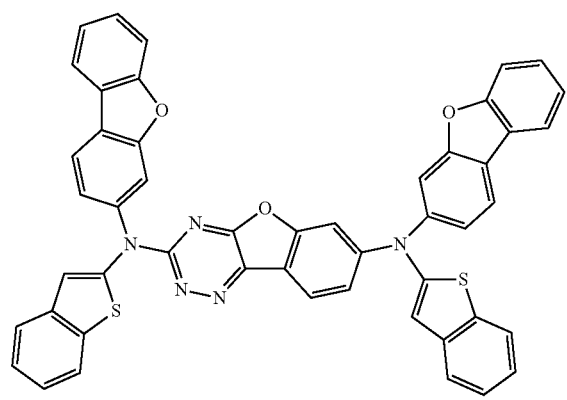
M266
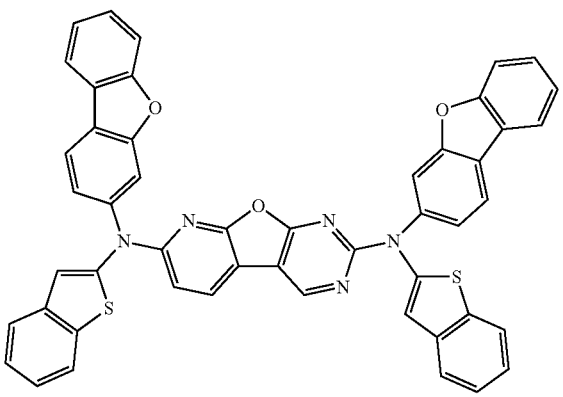
M267
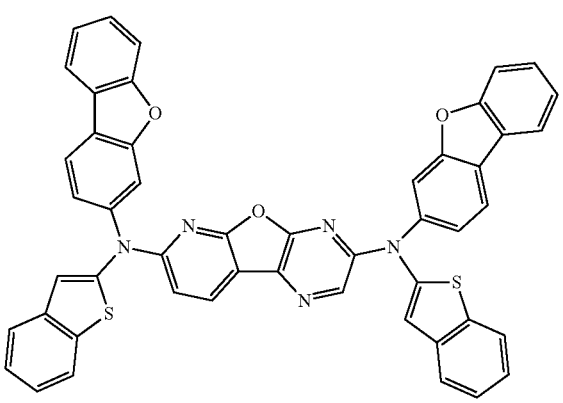
M268
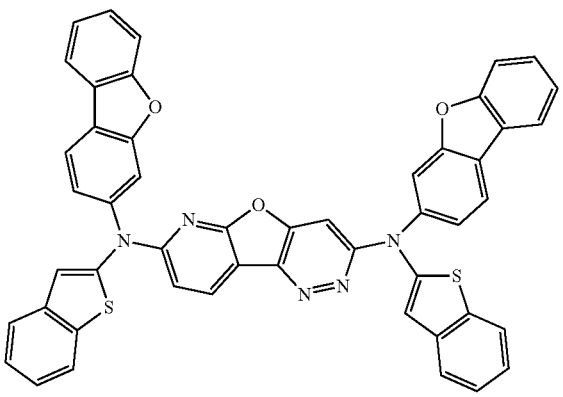
M269
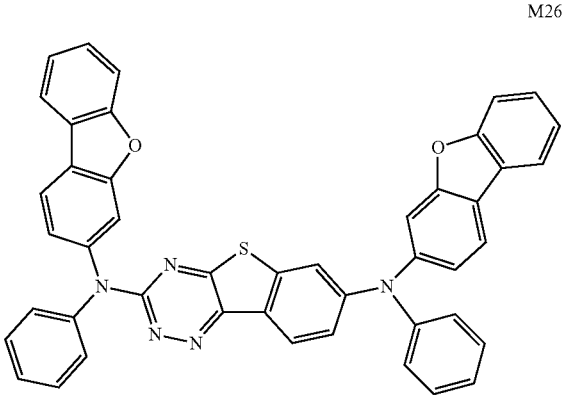

M270
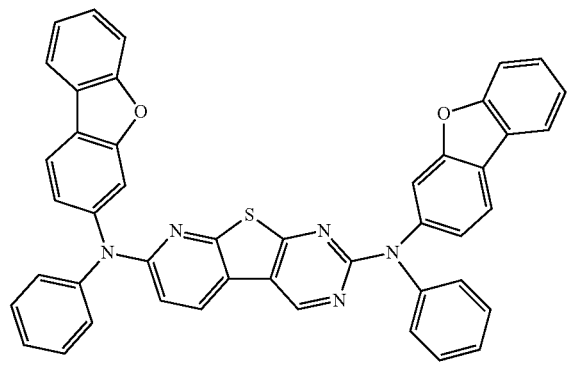
M271
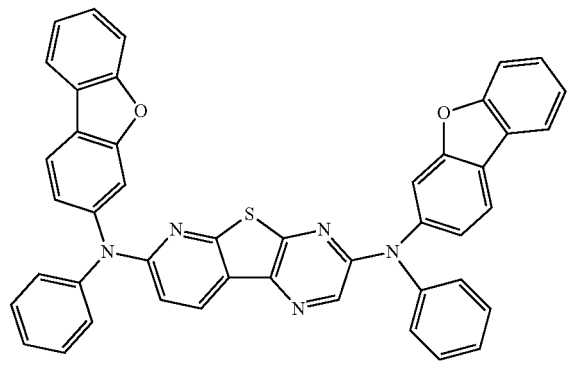
M272
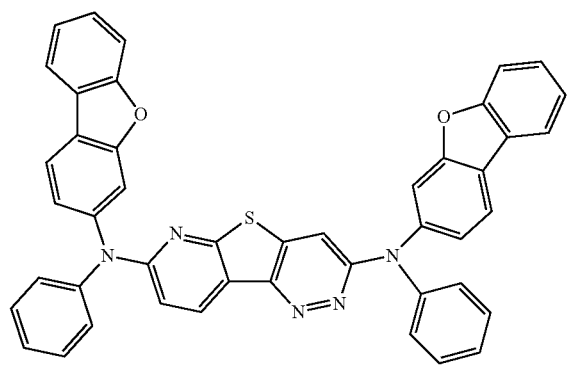
M273
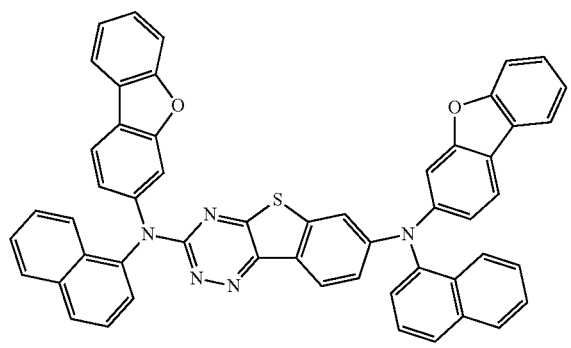
M274
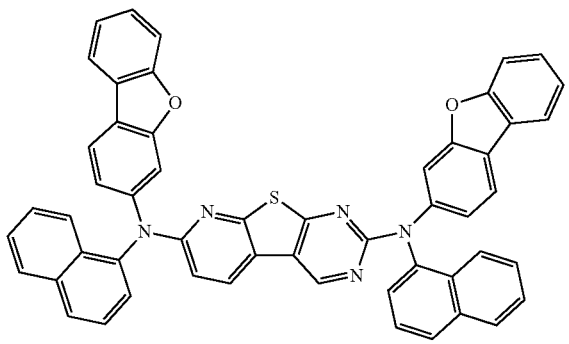
M275
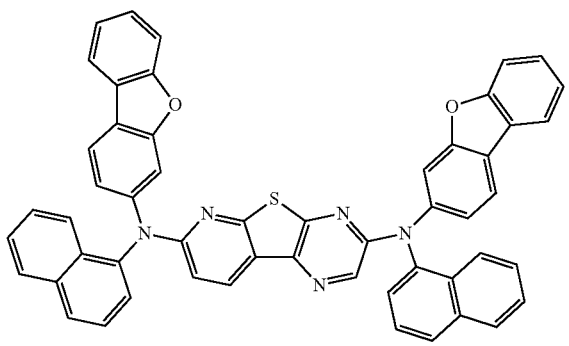
M276
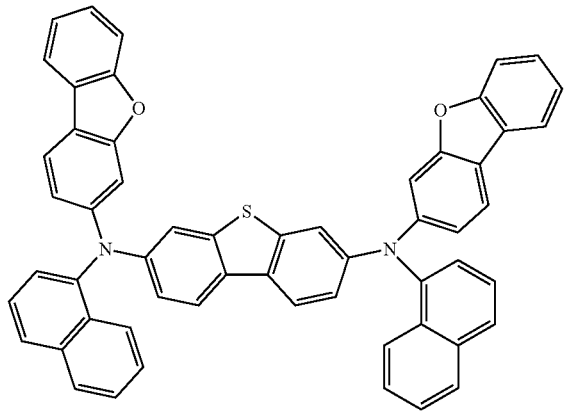
M277
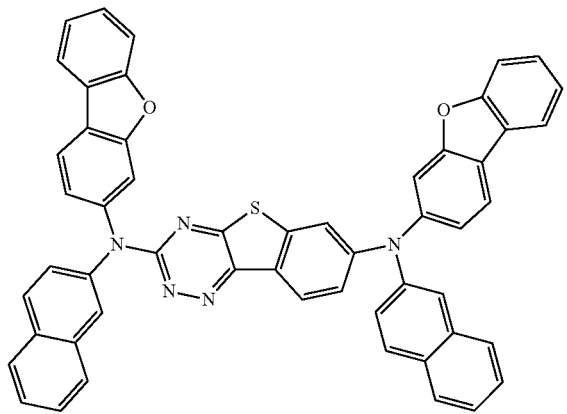

-continued
M278
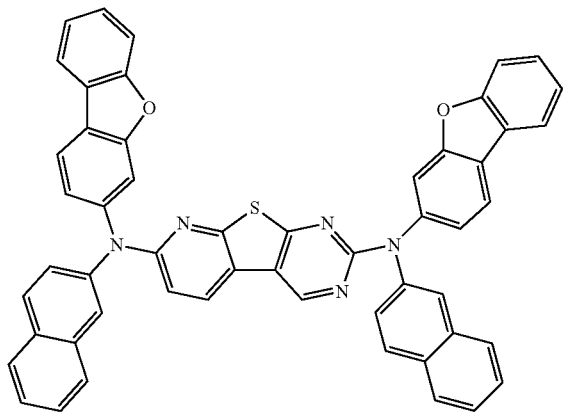
M279
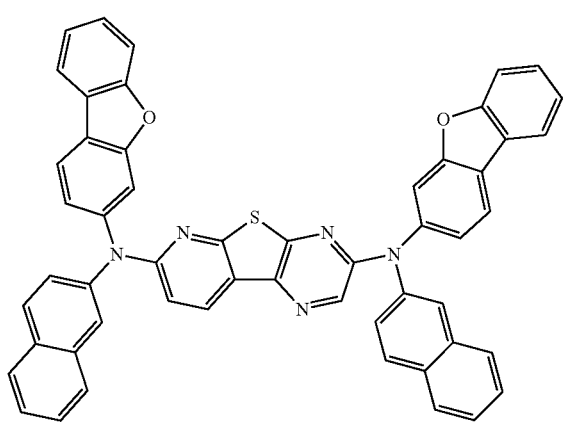
M280
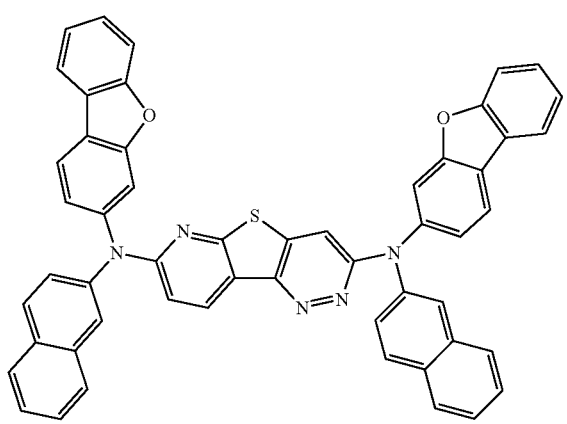
-continued
M281
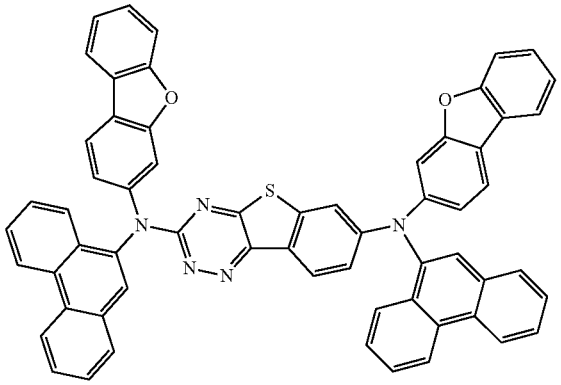
M282
M283
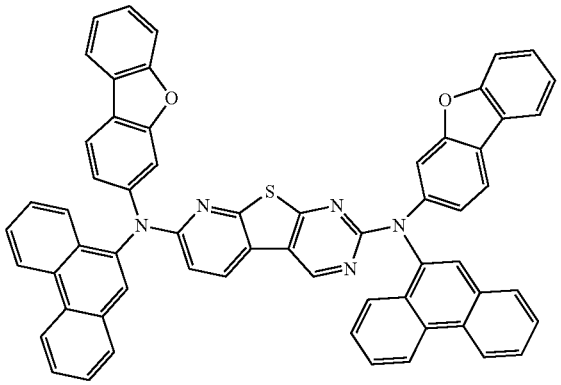
M284
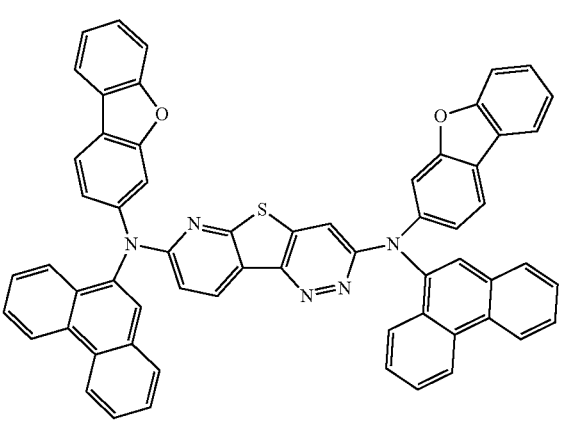

M285
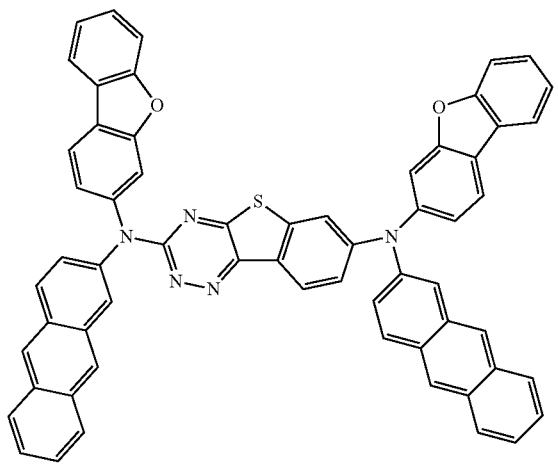
M288
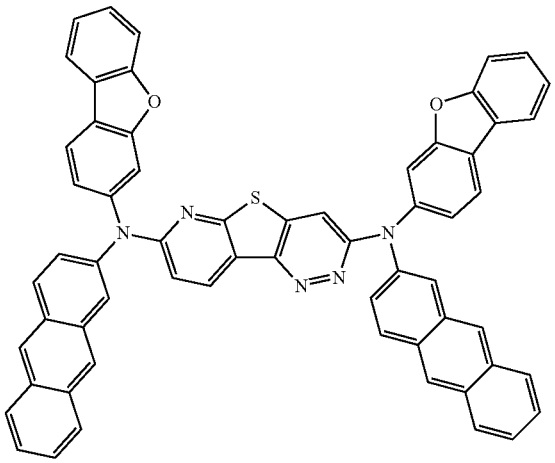
M286
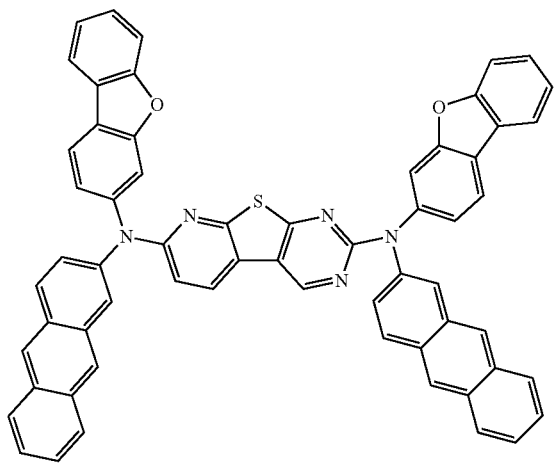
M289
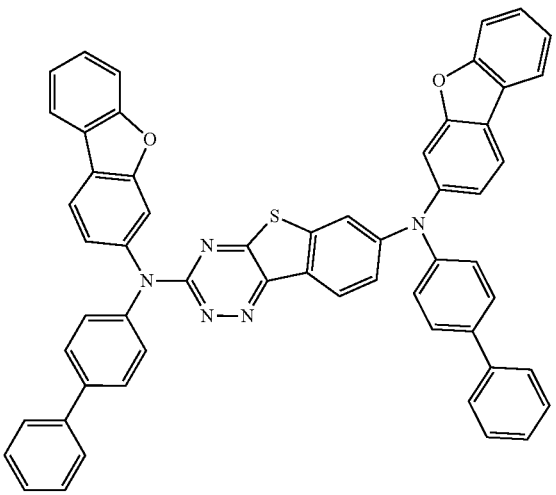
M287
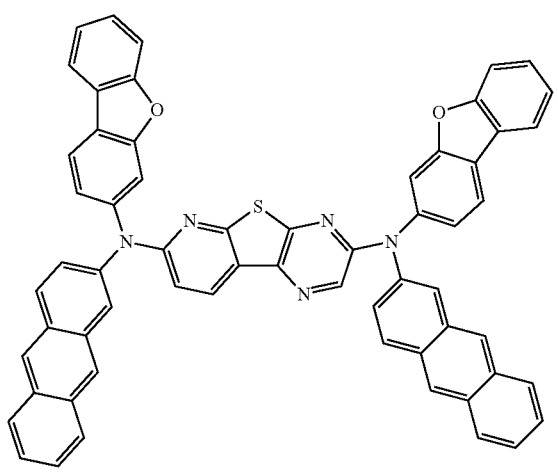
M290
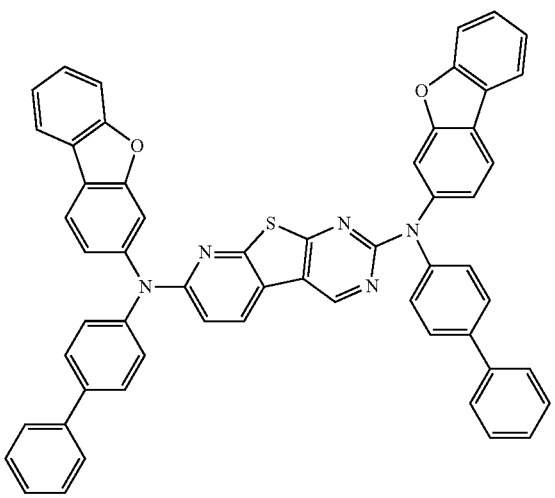

M291
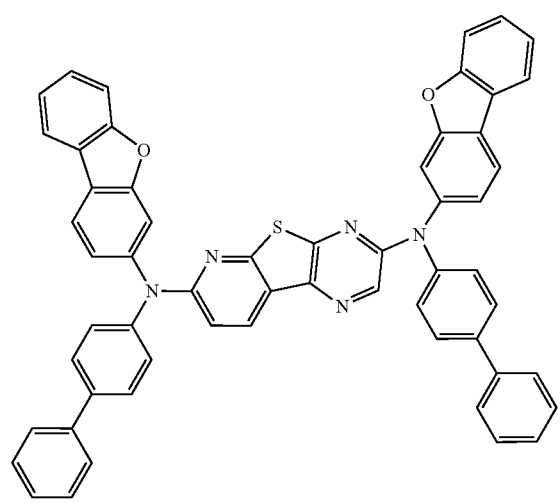
M292
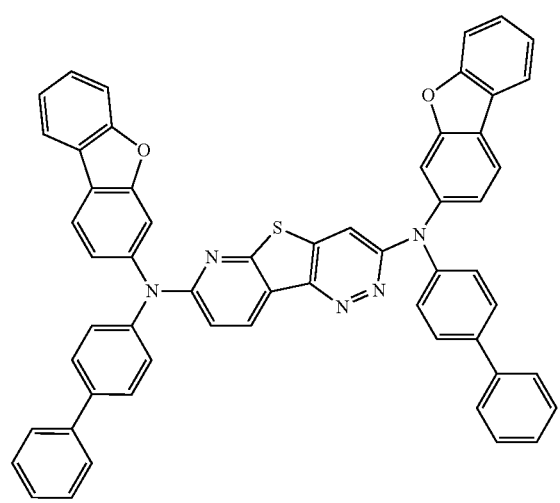
M293
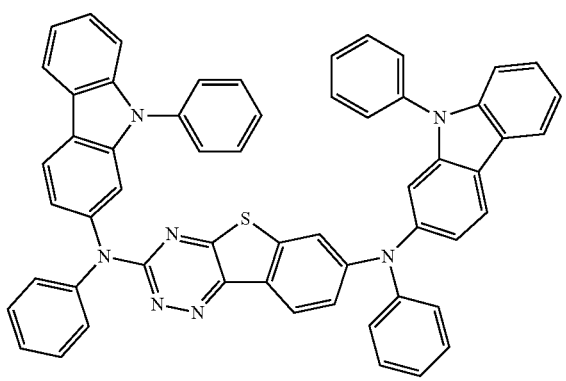
M294
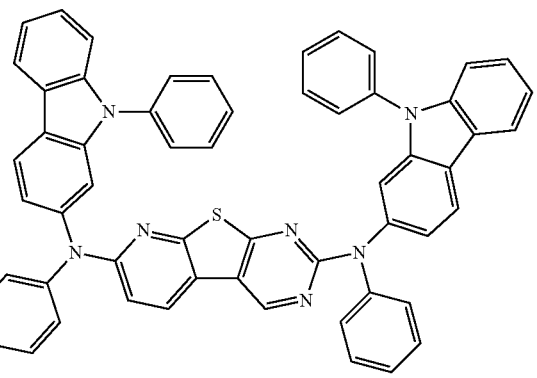
M295
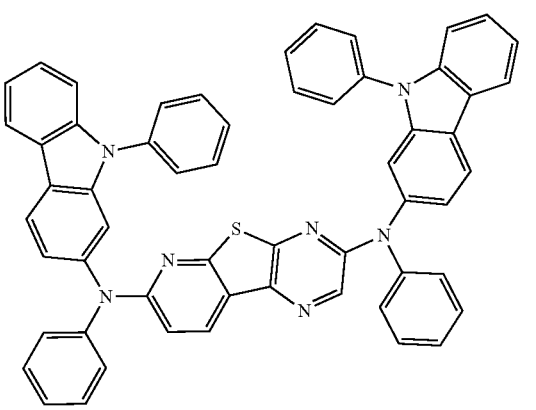
M296
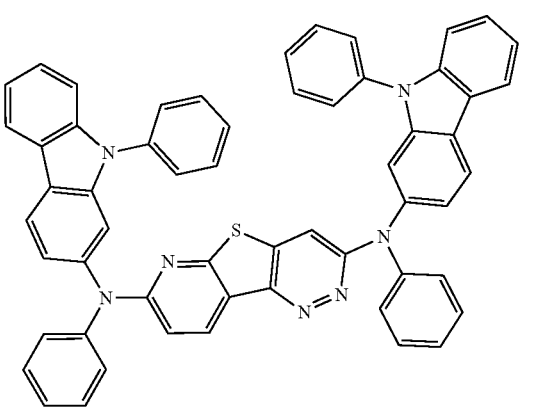
M297
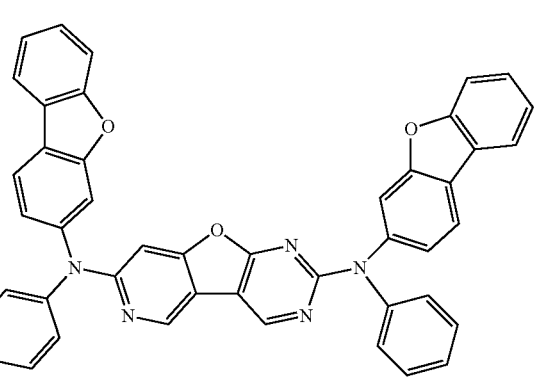

M298
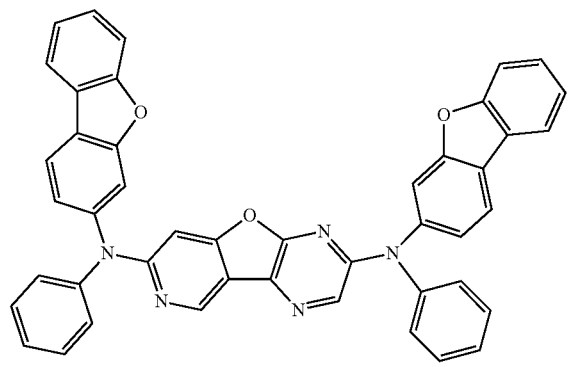
M299
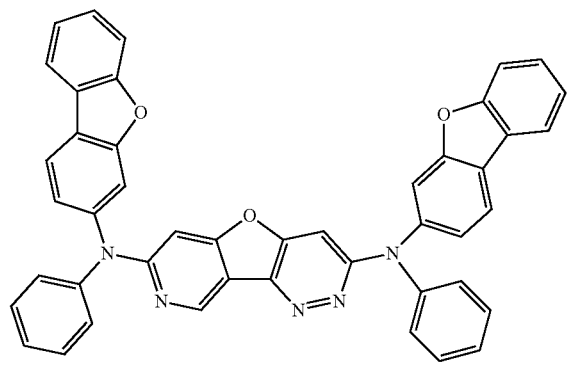
M300
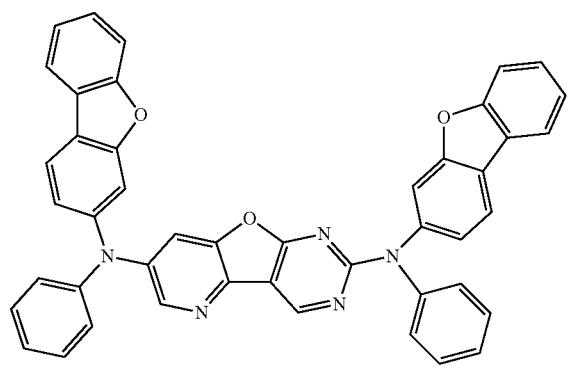
M301
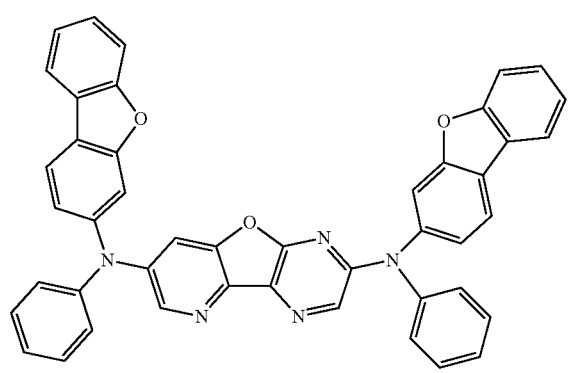
M302
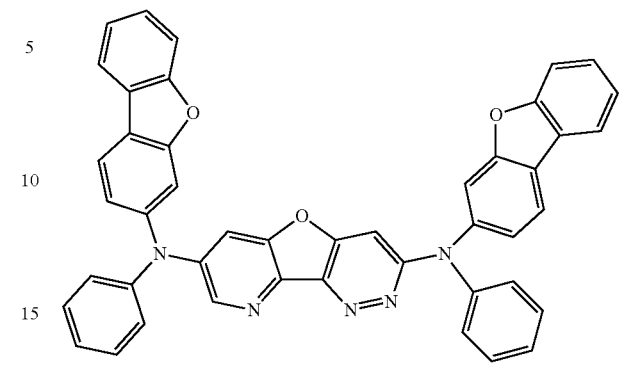
M303
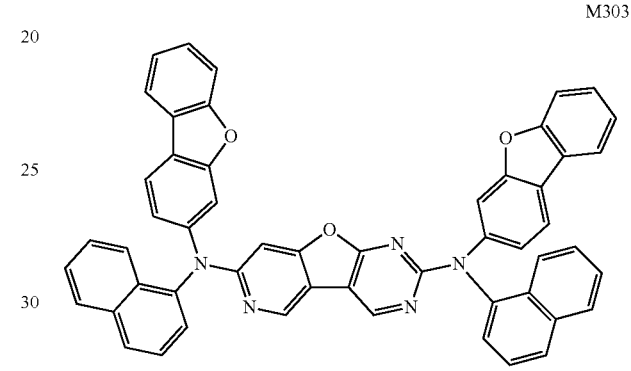
M304
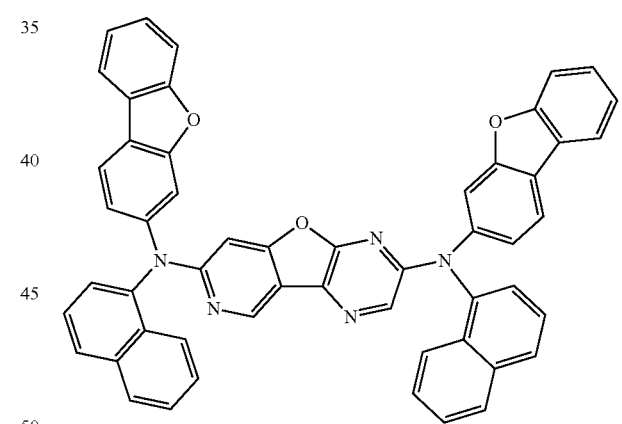
M305
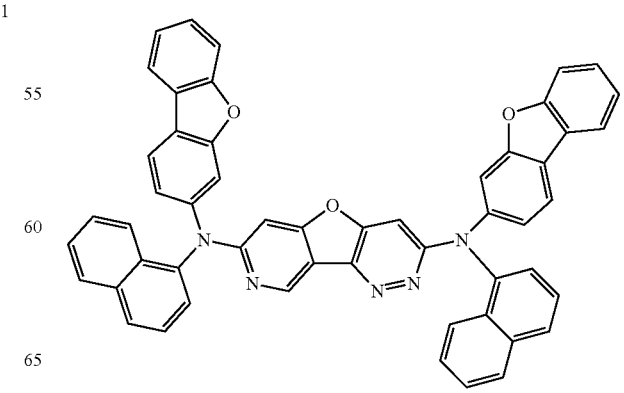

M306
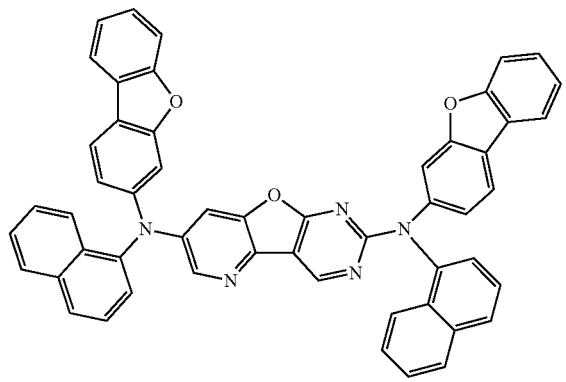
M309
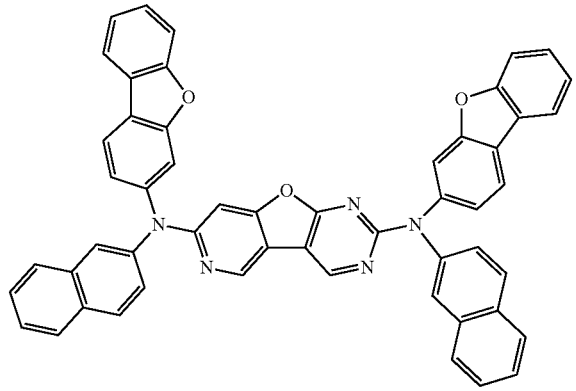
M307
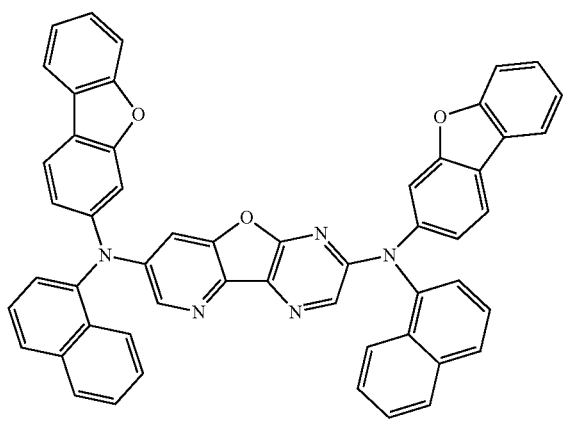
M310
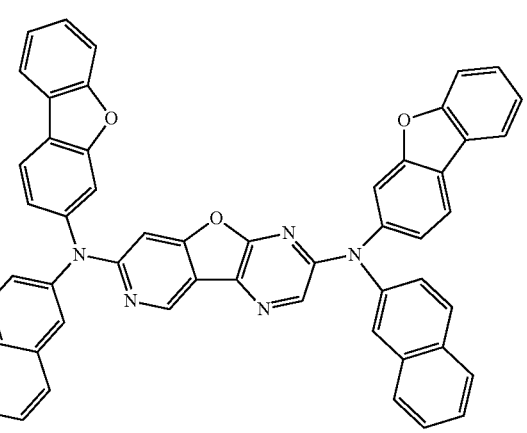
M308
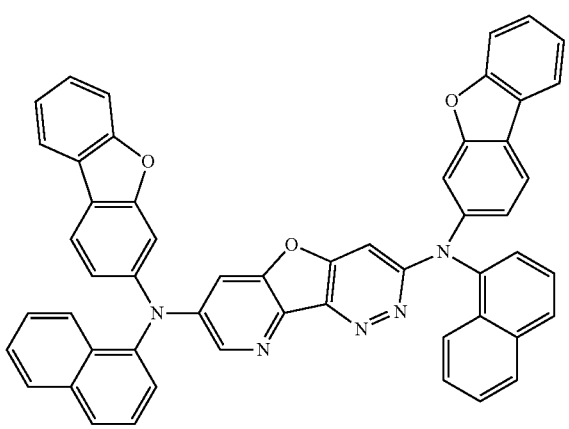
M311
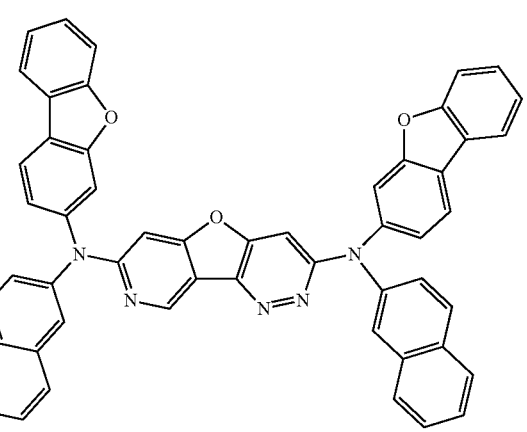

M312
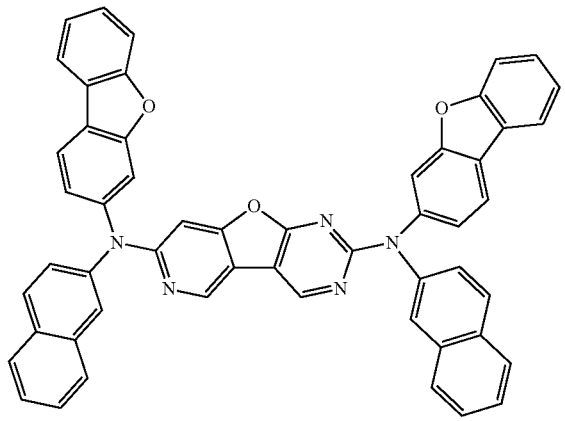
M315
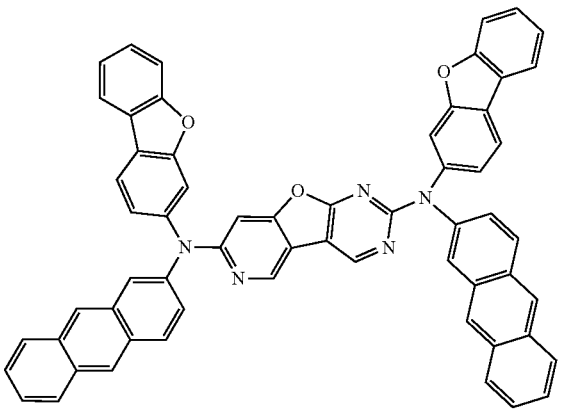
M313
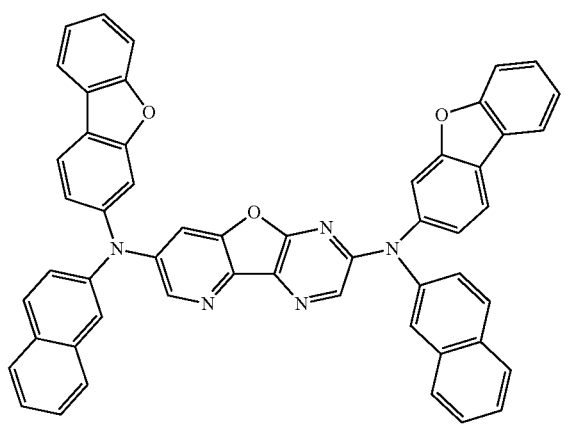
M316
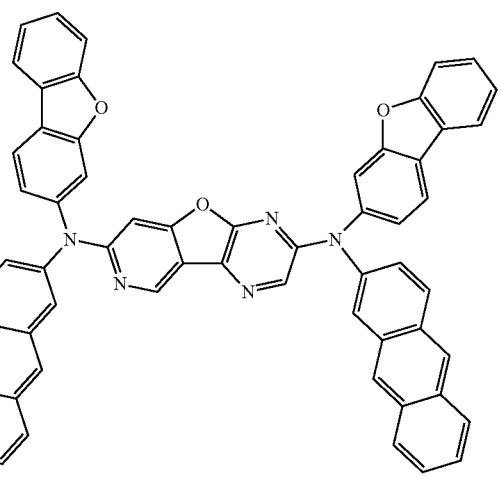
M314
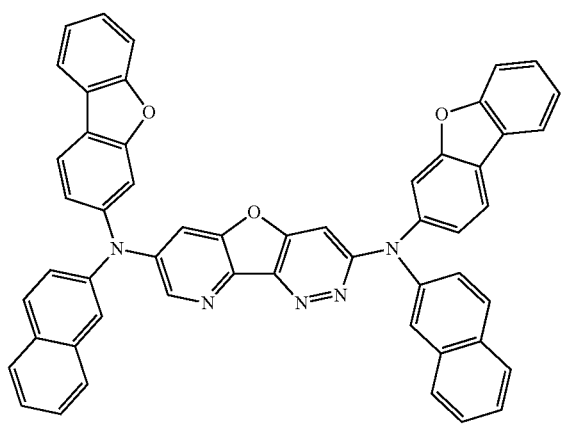
M317
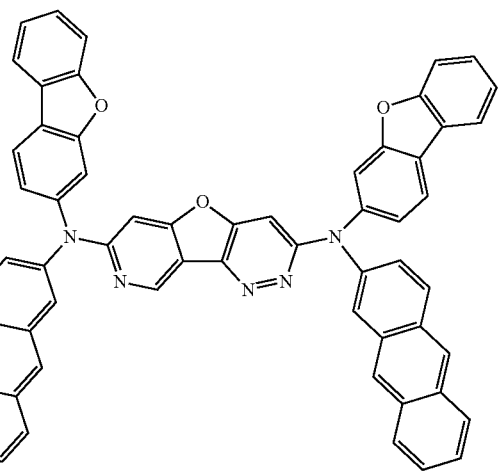

M318
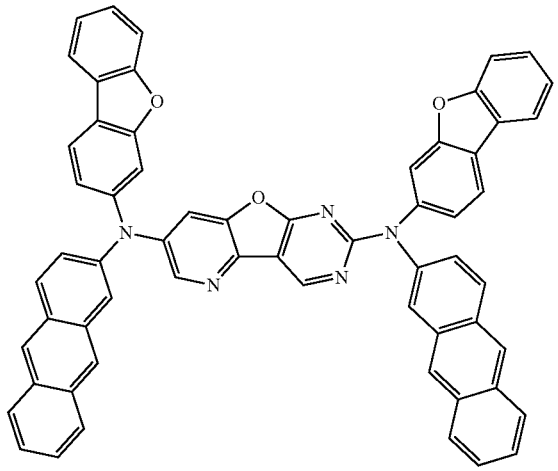
M319
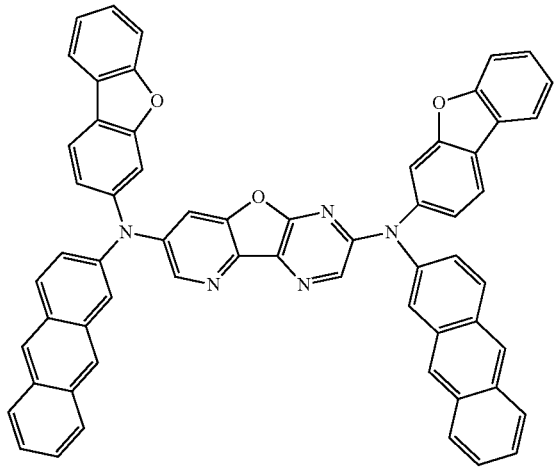
M320
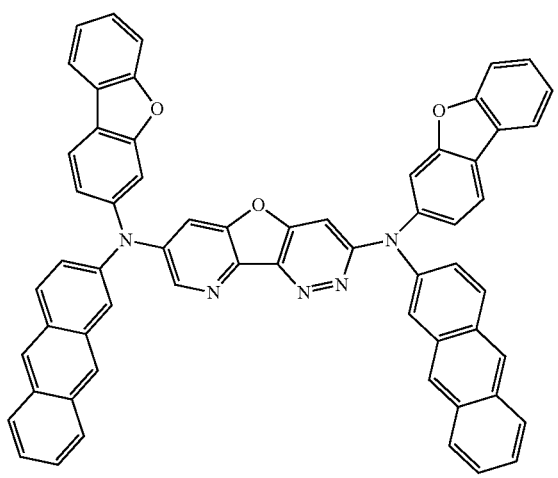
M321
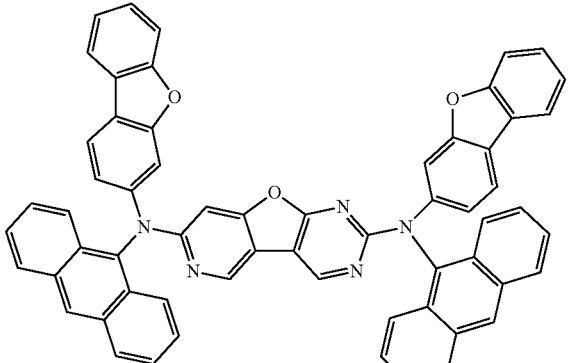
M322
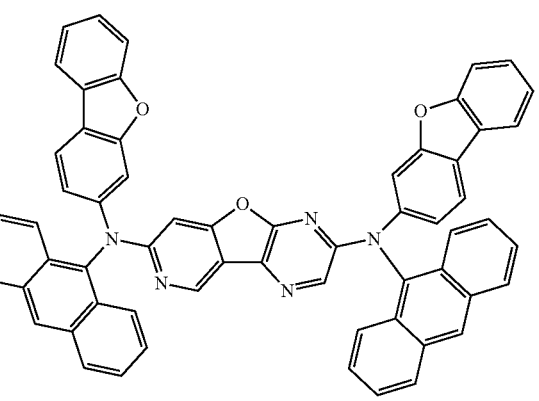
M323
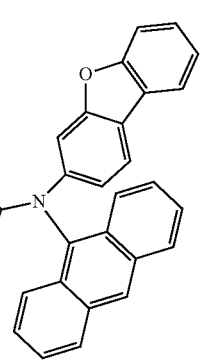
M324
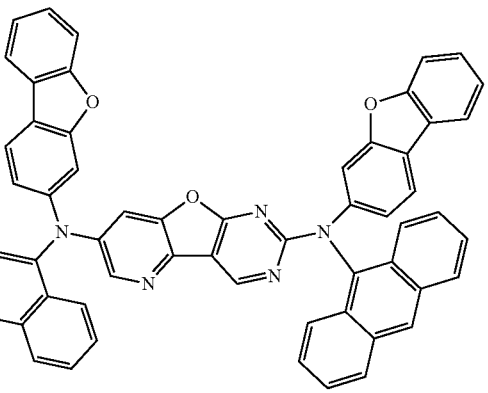

-continued
M325
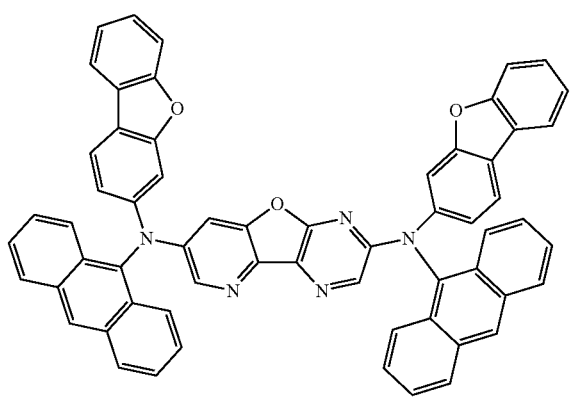
M326
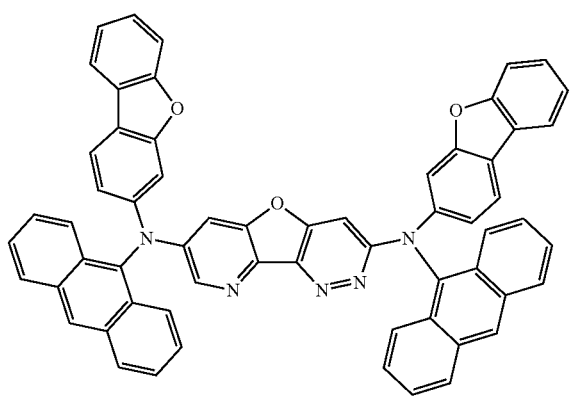
M327
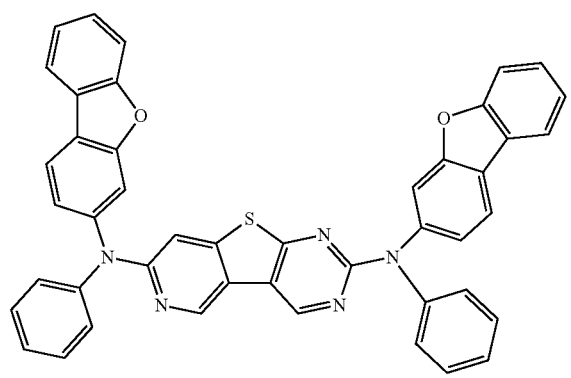
M328
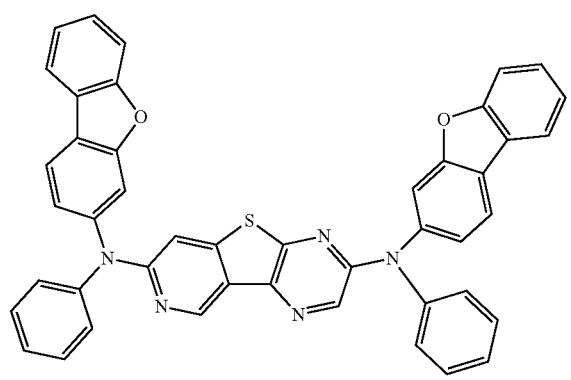
-continued
M329
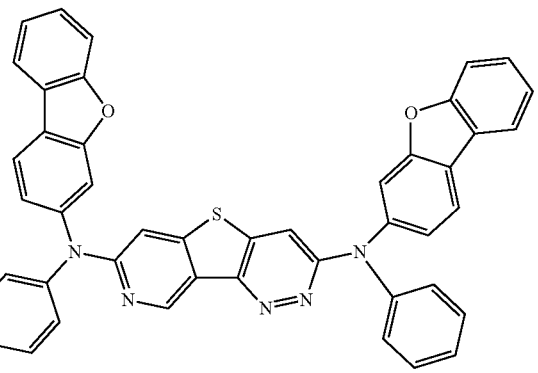
M330
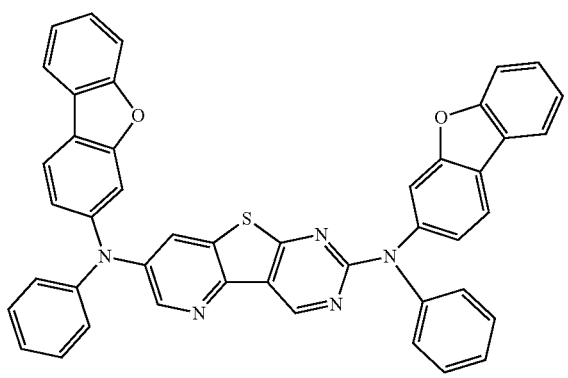
M331
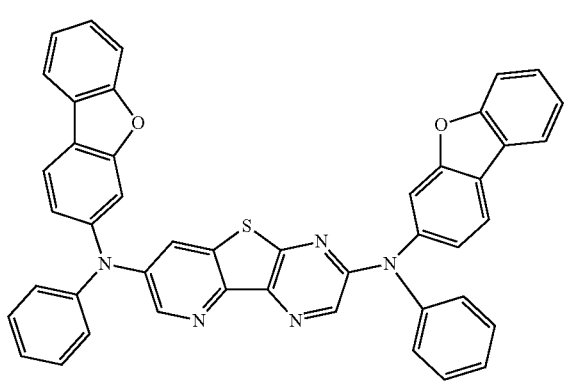
M332
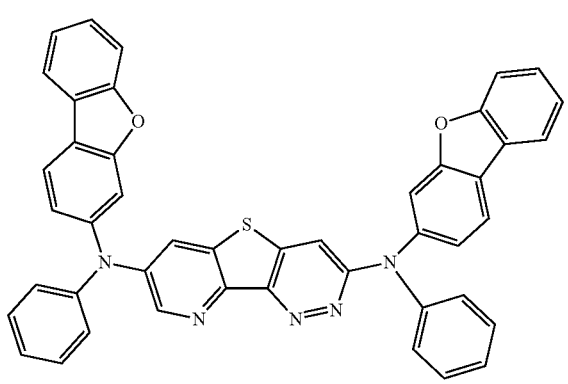

M333
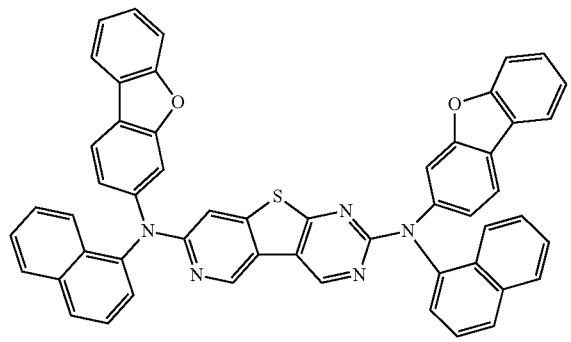
M334
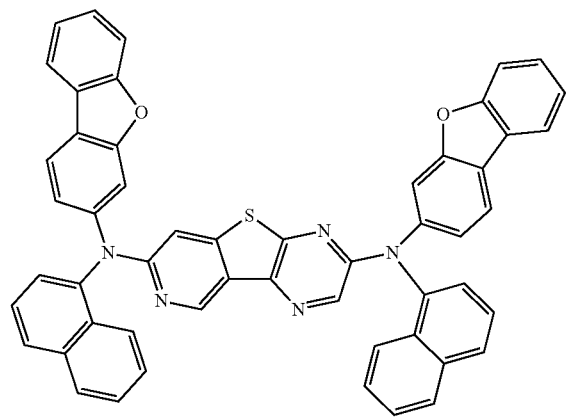
M335
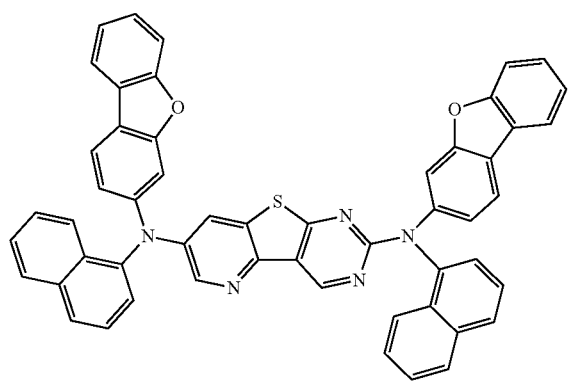
M336
M337
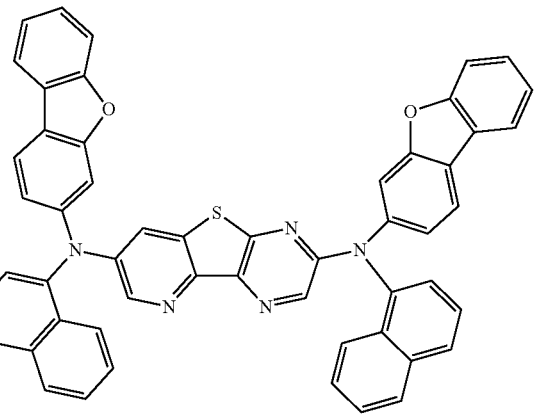
M338
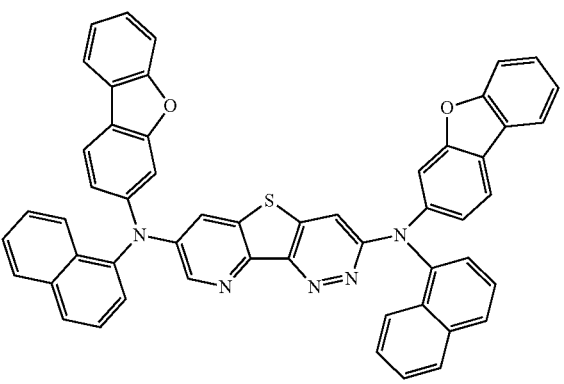
M339
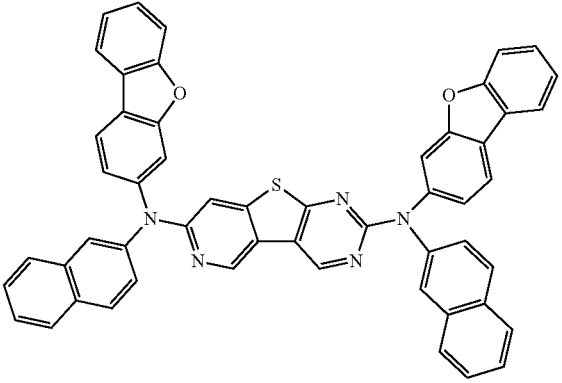

M340
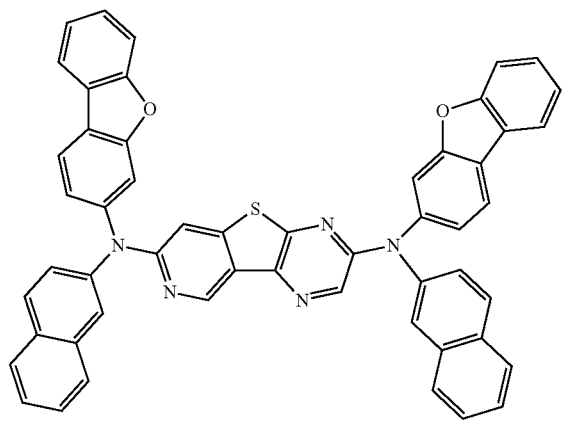
M341
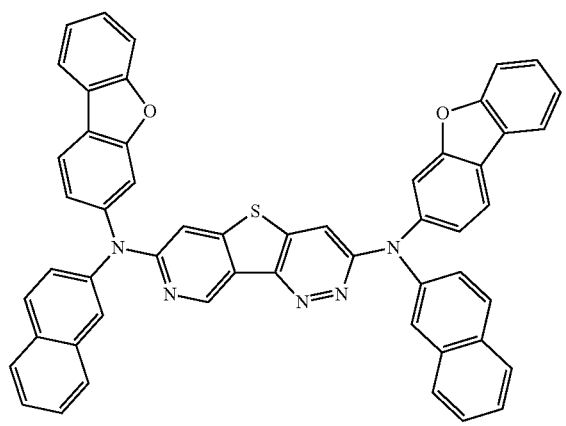
M342
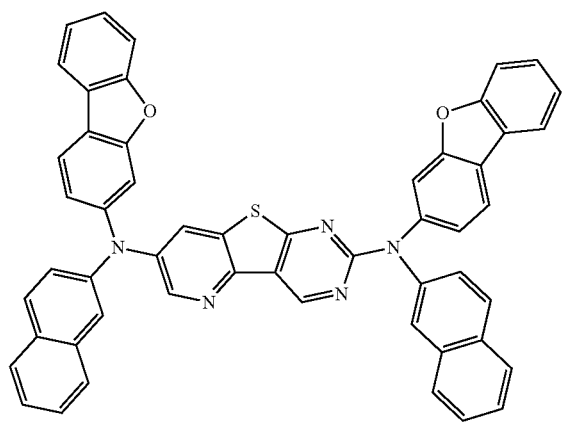
M343
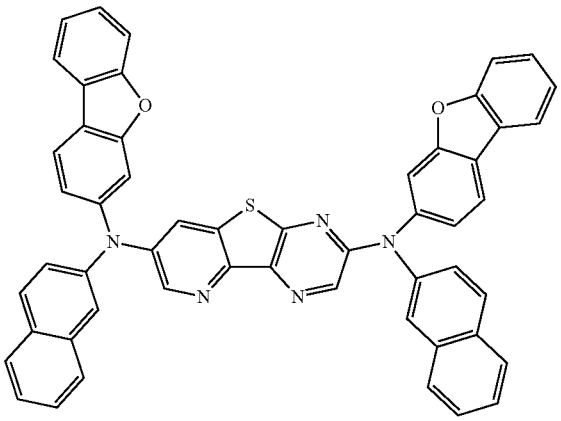
M344
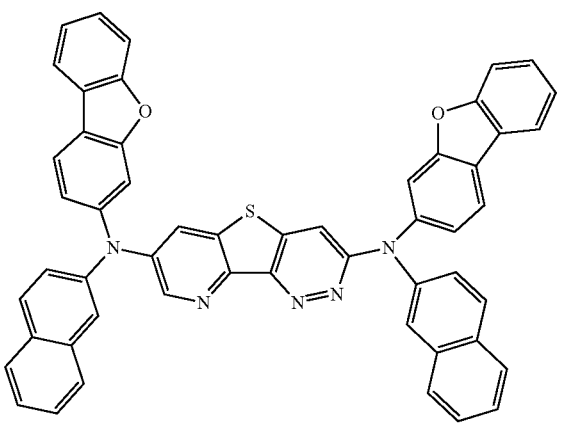
M345
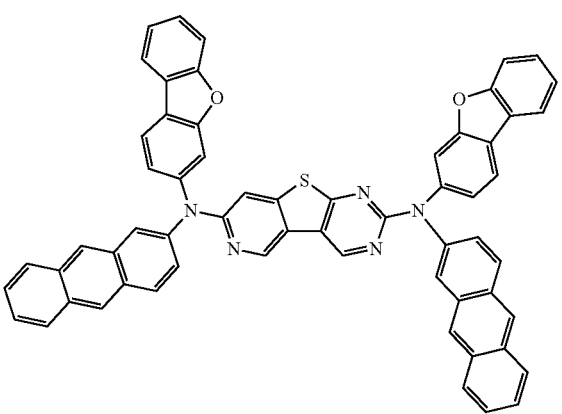

M346
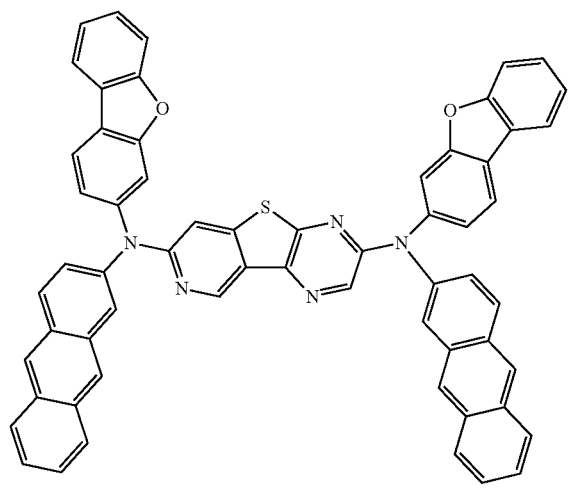
M349
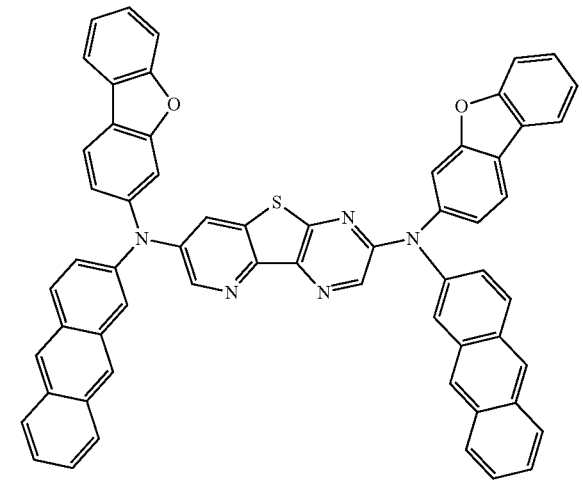
M347
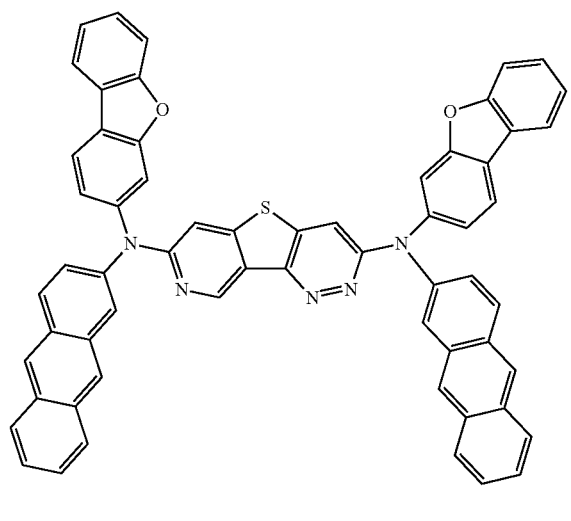
M350
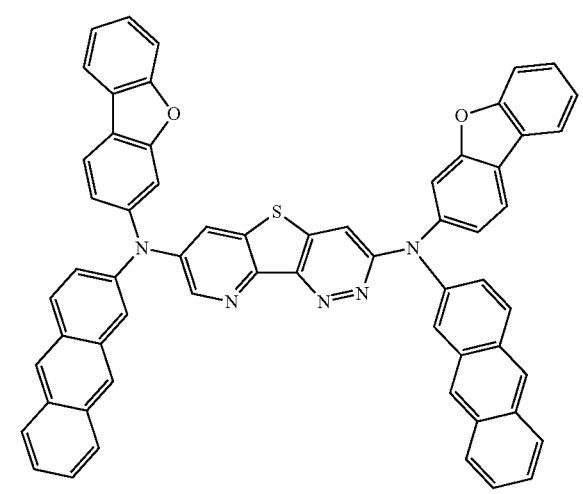
M348
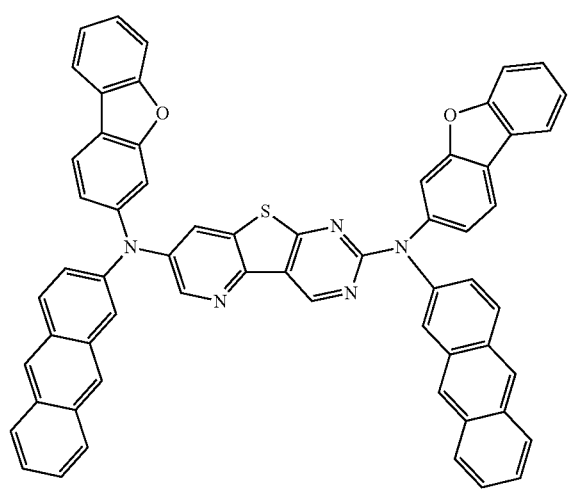
M351
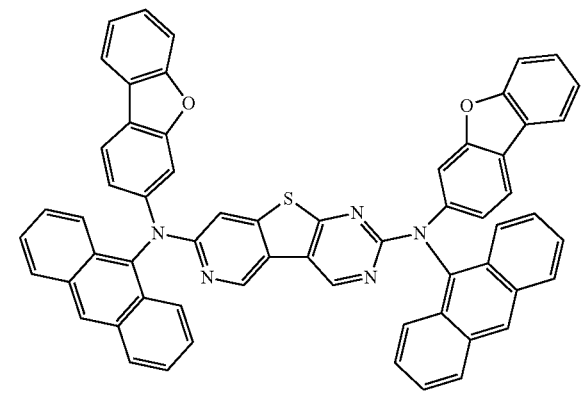

M352
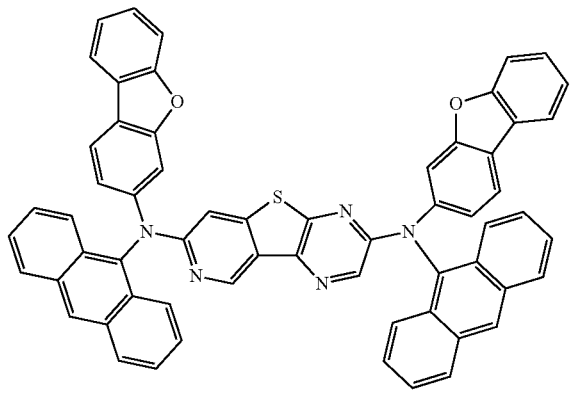
M353
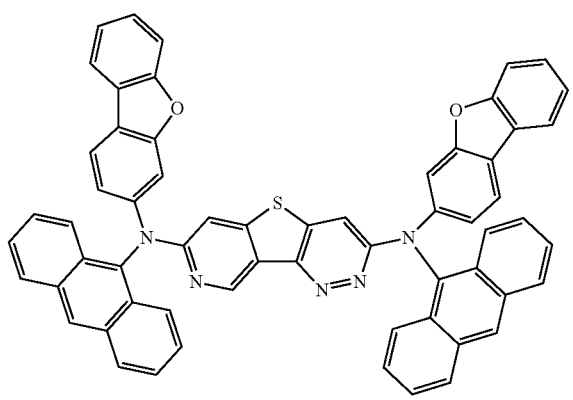
M354
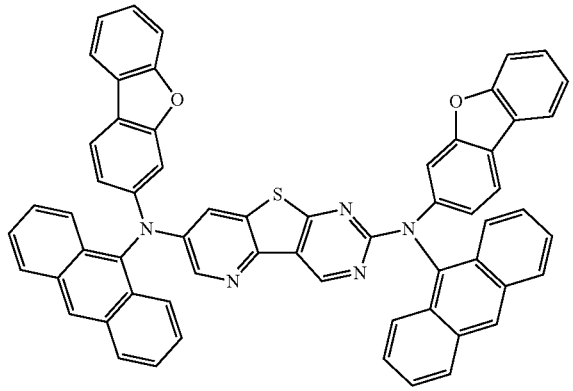
M355
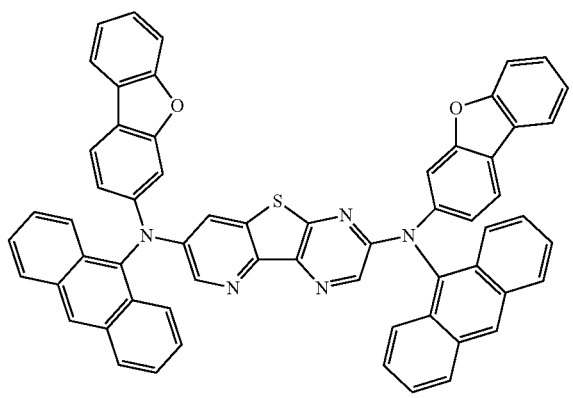
M356
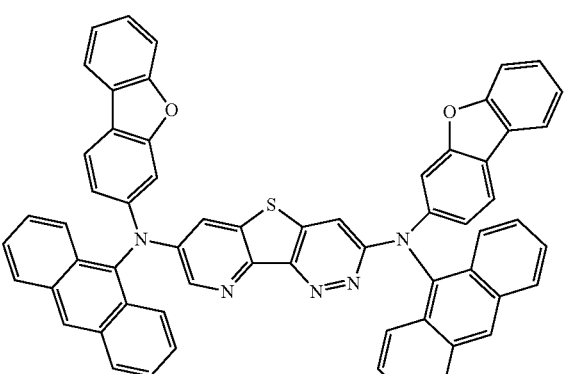
M357
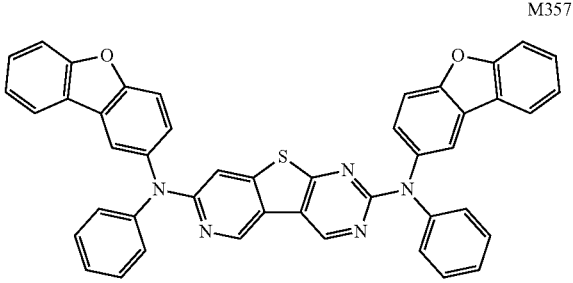
M358
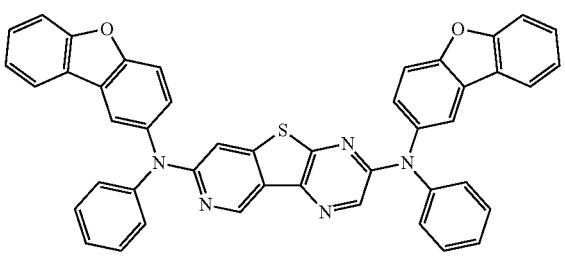
M359
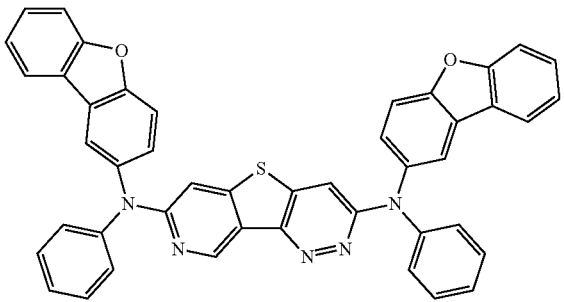
M360
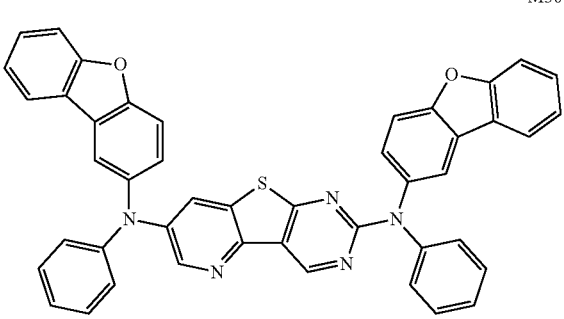

M361
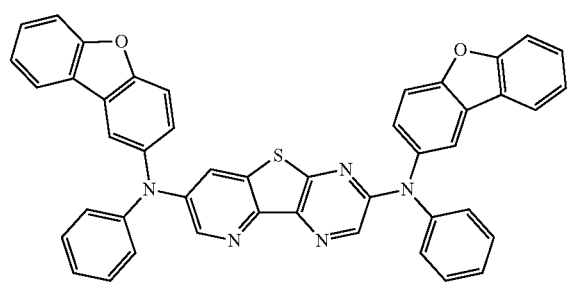
M362
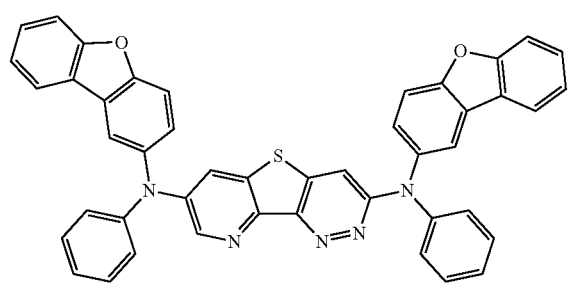
M363
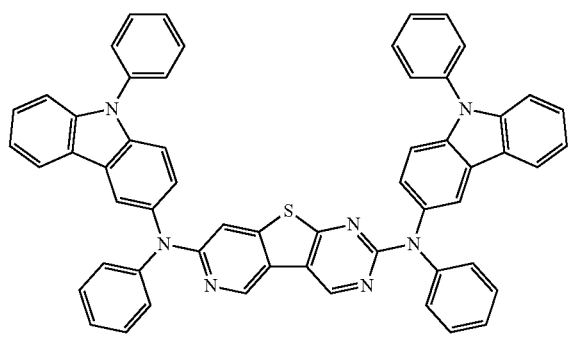
M364
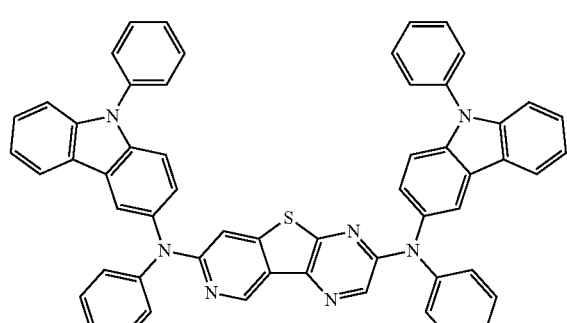
M365
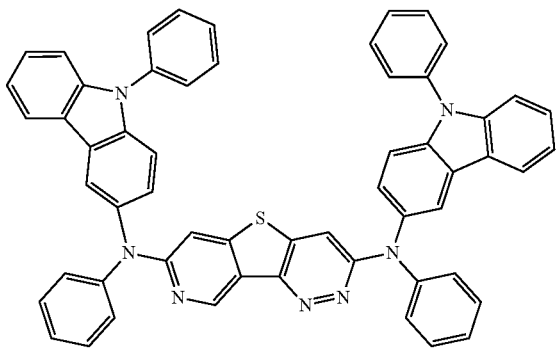
M366
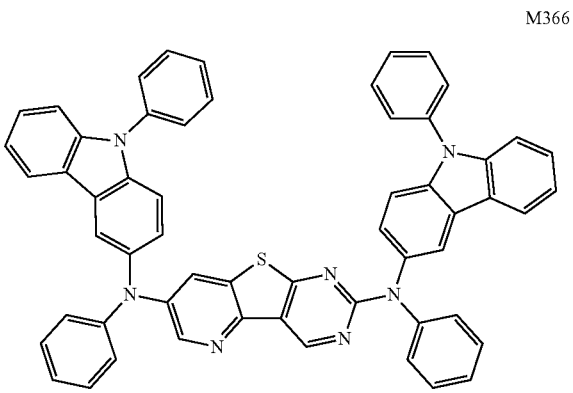
M367
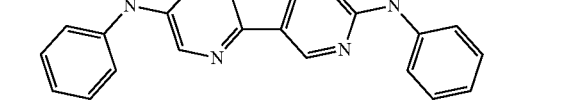
M368
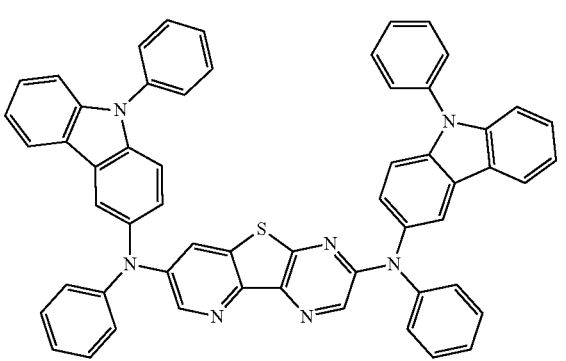
22. The heterocyclic compound according to claim 1, wherein the heterocyclic compound has any one of following structures:

-continued
M369
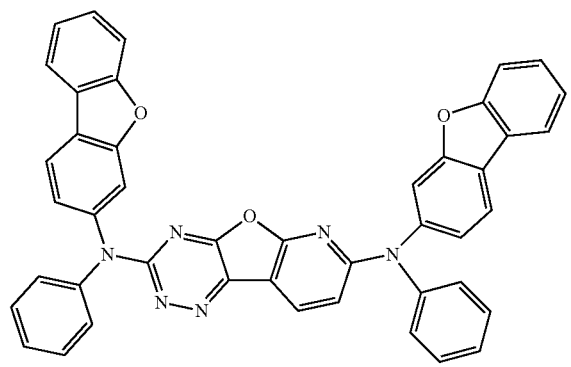
M373
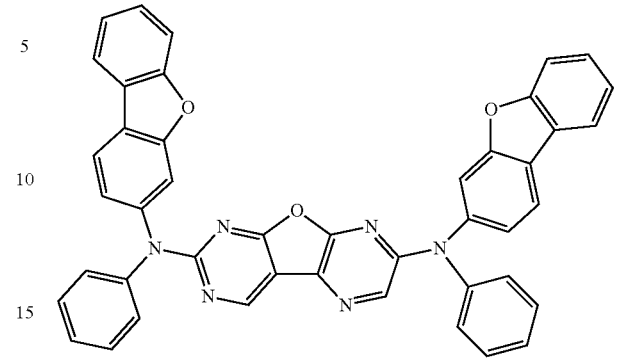
M370
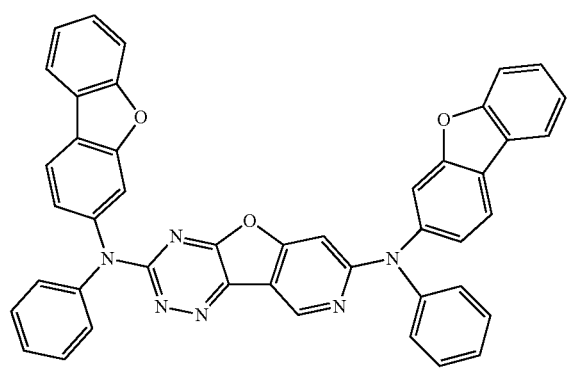
M374
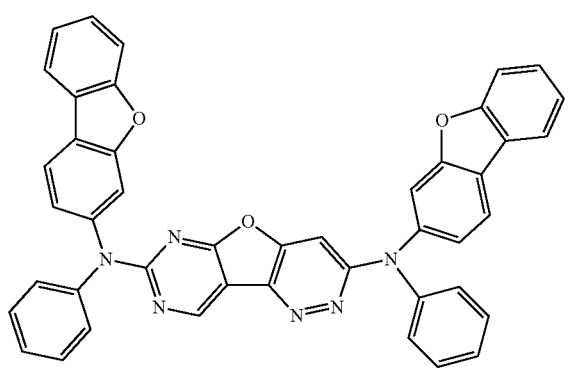
M371
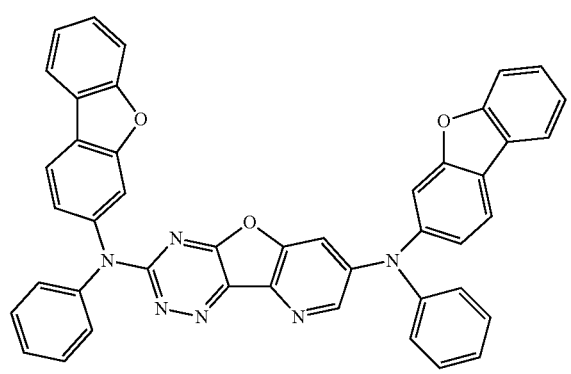
M375
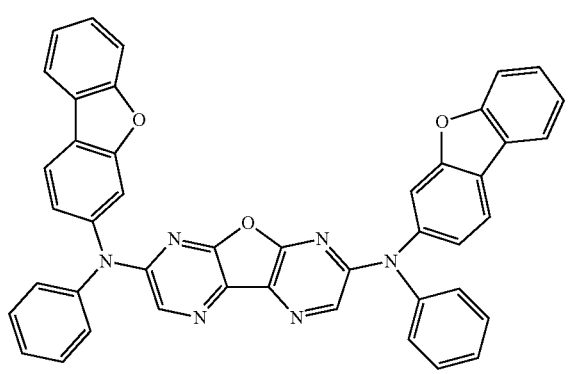
M372
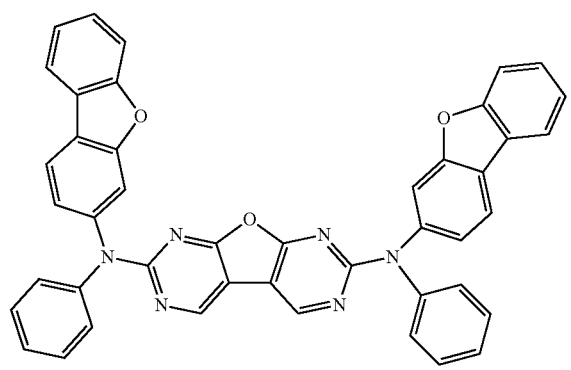
M376
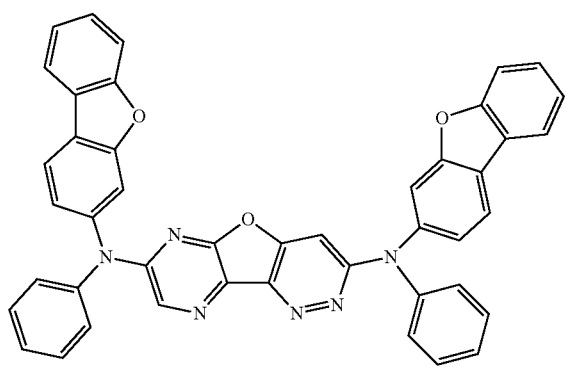

-continued
M377
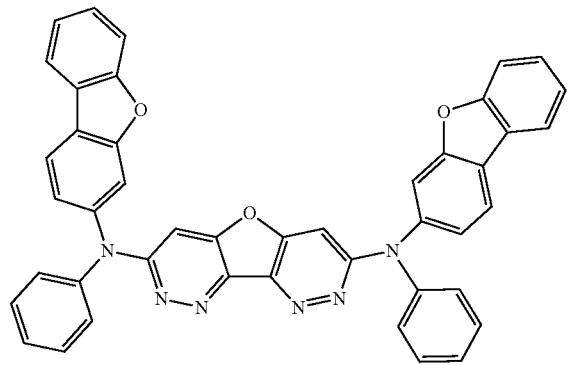
M378
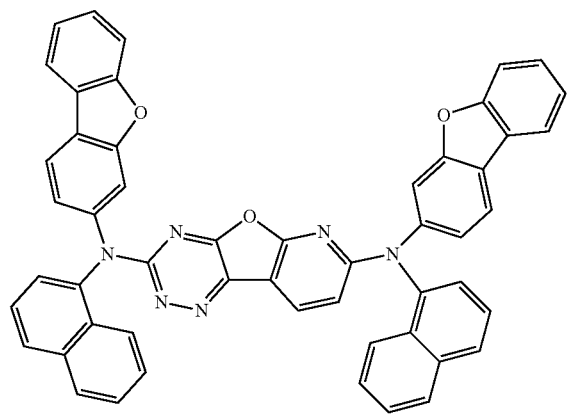
M379
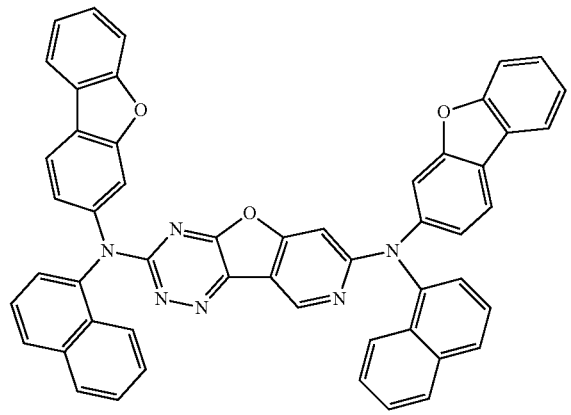
M380
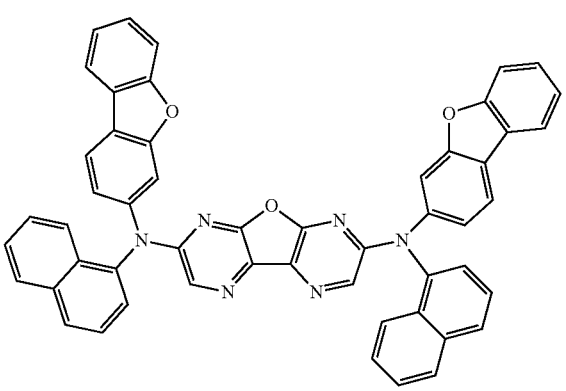
M381
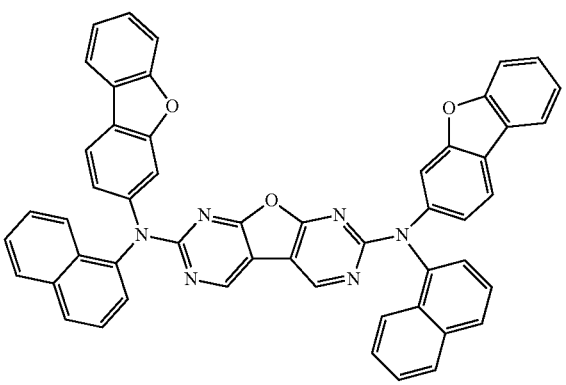
M382
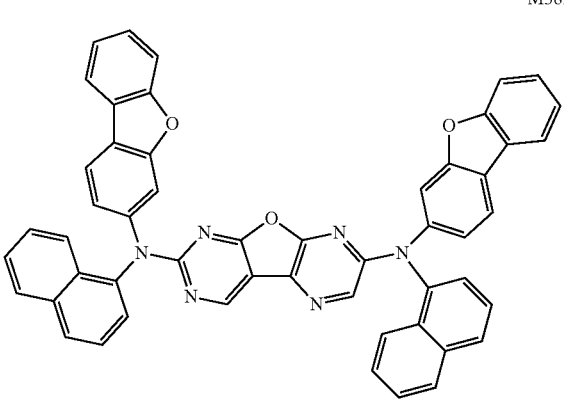
M383
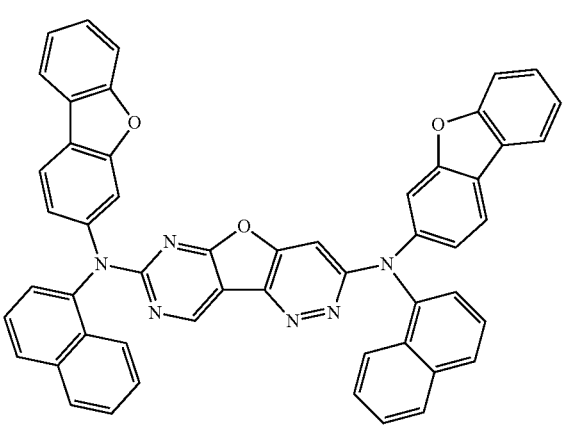
M384

M385
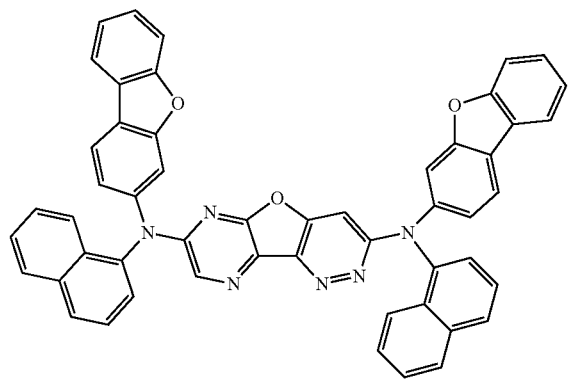
M386
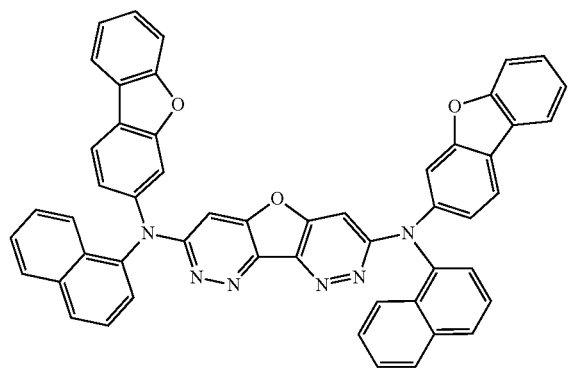
M387
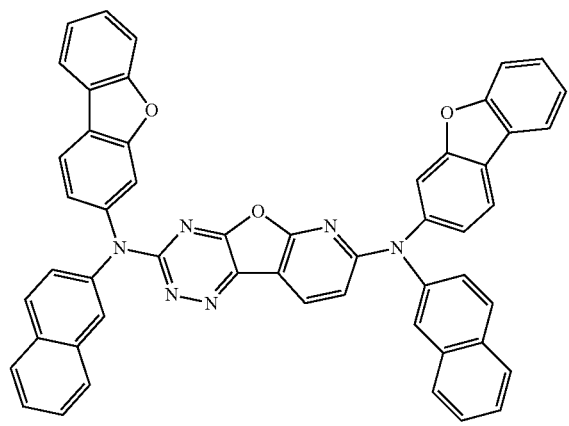
M388
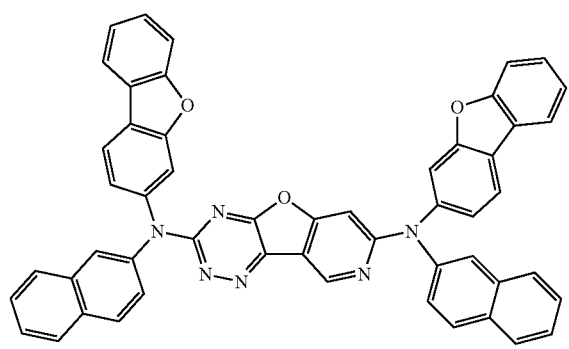
M389
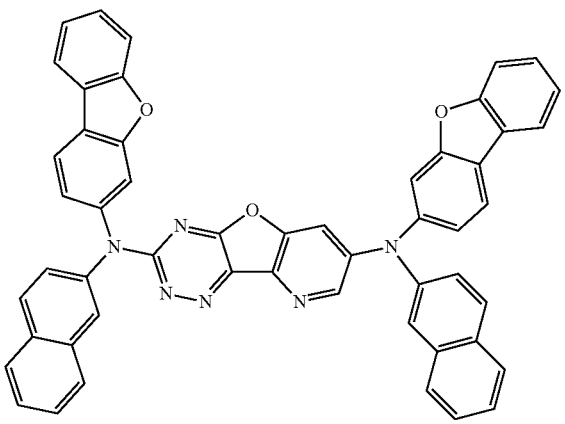
M390
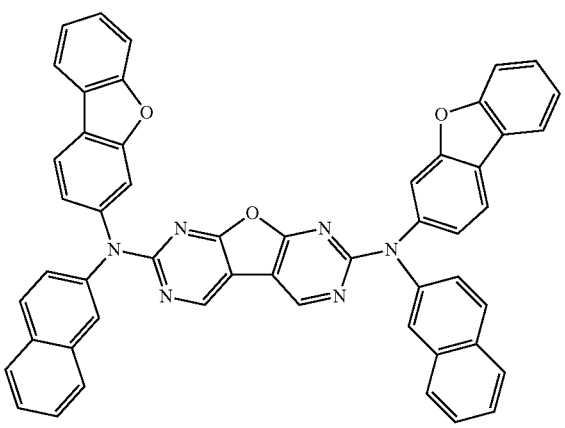
M391
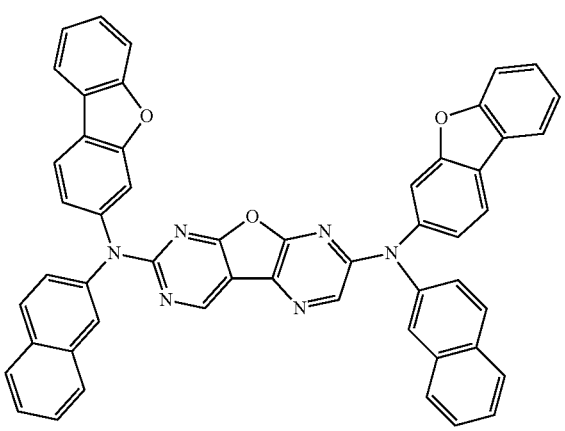

299
-continued
M392
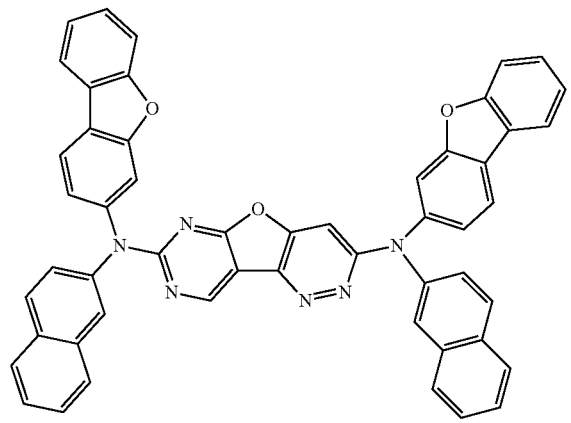
M393
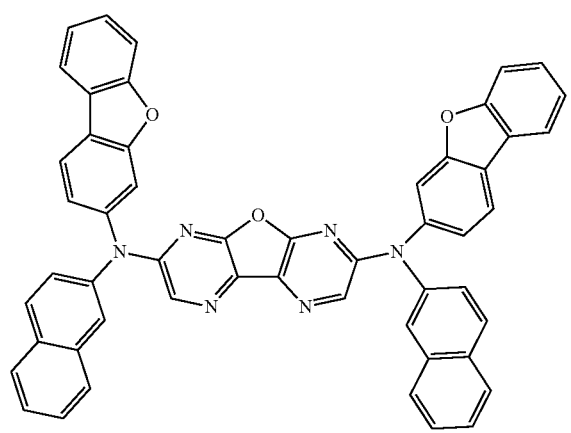
M394
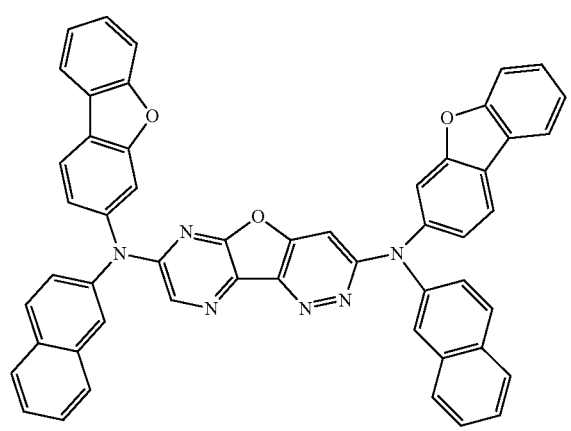
300
-continued
M395
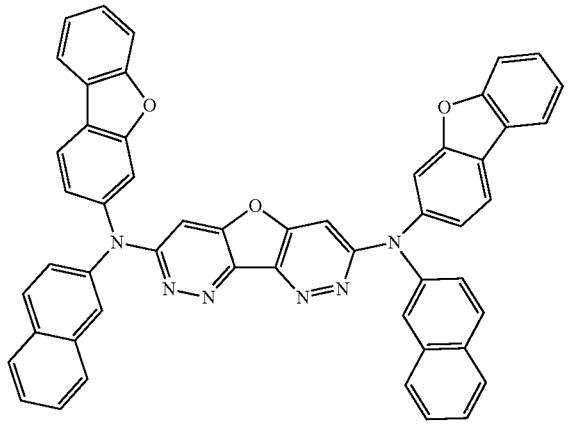
M396
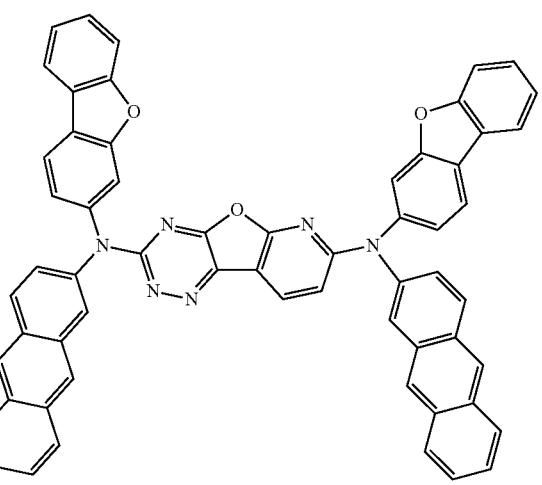
M397
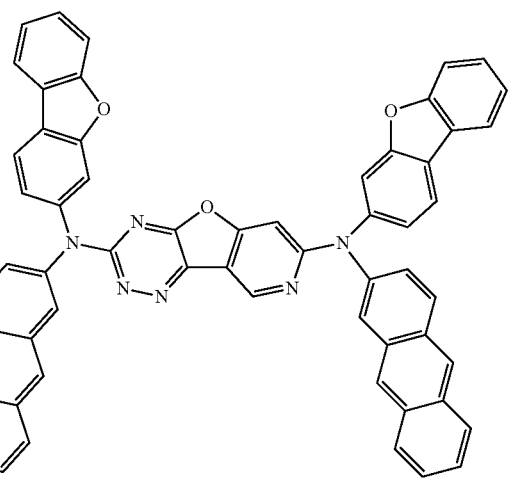

M398
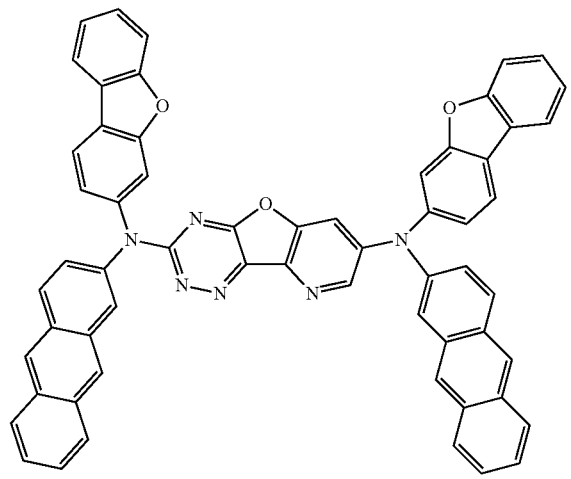
M399
M401
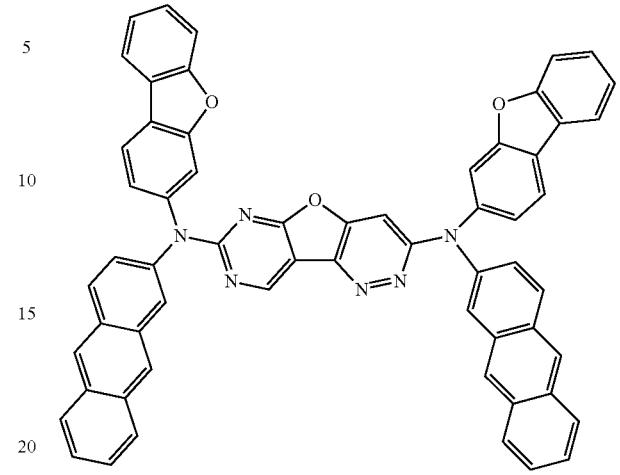
M402
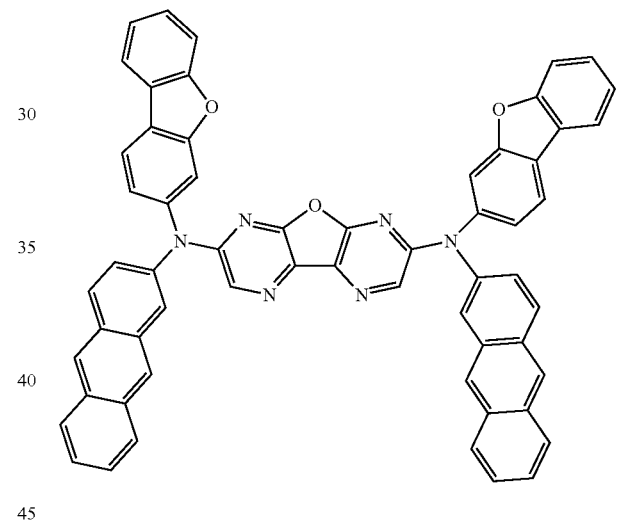
M400
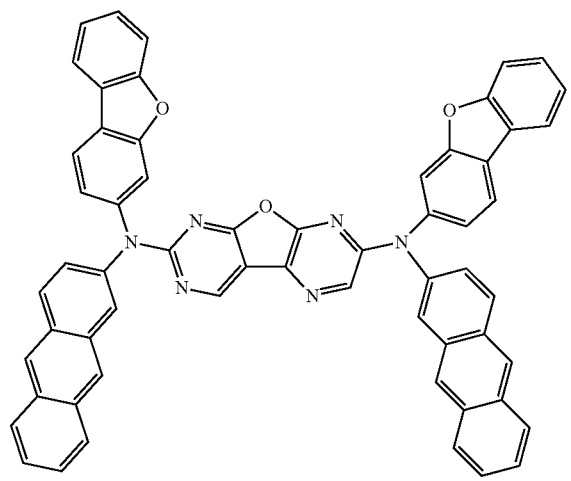
M403
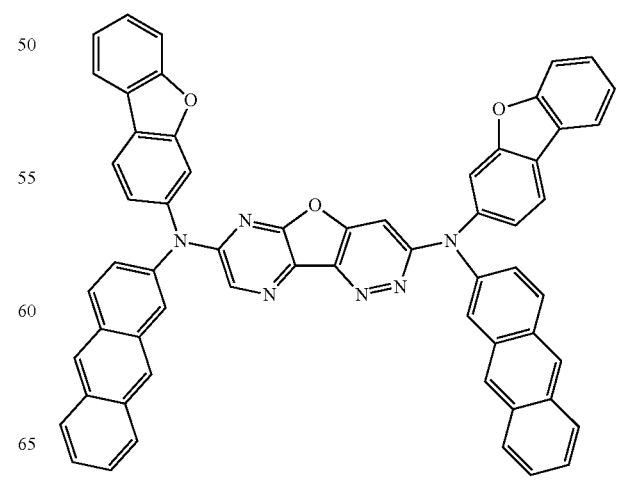

M404
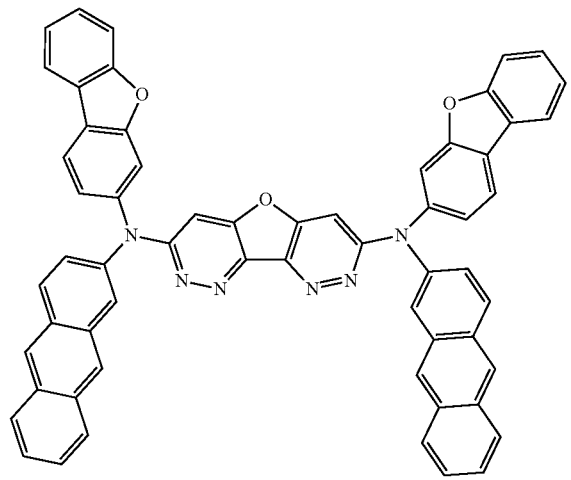
M405
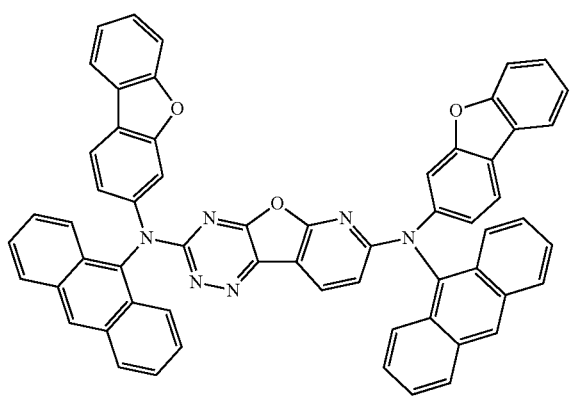
M406
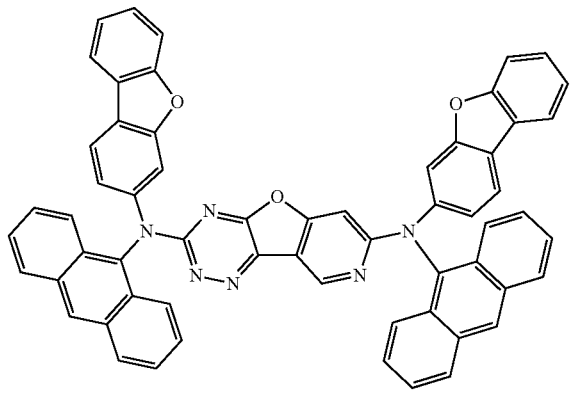
M407
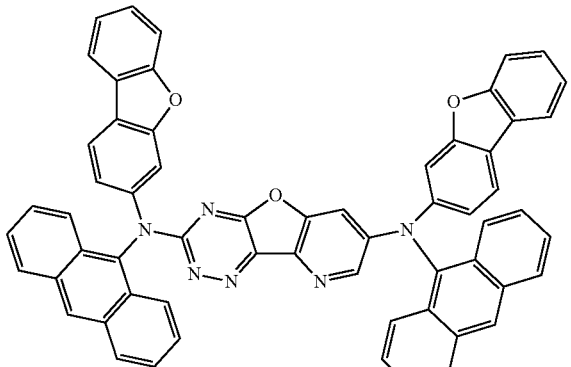
M408
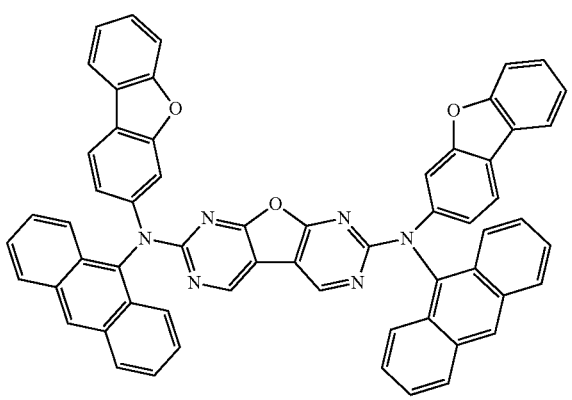
M409
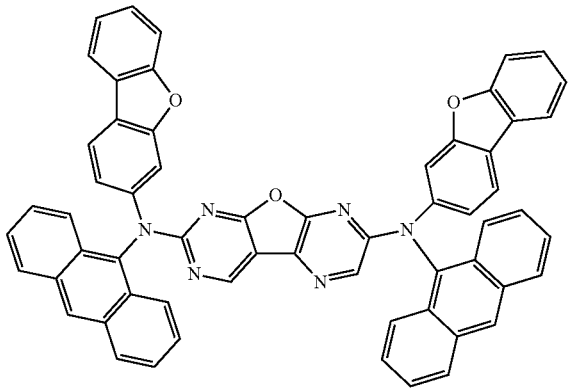
M410
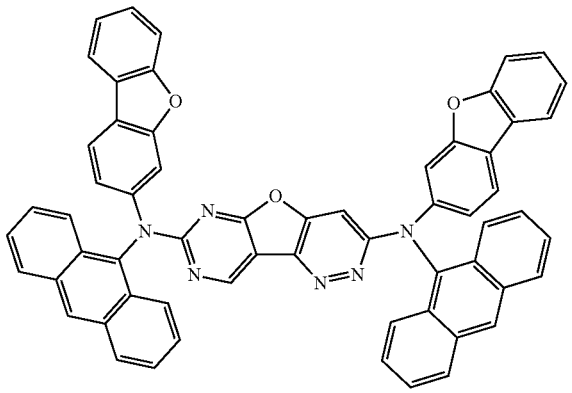

305
-continued
M411
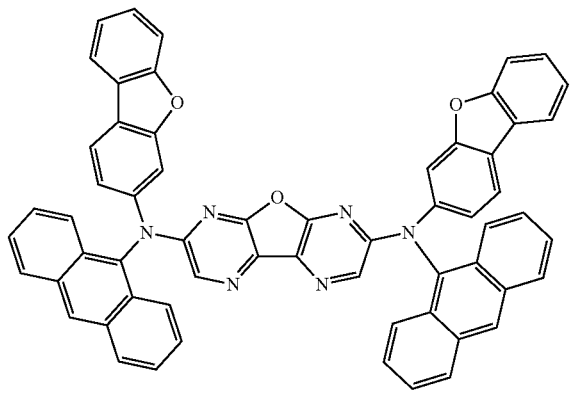
M412
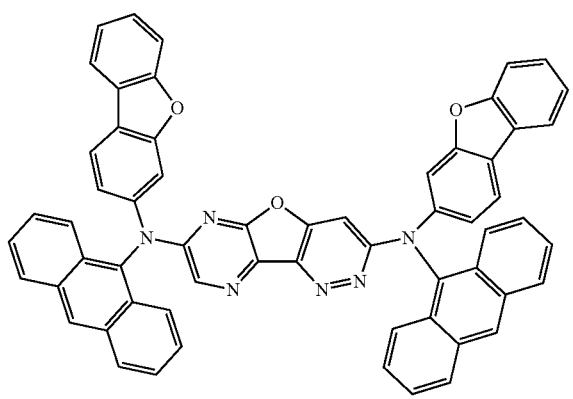
M413
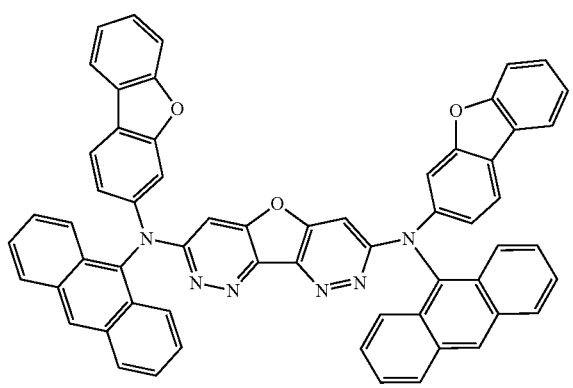
M414
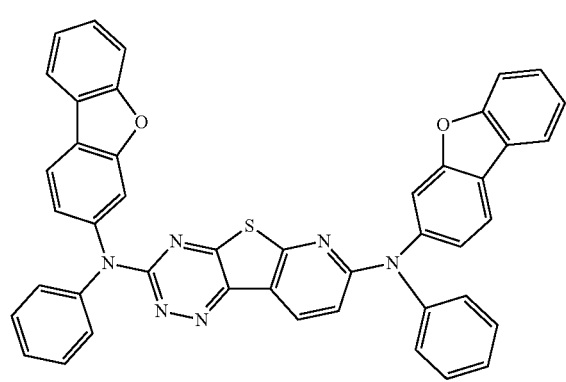
306
-continued
M415
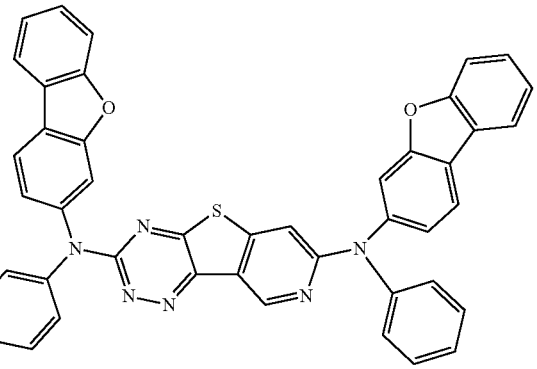
M416
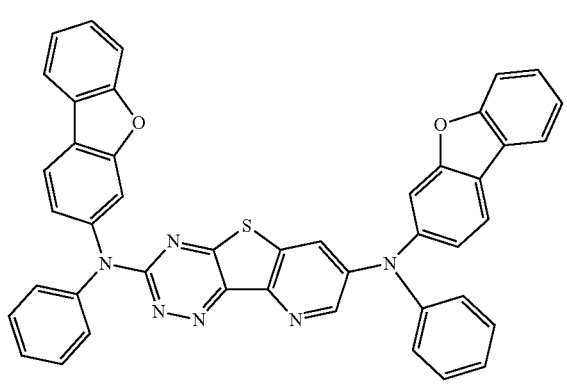
M417
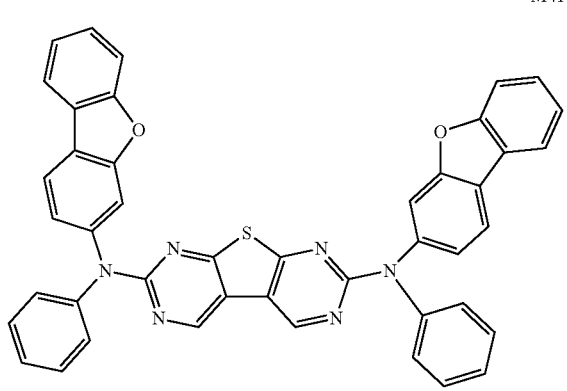
M418
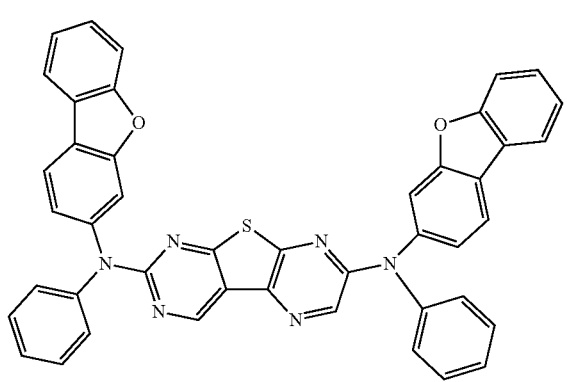

307
-continued
M419
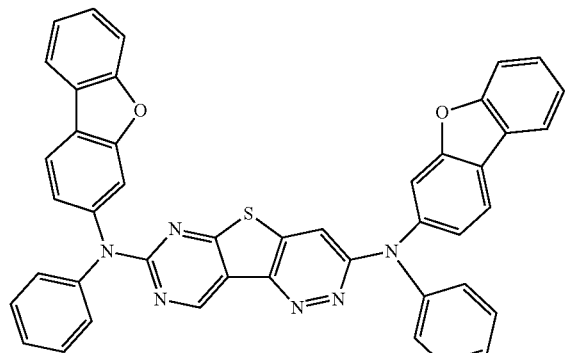
M420
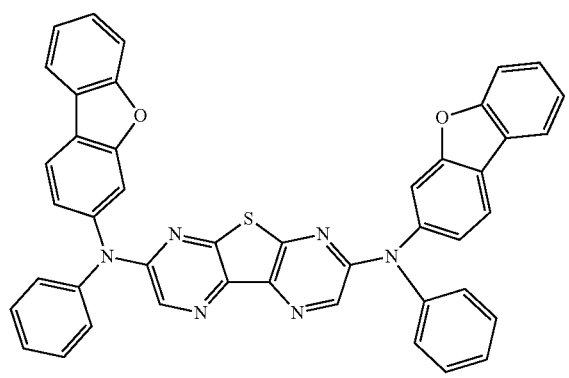
M421
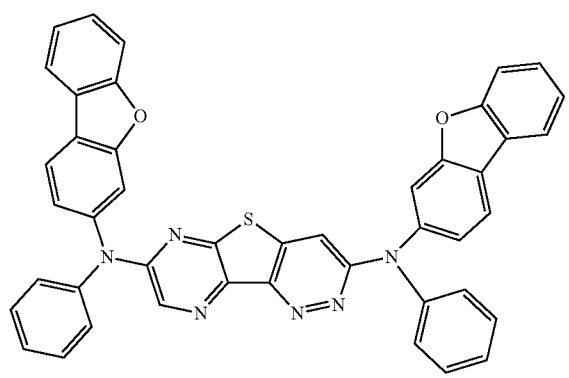
M422
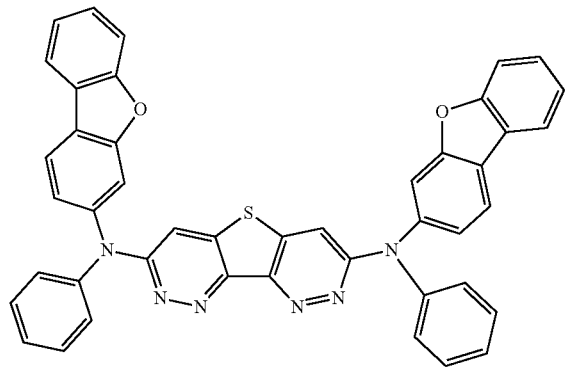
308
-continued
M423
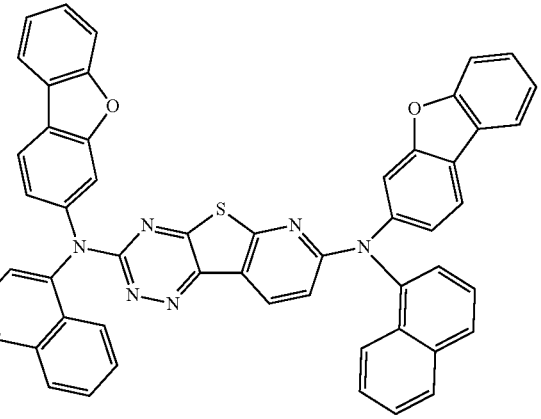
M424
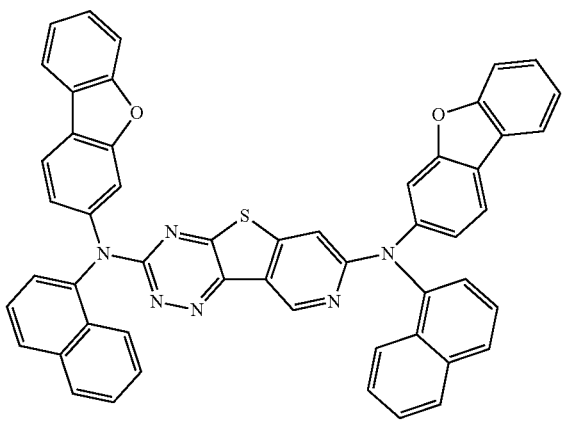
M425
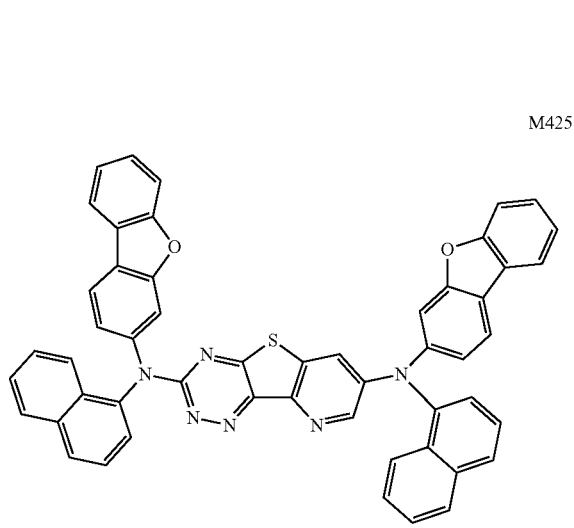

M426
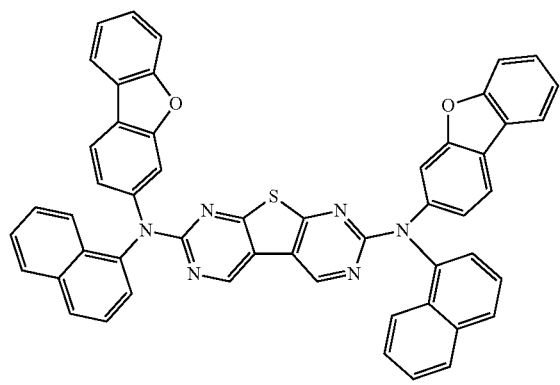
M427
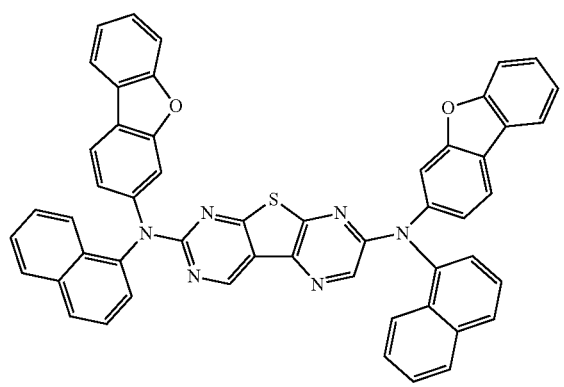
M428
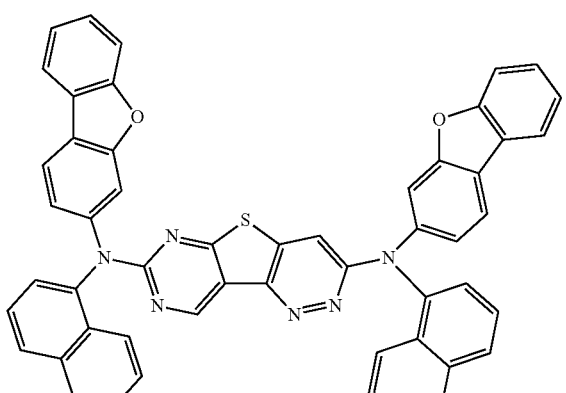
M429
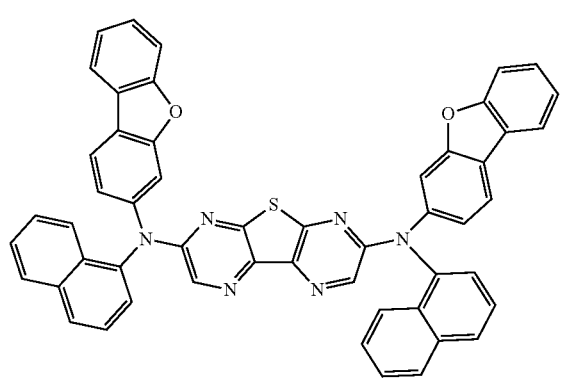
M430
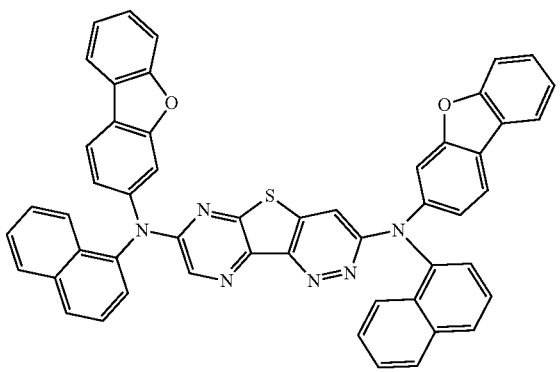
M431
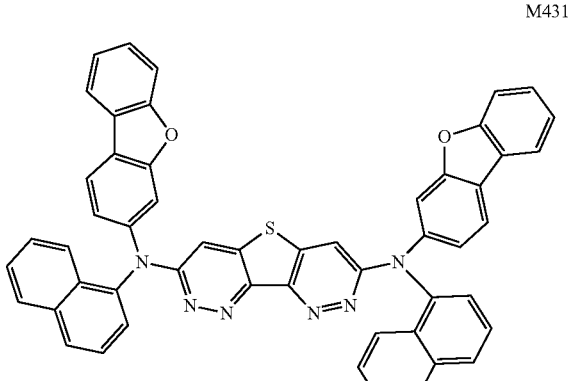
M432
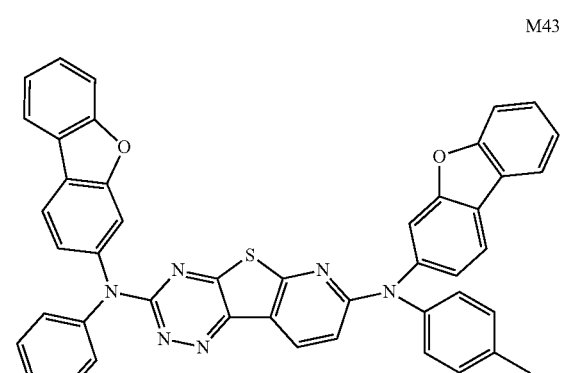
M433
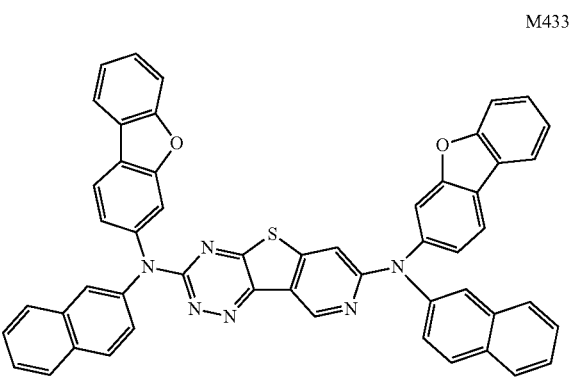

311
-continued
M434
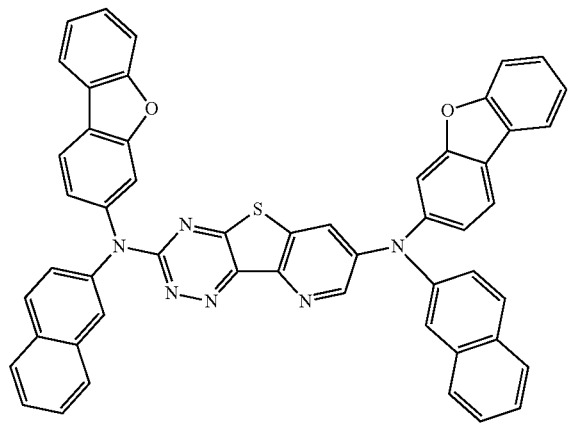
M435
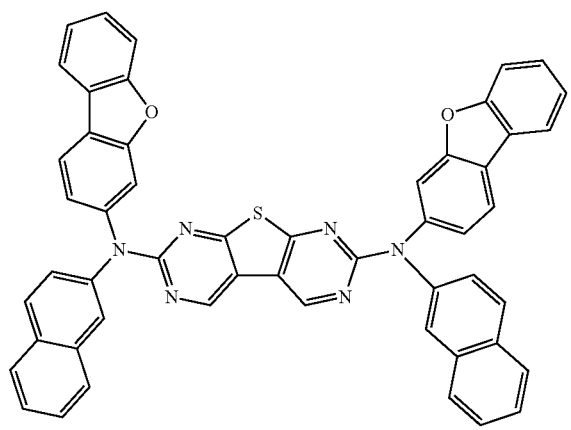
M436
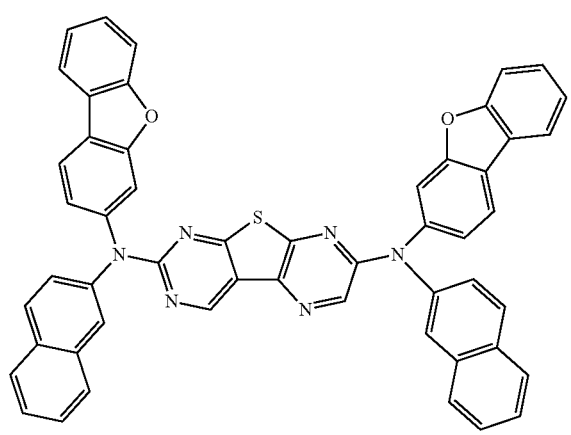
312
-continued
M437
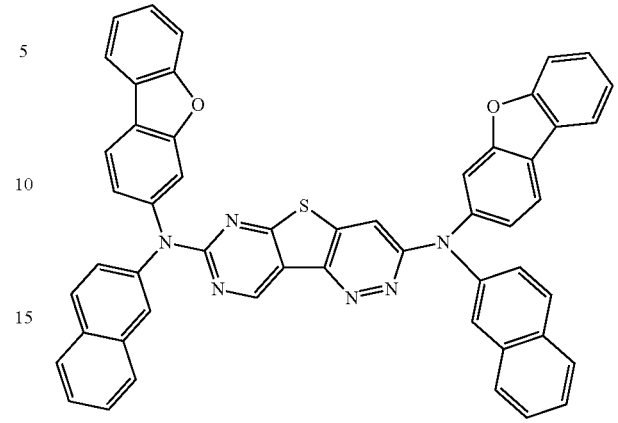
M438
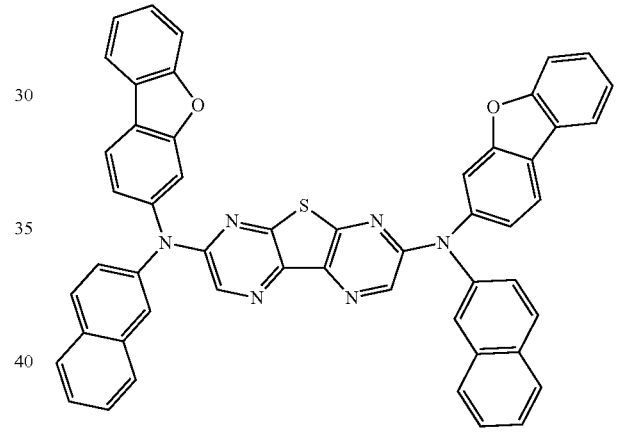
M439
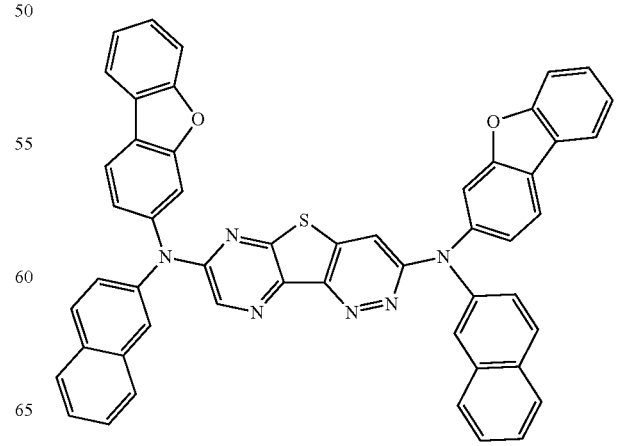

M440
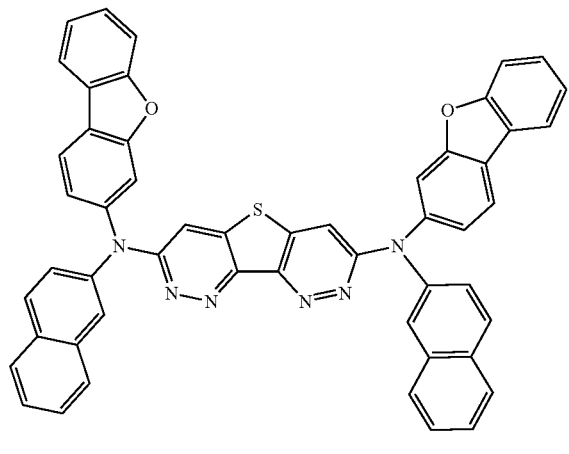
M443
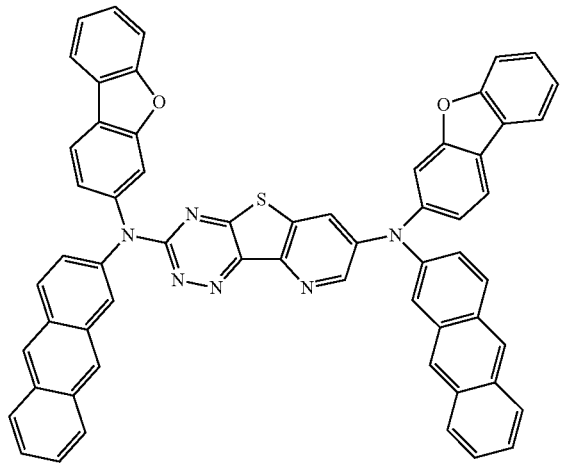
M441
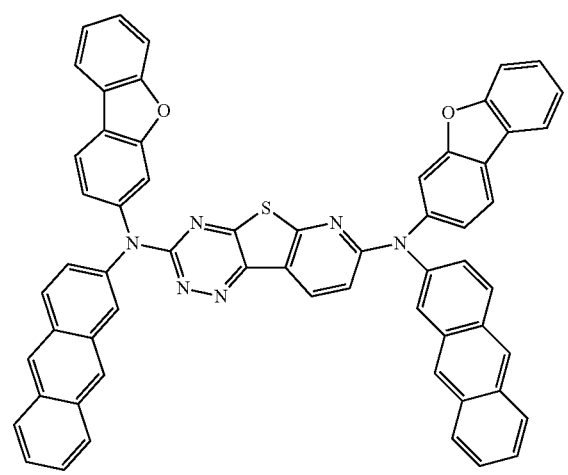
M444
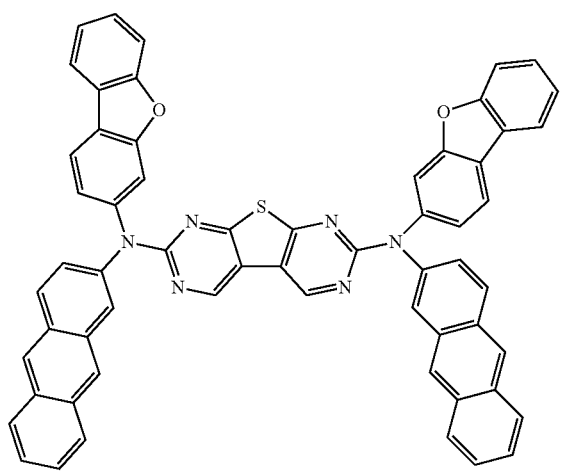
M442
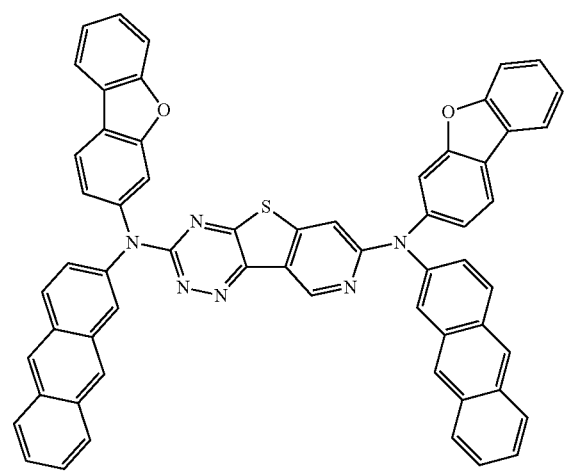
M445
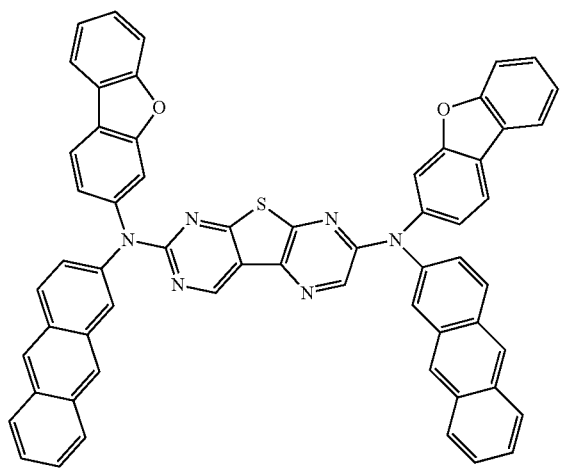

M446
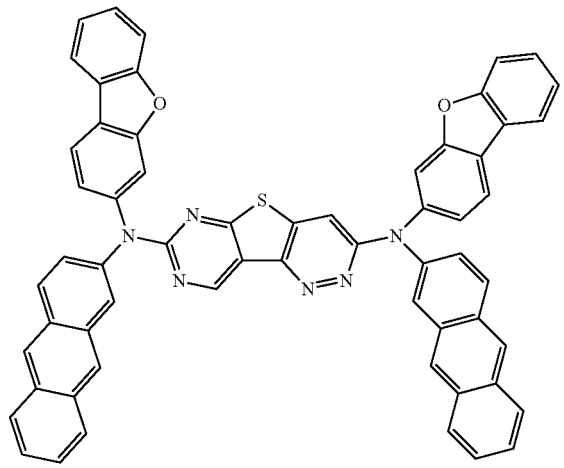
M447
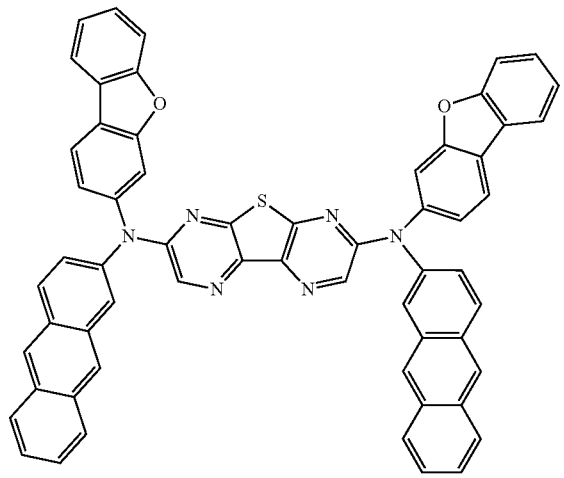
M448
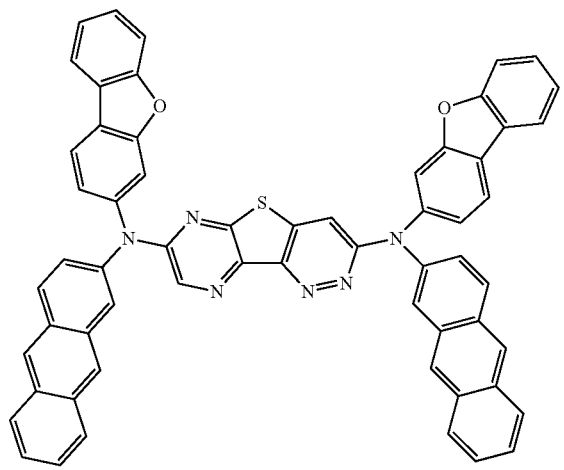
M449
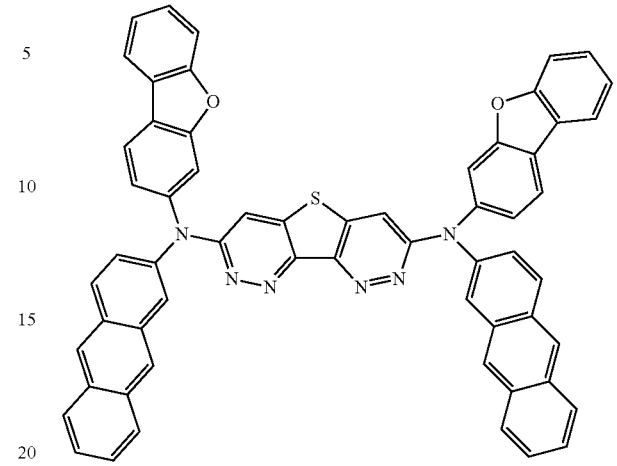
M450
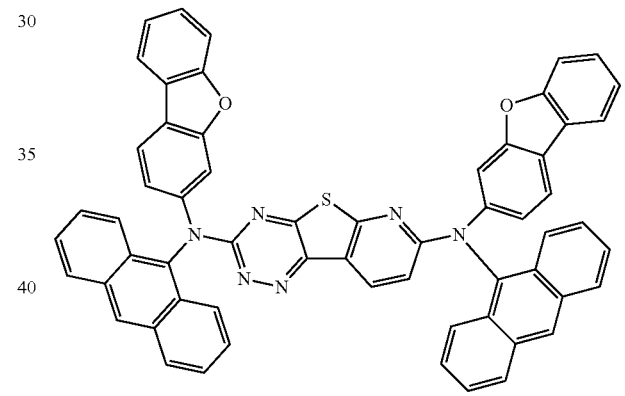
M451
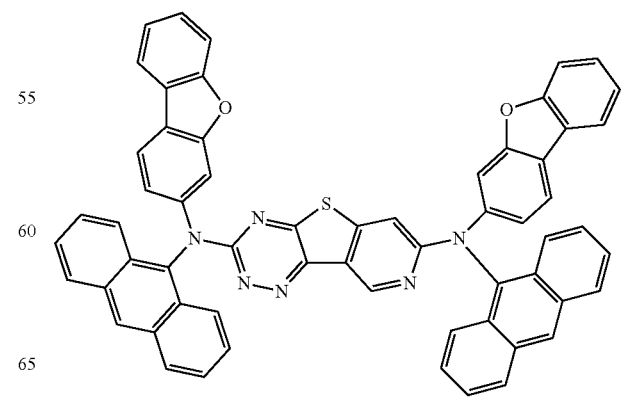

M452
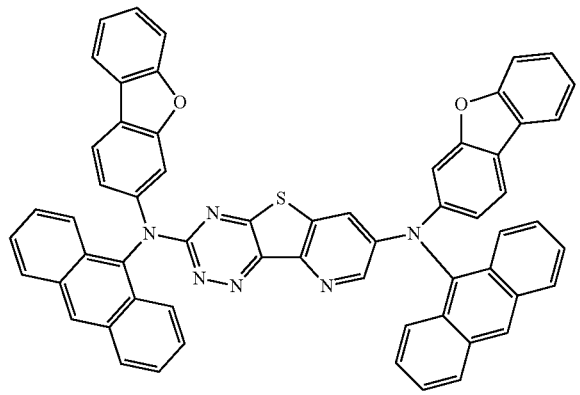
M453
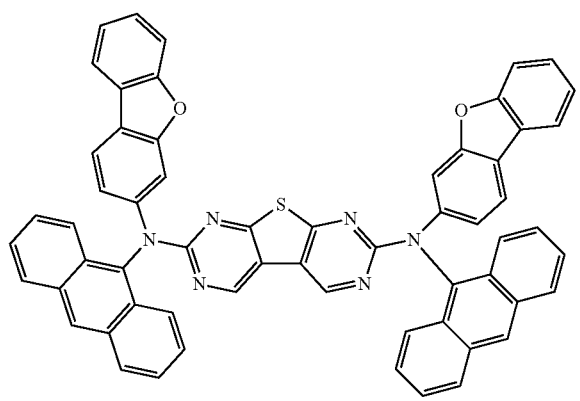
M454
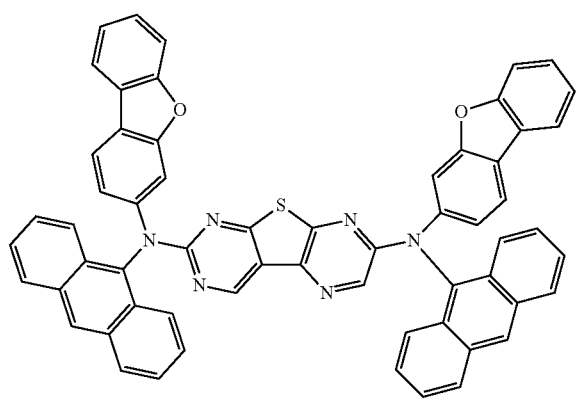
M455
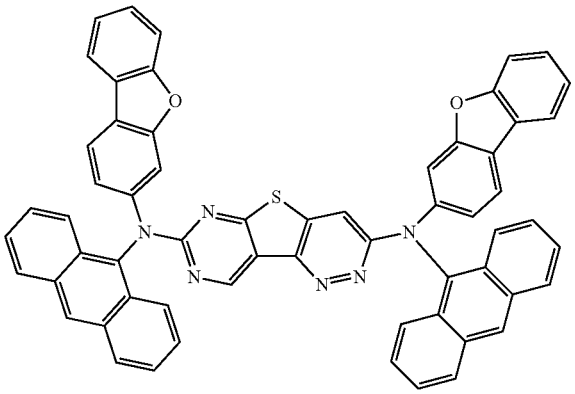
M456
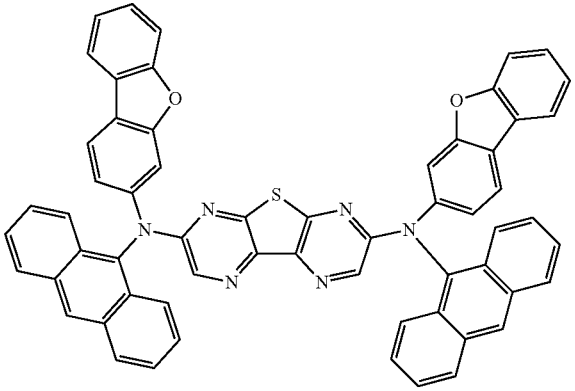
M457
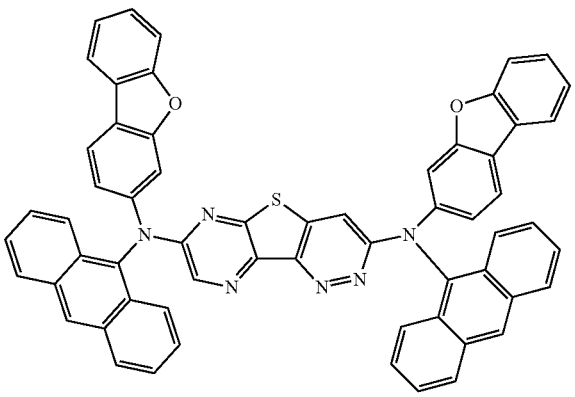
M458
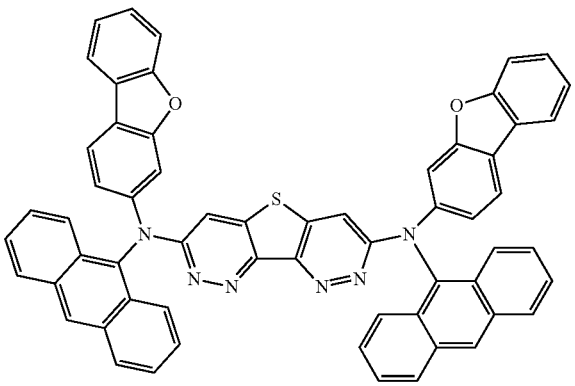

-continued
M459
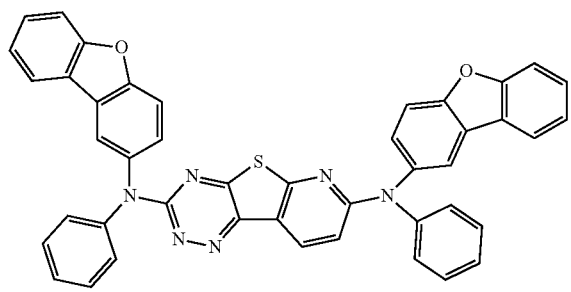
M460
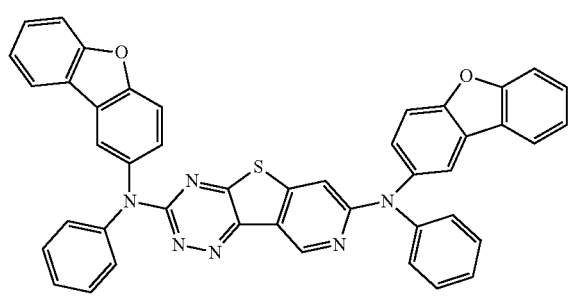
M461
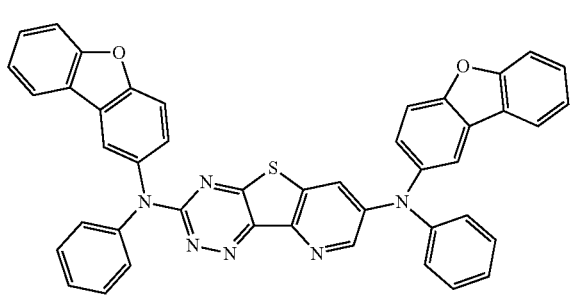
M462
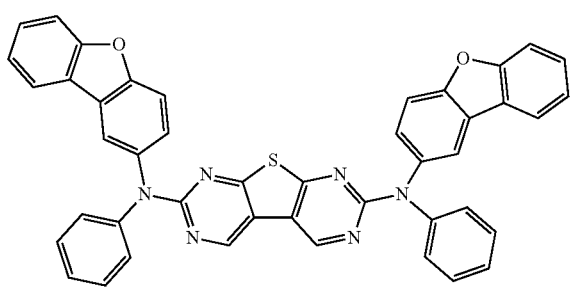
M463
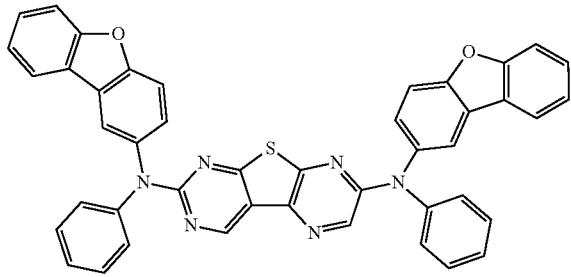
-continued
M464
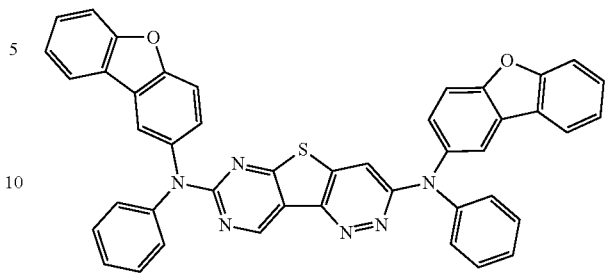
M465
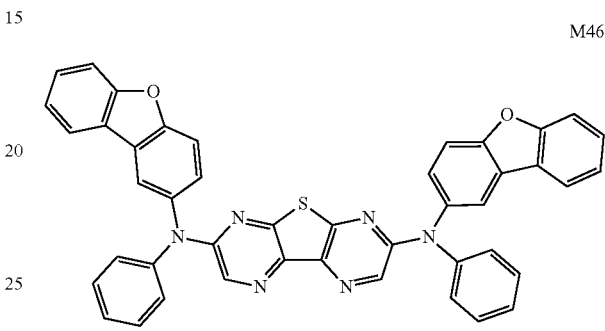
M466
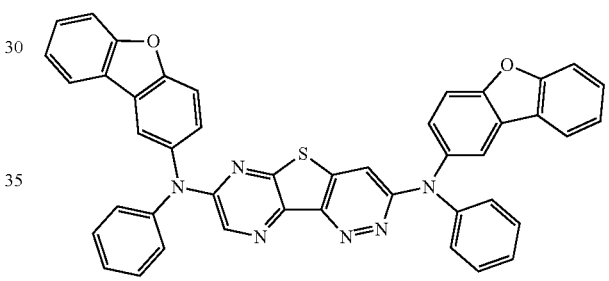
M467
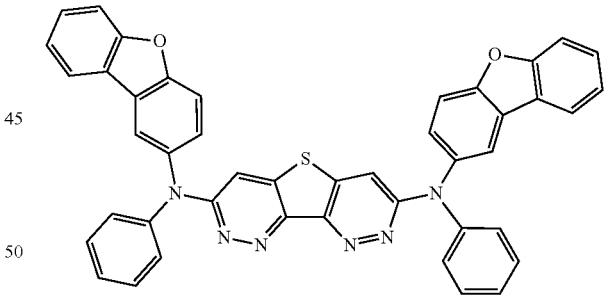
M468
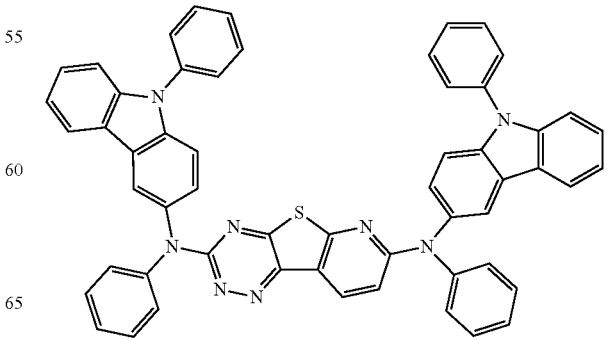

321
-continued
M469
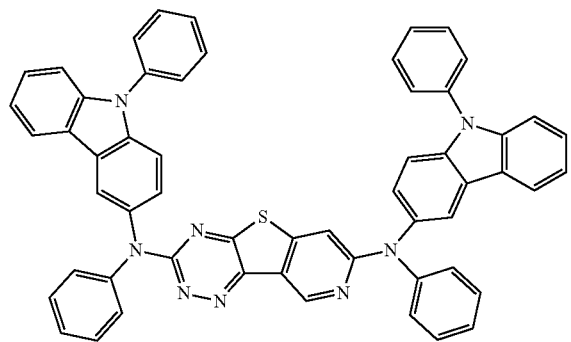
M470
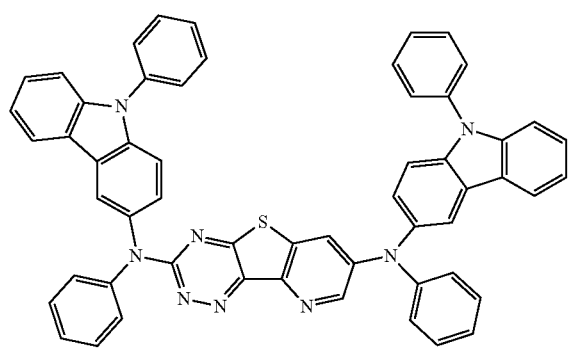
M471
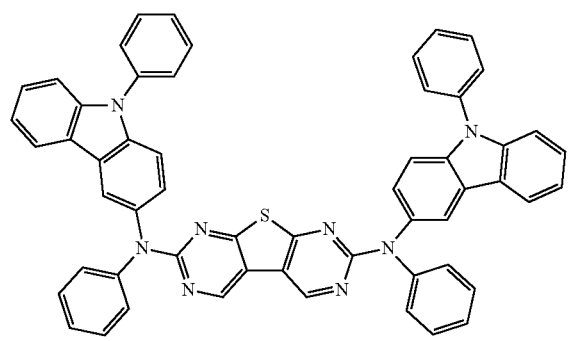
M472
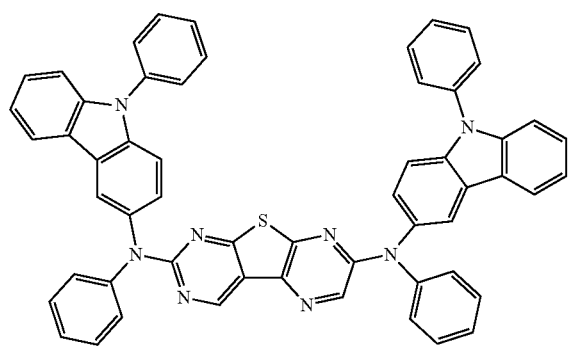
322
-continued
M473
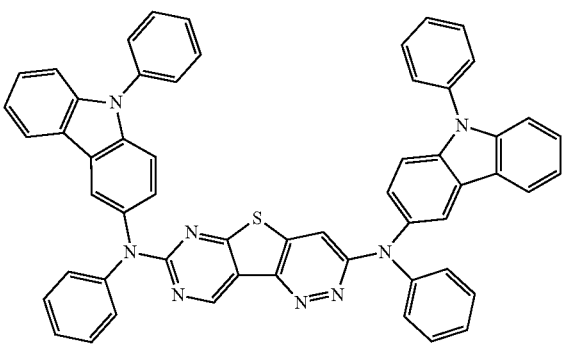
M474
M475
M476
23. The heterocyclic compound according to claim 1, wherein the heterocyclic compound has any one of following structures:

-continued
M477
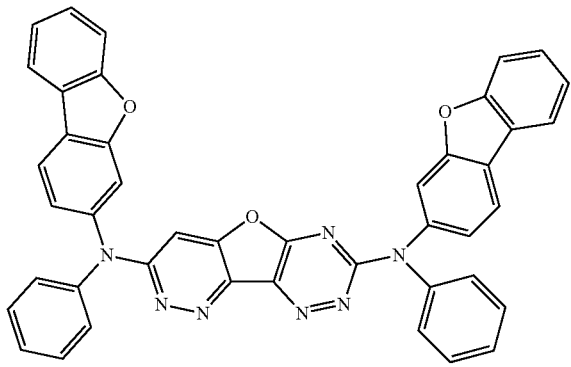
M480
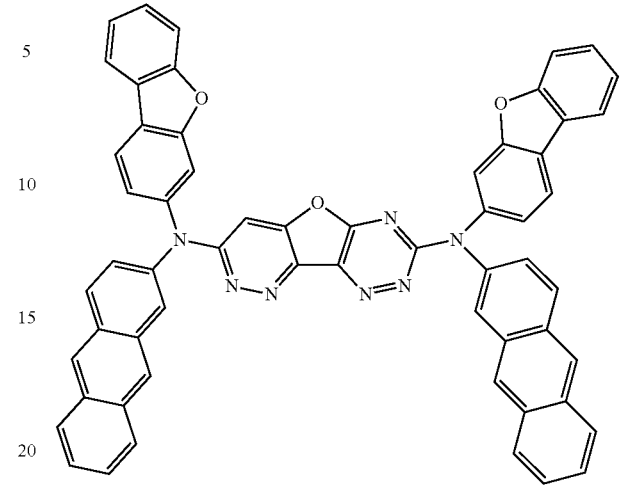
M478
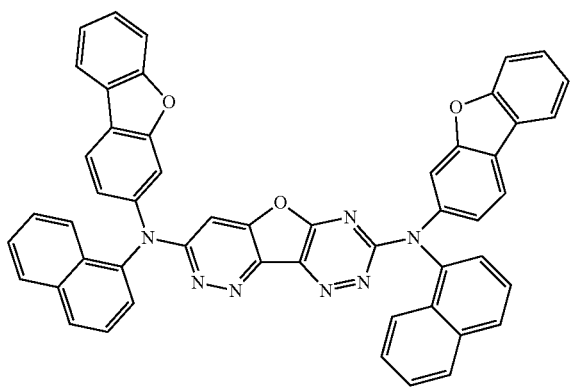
M481
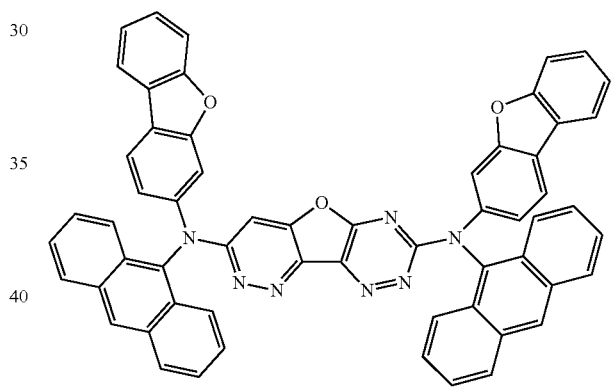
M479
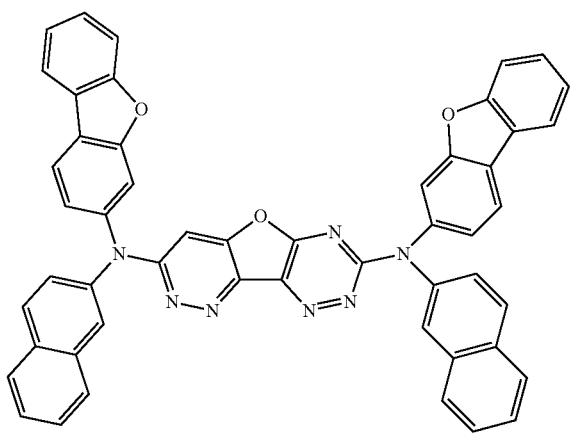
M482
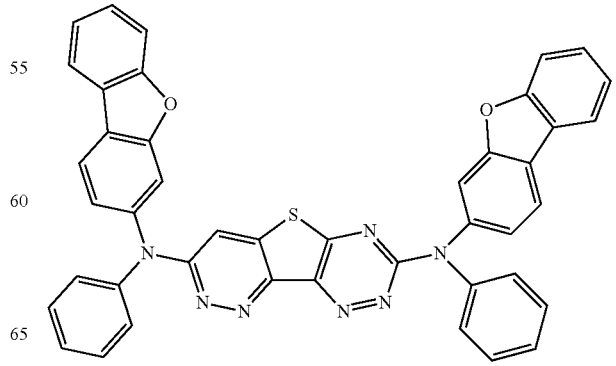

-continued
M483
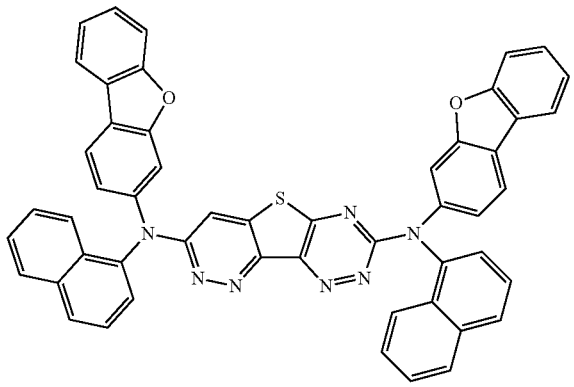
M484
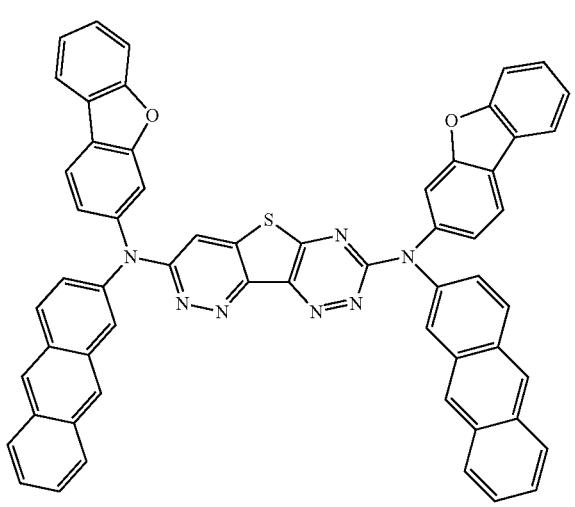
M485
-continued
M486
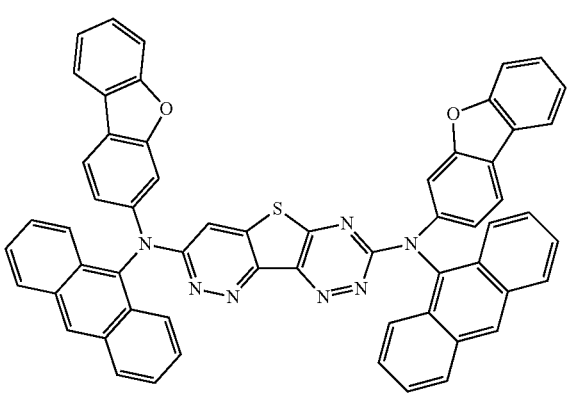
M487
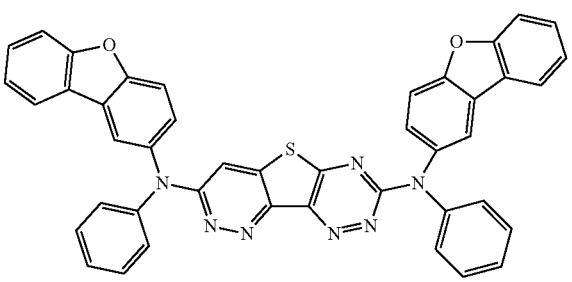
M488
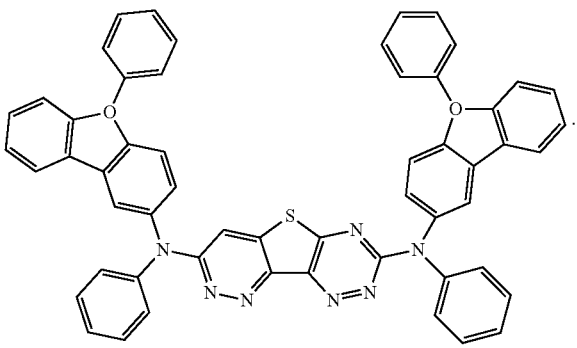
24. The heterocyclic compound according to claim 1, wherein the heterocyclic compound has any one of following structures:
M489
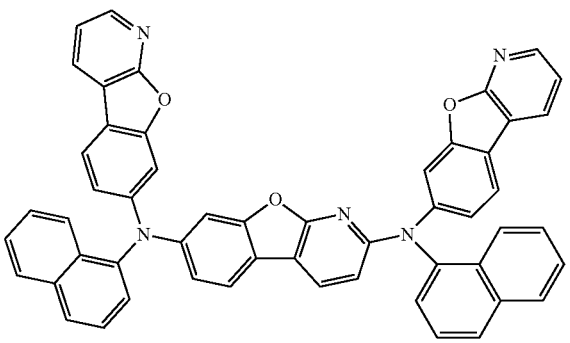

327
-continued
M490
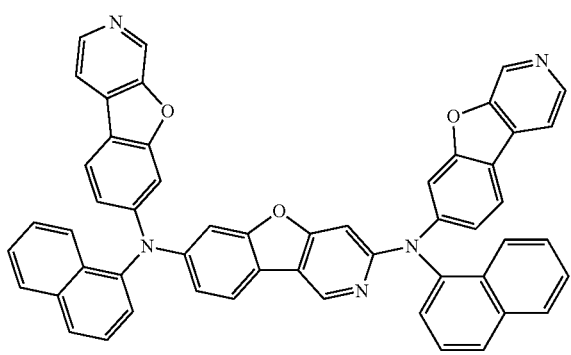
M491
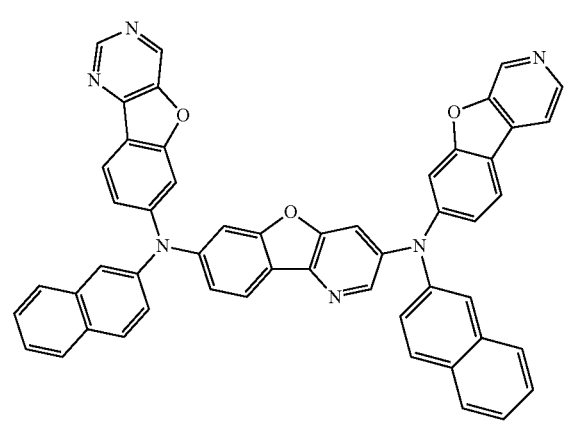
M492
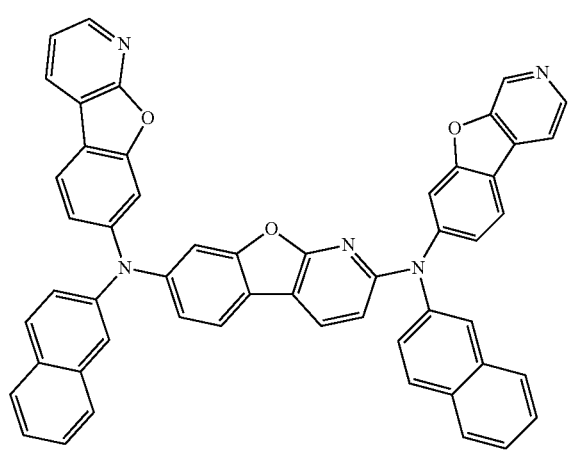
328
-continued
M493
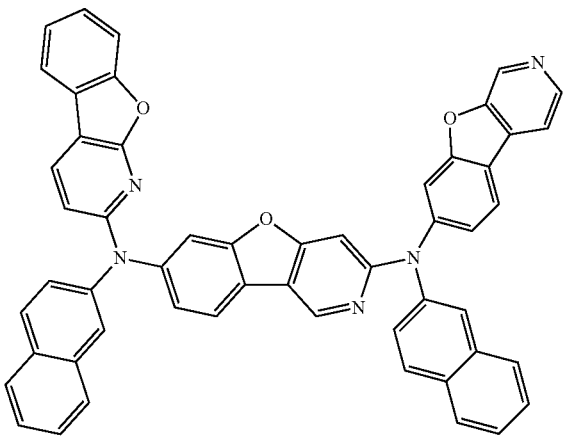
M494
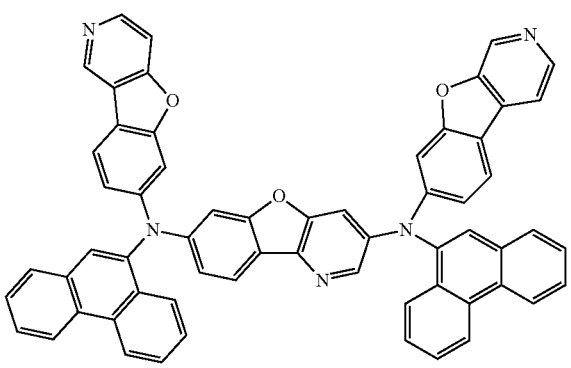
M495
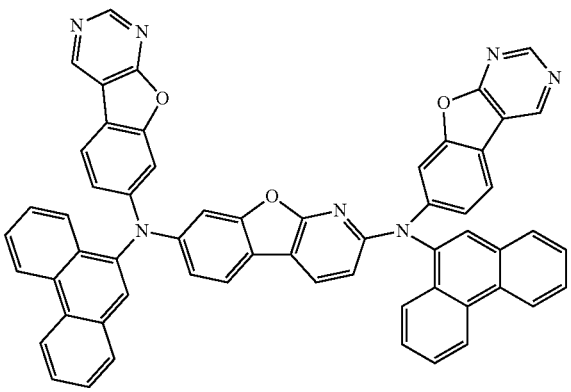
M496
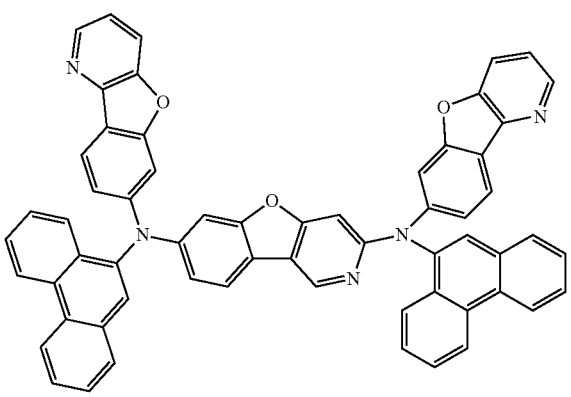

M497
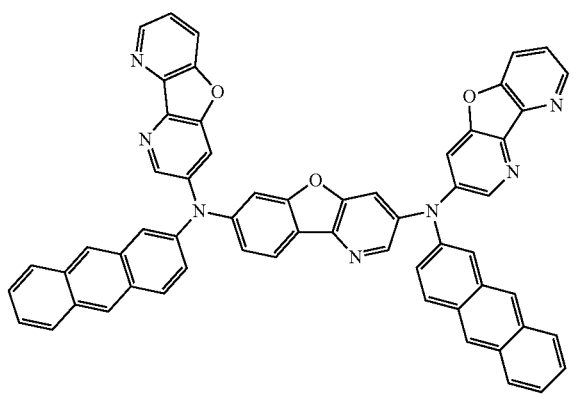
M498
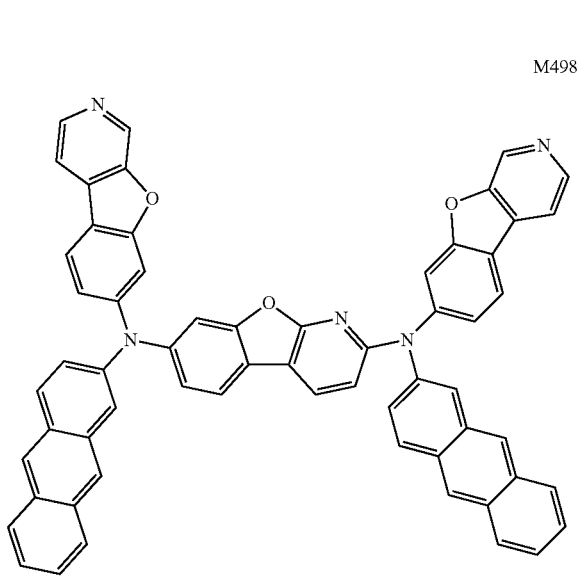
M499
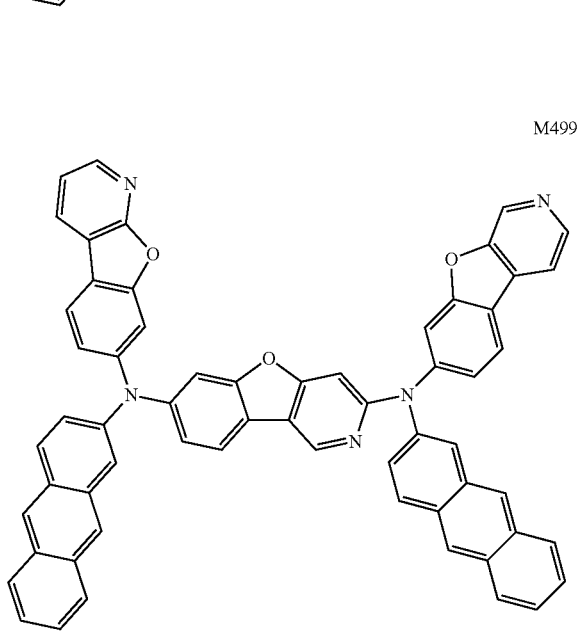
M500
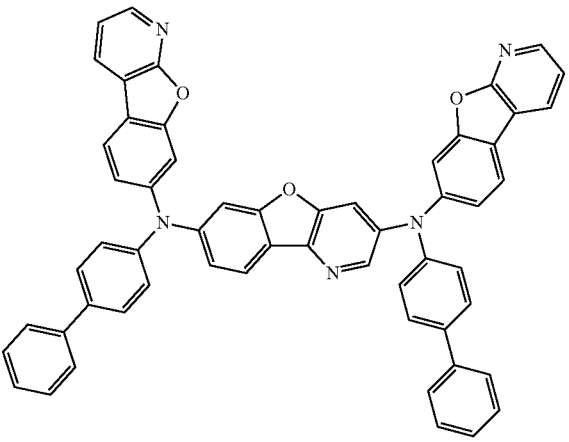
M501
M502
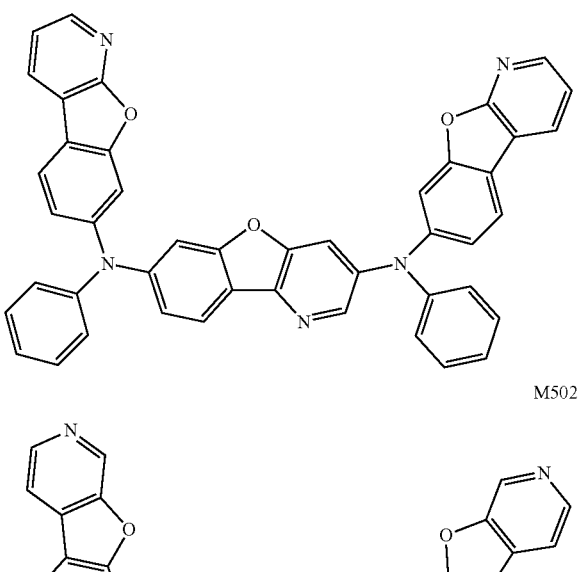
M503
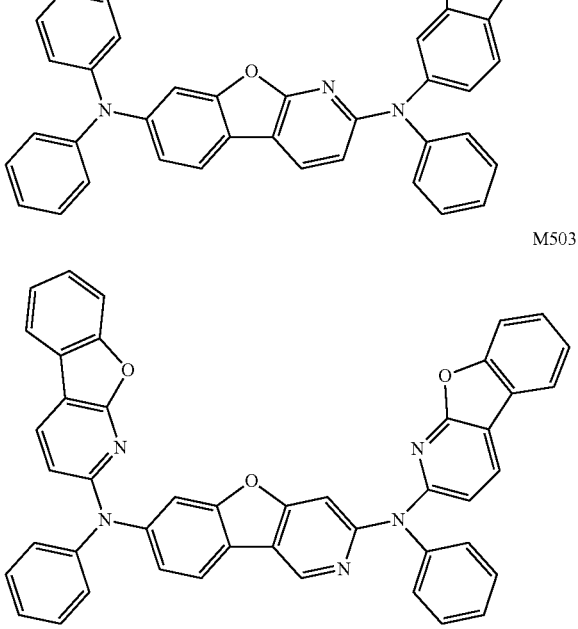

-continued

M504

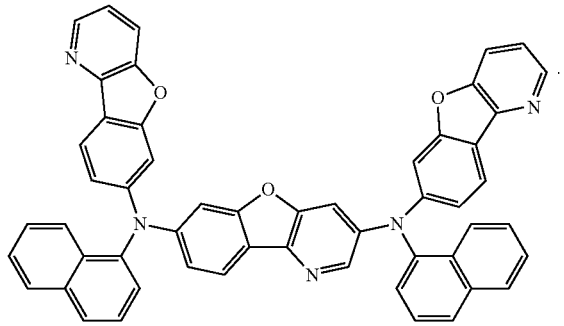

25. A display panel, comprising an organic light-emitting device, wherein the organic light-emitting device includes an anode, a cathode, and an organic thin film layer between the anode and the cathode; the cathode is covered with a capping layer (CPL); and the CPL layer contains at least a heterocyclic compound, having a structure shown in formula I, the heterocyclic compound comprising:

formula I

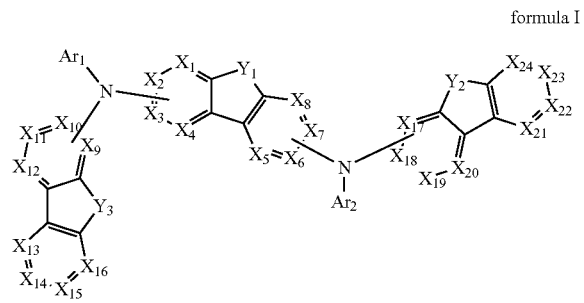

wherein:

$Y_1$ is selected from O or S;

$X_1$, $X_2$, $X_3$, $X_4$, $X_5$, $X_6$, $X_7$, and $X_8$ are independently selected from $CR_a$ or N, and at least one of $X_1$, $X_2$, $X_3$, $X_4$, $X_5$, $X_6$, $X_7$, and $X_8$ is N;

$X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, and $X_{24}$ are independently selected from $CR_1$ or N;

when there are a plurality of $CR_a$ in $X_1$-$X_8$, $R_a$ are same or different; and $R_a$ is independently selected from hydrogen, deuterium, tritium, halogen, nitrile, cyano, nitro, hydroxyl, carbonyl, ester, carboxyl, imide, amide, substituted or unsubstituted C1-C20 alkoxy, substituted or unsubstituted C1-C20 alkyl, substituted or unsubstituted C3-C20 cycloalkyl, substituted or unsubstituted C2-C20 alkenyl, substituted or unsubstituted C3-C20 cycloalkenyl, substituted or unsubstituted silyl, substituted or unsubstituted boron, substituted or unsubstituted phosphine oxide, substituted or unsubstituted phosphine, substituted or unsubstituted sulfonyl, substituted or unsubstituted amine, substituted or unsubstituted C6-C30 aryl, substituted or unsubstituted C3-C30 heteroaryl, or a ring structure formed by bonding adjacent groups;

$Y_2$, and $Y_3$ are independently selected from O, S or $NR_2$;

$Ar_1$ and $Ar_2$ are independently selected from substituted or unsubstituted aryl, or substituted or unsubstituted heteroaryl; and $R_1$ and $R_2$ are independently selected from hydrogen, deuterium, substituted or unsubstituted C1-C20 alkyl, substituted or unsubstituted C6-C30 aryl, or substituted or unsubstituted C3-C30 heteroaryl.

26. A display panel, comprising an organic light-emitting device, wherein the organic light-emitting device includes an anode, a cathode, and an organic thin film layer between the anode and the cathode; the organic thin film layer includes a hole transport layer and/or an electron transport layer, wherein at least one of the hole transport layer and the electron transport layer contains at least a heterocyclic compound, having a structure shown in formula I, the heterocyclic compound comprising:

formula I

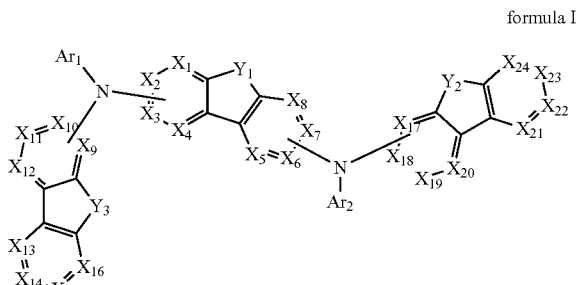

wherein:

$Y_1$ is selected from O or S;

$X_1$, $X_2$, $X_3$, $X_4$, $X_5$, $X_6$, $X_7$, and $X_8$ are independently selected from $CR_a$ or N, and at least one of $X_1$, $X_2$, $X_3$, $X_4$, $X_5$, $X_6$, $X_7$, and $X_8$ is N;

$X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, and $X_{24}$ are independently selected from $CR_1$ or N;

when there are a plurality of $CR_a$ in $X_1$-$X_8$, $R_a$ are same or different; and $R_a$ is independently selected from hydrogen, deuterium, tritium, halogen, nitrile, cyano, nitro, hydroxyl, carbonyl, ester, carboxyl, imide, amide, substituted or unsubstituted C1-C20 alkoxy, substituted or unsubstituted C1-C20 alkyl, substituted or unsubstituted C3-C20 cycloalkyl, substituted or unsubstituted C2-C20 alkenyl, substituted or unsubstituted C3-C20 cycloalkenyl, substituted or unsubstituted silyl, substituted or unsubstituted boron, substituted or unsubstituted phosphine oxide, substituted or unsubstituted phosphine, substituted or unsubstituted sulfonyl, substituted or unsubstituted amine, substituted or unsubstituted C6-C30 aryl, substituted or unsubstituted C3-C30 heteroaryl, or a ring structure formed by bonding adjacent groups;

$Y_2$, and $Y_3$ are independently selected from O, S or $NR_2$;

$Ar_1$ and $Ar_2$ are independently selected from substituted or unsubstituted aryl, or substituted or unsubstituted heteroaryl; and $R_1$ and $R_2$ are independently selected from hydrogen, deuterium, substituted or unsubstituted C1-C20 alkyl, substituted or unsubstituted C6-C30 aryl, or substituted or unsubstituted C3-C30 heteroaryl.

\* \* \* \* \*